US010374170B2

(12) United States Patent
Parham et al.

(10) Patent No.: US 10,374,170 B2
(45) Date of Patent: Aug. 6, 2019

(54) SUBSTITUTED OXEPINES

(71) Applicant: Merck Patent GmbH, Darmstadt (DE)

(72) Inventors: Amir Hossain Parham, Frankfurt am Main (DE); Arne Buesing, Frankfurt am Main (DE); Philipp Stoessel, Frankfurt am Main (DE); Anja Gerhard, Egelsbach (DE); Christof Pflumm, Darmstadt (DE); Thomas Eberle, Landau (DE); Anja Jatsch, Frankfurt am Main (DE); Jonas Valentin Kroeber, Frankfurt am Main (DE); Lars Dobelmann-Mara, Darmstadt (DE)

(73) Assignee: Merck Patent GmbH (DE)

( * ) Notice: Subject to any disclaimer, the term of this patent is extended or adjusted under 35 U.S.C. 154(b) by 48 days.

(21) Appl. No.: 15/101,219

(22) PCT Filed: Nov. 18, 2014

(86) PCT No.: PCT/EP2014/003071
§ 371 (c)(1),
(2) Date: Jun. 2, 2016

(87) PCT Pub. No.: WO2015/082046
PCT Pub. Date: Jun. 11, 2015

(65) Prior Publication Data
US 2016/0308146 A1    Oct. 20, 2016

(30) Foreign Application Priority Data

Dec. 6, 2013   (EP) .................................. 13005698

(51) Int. Cl.
| | | |
|---|---|---|
| *H01L 51/00* | (2006.01) | |
| *C07D 313/06* | (2006.01) | |
| *C07D 405/10* | (2006.01) | |
| *A61N 5/06* | (2006.01) | |
| *C07D 405/04* | (2006.01) | |
| *C07D 405/14* | (2006.01) | |
| *C07D 407/04* | (2006.01) | |
| *C07D 407/10* | (2006.01) | |
| *C07D 407/12* | (2006.01) | |
| *C07D 407/14* | (2006.01) | |
| *C07D 487/04* | (2006.01) | |
| *C07D 491/044* | (2006.01) | |
| *C09K 11/02* | (2006.01) | |
| *C09K 11/06* | (2006.01) | |
| *H01L 51/50* | (2006.01) | |
| *A61N 5/067* | (2006.01) | |

(52) U.S. Cl.
CPC ........ *H01L 51/0073* (2013.01); *A61N 5/0616* (2013.01); *C07D 313/06* (2013.01); *C07D 405/04* (2013.01); *C07D 405/10* (2013.01); *C07D 405/14* (2013.01); *C07D 407/04* (2013.01); *C07D 407/10* (2013.01); *C07D 407/12* (2013.01); *C07D 407/14* (2013.01); *C07D 487/04* (2013.01); *C07D 491/044* (2013.01); *C09K 11/025* (2013.01); *C09K 11/06* (2013.01); *H01L 51/006* (2013.01); *H01L 51/0052* (2013.01); *H01L 51/0053* (2013.01); *H01L 51/0054* (2013.01); *H01L 51/0058* (2013.01); *H01L 51/0059* (2013.01); *H01L 51/0061* (2013.01); *H01L 51/0067* (2013.01); *H01L 51/0071* (2013.01); *H01L 51/0072* (2013.01); *H01L 51/0085* (2013.01); *H01L 51/0087* (2013.01); *A61N 2005/067* (2013.01); *A61N 2005/0653* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1059* (2013.01); *C09K 2211/1088* (2013.01); *C09K 2211/185* (2013.01); *H01L 51/0002* (2013.01); *H01L 51/0003* (2013.01); *H01L 51/0056* (2013.01); *H01L 51/5012* (2013.01); *H01L 51/5016* (2013.01); *H01L 51/5056* (2013.01); *H01L 51/5072* (2013.01); *H01L 51/5076* (2013.01); *H01L 2251/5384* (2013.01); *Y02E 10/549* (2013.01); *Y02P 70/521* (2015.11)

(58) Field of Classification Search
CPC ..................... A01N 2300/00; G01N 33/582
See application file for complete search history.

(56) References Cited

U.S. PATENT DOCUMENTS

| | | | |
|---|---|---|---|
| 7,976,739 B2 | 7/2011 | Izumi et al. | |
| 8,039,126 B2 | 10/2011 | Stossel et al. | |
| 8,598,306 B2 | 12/2013 | McKiernan et al. | |
| 9,879,177 B2 | 1/2018 | Heun et al. | |
| 2010/0045171 A1* | 2/2010 | Katakura | C09K 11/06 313/504 |

FOREIGN PATENT DOCUMENTS

| | | | |
|---|---|---|---|
| CN | 102395549 A | 3/2012 | |
| JP | 2009532396 A | 9/2009 | |
| WO | WO-2008023828 A1 | 2/2008 | |
| WO | WO 2010119274 A1 * | 10/2010 | ............ C07C 25/22 |
| WO | WO-2010119274 A1 | 10/2010 | |
| WO | WO-2013174471 A1 | 11/2013 | |

OTHER PUBLICATIONS

International Search Report for PCT/EP2014/003071 dated Jun. 3, 2015.
Luo, J., et al., "Curved Polycyclic Aromatic Molecules That Are π-Isoelectronic to Hexabenzocoronene", Journal of the American Chemical Society, vol. 134, No. 33, (2012), pp. 13796-13803.

(Continued)

*Primary Examiner* — Michael J D Abreu
(74) *Attorney, Agent, or Firm* — Drinker Biddle & Reath LLP

(57) ABSTRACT

The invention relates to materials, to electroluminescence devices comprising said materials and to the use thereof.

22 Claims, No Drawings

(56) References Cited

OTHER PUBLICATIONS

Ohishi, T., et al., "High-yielding TfOH-catalyzed condensation of phenols with aromatic aldehydes at high pressure. A model synthesis of the benzylidene biphenol key skeleton of blepharismins", Tetrahedron Letters, vol. 42, No. 13, (2001), pp. 2493-2496.

Wei, Y., et al., "Emission Mechanism of Doubly ortho-Linked Quinoxaline/Diphenylfluorene or cis-Stilbene/Fluorene Hybrid Compounds Based on the Transient Absorption and Emission Measurements during Pulse Radiolysis", Journal of the American Chemical Society, vol. 131, No. 19, (2009), pp. 6698-6707.

European Examination Report for European Application No. EP 14818867.5, dated Jun. 27, 2017.

"CASEANNEX", REAXYS database, 2015, pp. 1-87.

Baidossi, W., et al., "Selective Transformations of Phenylated Diynes to Polycyclic Compounds by the $RhCl_3$-and $PtCl_4$-Aliquat 336® Ion Pair Catalysts", Tetrahedron, 1996, vol. 52, No. 24, pp. 8349-8364.

Büttner, F., et al., "Two novel series of allocolchicinoids with modified seven membered B-rings: design, synthesis, inhibition of tubulin assembly and cytotoxicity", Bioorganic & Medicinal Chemistry, 2005, vol. 13, No. 10, pp. 3497-3511.

Kametani, T., et al., "A Synthesis of 10,11-dihydro-2,3-dimethoxydibenzo[b,f]oxepin.", Yakugaku Zasshi, 1964, vol. 84, No. 7, pp. 642-646.

Kametani, T., et al., "Cularine and Related Compound Part VI. A Total Synthesis of (±)-cularine", Journal of the Chemical Society, 1963, pp. 4289-4296.

Kimura, T., et al., "Effect of Thorough-Space Interaction on the Photolytic Desulfurization or Deselenization and Intramolecular Cyclization Reactions of 1,9-Disubstituted Dibenzochalcogenophenes", J. Org. Chem., 1994, vol. 59, No. 23, pp. 7117-7124.

Schwan, A.L., "Product Subclass 4: benzothiepins and Selenium/Tellurium Analogues", Science of Synthesis, 2004, vol. 17, pp. 717-748.

Tochtermann, W., et al., "An Optically Active Tribenzoxepin", Angew. Chem. Internat. Edit., 1969, vol. 8, No. 1, pp. 68-69.

Tochtermann, W., et al., "Preparation and thermolys is of tetraphenyltribenzocycloheptatrienyl chlorosulfite", Tetrahedron Letters, 1996, No. 15, pp. 1163-1166.

Tochtermann, W., et al., "Seven-member ring systems. III. Intermediary occurrence of 10, 11-dehydrodibenzo [b,f] thiepin S, S-dioxide and 10, 11-dehydrodibenzo [b,f] oxepin", Liebigs Ann. Chem., 1967, vol. 701, pp. 117-125.

Yamada, M., et al., "A Facile Method fro Deprotection of O-Allylphenols", Chemical & Pharaceutical Bulletin, 2003, vol. 51, No. 10, pp. 1220-1221.

Chinese Office Action with English Translation for Chinese Application No. 201480066602.5, dated Feb. 26, 2018.

Kumar, S., et al., "Heteroaromatic annulation studies on 10,11-dihydro-11-[bis(methylthio)methylene]dibenzoxepin-10-one: a facile access to novel dibenzoxepino[4,5]-fused heterocycles", Tetrahedron, 2007, vol. 63, pp. 10067-10076.

* cited by examiner

SUBSTITUTED OXEPINES

CROSS-REFERENCE TO RELATED APPLICATIONS

This application is a national stage application (under 35 U.S.C. § 371) of PCT/EP2014/003071, filed Nov. 18, 2014, which claims benefit of European Application No. 13005698.9, filed Dec. 6, 2013, both of which are incorporated herein by reference in their entirety.

The present invention relates to a novel class of organic compounds, to compositions and formulations comprising these, and to the preparation thereof and to optoelectronic devices comprising the compounds.

Optoelectronic devices have been the subject of intensive research for many years. Among the optoelectronic devices, organic electroluminescent devices in particular have piqued the interest of research and development in industry and universities. These include, for example, the organic light-emitting diodes (OLEDs and PLEDs) and the organic light-emitting electrochemical cells (OLECs, LECs or LEECs).

The structure of organic electroluminescent devices (for example OLEDs) in which organic semiconductors are used as functional materials is described, for example, in U.S. Pat. Nos. 4,539,507, 5,151,629, EP 0676461 and WO 98/27136. Emitting materials used here, as well as fluorescent emitters, are increasingly organometallic complexes which exhibit phosphorescence (M. A. Baldo et al., Appl. Phys. Lett. 1999, 75, 4-6). For quantum-mechanical reasons, up to four times the energy efficiency and power efficiency is possible using organometallic compounds as phosphorescent emitters. In general terms, both in the case of OLEDs which exhibit singlet emission and in the case of OLEDs which exhibit triplet emission, there is still a need for improvement, especially with regard to efficiency, operating voltage and lifetime. This is especially true of OLEDs which emit in the shorter-wave range, i.e. green and especially blue.

The properties of OLEDs are determined not just by the emitters used. Also of particular significance here are especially the other materials used, such as matrix materials, hole blocker materials, electron transport materials, hole transport materials and electron or exciton blocker materials. Improvements to these materials can thus also lead to distinct improvements in the OLED properties.

However, there is still a need for improvement in the case of use of these host and matrix materials, and likewise of other matrix materials, especially in relation to the efficiency and lifetime of the device.

Even though some of the OLEDs based on small molecules (SMOLEDs) exhibit quite good efficiencies, lifetimes and/or operating voltage, thermal vapor deposition methods under reduced pressure are necessary, these being restricted to a particular device size. For mass production and for larger displays, however, it is desirable to apply the organic materials from solution, for example by means of spin-coating or inkjet methods, by means of which it is additionally possible to lower the production costs. Usually, light-emitting polymers, oligomers and/or dendrimers are used to process electroluminescent devices from solution. These compounds often exhibit good solubility in organic aromatic solvents and have good film-forming properties. A further way of improving processibility is, for example, to incorporate long alkyl chains as solubility-imparting groups into a molecule. Regrettably, the devices processed from solution using polymers, oligomers and/or dendrimers or molecules having alkyl chains usually have poorer performance than comparable small molecules in terms of efficiency, lifetime and operating voltage.

It is an object of the present invention to provide compounds suitable for use in a fluorescent or phosphorescent OLED, for example as matrix material or as hole transport/electron blocker material or exciton blocker material, or as electron transport or hole blocker material, and which lead to good device properties when used in an OLED, and to provide the corresponding electronic device.

It is a further object of the present invention to provide the molecules which have improved solubility and can therefore be processed from solution in the production of a light-emitting device. It is yet a further object of the present invention to provide molecules of particularly good suitability for production of light-emitting devices from the gas phase, i.e. to provide molecules which can be applied by vapor deposition in a particularly efficient manner.

It has been found that, surprisingly, particular compounds described in detail below achieve these objects and lead to good properties of the organic electronic devices, especially in organic electroluminescent device, especially with regard to lifetime, efficiency, operating voltage and processibility. Electronic devices, especially organic electroluminescent devices, containing such compounds, and the corresponding preferred compounds, are therefore provided by the present invention.

The present invention relates to a compound of the general formula (1)

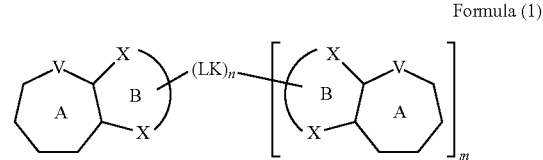

Formula (1)

where the B ring is an aromatic or heteroaromatic ring or ring system fused onto the A ring, where further rings that may be fused onto the A ring may be substituted independently by one or more $R^1$ radicals which may be the same or different at each instance, and where the further symbols and indices are:

V
  is either O, S or $C(R^4)_2$, preferably O or S and very preferably O;

X
  is the same or different at each instance and is N or $CR^1$, preferably $CR^1$;

m
  is 0 (monomer), 1 (dimer) or 2 (trimer);

n
  is 0 or 1, where:
  n=0 when m=0 and
  n=1 when m=1 or when m=2;

LK
  in the case that m=1 is a single bond or a bifunctional linker, where, in the case of a single bond, the two B rings are joined via a single bond; LK may be substituted by one or more $R^1$ radicals, where the $R^1$ radicals may be the same or different at each instance;
  when m=2 is a trifunctional linker, where the linker may be substituted by one or more $R^1$ radicals, where the $R^1$ radicals may be the same or different at each instance;
  when n=0 is absent, and so a monomer is present;

$R^1$ is the same or different at each instance and is H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^2$ radicals, where one or more nonadjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy, arylalkoxy or heteroaryloxy group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals, or a combination of two or more of these groups or a crosslinkable Q group; at the same time, two or more adjacent $R^1$ radicals together may form a mono- or polycyclic, aliphatic or aromatic or heteroaromatic ring system which may be substituted by one or more $R^2$ radicals, where it is preferable when two or more adjacent $R^1$ radicals together do not form a mono- or polycyclic, aliphatic or aromatic or heteroaromatic ring system;

$R^2$ is the same or different at each instance and is H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^3$ radicals, where one or more nonadjacent $CH_2$ groups may be replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy, arylalkoxy or heteroaryloxy group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of two or more of these groups; at the same time, two or more adjacent $R^2$ radicals together may form a mono- or polycyclic, aliphatic or aromatic or heteroaromatic ring system, where it is preferable when two or more adjacent $R^2$ radicals together do not form a mono- or polycyclic, aliphatic or aromatic or heteroaromatic ring system;

$R^3$ is the same or different at each instance and is H, D, F or an aliphatic, aromatic and/or heteroaromatic hydrocarbyl radical having 1 to 40 carbon atoms, in which one or more hydrogen atoms may also be replaced by F; at the same time, two or more $R^3$ substituents together may also form a mono- or polycyclic, aliphatic or aromatic or heteroaromatic ring system, where it is preferable when two or more adjacent $R^3$ radicals together do not form a mono- or polycyclic, aliphatic or aromatic or heteroaromatic ring system;

$R^4$ is as defined for $R^1$, but the two $R^4$ radicals must not form a ring closure;

with the proviso that the A rings, in addition to the fused aromatic or heteroaromatic B ring, each contain either another 2 or another 3 further aromatic or heteroaromatic rings or ring systems fused directly to the 7-membered A ring of formula (1), where the further rings or ring systems fused to the A ring may be substituted by one or more $R^1$ radicals, where the $R^1$ radicals may be the same or different at each instance, and with the proviso that, when m=0, at least one of the $R^1$ radicals is not H.

When m is 0, it is further preferable when at least one of the $R^1$ radicals is not H, where:

$R^1$ is the same or different at each instance and is H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^2$ radicals, where one or more nonadjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy, arylalkoxy or heteroaryloxy group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals, or a combination of two or more of these groups or a crosslinkable Q group; at the same time, two or more adjacent $R^1$ radicals together may not form a mono- or polycyclic, aliphatic or aromatic or heteroaromatic ring system which may be substituted by one or more $R^2$ radicals;

$R^2$ is the same or different at each instance and is H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^3$ radicals, where one or more nonadjacent $CH_2$ groups may be replaced by $R^3C=CR^3$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy, arylalkoxy or heteroaryloxy group which has 5 to 60 aromatic ring atoms and may be substituted by one or more $R^3$ radicals, or a diarylamino group, diheteroarylamino group or arylheteroarylamino group which has 10 to 40 aromatic ring atoms and may be substituted by one or more $R^3$ radicals, or a combination of two or more of these groups; at the same time, two or more adjacent $R^2$ radicals together may not form a mono- or polycyclic, aliphatic or aromatic or heteroaromatic ring system;

$R^3$
is the same or different at each instance and is H, D, F or an aliphatic, aromatic and/or heteroaromatic hydrocarbyl radical having 1 to 40 carbon atoms, in which one or more hydrogen atoms may also be replaced by F; at the same time, two or more $R^3$ substituents together may not also form a mono- or polycyclic, aliphatic or aromatic or heteroaromatic ring system.

It is preferable when the further ring(s) fused to the A ring are themselves aromatic rings or heteroaromatic rings, it being very preferable when they are aromatic rings. It may be the case here that the further ring(s) do not just form a fused ring system with the A ring but are simultaneously also fused to the B ring.

As described above, there is no ring closure between the two $R^4$ radicals. Since the $R^4$ radicals are otherwise as defined for the $R^1$ radicals and $R^1$ may be substituted by $R^2$ and further by $R^3$, it is also possible for the two $R^4$ radicals to be substituted by $R^2$ and further by $R^3$, where there is no ring closure between the $R^2$ radicals or between the $R^3$ radicals either.

It is preferable when m is 0 or 1, very preferable when m is 0, i.e. when the compounds of the invention are in the form of monomers.

It is preferable when the B ring is an aromatic or heteroaromatic ring or ring system having 5 to 60 ring atoms, it being very preferable when B is an aromatic ring or an aromatic ring system having 6 to 60 ring atoms.

In a preferred embodiment, m=n=0 (monomer). In a further preferred embodiment, m=n=1 (dimer). In yet a further preferred embodiment, m=2 and n=1 (trimer). It is most preferred in this connection when m=n=0.

The present invention preferably relates to a compound of the general formula (2)

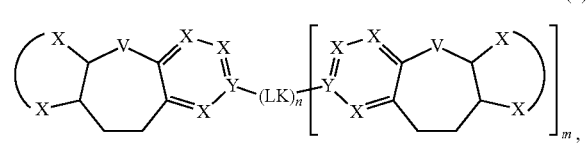

Formula (2)

where the above definitions and provisos apply and where:

Y
is an $sp^2$-hybridized carbon atom when m is not 0 or is X when m=0;

where preferred embodiments of the indices and symbols used that are specified elsewhere also constitute preferred embodiments for the compound of the formula (2).

The present invention very preferably relates to a compound of the general formula (3)

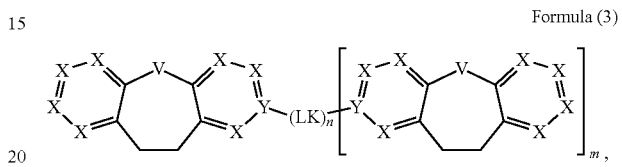

Formula (3)

where preferred embodiments of the indices and symbols used that are specified elsewhere also constitute preferred embodiments for the compound of the formula (3).

In a particularly preferred embodiment, the present invention relates to a compound of the general formula (4), where preferred embodiments of the indices and symbols used that are specified elsewhere also constitute preferred embodiments for the compound of the formula (4).

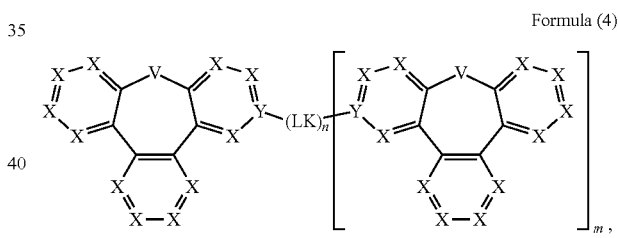

Formula (4)

As already described above, X is preferably $CR^1$, i.e. a very preferred compound in this connection is one of the general formula (5), where preferred embodiments of the indices and symbols used that are specified elsewhere also constitute preferred embodiments for the compound of the formula (5).

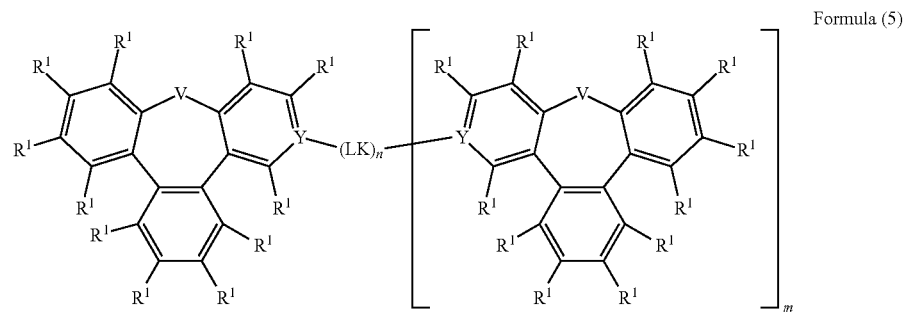

Formula (5)

It is further preferable here when at least one or two of the $R^1$ radicals in formula (5) is/are not H.

In a very particularly preferred embodiment, the present invention relates to a compound of the general formula (5), where preferred embodiments of the indices and symbols used that are specified elsewhere also constitute preferred embodiments for the compound of the formula (6).

Formula (6)

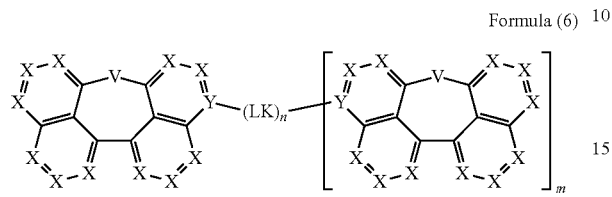

As already described above, X is preferably $CR^1$, i.e. a very preferred compound in this connection is one of the general formula (7), where preferred embodiments of the indices and symbols used that are specified elsewhere also constitute preferred embodiments for the compound of the formula (7).

Formula (7)

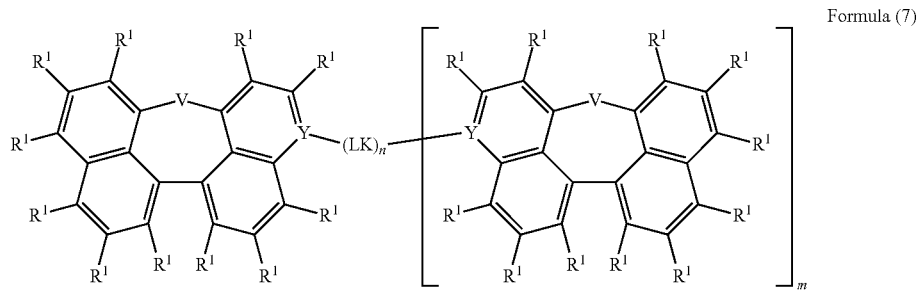

In a further preferred embodiment, the present invention relates to a compound of the general formula (8), where preferred embodiments of the indices and symbols used that are specified elsewhere also constitute preferred embodiments for the compound of the formula (8).

Formula (8)

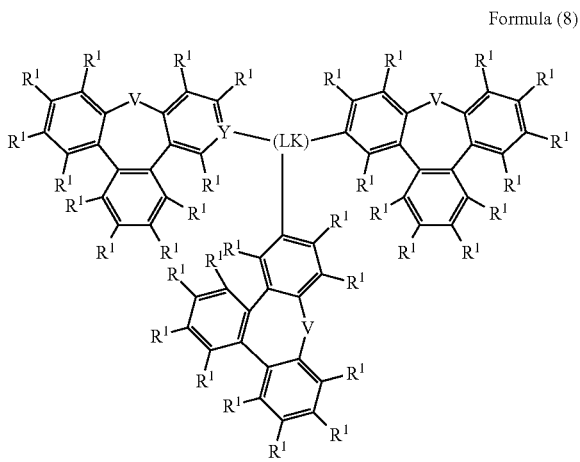

In yet a further preferred embodiment, the present invention relates to a compound of the general formula (9), where preferred embodiments of the indices and symbols used that are specified elsewhere also constitute preferred embodiments for the compound of the formula (9).

Formula (9)

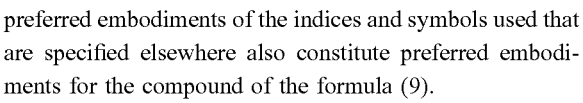
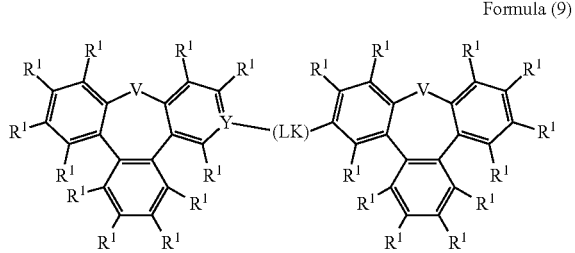

In a very preferred embodiment, the present invention relates to a compound of the general formula (10), where preferred embodiments of the indices and symbols used that are specified elsewhere also constitute preferred embodiments for the compound of the formula (10).

Formula (10)

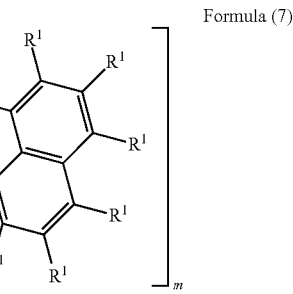
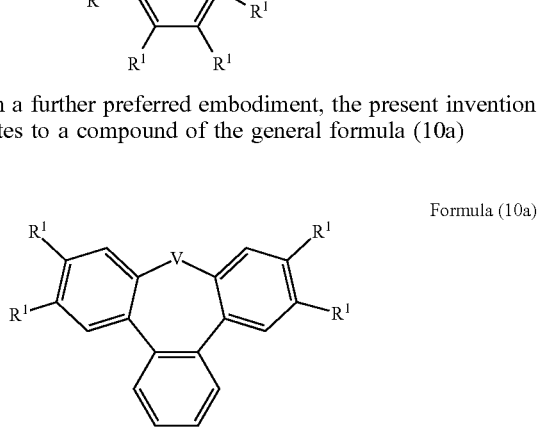

In a further preferred embodiment, the present invention relates to a compound of the general formula (10a)

Formula (10a)

where it is especially preferred for the compound of the general formula (10a) when the adjacent $R^1$ radicals enter into a ring closure.

In a further preferred embodiment, the present invention relates to a compound of the general formula (10b)

Formula (10b)

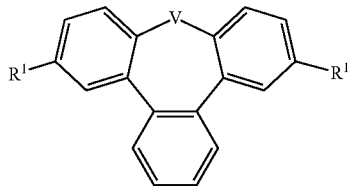

It is preferable when neither $R^1$ radical in the compound of the formula (10b) is H.

In a further preferred embodiment, the present invention relates to a compound of the general formula (10c)

Formula (10c)

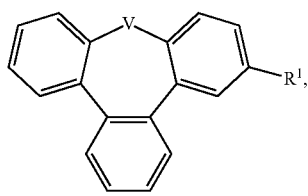

In a further preferred embodiment, the present invention relates to a compound of the general formula (10d)

Formula (10d)

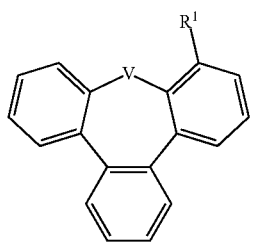

In a further preferred embodiment, the present invention relates to a compound of the general formula (11), where preferred embodiments of the indices and symbols used that are specified elsewhere also constitute preferred embodiments for the compound of the formula (11).

Formula (11)

In yet a further preferred embodiment, the present invention relates to a compound of the general formula (12), where preferred embodiments of the indices and symbols used that are specified elsewhere also constitute preferred embodiments for the compound of the formula (12).

Formula (12)

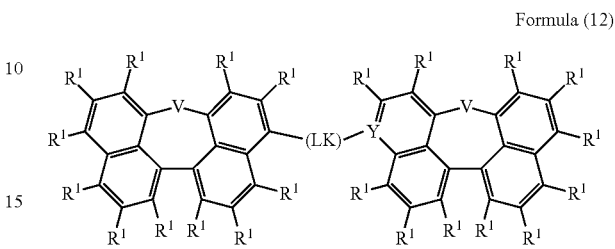

In a very preferred embodiment, the present invention relates to a compound of the general formula (13), where preferred embodiments of the indices and symbols used that are specified elsewhere also constitute preferred embodiments for the compound of the formula (13).

Formula (13)

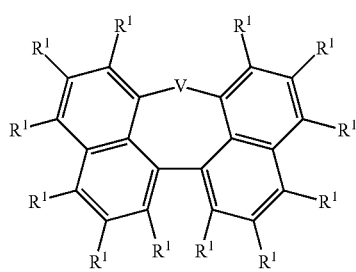

In a very particularly preferred embodiment, the present invention relates to a compound of the general formula (14), where preferred embodiments of the indices and symbols used that are specified elsewhere also constitute preferred embodiments for the compound of the formula (14).

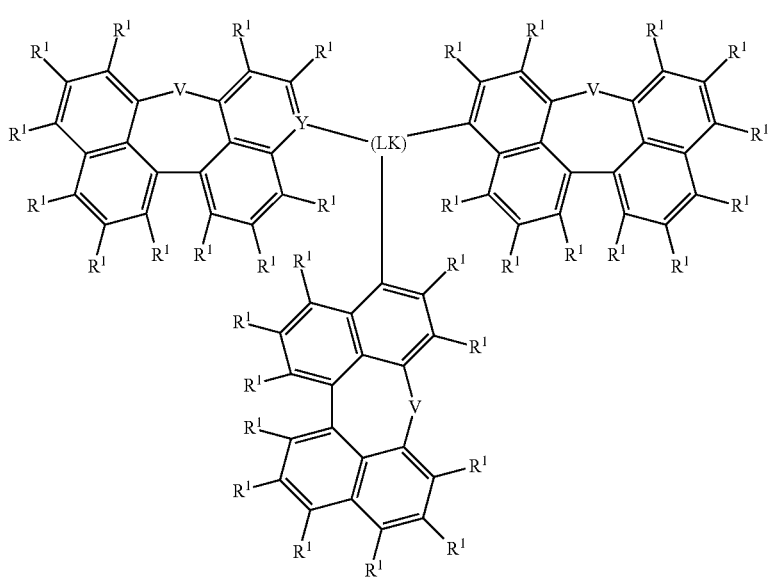

Formula (14)

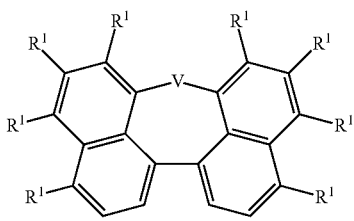

In an additionally very particularly preferred embodiment, the present invention relates to a compound of the general formula (15), where preferred embodiments of the indices and symbols used that are specified elsewhere also constitute preferred embodiments for the compound of the formula (15).

Formula (15)

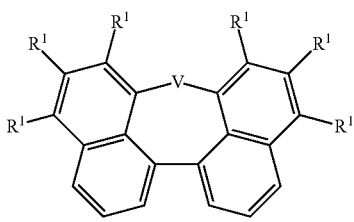

In an additionally very particularly preferred embodiment, the present invention relates to a compound of the general formula (16), where preferred embodiments of the indices and symbols used that are specified elsewhere also constitute preferred embodiments for the compound of the formula (16).

Formula (16)

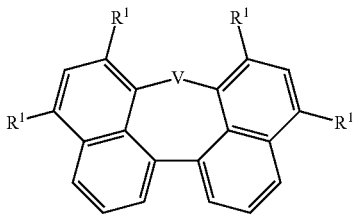

In an additionally very particularly preferred embodiment, the present invention relates to a compound of the general formula (17), where preferred embodiments of the indices and symbols used that are specified elsewhere also constitute preferred embodiments for the compound of the formula (17).

Formula (17)

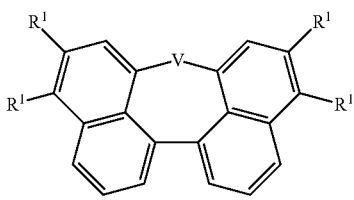

In an especially preferred embodiment, the present invention relates to a compound of the general formula (18), where preferred embodiments of the indices and symbols used that are specified elsewhere also constitute preferred embodiments for the compound of the formula (18).

Formula (18)

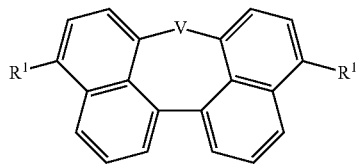

In another especially preferred embodiment, the present invention relates to a compound of the general formula (19), where preferred embodiments of the indices and symbols used that are specified elsewhere also constitute preferred embodiments for the compound of the formula (19).

Formula (19)

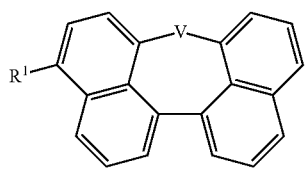

LK in the compounds specified herein is either a single bond or a bifunctional or trifunctional linker. The person skilled in the art will have no difficulty at all in selecting suitable linkers.

In a preferred embodiment of the present invention, the linker LK is a single bond or a bifunctional group, i.e. n=1 and m=1. If LK is a single bond, the two B rings specified in the compound of the general formula (1) are directly covalently bonded to one another.

Preferred bifunctional linkers LK in the context of the present invention are selected from $NR^1$, $C(=O)$, $P(=O)$, $P(=O)R^1$, a straight-chain alkyl, alkoxy or thioalkoxy group having 1 to 10 carbon atoms or a straight-chain alkenyl or alkynyl group having 2 to 10 carbon atoms or a branched or cyclic alkyl, alkenyl, alkynyl, alkoxy, alkylalkoxy or thioalkoxy group having 3 to 20 carbon atoms, each of which may be substituted by one or more $R^1$ radicals, where one or more nonadjacent $CH_2$ groups may be replaced by $R^1C=CR^1$, $C≡C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$, or an aromatic or heteroaromatic ring system which has 5 to 30 aromatic ring atoms and may be substituted in each case by one or more $R^1$ radicals, or an aryloxy, arylalkoxy or heteroaryloxy group which has 5 to 30 aromatic ring atoms and may be substituted by one or more $R^1$ radicals.

Very particularly preferred bifunctional linkers LK are selected from $NR^1$, $C(=O)$, $P(=O)$, $P(=O)R^1$ and an aromatic or heteroaromatic ring system having 5 to 30 aromatic ring atoms, each of which may be substituted by one or more $R^1$ radicals.

Among the aromatic rings and heteroaromatic rings as bifunctional LK group, very particular preference is given to a phenylene, biphenylene, terphenylene, naphthylene, anthracenylene, pyridylene, pyridazylene, pyrimidylene, pyrazinylene, triazylene, fluorenylene, indenofluorenylene, dibenzofuranylene, dibenzothiophenylene, carbazoylene, indenocarbazoylene and indolocarbazoylene group, each of which may be substituted by one or more independent $R^1$ radicals, where the phenylenes are very particularly preferred bifunctional linkers. Especially preferred is a meta or para linkage to the phenylene.

Preferred trifunctional linkers in the context of the present invention are selected from N, P(=O), a branched or cyclic alkyl, alkenyl, alkynyl, alkoxy, alkylalkoxy or thioalkoxy group having 3 to 20 carbon atoms, each of which may be substituted by one or more $R^1$ radicals, where one or more nonadjacent $CH_2$ groups may be replaced by $R^1C=CR^1$, C≡C, $Si(R^1)_2$, $Ge(R^1)_2$, $Sn(R^1)_2$, C=O, C=S, C=Se, C=$NR^1$, P(=O)($R^1$), SO, $SO_2$, $NR^1$, O, S or $CONR^1$ and where one or more hydrogen atoms may be replaced by D, F, Cl, Br, I, CN or $NO_2$, or an aromatic or heteroaromatic ring system which has 5 to 30 aromatic ring atoms and may be substituted in each case by one or more $R^1$ radicals, or an aryloxy, arylalkoxy or heteroaryloxy group which has 5 to 30 aromatic ring atoms and may be substituted by one or more independent $R^1$ radicals.

Very preferred trifunctional linkers LK are selected from N, P(=O) and an aromatic or heteroaromatic ring system having 5 to 30 aromatic ring atoms, each of which may be substituted by one or more independent $R^1$ radicals.

Among the aromatic rings and heteroaromatic rings as bifunctional LK group, very particular preference is given to a phenylene, biphenylene, terphenylene, naphthylene, anthracenylene, pyridylene, pyridazylene, pyrimidylene, pyrazinylene, triazylene, fluorenylene, indenofluorenylene, dibenzofuranylene, dibenzothiophenylene, carbazoylene, indenocarbazoylene and indolocarbazoylene group, each of which may be substituted by one or more independent $R^1$ radicals, where the phenylenes and triazinylenes are very particularly preferred trifunctional linkers. Especially preferred is a 1,3,5 linkage to the phenylene.

In the compounds of the invention, the specified $R^1$ radicals may all also be H. In a preferred embodiment, however, at least one of the $R^1$ radicals is not H.

It is preferable when the $R^1$ radical is the same or different at each instance and is selected from the group consisting of H, D, $N(R^2)_2$, CN, $B(OR^2)_2$, C(=O)$R^2$, P(=O)$(R^2)_2$, S(=O)$R^2$, S(=O)$_2R^2$, $OSO_2R^2$, a straight-chain alkyl, alkoxy or thioalkoxy group having 1 to 40 carbon atoms or a branched or cyclic alkyl, alkoxy, alkylalkoxy or thioalkoxy group having 3 to 40 carbon atoms, each of which may be substituted by one or more $R^2$ radicals, or an aromatic or heteroaromatic ring system which has 5 to 60 aromatic ring atoms and may be substituted in each case by one or more $R^2$ radicals, or an aryloxy, arylalkoxy or heteroaryloxy group which has 5 to 60 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals, or a combination of two or more of these groups; at the same time, two or more adjacent $R^1$ radicals together may form a mono- or polycyclic, aliphatic or aromatic or heteroaromatic ring system which may be substituted by one or more $R^2$ radicals.

It is very preferable when the $R^1$ radical is the same or different at each instance and is selected from the group consisting of H, D, $N(R^2)_2$, a straight-chain alkyl, alkoxy or thioalkoxy group having 1 to 40 carbon atoms or a branched or cyclic alkyl, alkoxy, alkylalkoxy or thioalkoxy group having 3 to 40 carbon atoms, each of which may be substituted by one or more $R^2$ radicals, or an aromatic or heteroaromatic ring system which has 5 to 60 aromatic ring atoms and may be substituted in each case by one or more $R^2$ radicals, or a diarylamino group, diheteroarylamino group or arylheteroarylamino group which has 10 to 40 aromatic ring atoms and may be substituted by one or more $R^2$ radicals, or a combination of two or more of these groups; at the same time, two or more adjacent $R^1$ radicals together may form a mono- or polycyclic, aliphatic or aromatic or heteroaromatic ring system which may be substituted by one or more $R^2$ radicals.

It is particularly preferable when the $R^1$ radical is the same or different at each instance and is selected from the group consisting of H, D, a straight-chain alkyl group having 1 to 40 carbon atoms, an aromatic or heteroaromatic ring system which has 5 to 60 aromatic ring atoms and may be substituted in each case by one or more $R^2$ radicals; at the same time, two or more adjacent $R^1$ radicals together may form a mono- or polycyclic, aliphatic or aromatic or heteroaromatic ring system which may be substituted by one or more $R^2$ radicals.

It is very particularly preferable when the $R^1$ radical is the same or different at each instance and is selected from the group consisting of H, a straight-chain alkyl group having 1 to 40 carbon atoms, an aromatic or heteroaromatic ring system which has 5 to 60 aromatic ring atoms and may be substituted in each case by one or more $R^2$ radicals; at the same time, two or more adjacent $R^1$ radicals together may form a mono- or polycyclic, aliphatic or aromatic or heteroaromatic ring system which may be substituted by one or more $R^2$ radicals.

It is especially preferable when the $R^1$ radical is the same or different at each instance and is selected from the group consisting of H, an aromatic or heteroaromatic ring system which has 5 to 60 aromatic ring atoms and may be substituted in each case by one or more $R^2$ radicals; at the same time, two or more adjacent $R^1$ radicals together may form a mono- or polycyclic, aliphatic or aromatic or heteroaromatic ring system which may be substituted by one or more $R^2$ radicals.

The following overview shows some particularly preferred $R^1$ radicals, where the radicals shown may also be substituted by one or more $R^2$ radicals which may be the same or different at each instance:

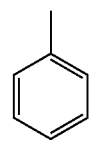

Formula (R1-1)

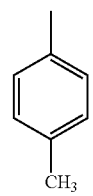

Formula (R1-2)

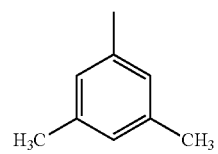

Formula (R1-3)

-continued
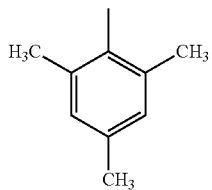
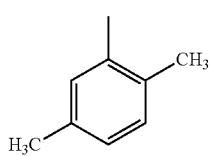
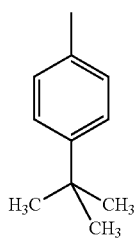
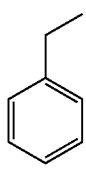
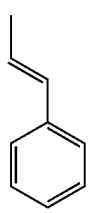
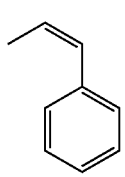
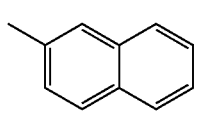
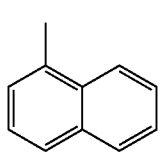
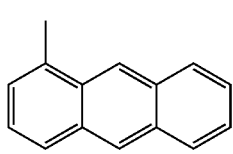
-continued
Formula (R1-4)
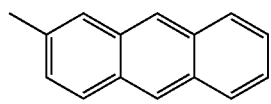
Formula (R1-5)
Formula (R1-6)
Formula (R1-7)
Formula (R1-8)
Formula (R1-9)
Formula (R1-10)
Formula (R1-11)
Formula (R1-12)
Formula (R1-13)
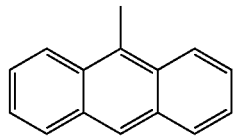
Formula (R1-14)
Formula (R1-15)
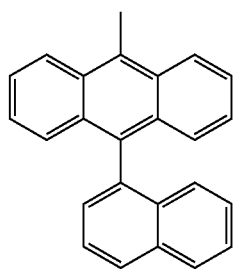
Formula (R1-16)
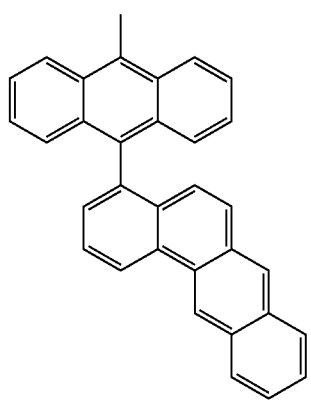
Formula (R1-17)
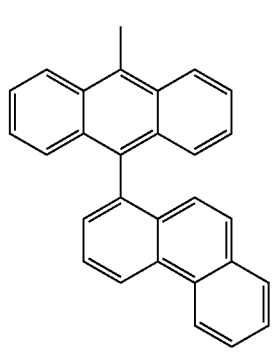
Formula (R1-18)
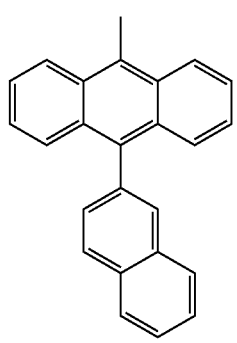

Formula (R1-19)
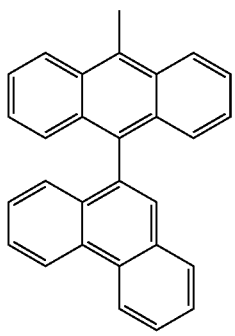
Formula (R1-20)
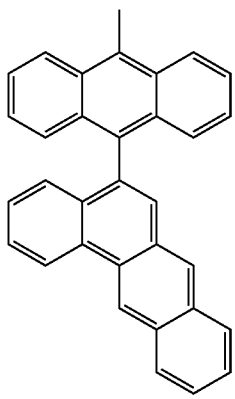
Formula (R1-21)
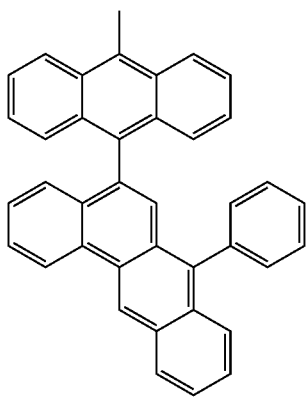
Formula (R1-22)
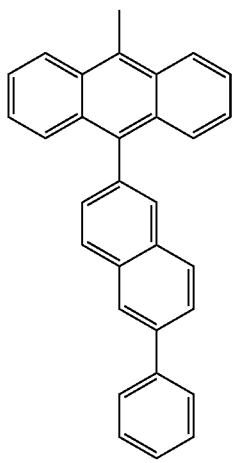
Formula (R1-23)
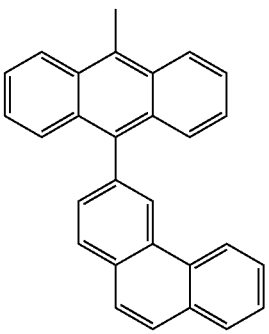
Formula (R1-24)
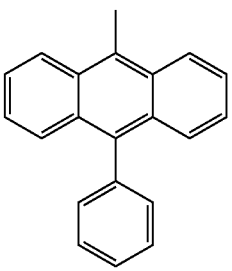
Formula (R1-25)
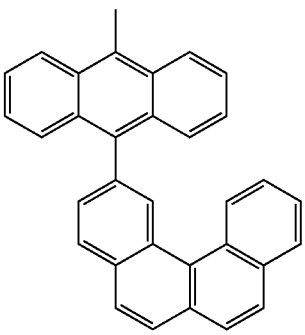
Formula (R1-26)
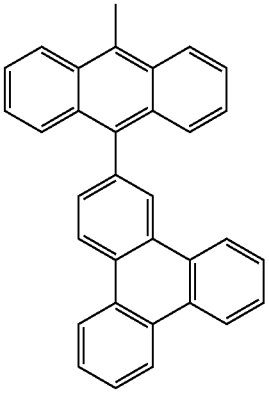

Formula (R1-27)
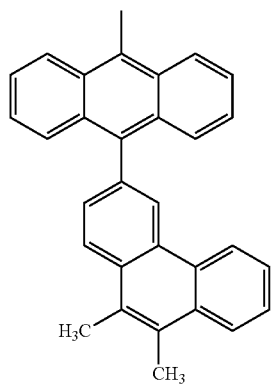
Formula (R1-28)
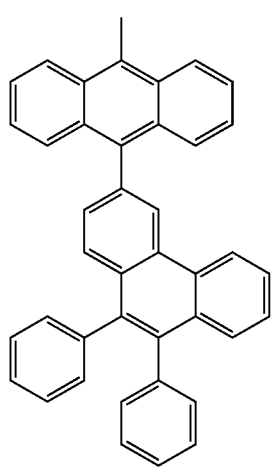
Formula (R1-29)
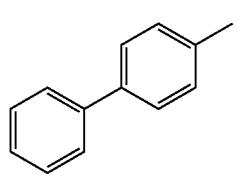
Formula (R1-30)
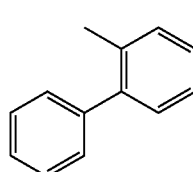
Formula (R1-31)
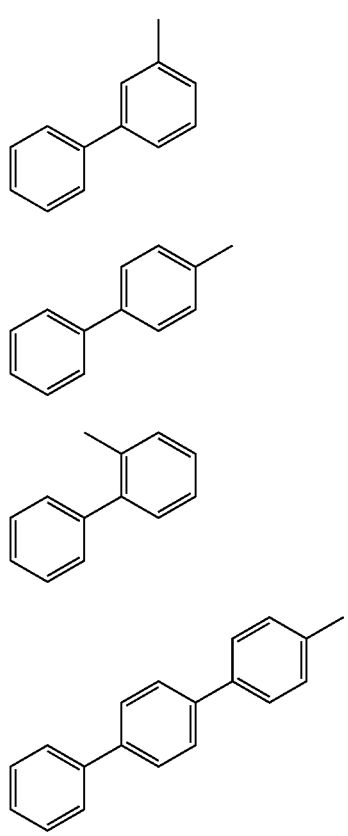
Formula (R1-32)
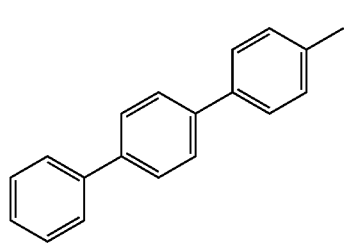
Formula (R1-33)
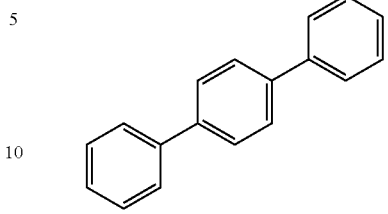
Formula (R1-34)
Formula (R1-35)
Formula (R1-36)
Formula (R1-37)
Formula (R1-38)

Formula (R1-39)
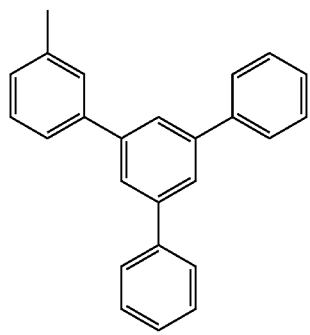
Formula (R1-40)
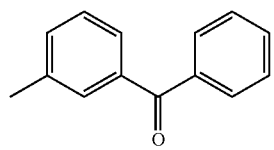
Formula (R1-41)
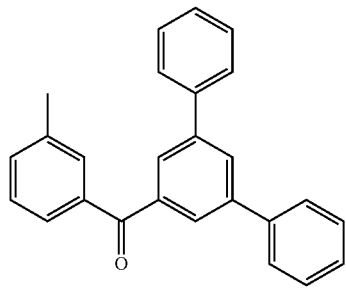
Formula (R1-42)
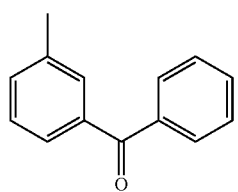
Formula (R1-43)
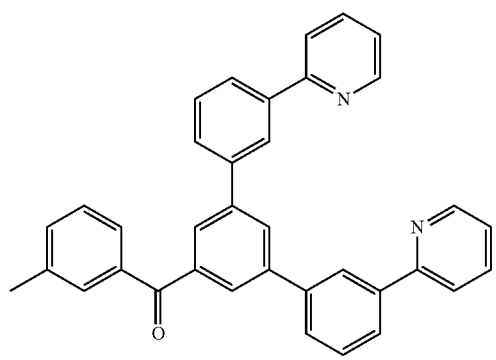
Formula (R1-44)
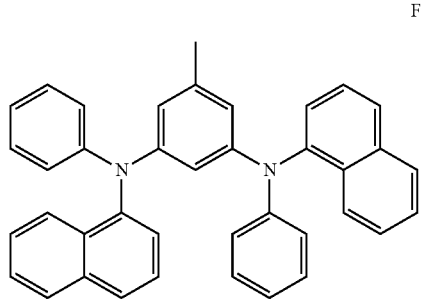
Formula (R1-45)
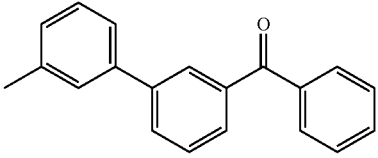
Formula (R1-46)
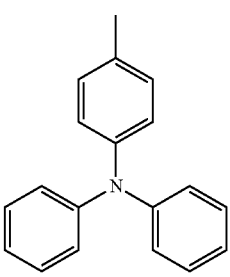
Formula (R1-47)
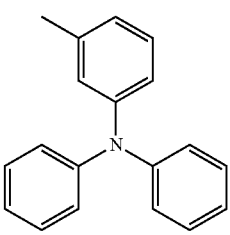
Formula (R1-48)
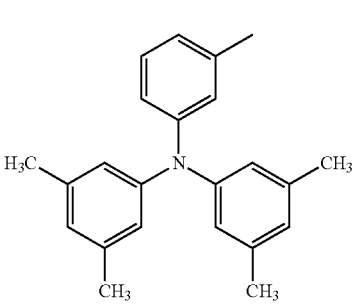
Formula (R1-49)
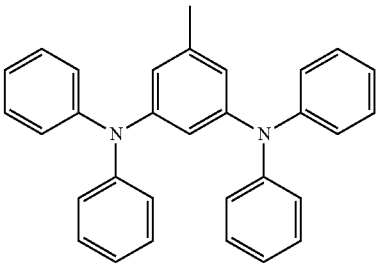
Formula (R1-50)
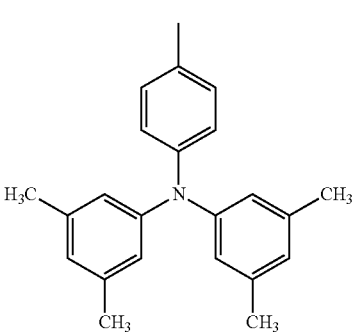

Formula (R1-51)
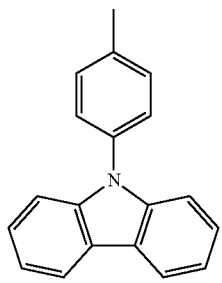
Formula (R1-52)
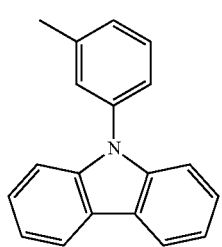
Formula (R1-53)
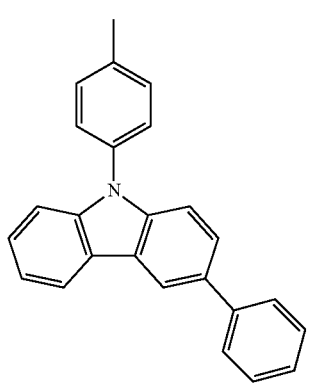
Formula (R1-54)
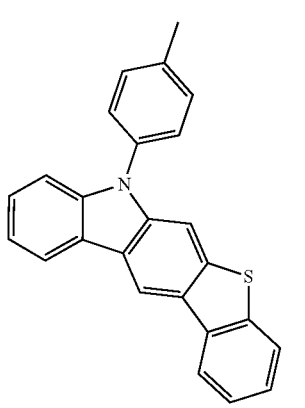
Formula (R1-55)
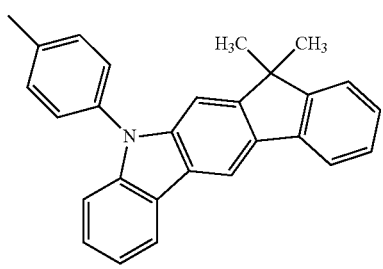
Formula (R1-56)
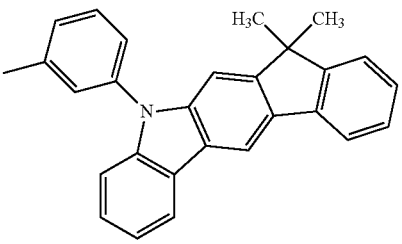
Formula (R1-57)
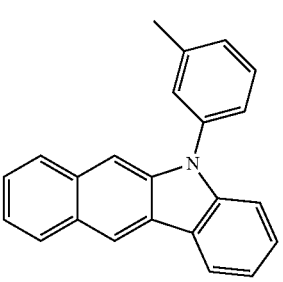
Formula (R1-58)
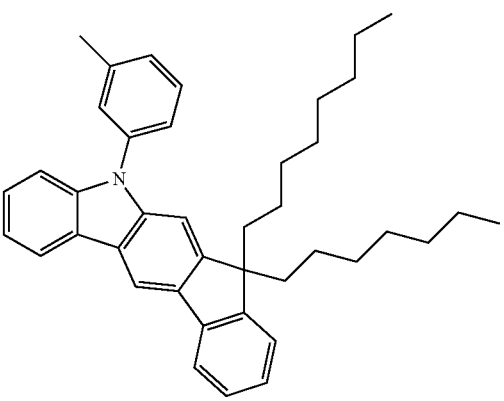
Formula (R1-59)
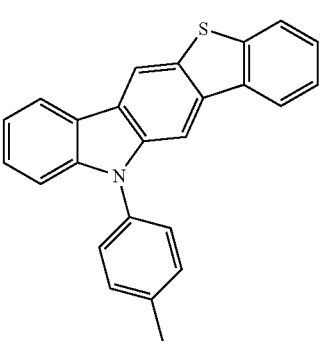

Formula (R1-60)
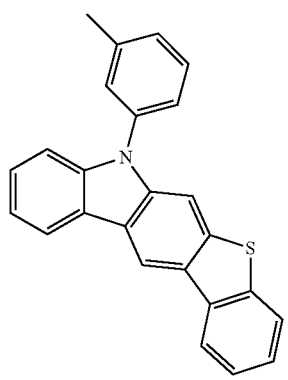
Formula (R1-64)
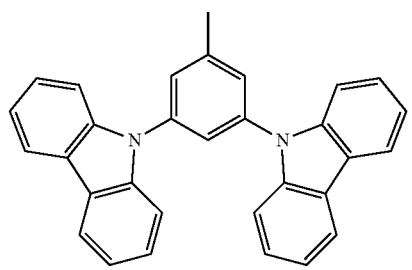
Formula (R1-61)
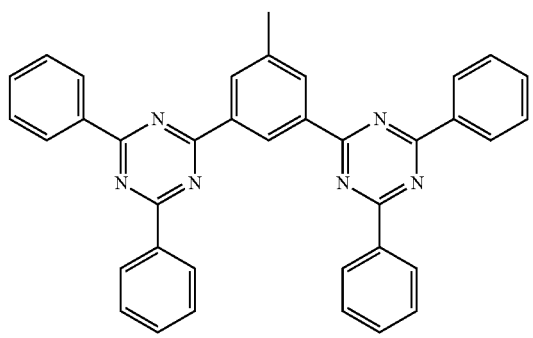
Formula (R1-65)
Formula (R1-62)
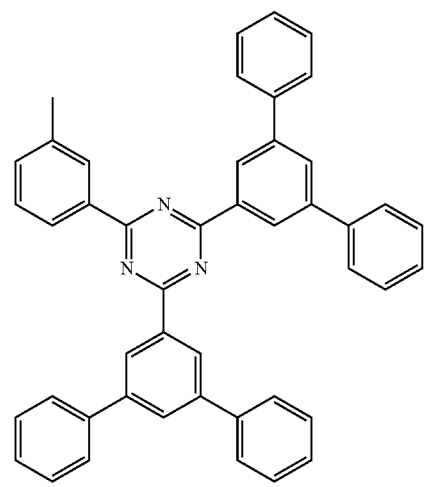
Formula (R1-66)
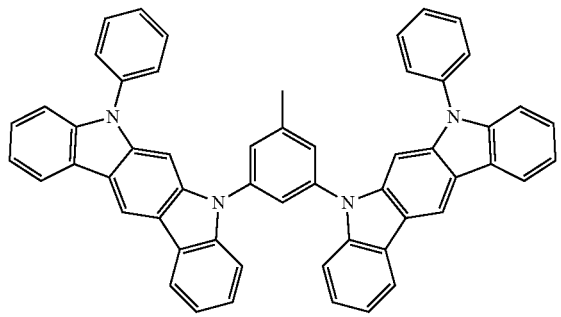
Formula (R1-67)
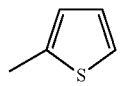
Formula (R1-68)
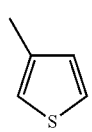
Formula (R1-63)
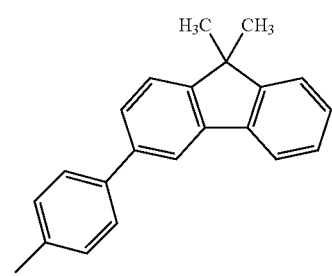
Formula (R1-69)
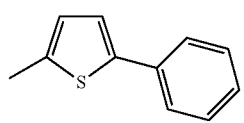
Formula (R1-70)
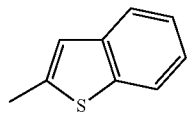

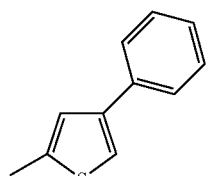
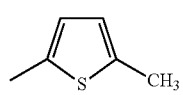
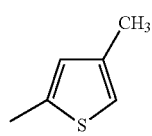
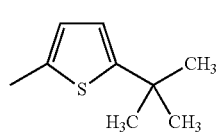
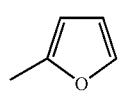
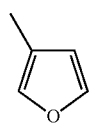
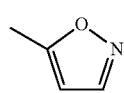
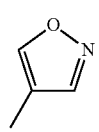
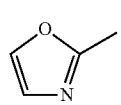
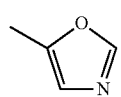
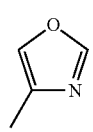
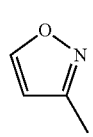
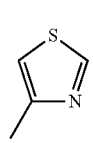
Formula (R1-71)
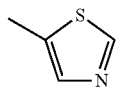
Formula (R1-72)
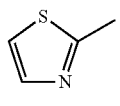
Formula (R1-73)
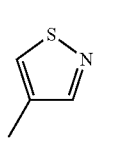
Formula (R1-74)
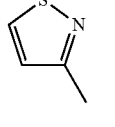
Formula (R1-75)
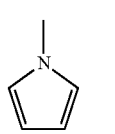
Formula (R1-76)
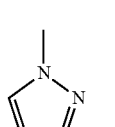
Formula (R1-77)
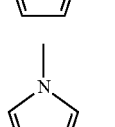
Formula (R1-78)
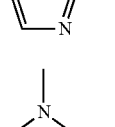
Formula (R1-79)
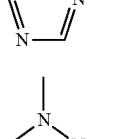
Formula (R1-80)
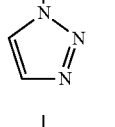
Formula (R1-81)
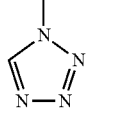
Formula (R1-82)
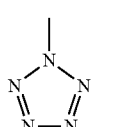
Formula (R1-83)
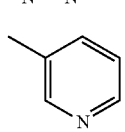
Formula (R1-84)
Formula (R1-85)
Formula (R1-86)
Formula (R1-87)
Formula (R1-88)
Formula (R1-89)
Formula (R1-90)
Formula (R1-91)
Formula (R1-92)
Formula (R1-93)
Formula (R1-94)
Formula (R1-95)
Formula (R1-96)

Formula (R1-97)
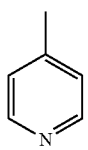
Formula (R1-98)
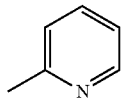
Formula (R1-99)
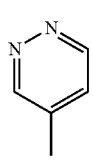
Formula (R1-100)
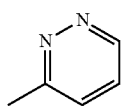
Formula (R1-101)
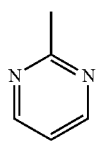
Formula (R1-102)
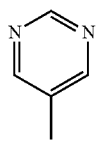
Formula (R1-103)
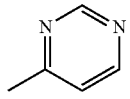
Formula (R1-104)
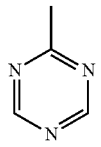
Formula (R1-105)
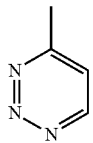
Formula (R1-106)
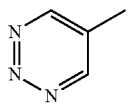
Formula (R1-107)
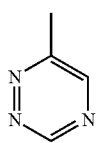
Formula (R1-108)
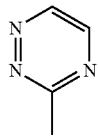
Formula (R1-109)
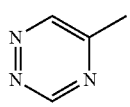
Formula (R1-110)
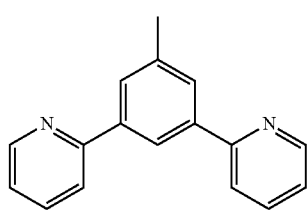
Formula (R1-111)
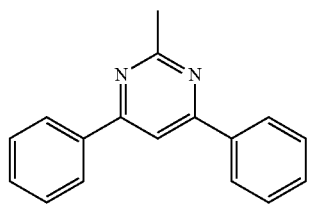
Formula (R1-112)
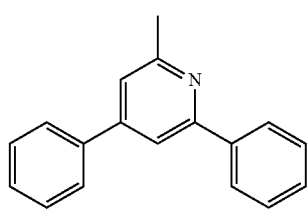
Formula (R1-113)
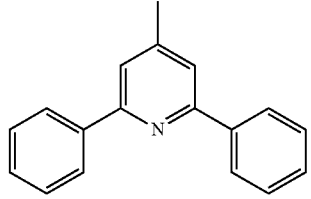
Formula (R1-114)
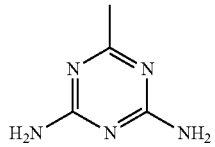
Formula (R1-115)
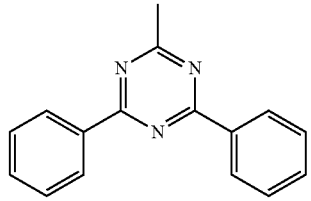

Formula (R1-116)
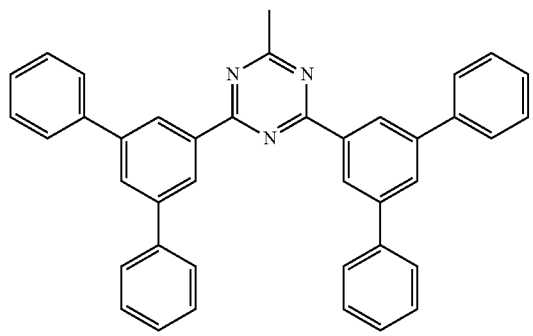
Formula (R1-117)
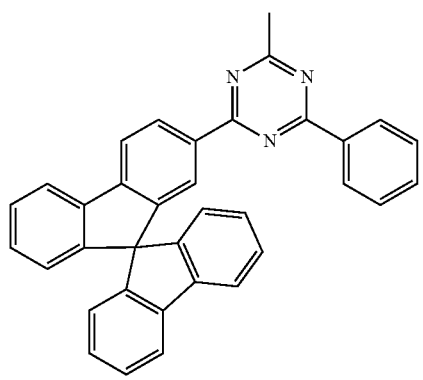
Formula (R1-118)
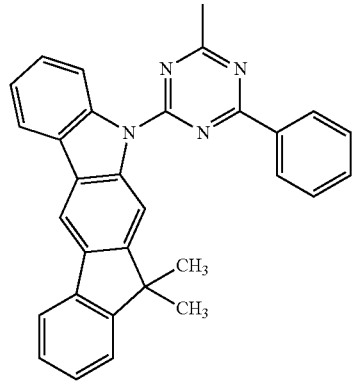
Formula (R1-119)
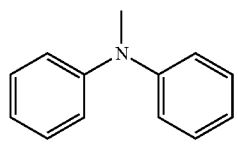
Formula (R1-120)
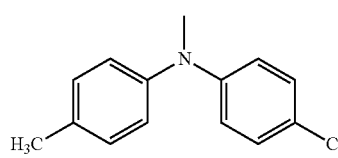
Formula (R1-121)
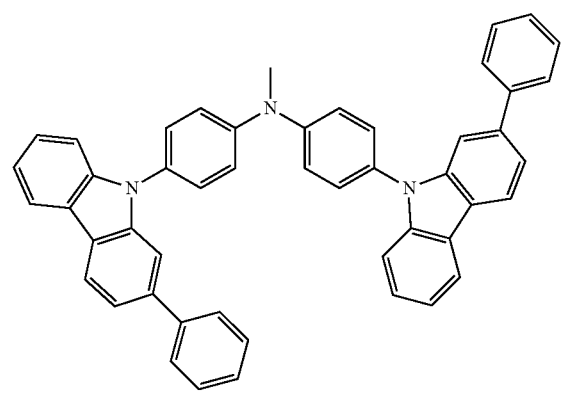
Formula (R1-122)
Formula (R1-123)
Formula (R1-124)
Formula (R1-125)
Formula (R1-126)
Formula (R1-127)

Formula (R1-128)
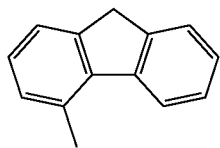
Formula (R1-129)
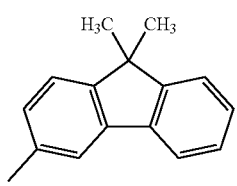
Formula (R1-130)
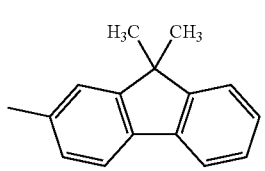
Formula (R1-131)
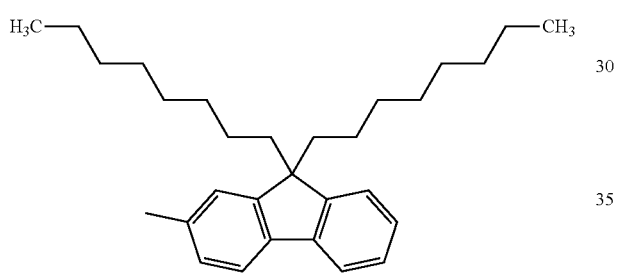
Formula (R1-132)
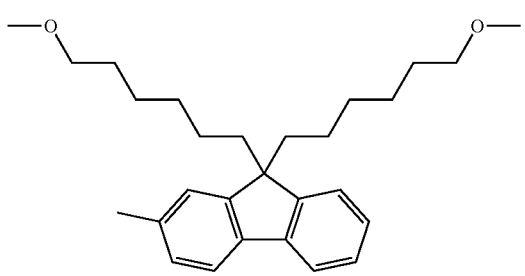
Formula (R1-133)
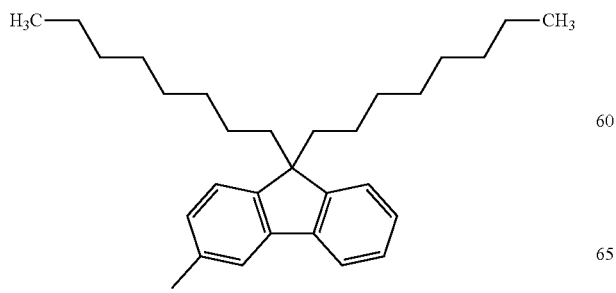
Formula (R1-134)
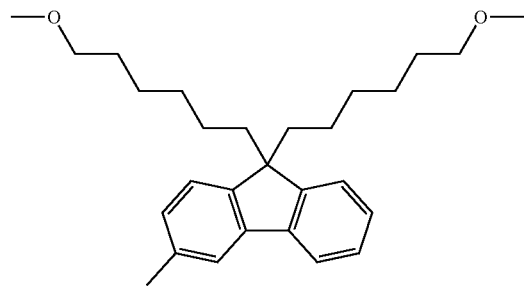
Formula (R1-135)
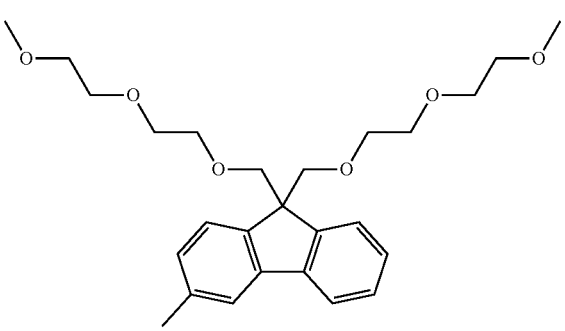
Formula (R1-136)
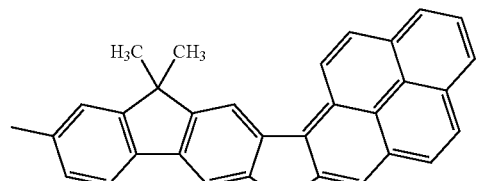
Formula (R1-137)
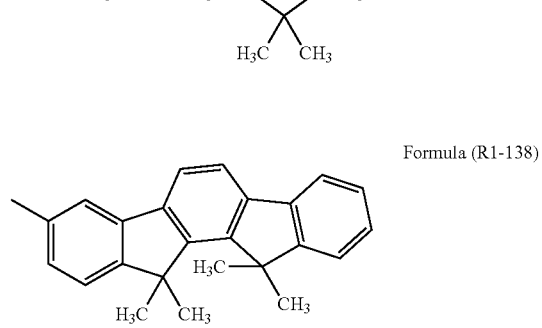
Formula (R1-138)

-continued
Formula (R1-139)
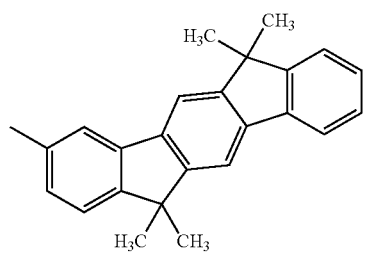
Formula (R1-140)
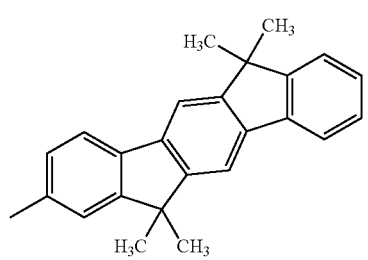
Formula (R1-141)
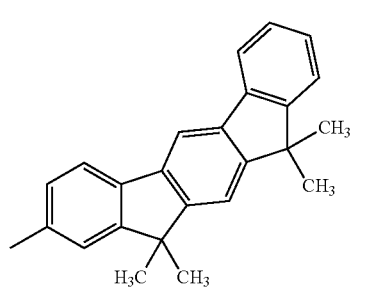
Formula (R1-142)
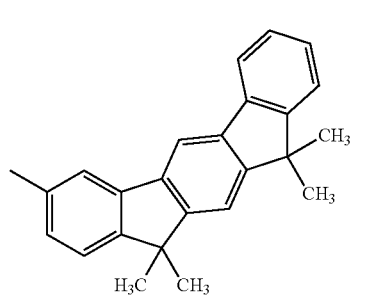
Formula (R1-143)
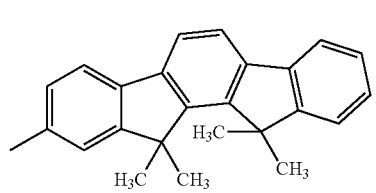
Formula (R1-144)
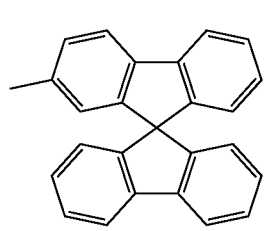
Formula (R1-145)
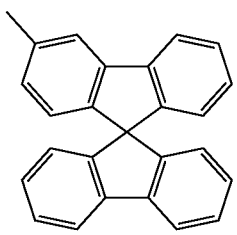
Formula (R1-146)
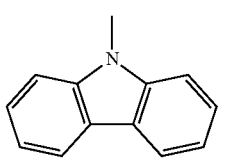
Formula (R1-147)
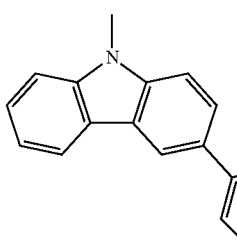
Formula (R1-148)
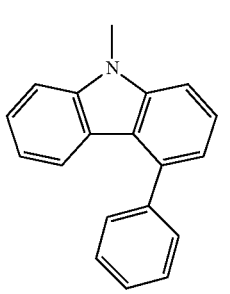
Formula (R1-149)
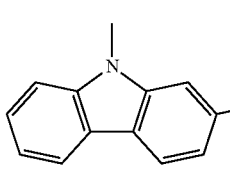
Formula (R1-150)
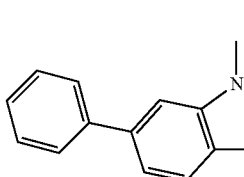
Formula (R1-151)
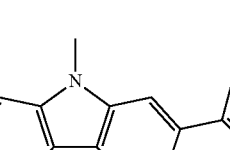

Formula (R1-152)
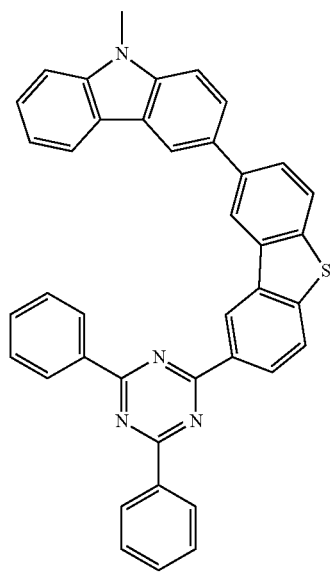
Formula (R1-153)
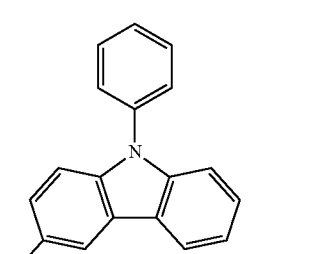
Formula (R1-154)
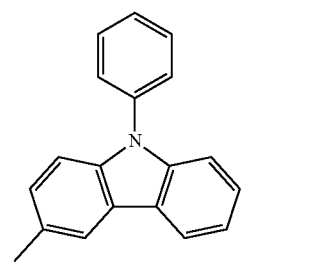
Formula (R1-155)
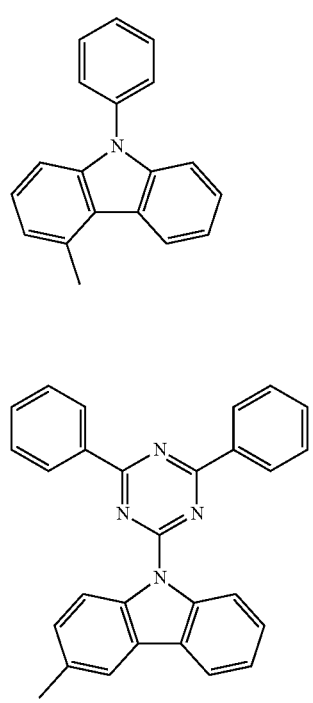
Formula (R1-156)
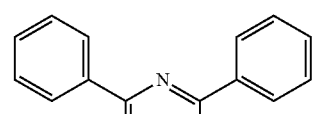
Formula (R1-157)
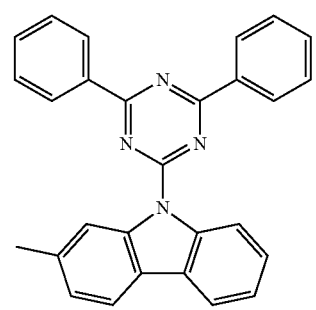
Formula (R1-158)
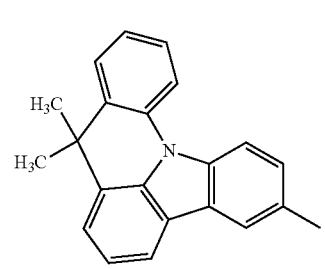
Formula (R1-159)
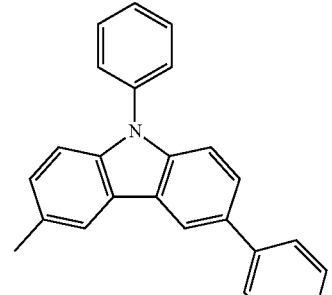
Formula (R1-160)
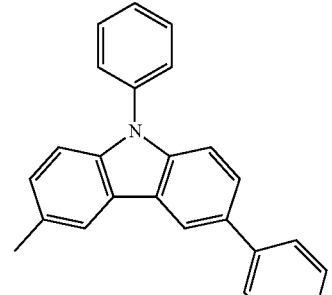
Formula (R1-161)
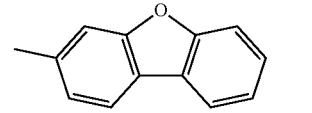

Formula (R1-162)
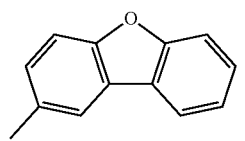
Formula (R1-163)
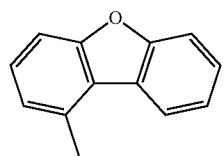
Formula (R1-164)
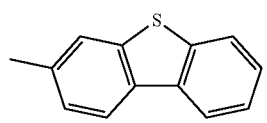
Formula (R1-165)
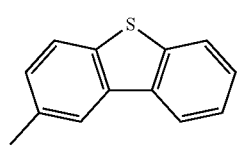
Formula (R1-166)
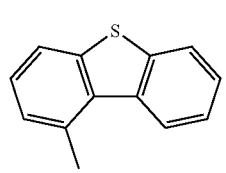
Formula (R1-167)
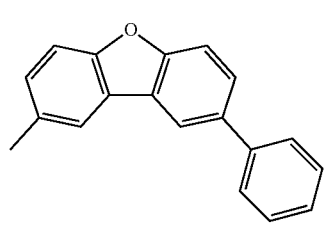
Formula (R1-168)
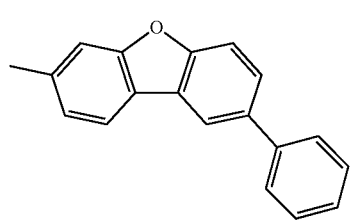
Formula (R1-169)
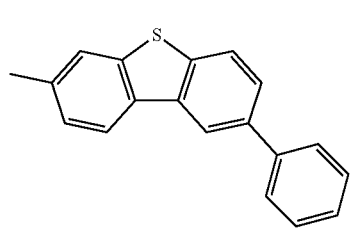
Formula (R1-170)
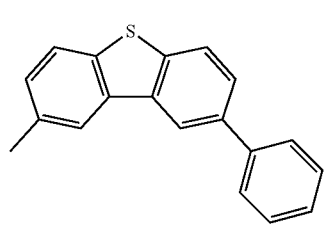
Formula (R1-171)
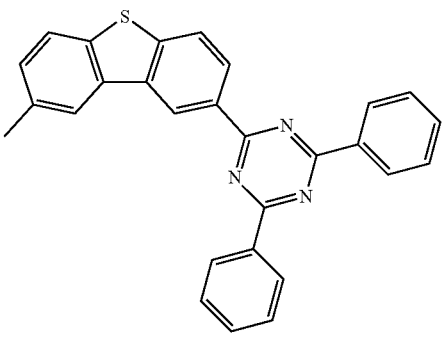
Formula (R1-172)
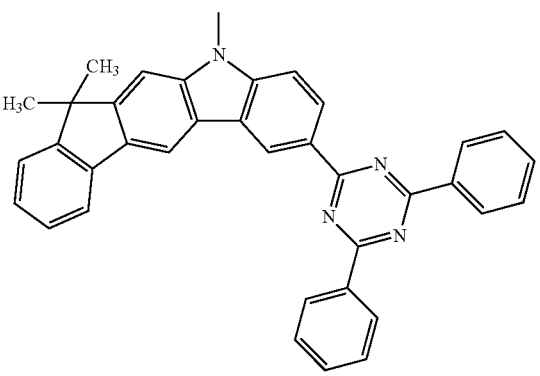
Formula (R1-173)
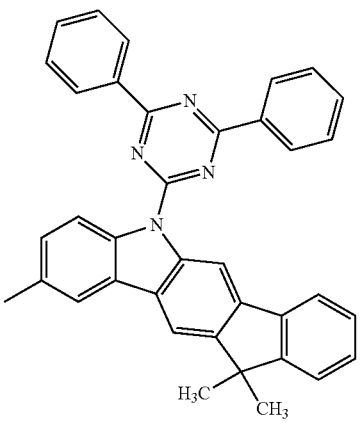
Formula (R1-174)
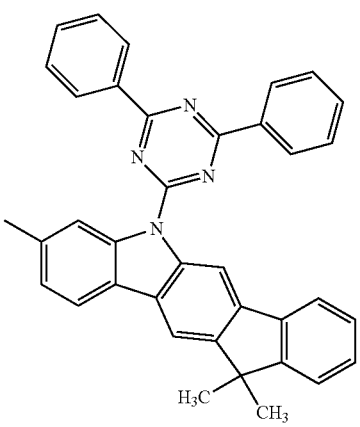

Formula (R1-175)
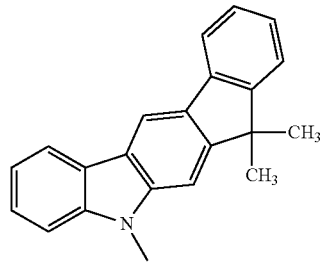
Formula (R1-176)
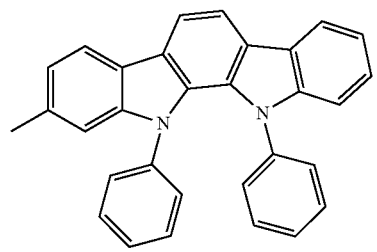
Formula (R1-177)
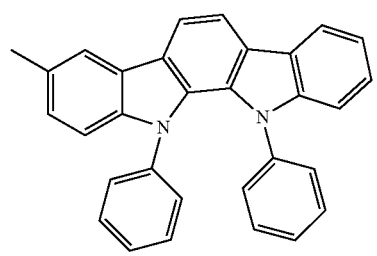
Formula (R1-178)
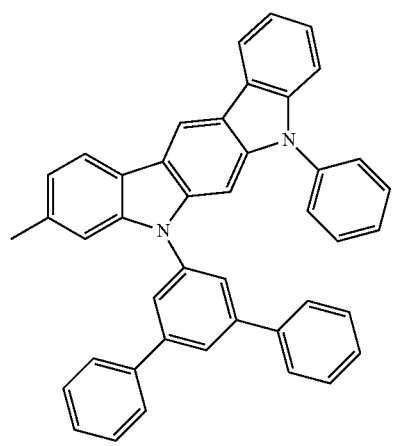
Formula (R1-179)
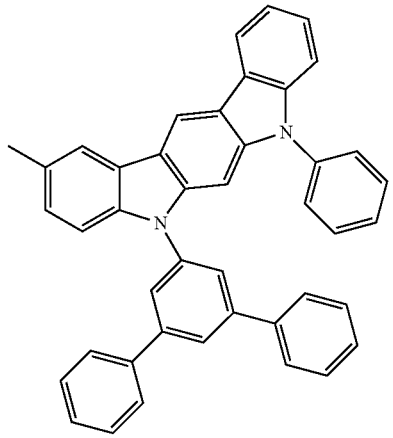
Formula (R1-180)
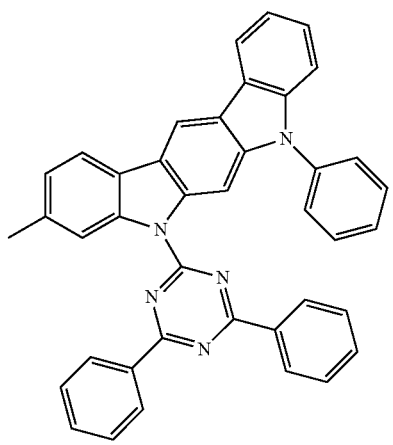
Formula (R1-181)
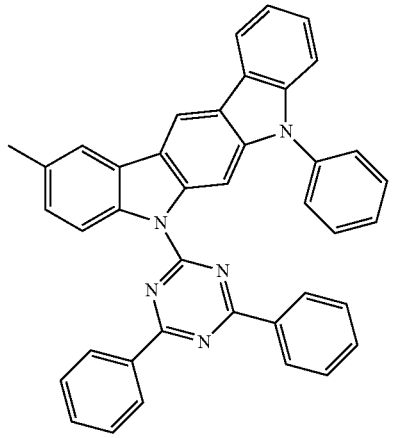
Formula (R1-182)
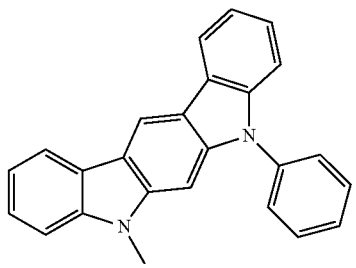

Formula (R1-183)
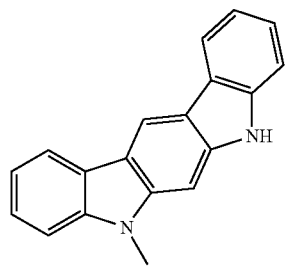
Formula (R-187)
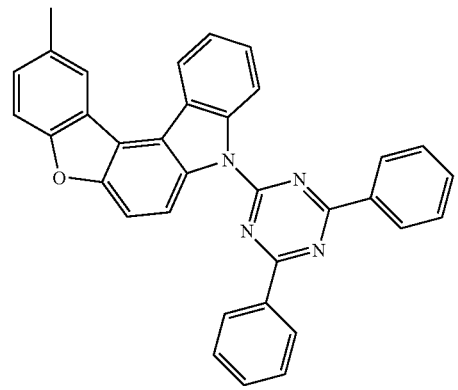
Formula (R1-184)
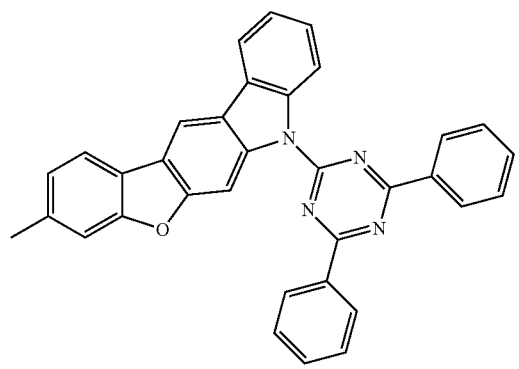
Formula (R-188)
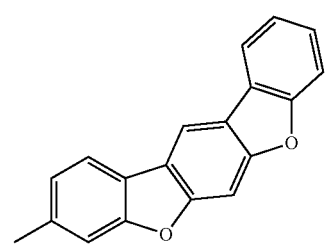
Formula (R1-185)
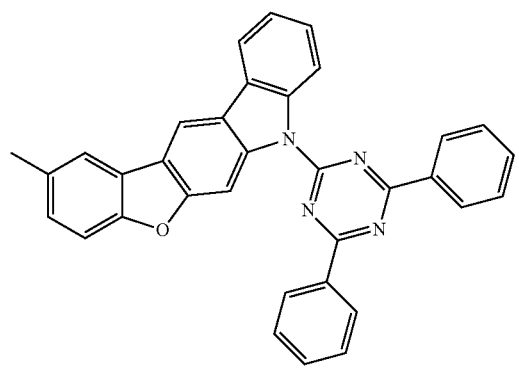
Formula (R-189)
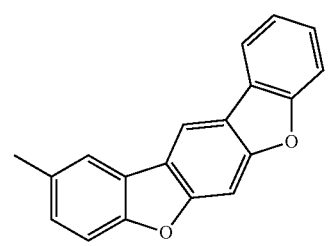
Formula (R1-186)
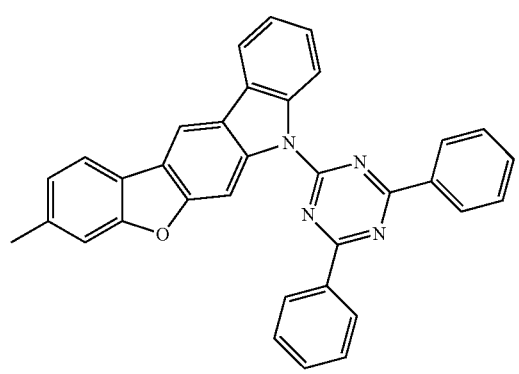
Formula (R-190)
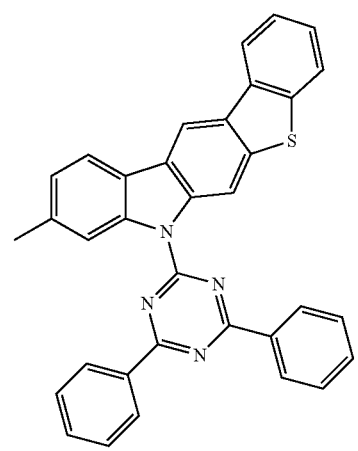

Formula (R-191)
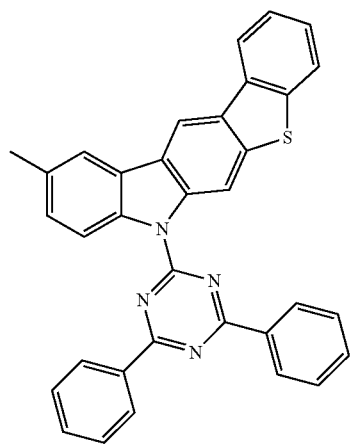
Formula (R1-192)
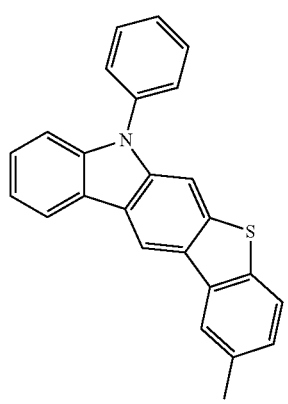
Formula (R1-193)
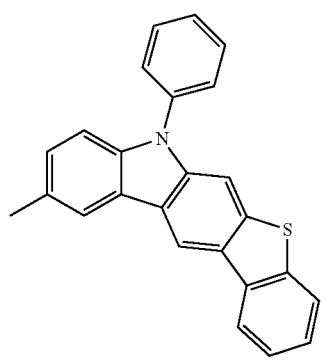
Formula (R1-194)
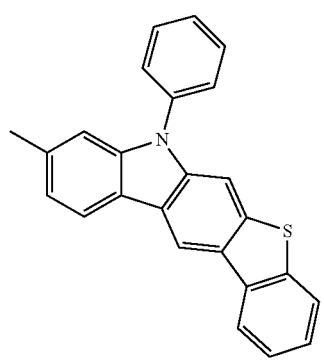
Formula (R1-195)
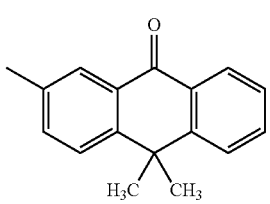
Formula (R1-196)
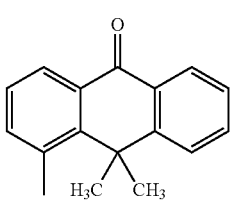
Formula (R1-197)
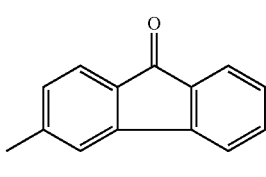
Formula (R1-198)
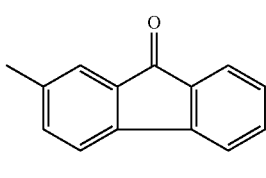
Formula (R1-199)
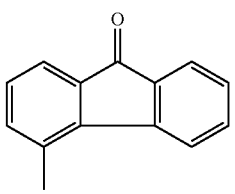
Formula (R1-200)
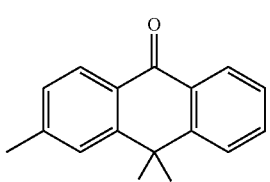
Formula (R1-201)
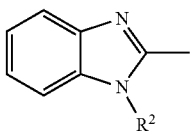
Formula (R1-202)
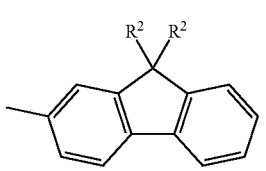
Formula (R1-203)

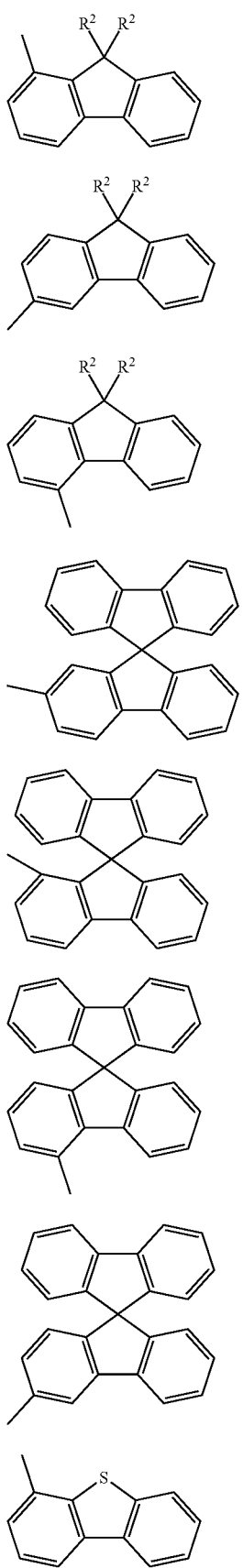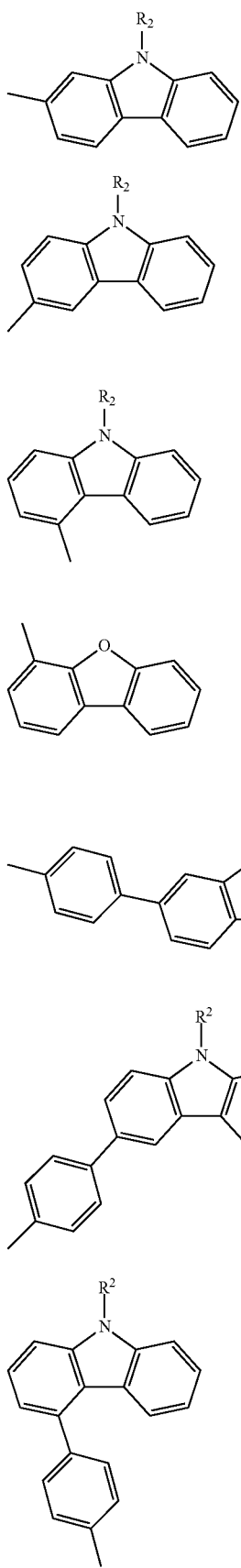

Formula (R1-219) 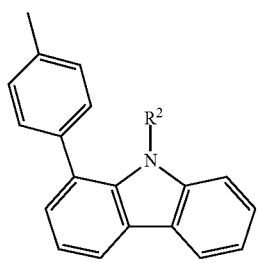

Formula (R1-220) 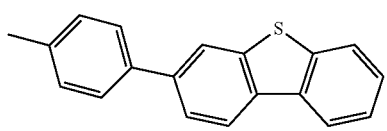

Formula (R1-221) 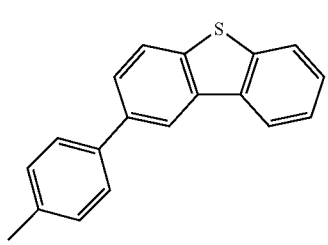

Formula (R1-222) 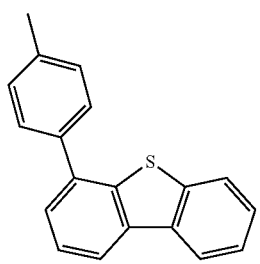

Formula (R1-223) 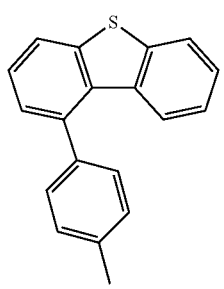

Formula (R1-224) 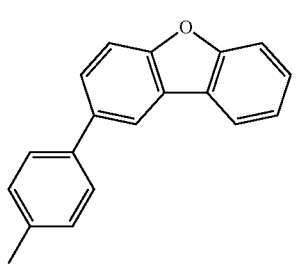

Formula (R1-225) 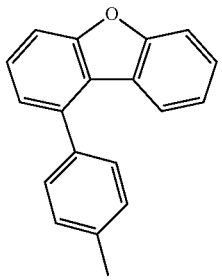

Formula (R1-226) 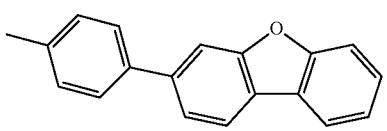

Formula (R1-227) 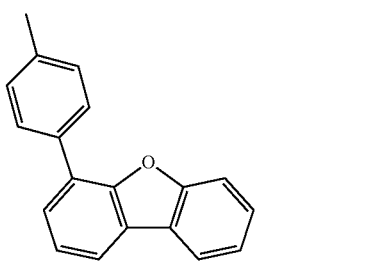

where the bond line indicates the position of the joining of the $R^1$ radical, Particularly preferred radicals are those of the formulae (R1-211), (R1-219), (R1-227).

The inventive compounds of the general formula (1) may assume different functions in an organic electronic device. The compounds may be used, for example, in the emission layer as fluorescent emitter or as matrix material. In addition, the compounds of the invention may be used as hole blocker material (HBM) in a hole blocker layer (HBL) or in an electron transport layer (ETL) as electron transport material (ETM). In addition, the compounds of the general formula (1) may be used as hole injection material (HIM), as hole transport material (HTM) or as electron blocker material (EBM). A further typical use for the inventive compounds of the general formula (1) is use in a mixed matrix system for fluorescent and more preferably phosphorescent emission layers.

The compound of the general formula (1) may be used here as pure material or in combination with other materials.

On the basis of his common art knowledge in the present technical field, the person skilled in the art will be aware that, depending on the use of the inventive compound of the general formula (1), the $R^1$ to $R^3$ radicals have to be chosen such that the optoelectronic properties of the compounds are matched to the particular applications.

If the compound of the general formula is used as electron-transporting compound, for example in an ETM, or as electron-transporting matrix in an emission layer, at least one of the $R^1$ to $R^3$ radicals contains an electron-transporting group ETG.

An ETG is an organic electron-transporting group (ETG) from the group of the electron-deficient heteroaromatic groups, the ETGs preferably being a heteroaryl group having 5 to 60 aromatic ring atoms, where N are very preferred heteroatoms, and very particularly preferred ETGs being selected from the group of triazines, pyrimidines, pyrazines, pyrazoles, pyridazines, quinoles, isoquinolines, thiazoles, benzothiazoles, oxazoles, benzoxazoles, imidazoles, benzimidazoles and pyridines.

Preferred ETGs are heteroaromatic groups having 6 aromatic ring atoms of which at least one, preferably 2 and very preferably at least three is a nitrogen atom, or heteroaromatic groups having 5 aromatic ring atoms of which at least 2 are heteroatoms, and preferably at least one of them a nitrogen atom, where further aryl or heteroaryl groups may also be fused onto each of these groups.

Preferred examples of electron-deficient heteroaromatic groups are: pyridines, pyrazines, pyrimidines, pyridazines, 1,2,4-triazines, 1,3,5-triazines, quinolines, isoquinolines, quinoxalines, pyrazoles, imidazoles, benzimidazoles, thiazoles, benzothiazoles, oxazoles or benzoxazoles, each of which may be substituted by $R^1$. Even more preferably, the electron-transporting group is a pyridine, pyrazine, pyrimidine, pyridazine and 1,3,5-triazine substituted by one or more $R^1$ radicals.

If the compound of the general formula (1) is used as electron-transporting compound, for example as matrix or in an ETL, it is further preferable when the compound of the formula (1) has a LUMO (lowest unoccupied molecular orbital) energy of less than −1.3 eV, very preferably less than −2.5 eV and most preferably less than −2.7 eV.

If the compound of the general formula (1) is used as electron-transporting compound, for example as matrix or in an ETL, it is further preferable when the electron mobility $\mu_-$ is $10^{-6}$ cm$^2$/(Vs) or more, very preferably 10 cm$^2$/(Vs) or more and most preferably $10^{-4}$ cm$^2$/(Vs) or more.

If the compound of the general formula is used as hole-transporting compound, for example in an HTM, or as hole-transporting matrix in an emission layer, at least one of the $R^1$ to $R^3$ radicals contains a hole-transporting group HTG.

An HTG is an organic hole-transporting group from the group of the electron-rich organic groups, the HTG preferably being selected from the group of the arylamines, triarylamines, bridged amines, preferred bridged amines being dihydroacridines, dihydrophenazines, phenoxazines and phenothiazines, carbazoles, bridged carbazoles, biscarbazoles, indenocarbazoles and indolocarbazoles.

If the compound of the general formula (1) is a hole-transporting compound, the compound preferably has a HOMO energy (HOMO$_L$) which is within the range of the electron work function of the anode used ($\Phi_{anode}$) plus +1.5 eV or lower, meaning that:

HOMO$_L \leq (\Phi_{anode} + 1.5$ eV)

When the anode used has an electron work function of −5 eV, HOMO$_L$ is −3.5 eV or lower (i.e. more negative than −3.5 eV). It is very preferable when HOMO$_L$ energy is equal to or less than the electron work function of the anode, most preferably less.

If the compound of the general formula (1) is a hole-transporting compound, the compound has a hole mobility $\mu_+$ of $10^{-6}$ cm$^2$/(Vs) or more, very preferably $10^{-5}$ cm$^2$/(Vs) or more and most preferably $10^{-4}$ cm$^2$/(Vs) or more.

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((*HEh*\*27.212)−0.9899)/1.1206

LUMO(eV)=((*LEh*\*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

"Crosslinkable group" in the context of the present invention means a functional group capable of reacting irreversibly. This forms a crosslinked material which is insoluble. The crosslinking can usually be promoted by means of heat or by means of UV radiation, microwave radiation, x-radiation or electron beams. As a result of the high stability of the polymer of the invention, there is less by-product formation in the crosslinking. In addition, the crosslinkable groups in the polymer of the invention crosslink very readily, such that small amounts of energy are required for the crosslinking (for example <200° C. in the case of thermal crosslinking).

Examples of crosslinkable Q groups are units containing a double bond, a triple bond, a precursor capable of in situ formation of a double or triple bond, or a heterocyclic additional-polymerizable radical. Preferred Q radicals include vinyl, alkenyl, preferably ethenyl and propenyl, C$_{4-20}$-cycloalkenyl, azide, oxirane, oxetane, di(hydrocarbyl)amino, cyanate ester, hydroxyl, glycidyl ether, C$_{1-10}$-alkyl acrylate, C$_{1-10}$-alkyl methacrylate, alkenyloxy, preferably ethenyloxy, perfluoroalkenyloxy, preferably perfluoroethenyloxy, alkynyl, preferably ethynyl, maleimide, tri(C$_{1-4}$)-alkylsiloxy and tri(C$_{1-4}$)-alkylsilyl. Particular preference is given to vinyl and alkenyl.

An aryl group in the context of this invention contains 6 to 40 carbon atoms; a heteroaryl group in the context of this invention contains 1 to 39 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms in the ring system. A heteroaromatic ring system in the context of this invention contains 1 to 59 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are interrupted, for example, by a short alkyl group. In addition, systems in which two or more aryl and/or heteroaryl groups are joined to one another by a single bond, for example biphenyl, terphenyl or bipyridine, shall be regarded as an aromatic or heteroaromatic ring system.

In the context of the present invention, an aliphatic hydrocarbyl radical or an alkyl group or an alkenyl or alkynyl group which may typically contain 1 to 40 or else 1 to 20 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, $SO$, $SO_2$, $NR^1$, O, S or $CONR^1$; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned $R^1$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The wording that two or more radicals together may form a ring, in the context of the present description, shall be understood to mean, inter alia, that the two radicals are joined to one another by a chemical bond. This is illustrated by the following scheme:

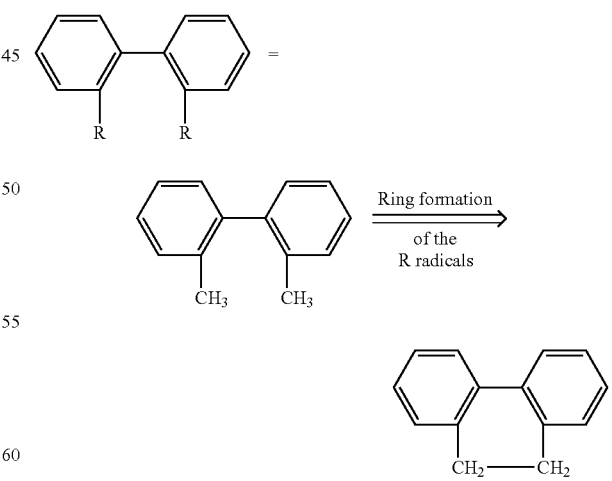

In addition, however, the abovementioned wording shall also be understood to mean that, if one of the two radicals is hydrogen, the second radical binds to the position to which the hydrogen atom was bonded, forming a ring. This shall be illustrated by the following scheme:

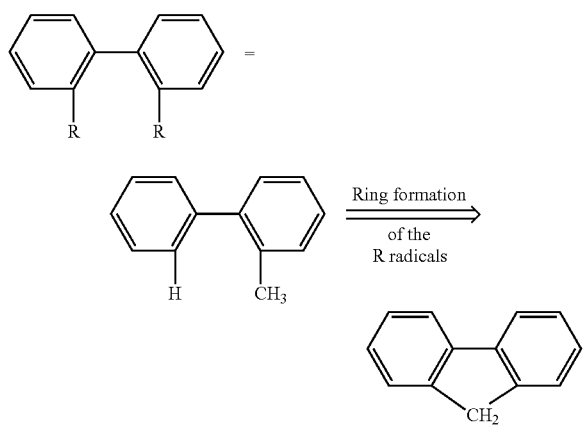

The compounds of the invention can be prepared according to schemes 1 to 7 which follow, where the first three schemes relate to the preparation of dinaphthoxepines and schemes 4 to 6 relate to the preparation of tribenzoxepines. The person skilled in the art will have no difficulty in successfully applying the synthesis route specified herein, within the scope of common art knowledge, to the synthesis of further derivatives.

The corresponding mono- and dibromides can be prepared by NBS bromination. Reaction of these mono- and dibromides via Suzuki coupling with the appropriate arylboronic acids or via Buchwald coupling or Ullmann coupling with appropriate aryl halides leads to the desired target compounds.

The bromide can also be used to prepare the corresponding boronic acids which can in turn be converted further via Suzuki coupling.

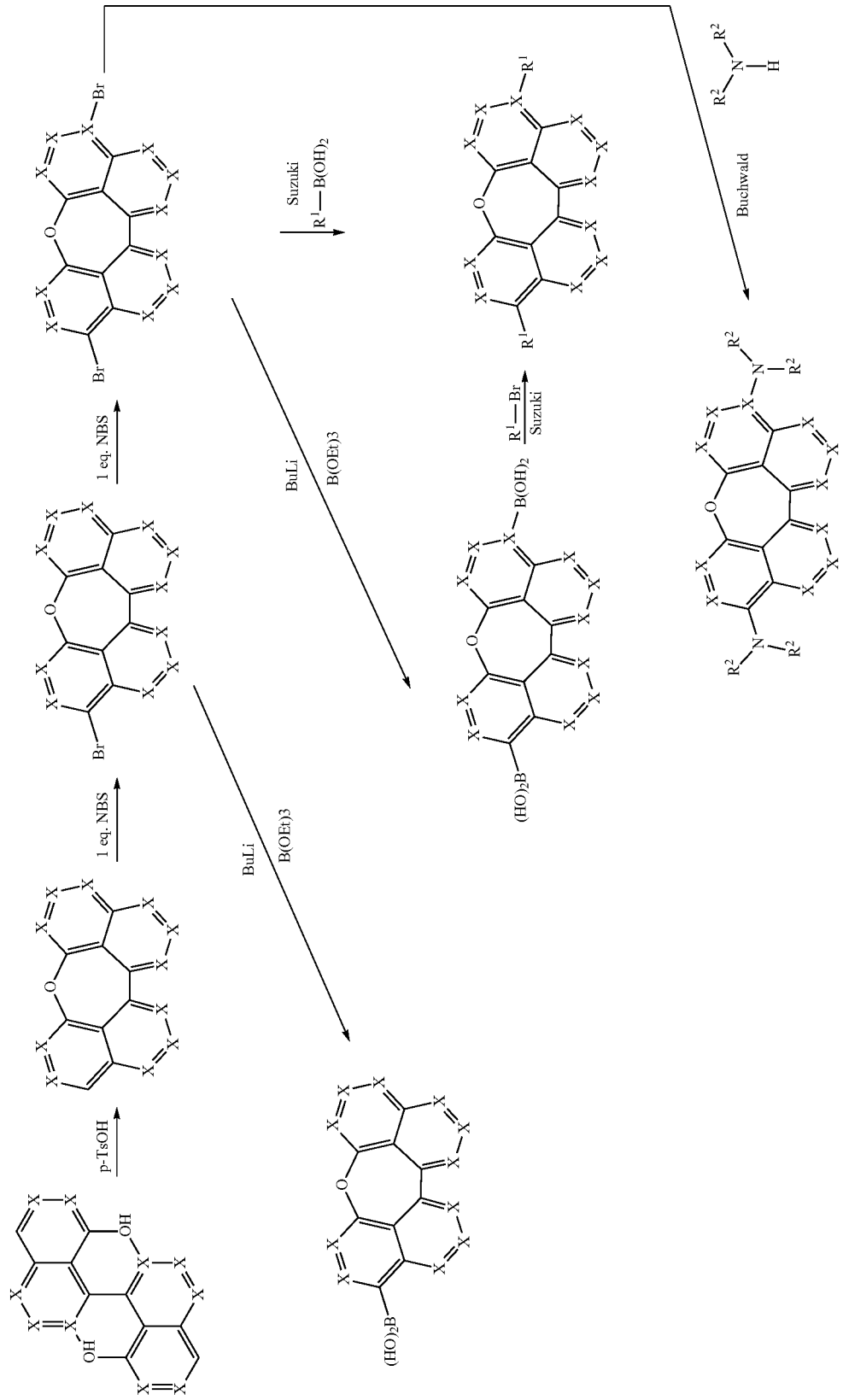

In a further step, the compounds thus obtained can again be selectively brominated with NBS and converted via Suzuki or Buchwald coupling or Ullmann coupling to further desired target compounds (schemes 2 and 3).
Scheme 2
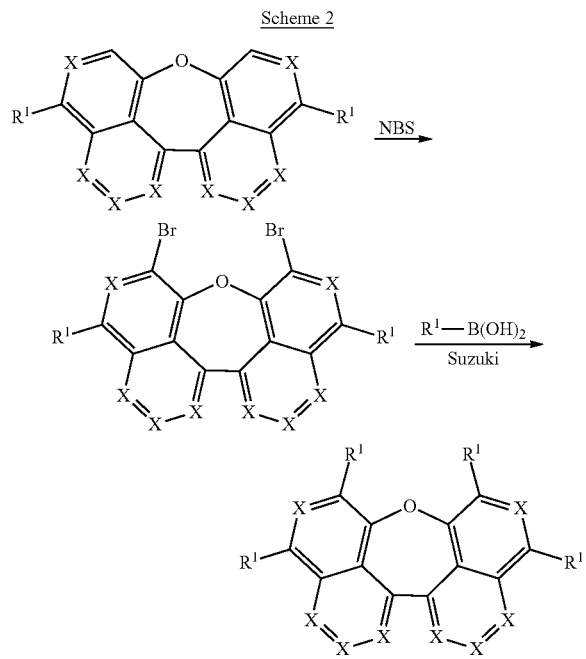
Scheme 3
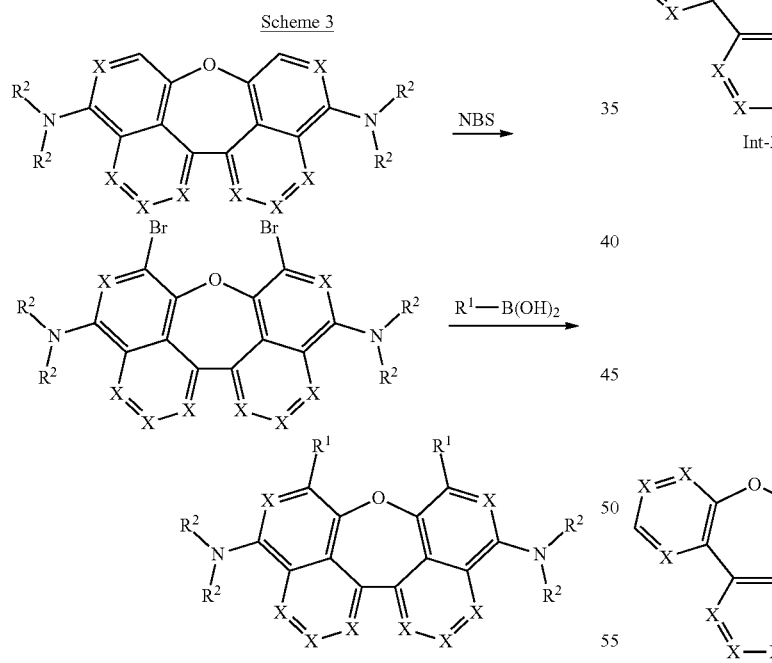
Tribenz[a,c,e]-oxepines of the invention can be prepared by the general scheme which follows.
Scheme 4
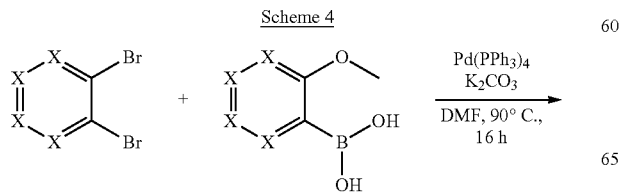
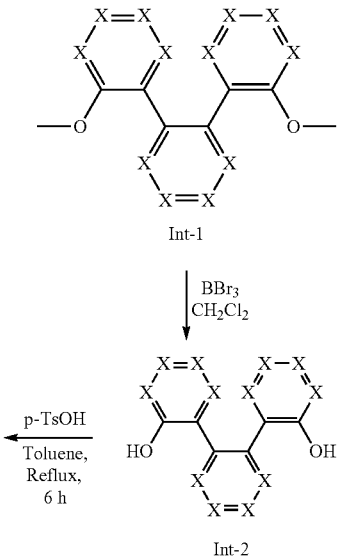
Scheme 5
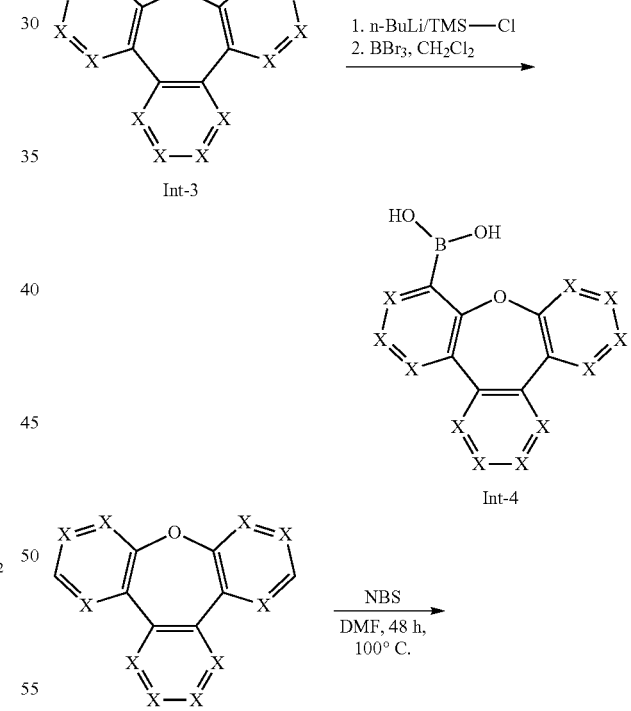
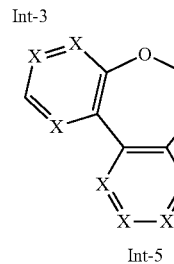

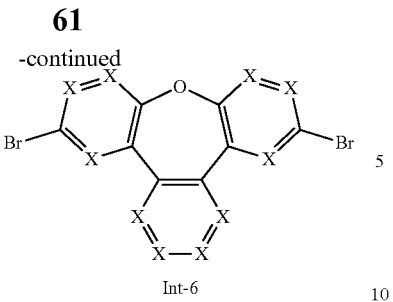
Int-6
Functionalization for further substitution is effected by ortho-metalation with n-butyllithium and by bromination with N-bromosuccinimide.
Scheme 6
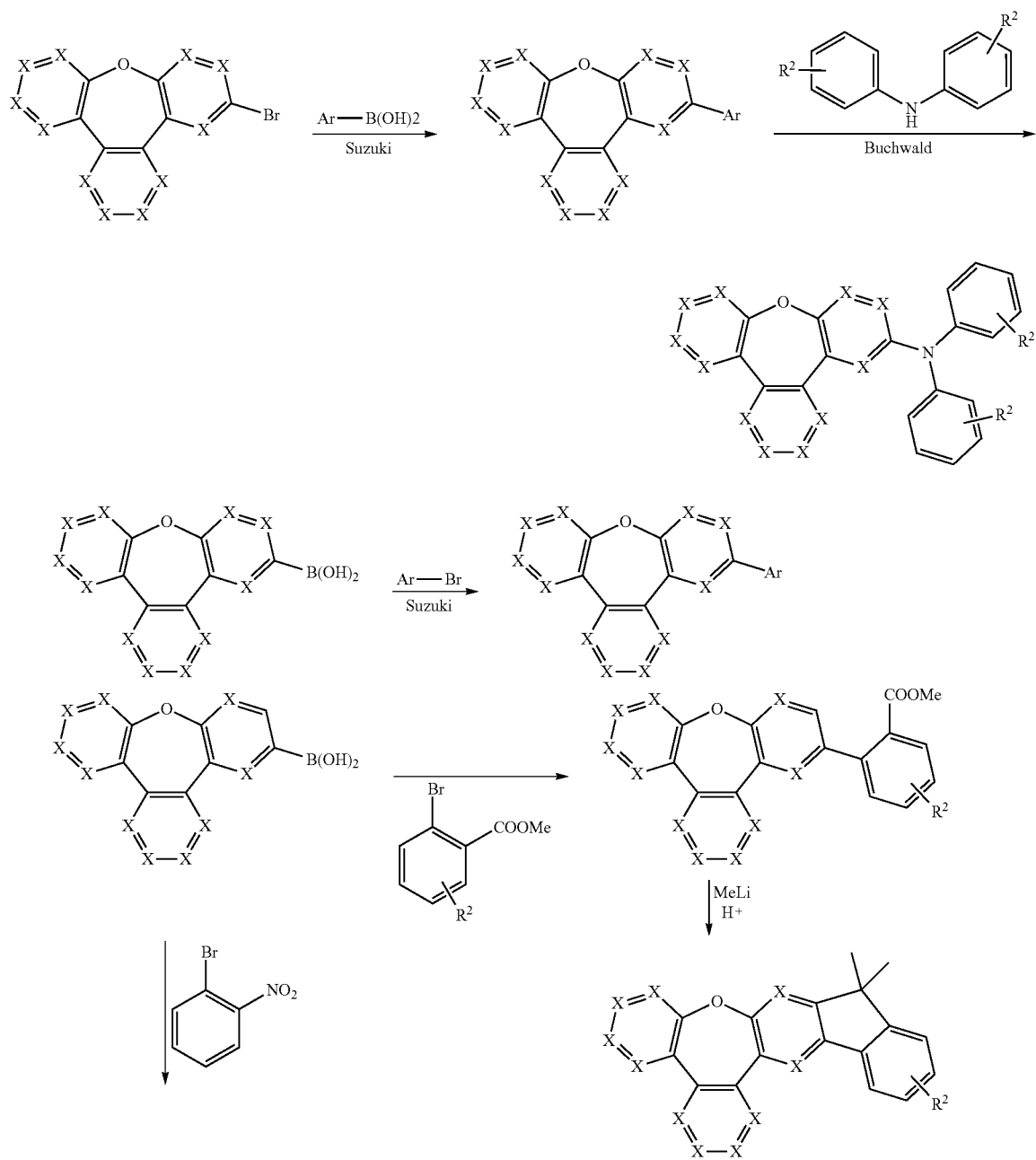

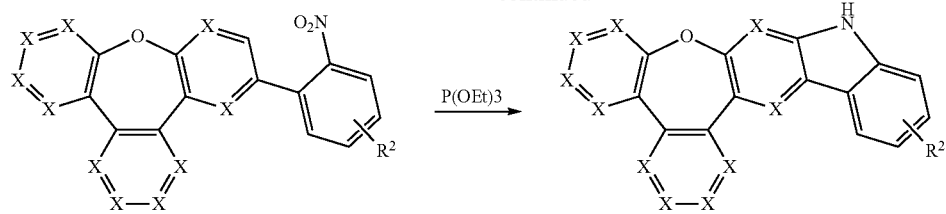

Further derivatizations of tribenz[a,c,e]oxepine can be undertaken as follows.
where Ar is an aromatic or heteroaromatic group as per the definition of $R^1$.

The preparation of the corresponding dibromides or diboronic acids is shown by the scheme which follows.

Scheme 7

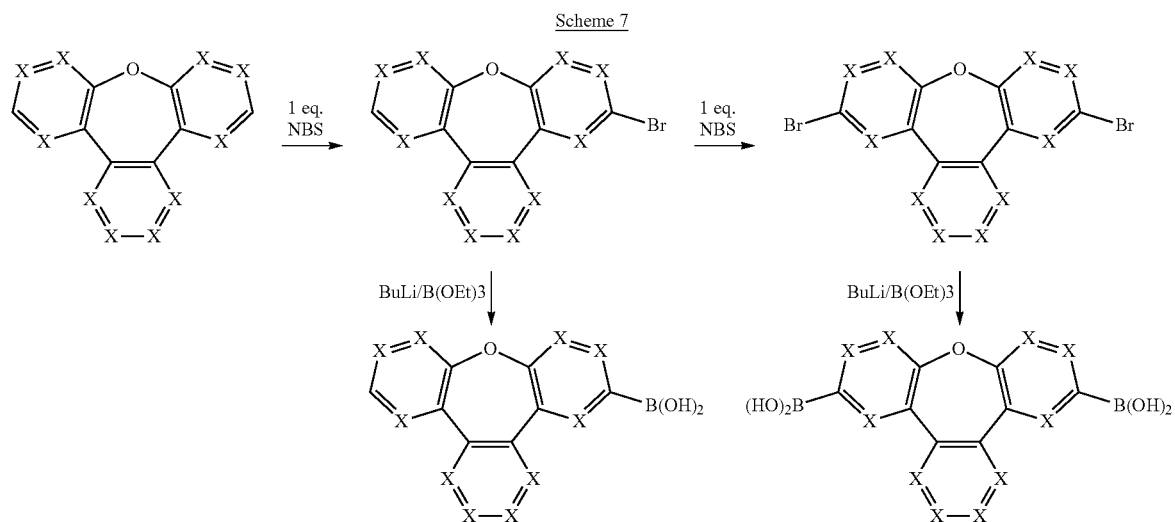

The overview which follows contains an illustration of compounds of the invention which can be prepared by one of the processes described herein.

Formula (A-1)

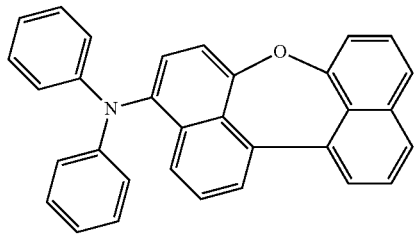

Formula (A-2)

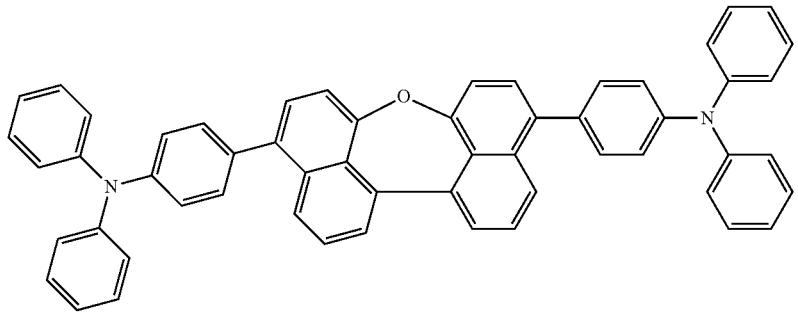

-continued
Formula (A-3)
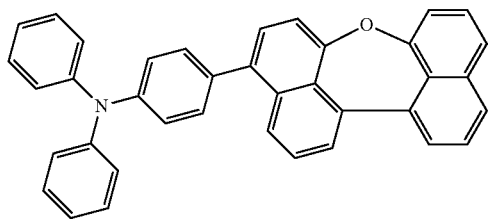
Formula (A-4)
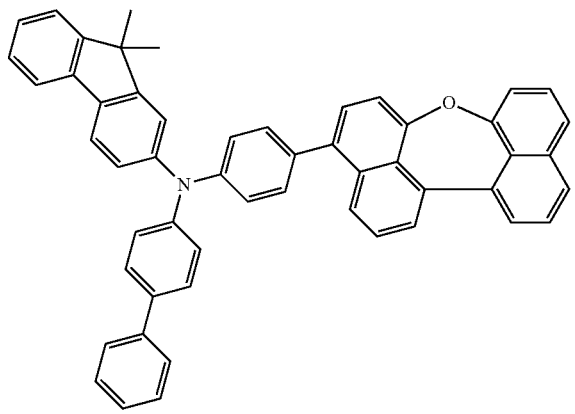
Formula (A-5)
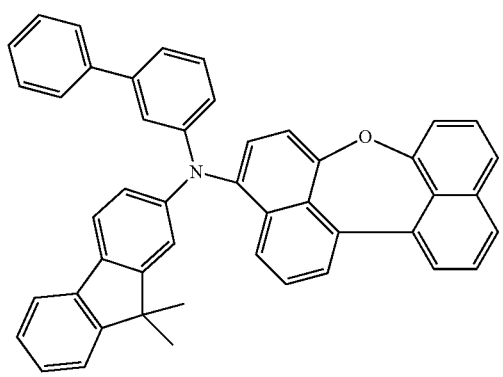
Formula (A-6)
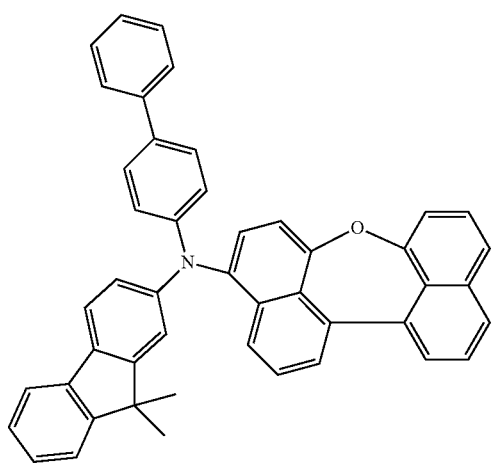
Formula (A-7)
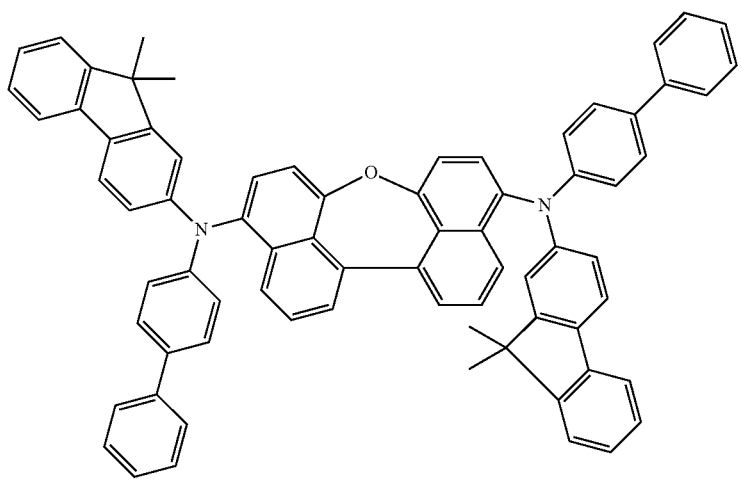

-continued
Formula (A-8)
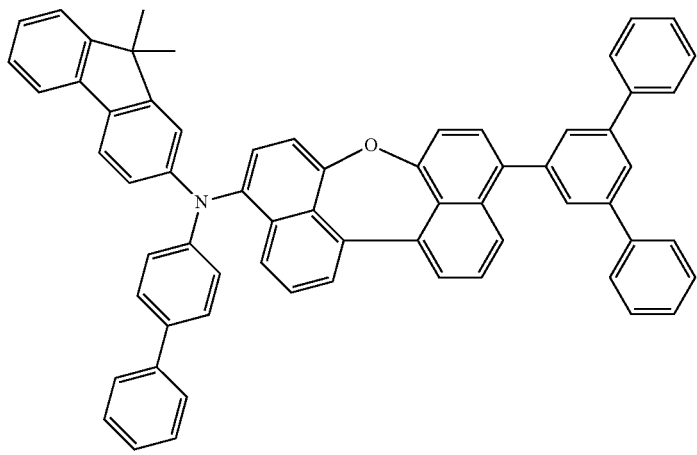
Formula (A-9)
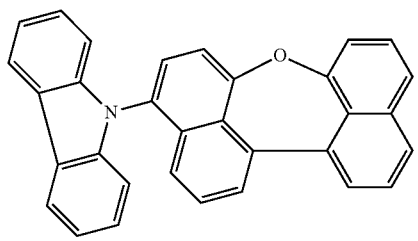
Formula (A-10)
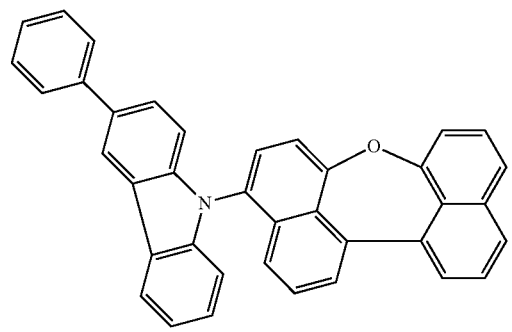
Formula (A-11)
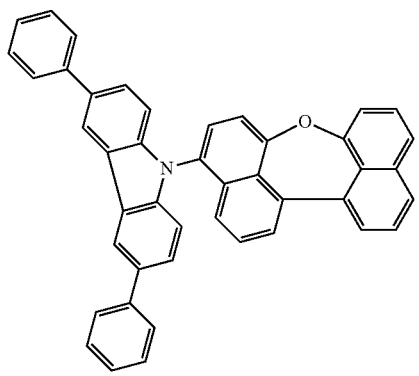
Formula (A-12)
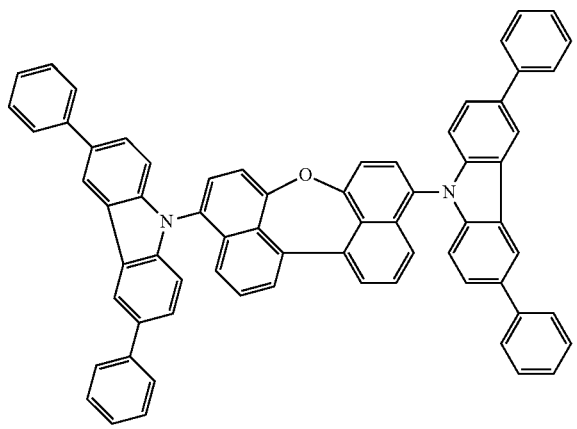
Formula (A-13)
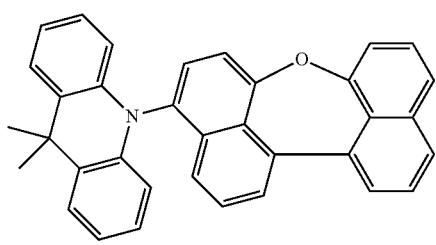
Formula (A-14)
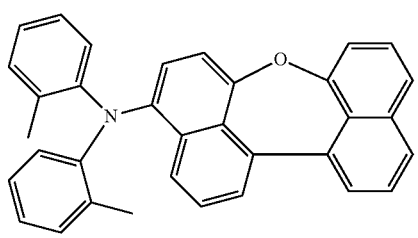

Formula (A-15)
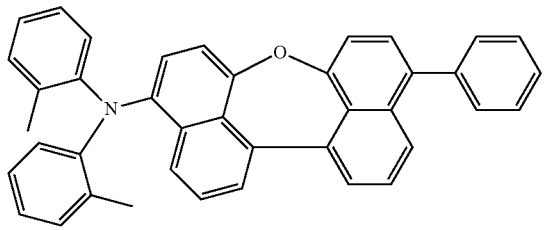
Formula (A-17)
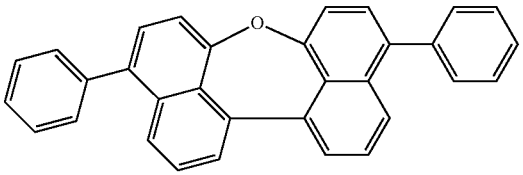
Formula (A-17)
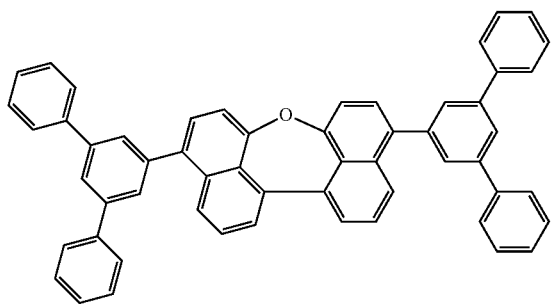
Formula (A-18)
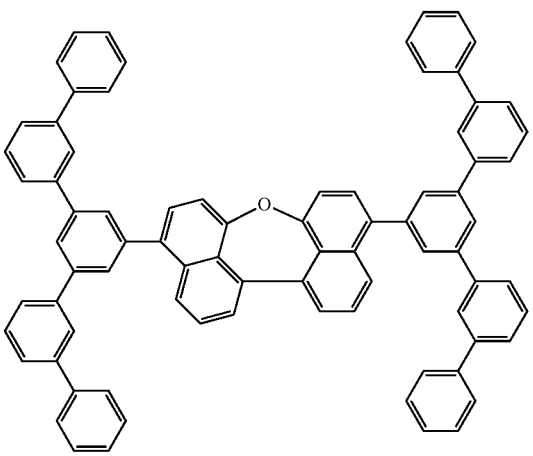
Formula (A-19)
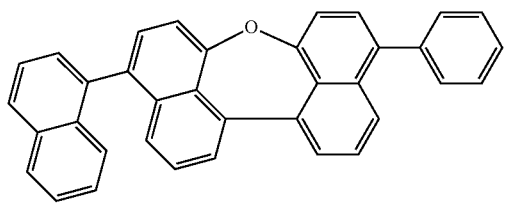
Formula (A-20)
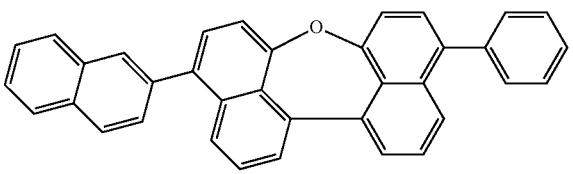
Formula (A-21)
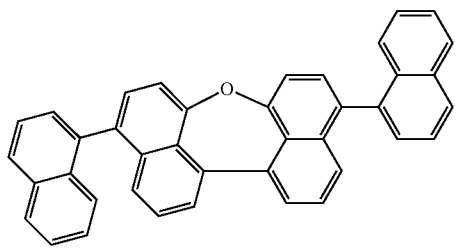
Formula (A-22)
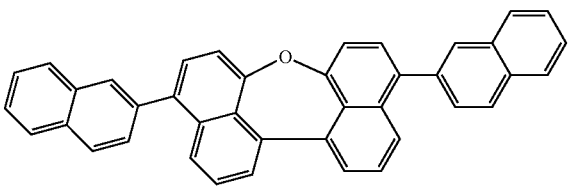
Formula (A-23)
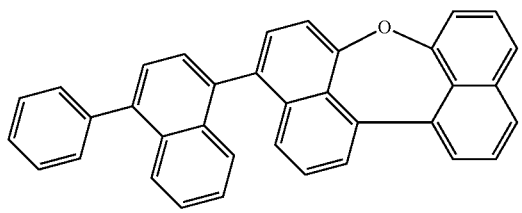
Formula (A-24)
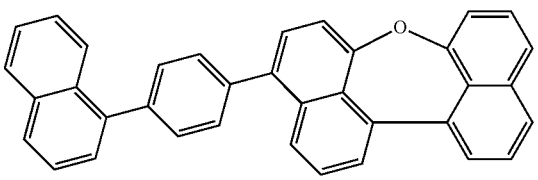

Formula (A-25)
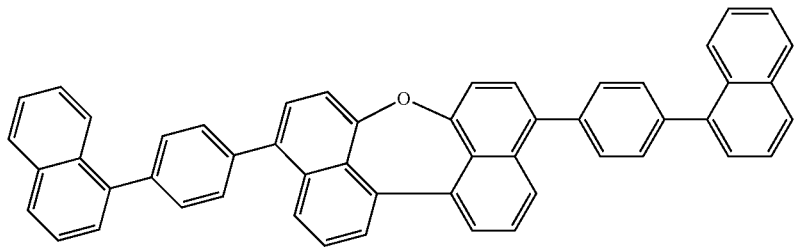
Formula (A-26)
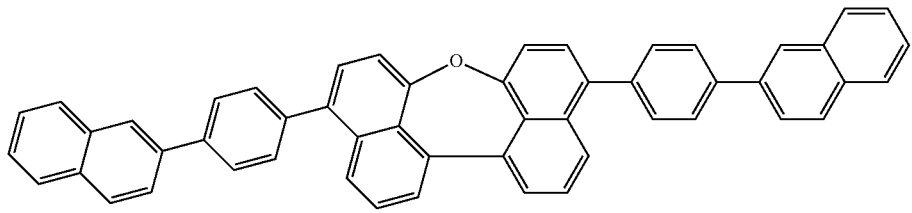
Formula (A-27)
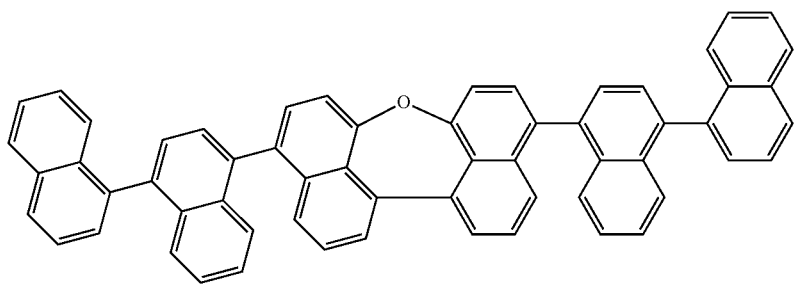
Formula (A-28)
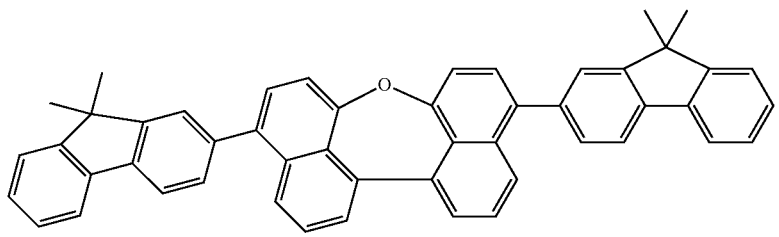
Formula (A-29)
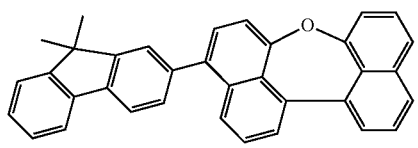
Formula (A-30)
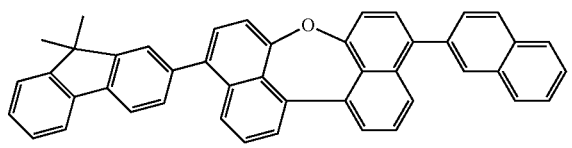
Formula (A-31)
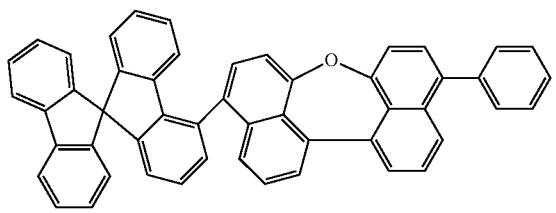

-continued
Formula (A-32)
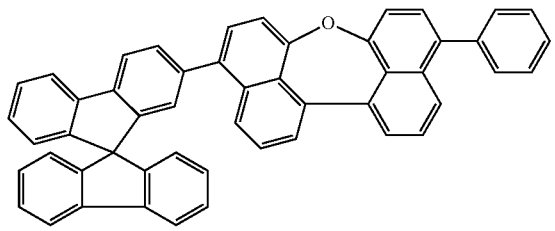
Formula (A-33)
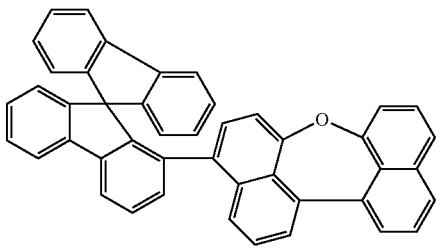
Formula (A-34)
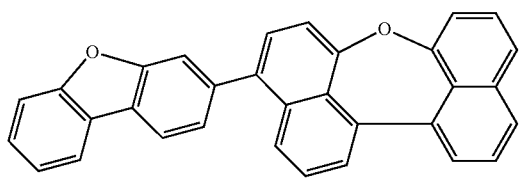
Formula (A-35)
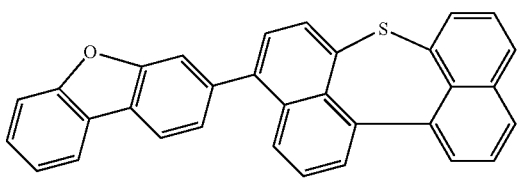
Formula (A-36)
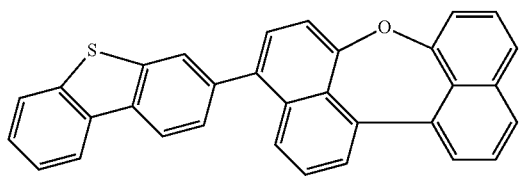
Formula (A-37)
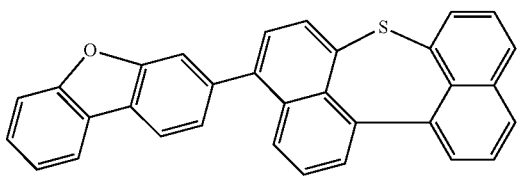
Formula (A-37)
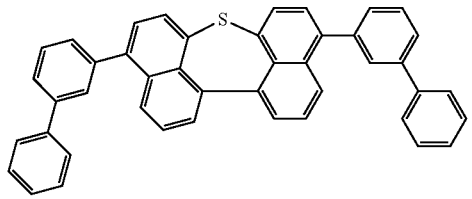
Formula (A-39)
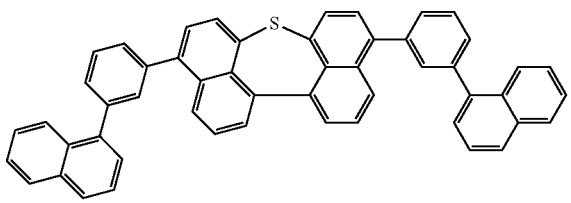
Formula (A-40)
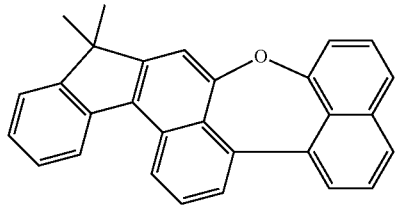
Formula (A-41)
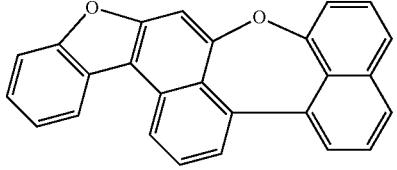
Formula (A-42)
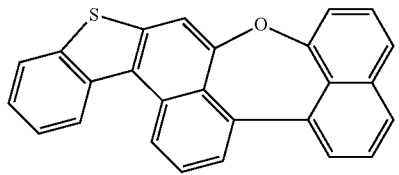
Formula (A-43)
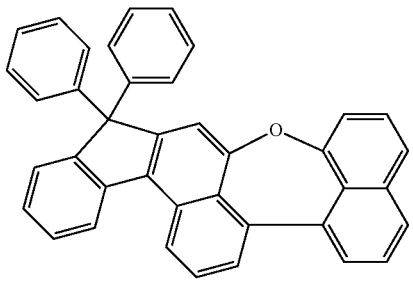

-continued
Formula (A-44)
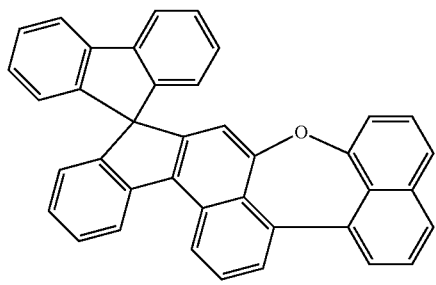
Formula (A-45)
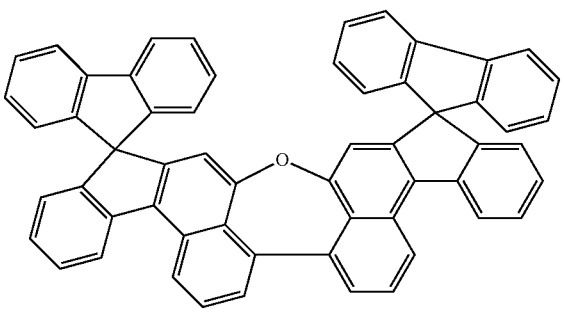
Formula (A-46)
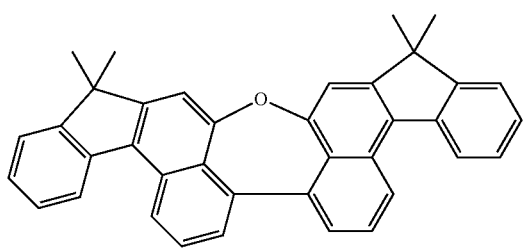
Formula (A-47)
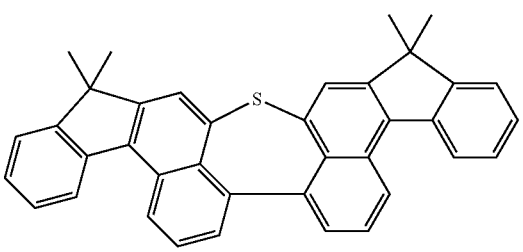
Formula (A-48)
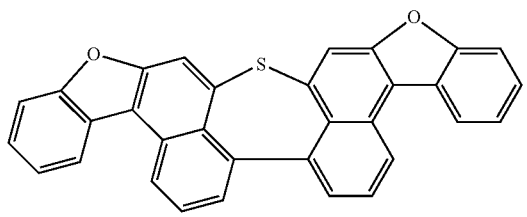
Formula (A-49)
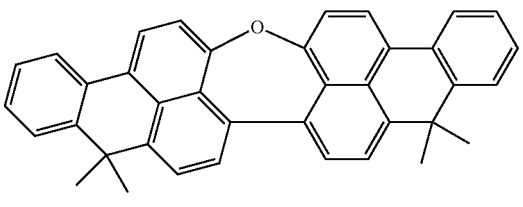
Formula (A-50)
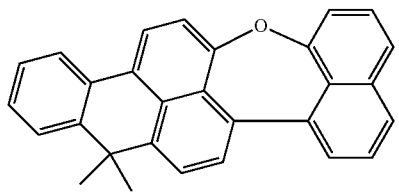
Formula (A-51)
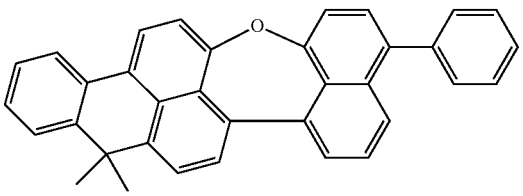
Formula (A-42)
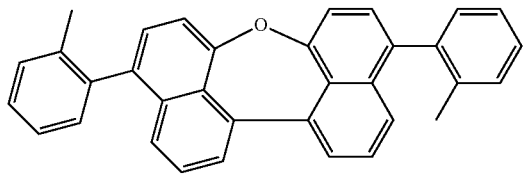
Formula (A-53)
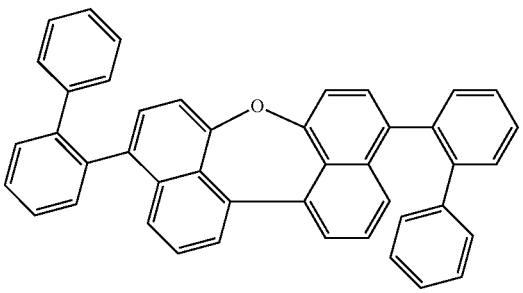
Formula (A-54)
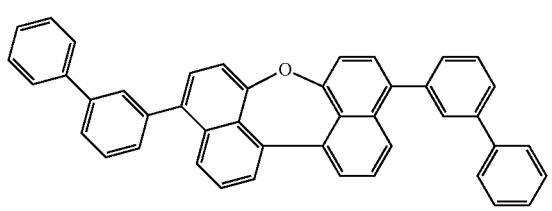
Formula (A-55)
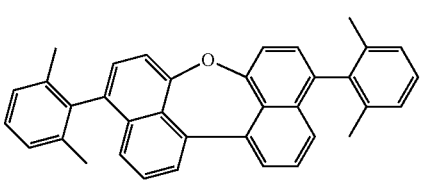

-continued
Formula (A-56)
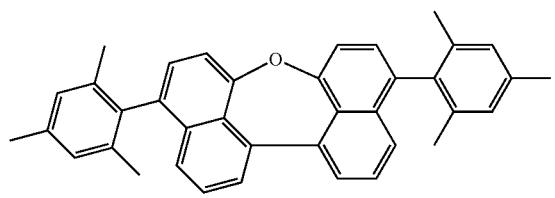
Formula (A-57)
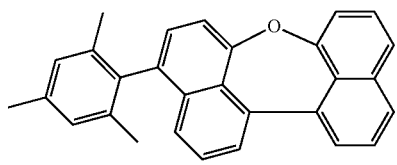
Formula (A-58)
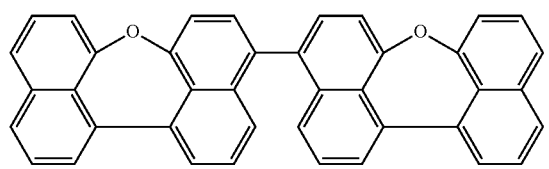
Formula (A-59)
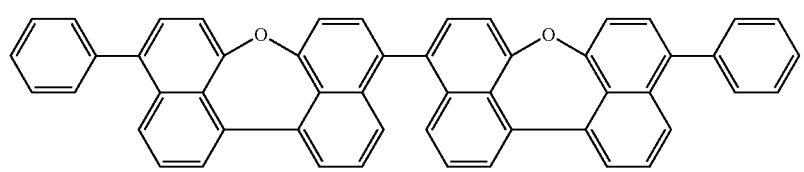
Formula (A-60)
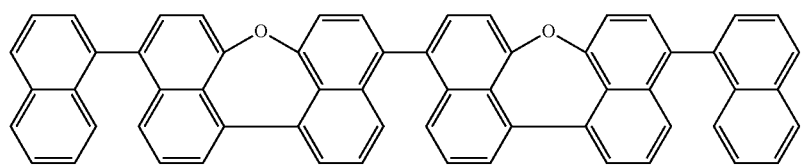
Formula (A-61)
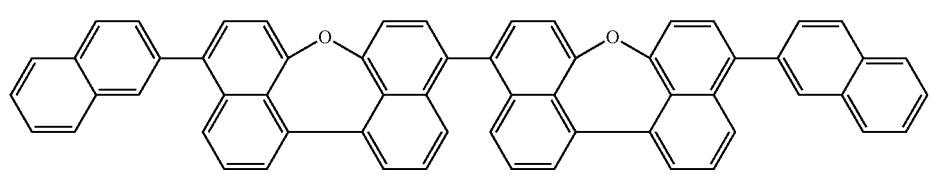
Formula (A-62)
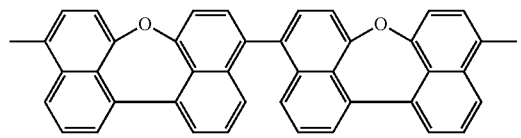
Formula (A-63)
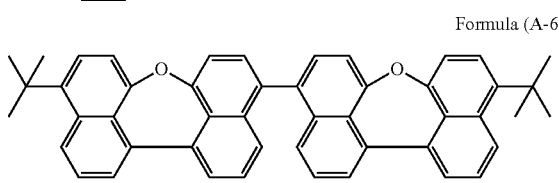
Formula (A-64)
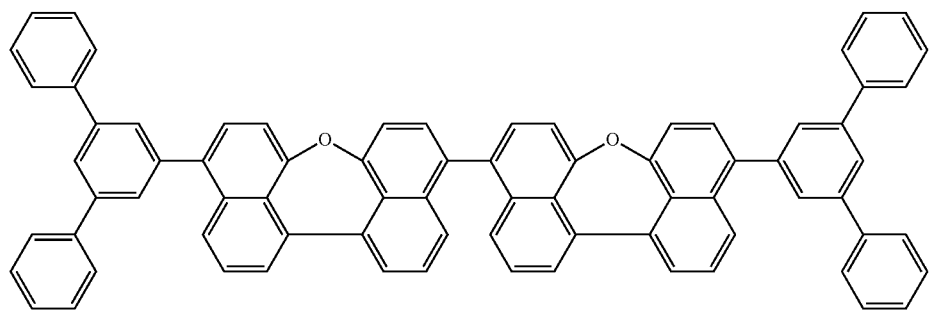
Formula (A-65)
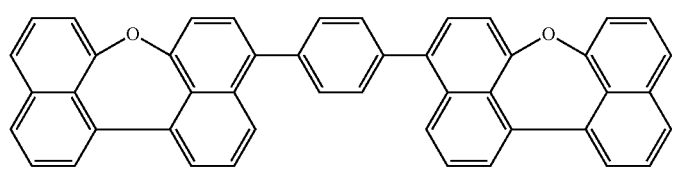

-continued
Formula (A-66)
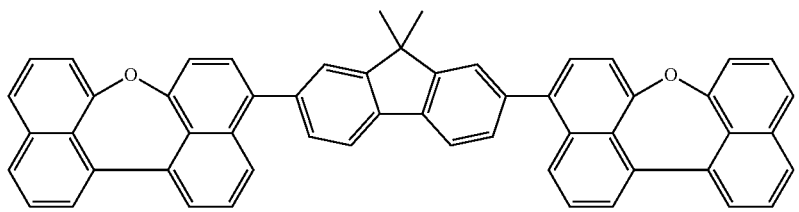
Formula (A-67)
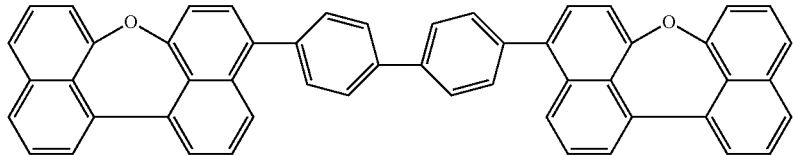
Formula (A-68)
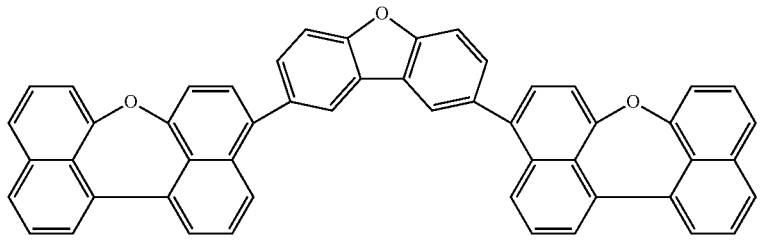
Formula (A-69)
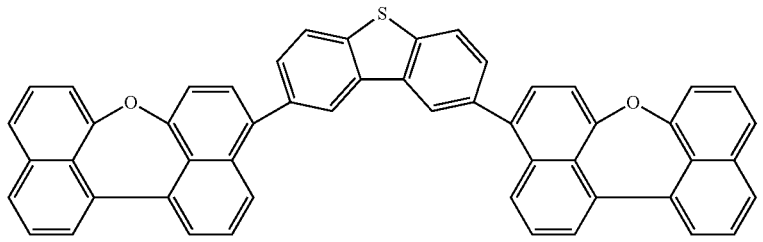
Formula (A-50)
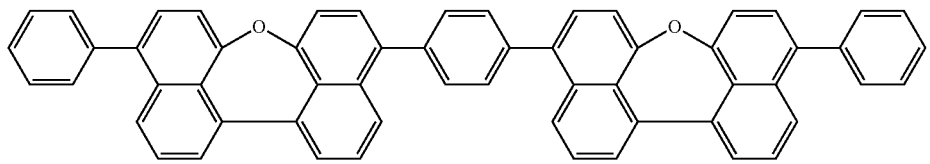
Formula (A-51)
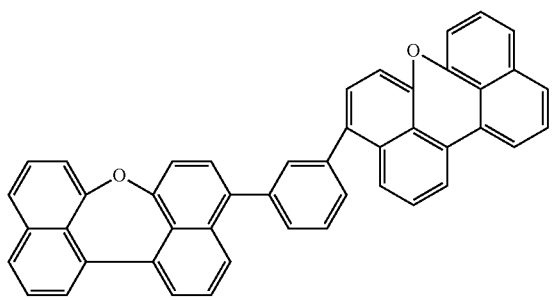
Formula (A-52)
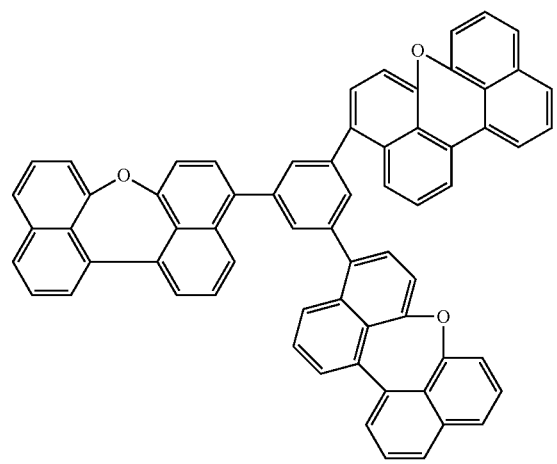

-continued
Formula (A-53)
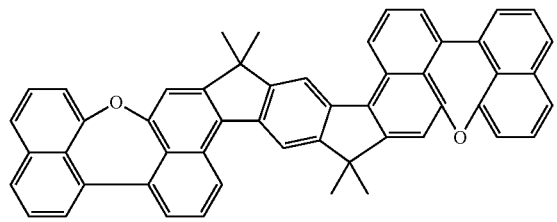
Formula (A-54)
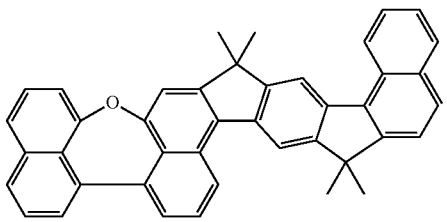
Formula (A-55)
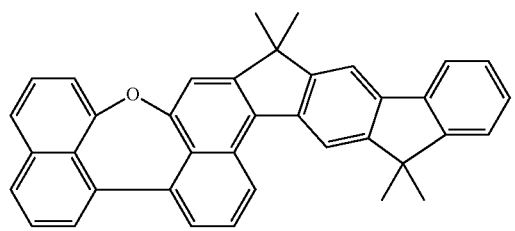
Formula (A-56)
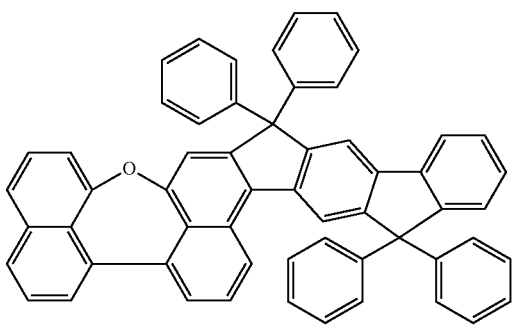
Formula (A-57)
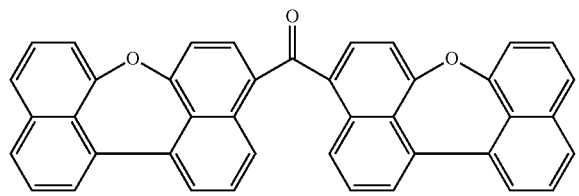
Formula (A-58)
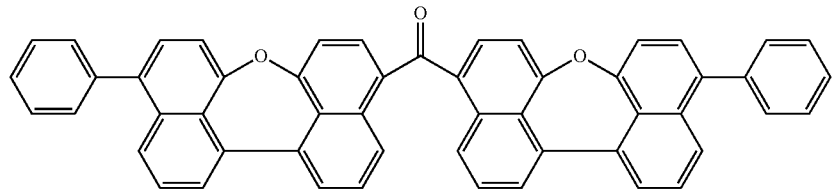
Formula (A-59)
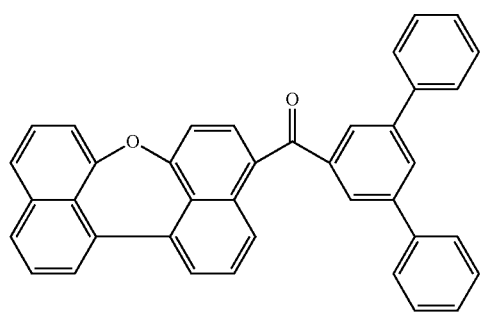
Formula (A-60)
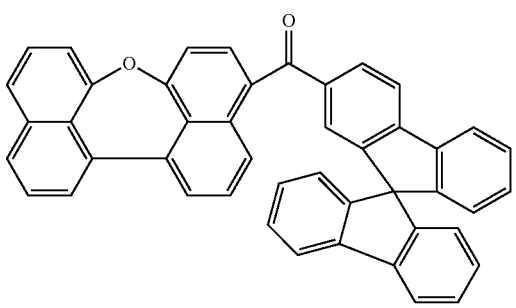

-continued
Formula (A-61)
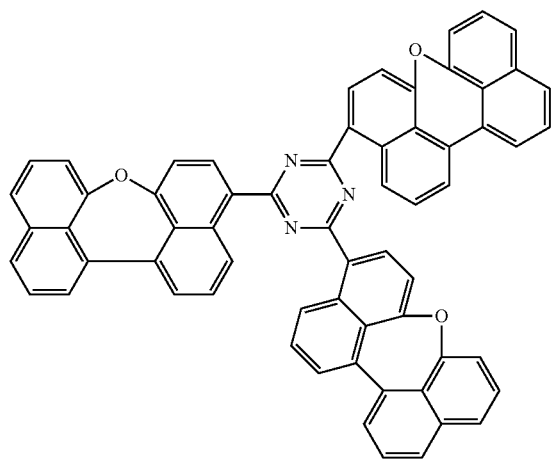
Formula (A-62)
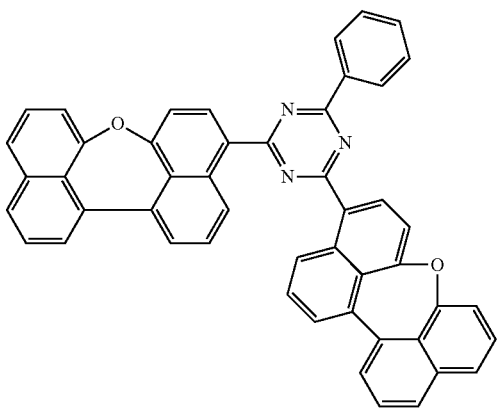
Formula (A-63)
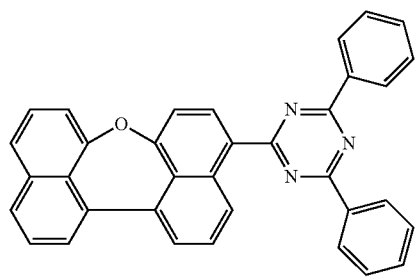
Formula (A-64)
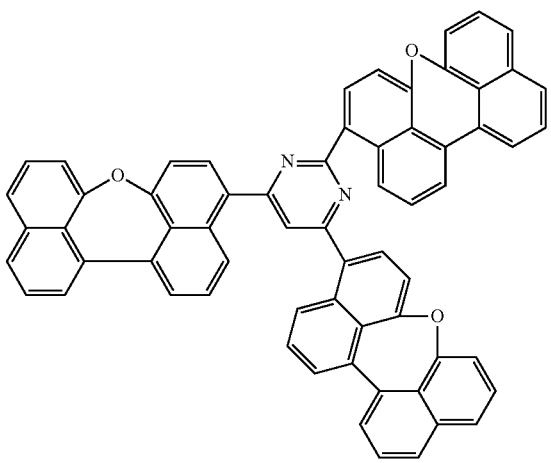
Formula (A-65)
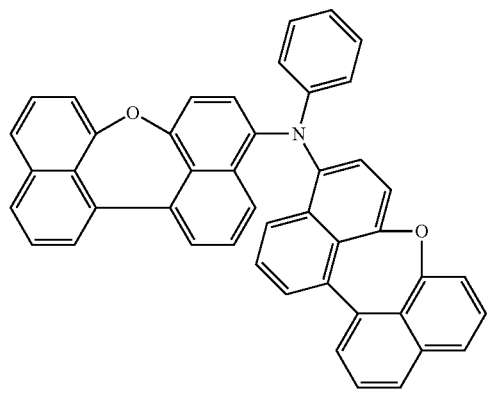
Formula (A-66)
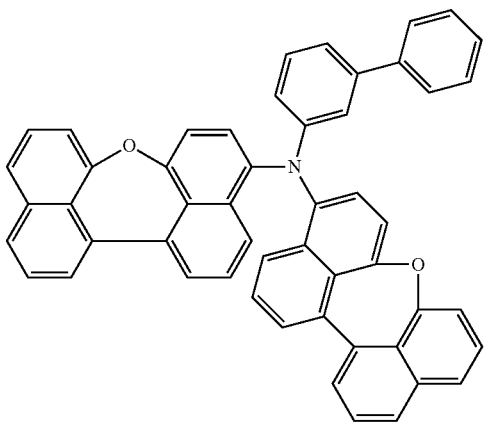

-continued
Formula (A-67)
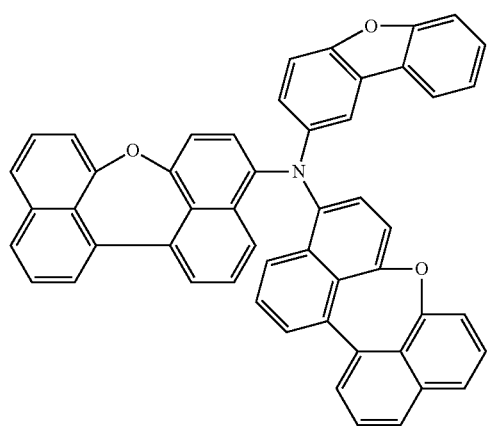
Formula (A-68)
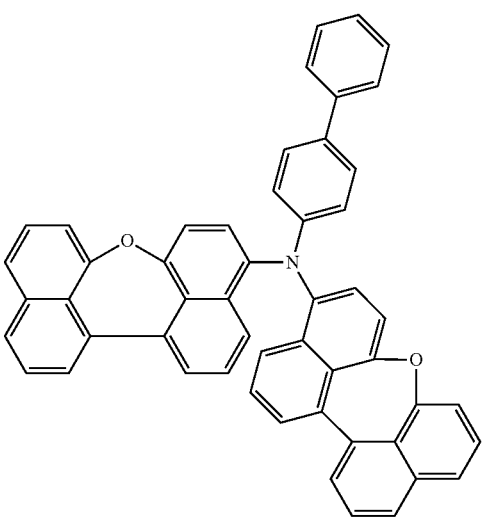
Formula (A-69)
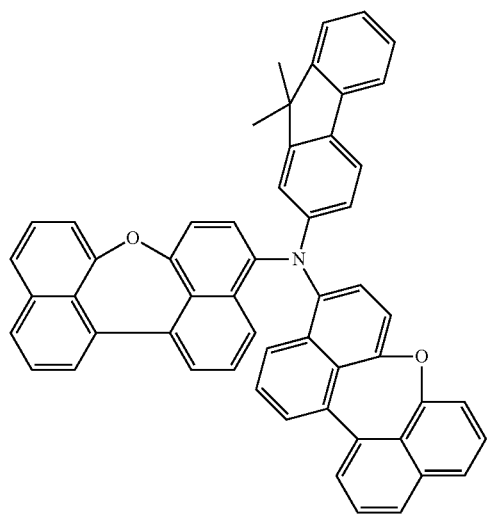
Formula (A-70)
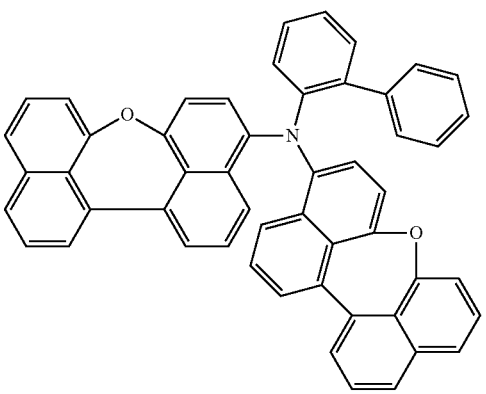
Formula (A-71)
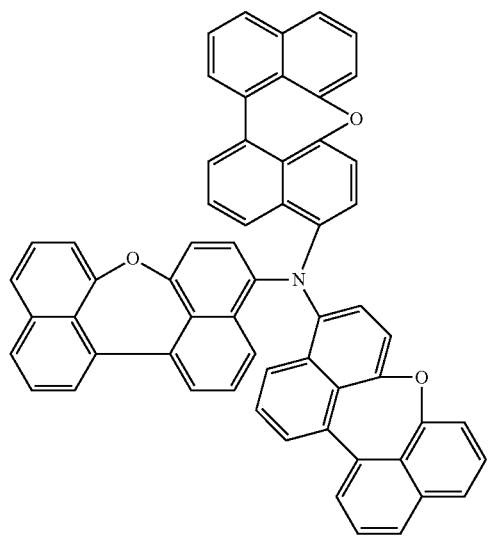
Formula (A-72)
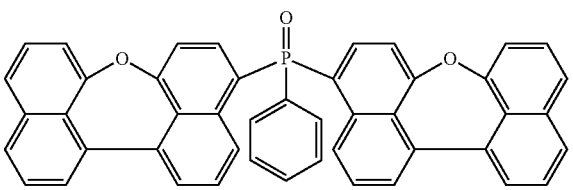

Formula (A-73)
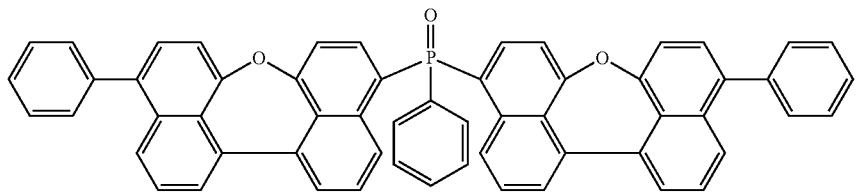
Formula (A-74)
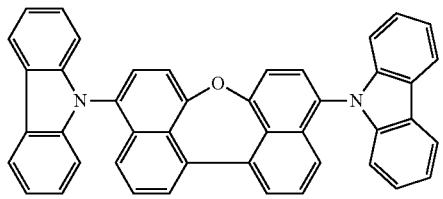
Formula (A-75)
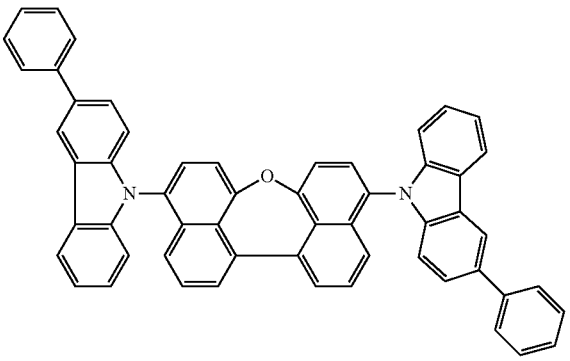
Formula (A-76)
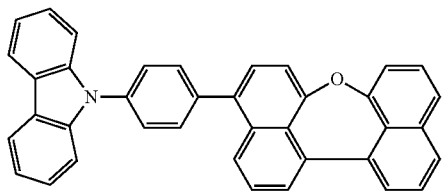
Formula (A-77)
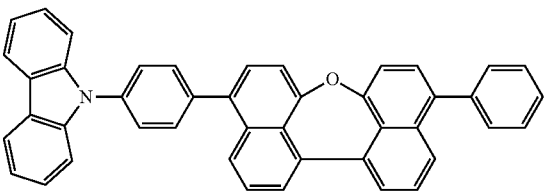
Formula (A-78)
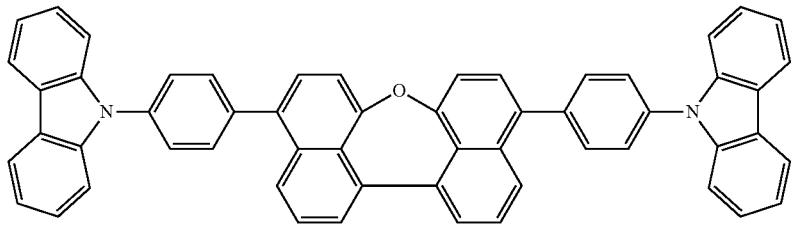
Formula (A-79)
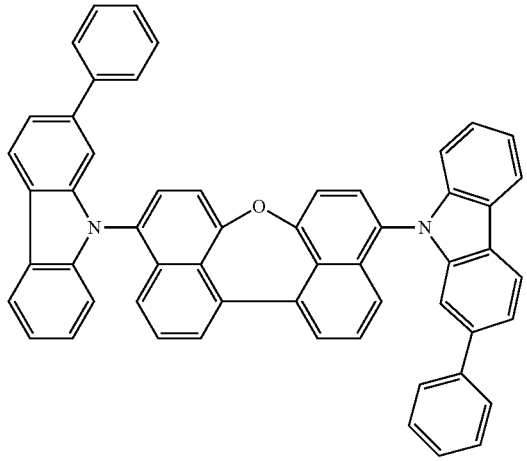
Formula (A-80)
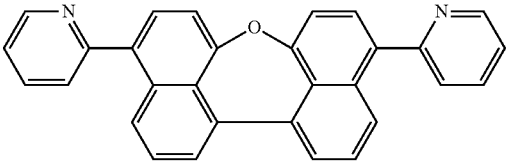

-continued
Formula (A-81)
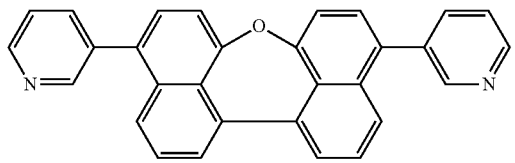
Formula (A-82)
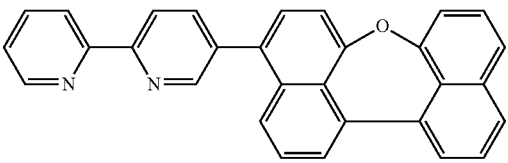
Formula (A-83)
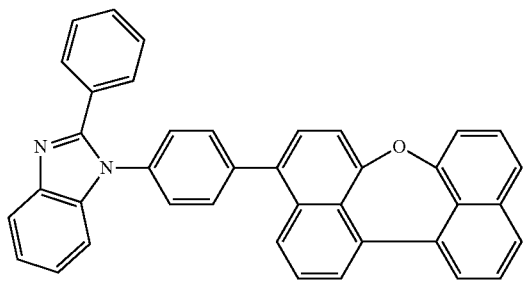
Formula (A-84)
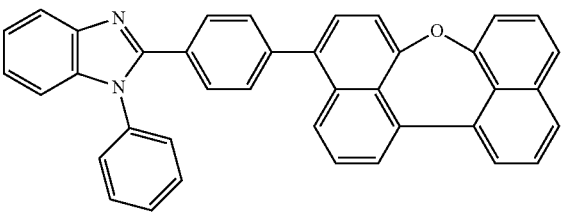
Formula (A-85)
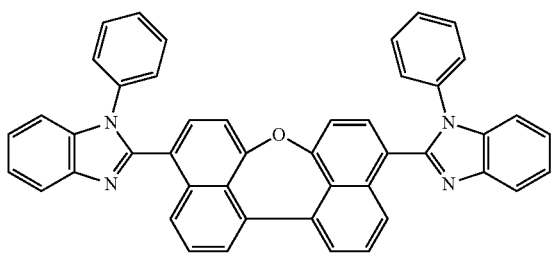
Formula (A-86)
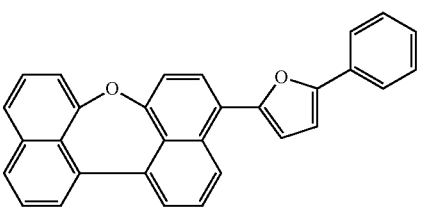
Formula (A-87)
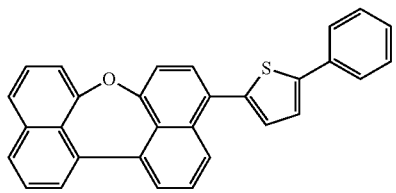
Formula (A-88)
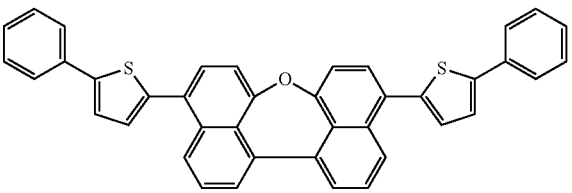
Formula (A-89)
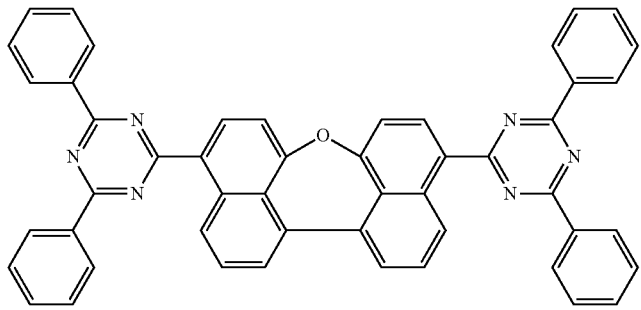
Formula (A-90)
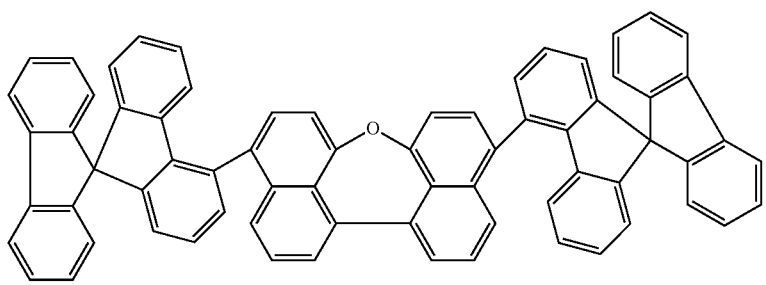

-continued
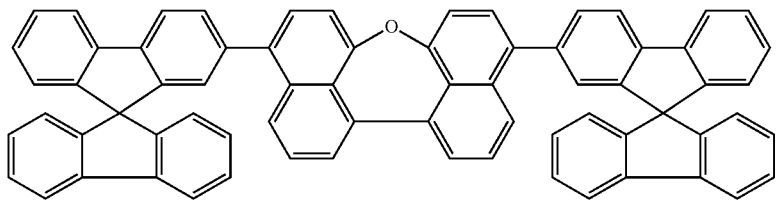
Formula (A-91)
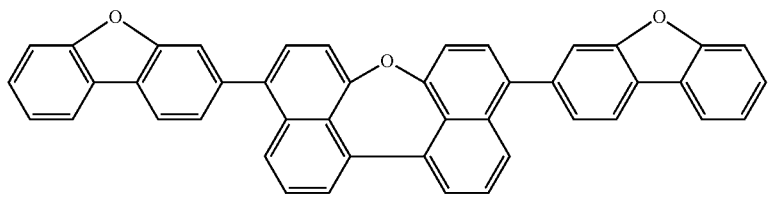
Formula (A-92)
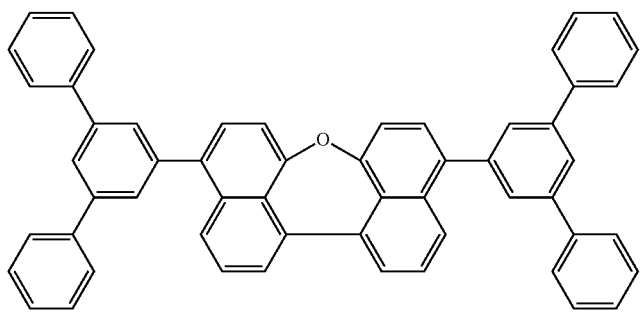
Formula (A-93)
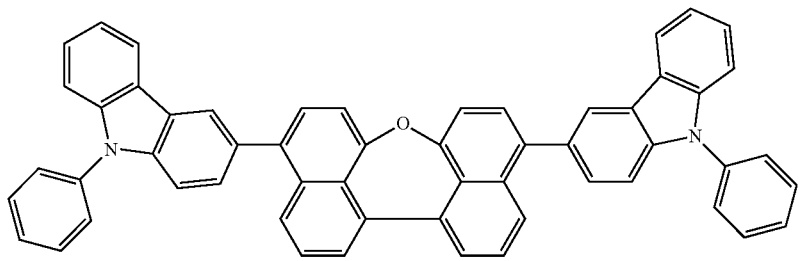
Formula (A-94)
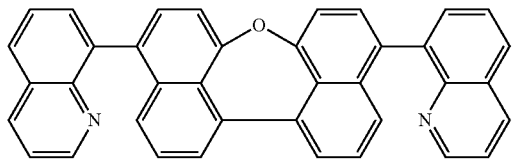
Formula (A-95)
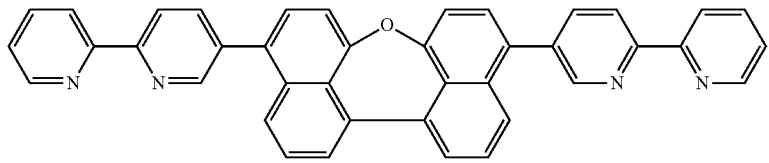
Formula (A-96)
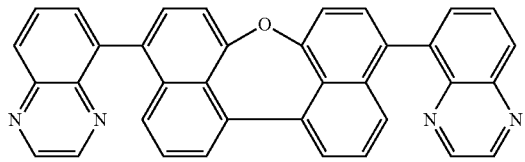
Formula (A-97)

Formula (A-98)
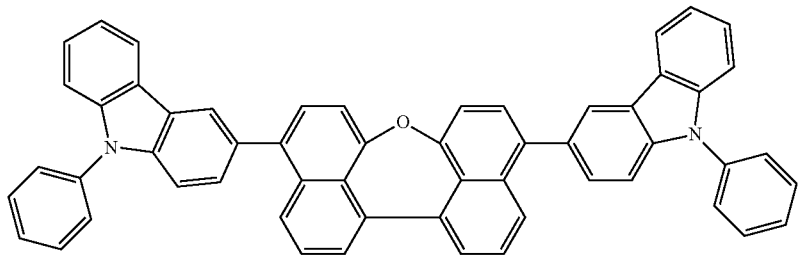
Formula (A-99)
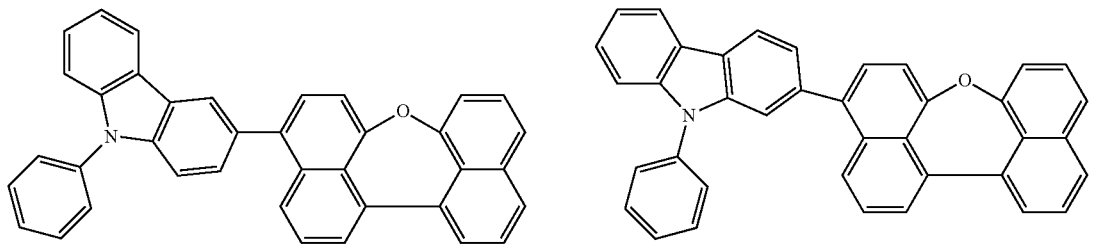
Formula (A-100)
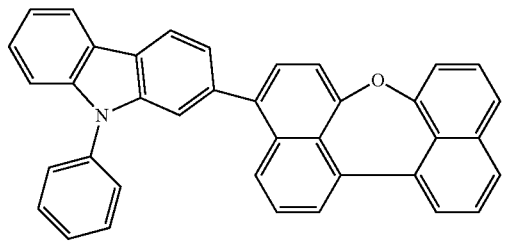
Formula (A-101)
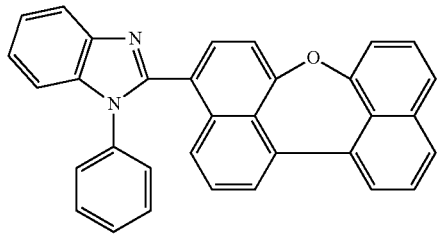
Formula (A-102)
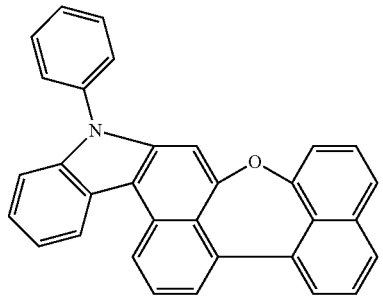
Formula (A-103)
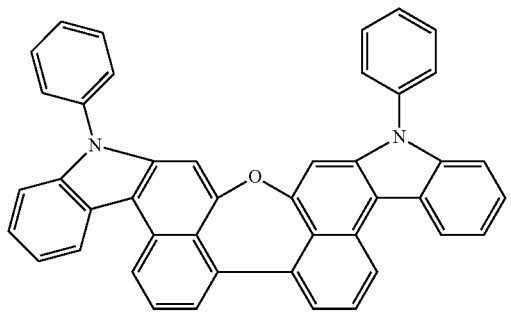
Formula (A-104)
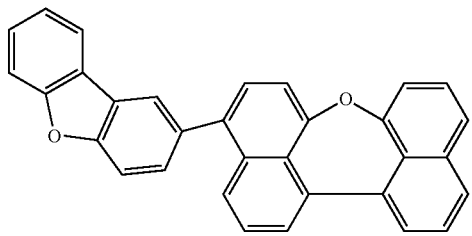
Formula (A-105)
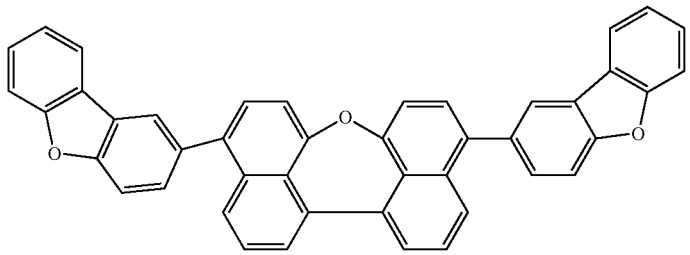

Formula (A-106)
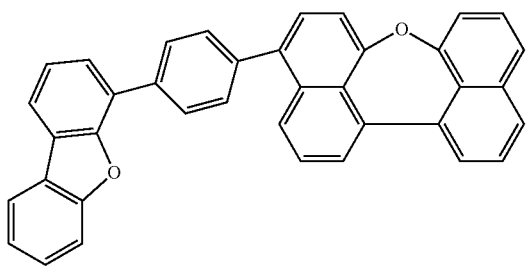
Formula (A-107)
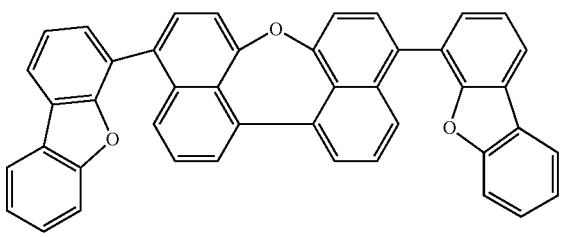
Formula (A-108)
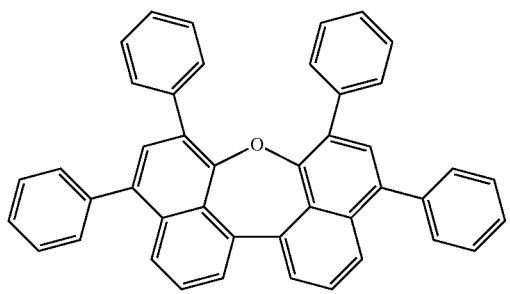
Formula (A-109)
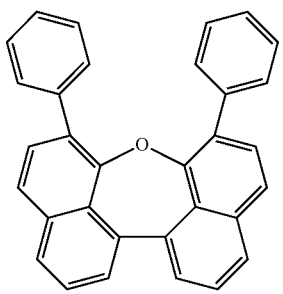
Formula (A-110)
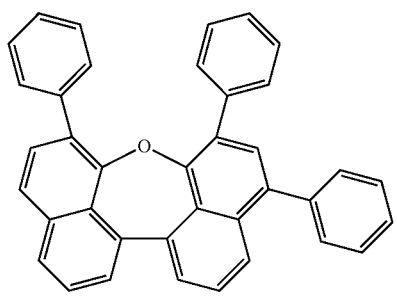
Formula (A-111)
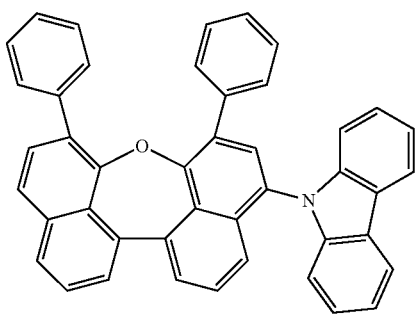
Formula (A-112)
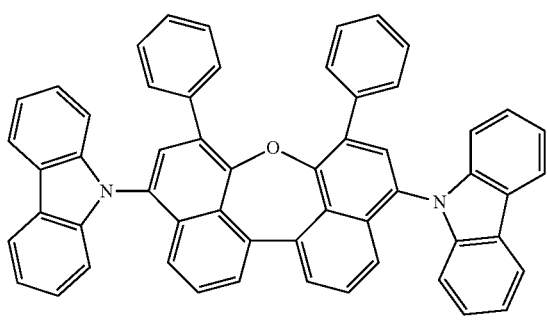

-continued
Formula (A-113)
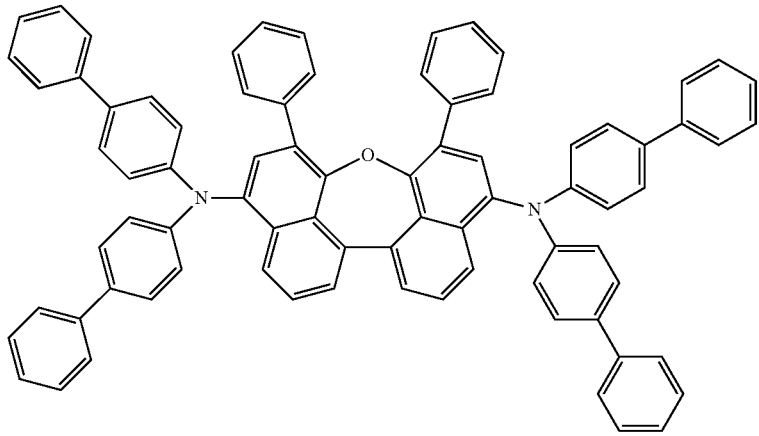
Formula (A-114)
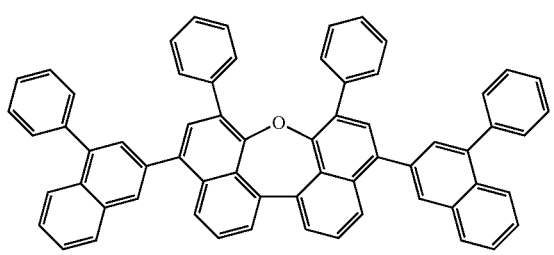
Formula (A-115)
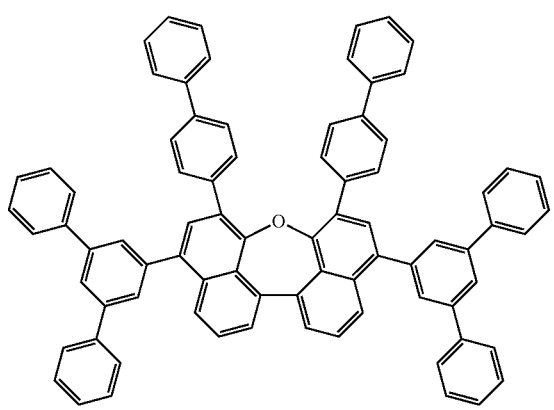
Formula (A-116)
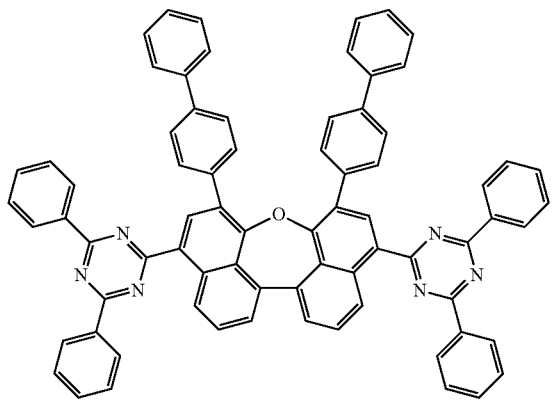
Formula (A-117)
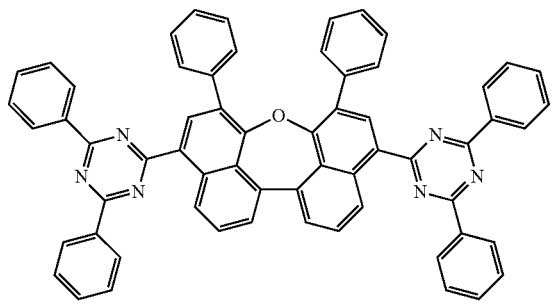
Formula (A-118)
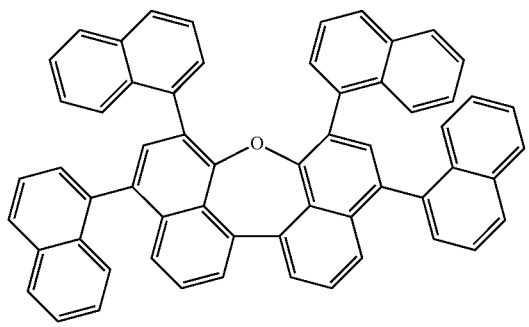
Formula (A-119)
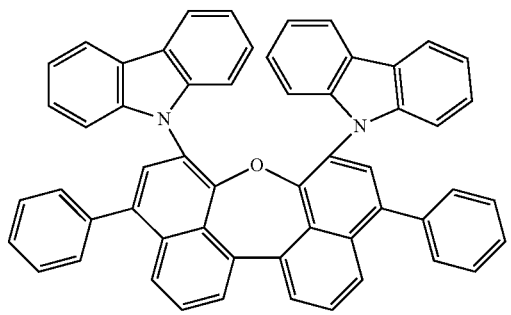

-continued
Formula (A-120)
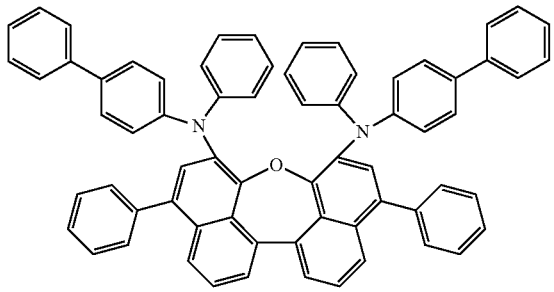
Formula (A-121)
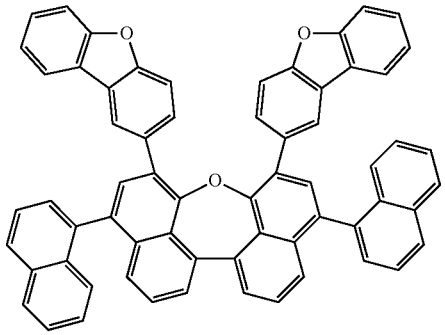
Formula (A-122)
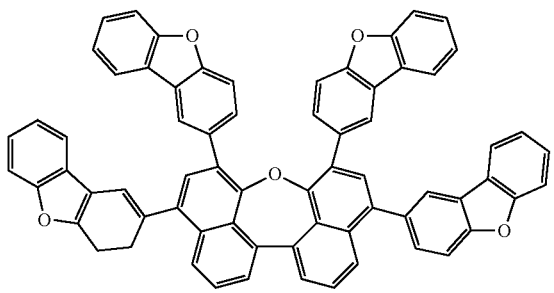
Formula (A-123)
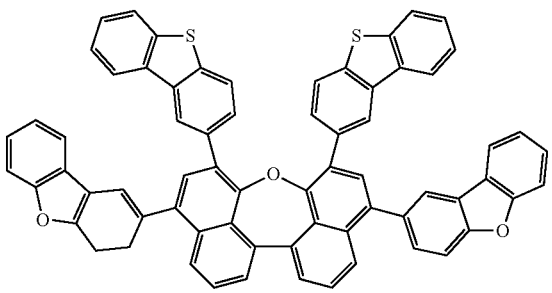
Formula (A-124)
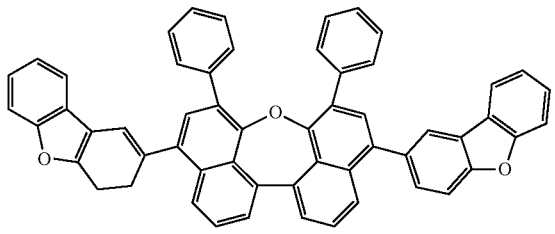
Formula (A-125)
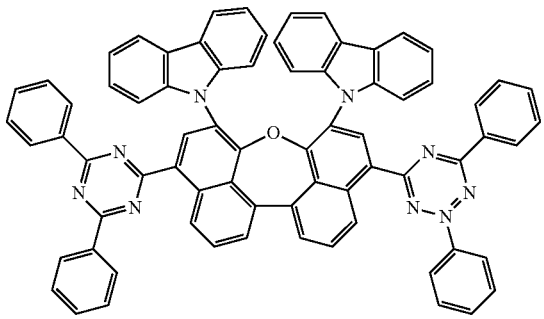
Formula (A-126)
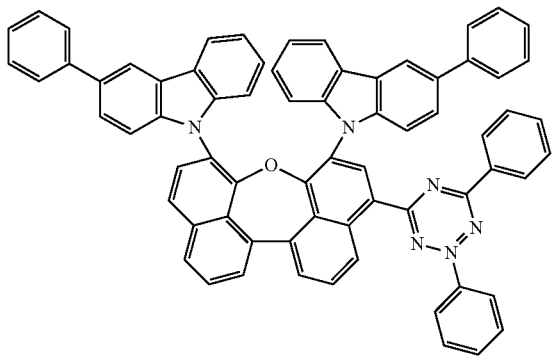
Formula (A-127)
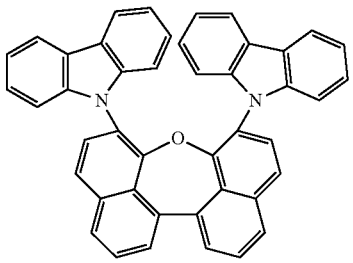

Formula (A-128)
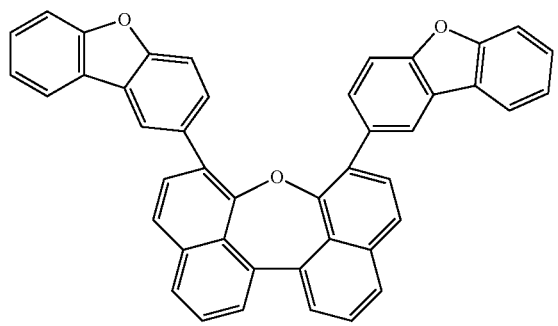
Formula (A-129)
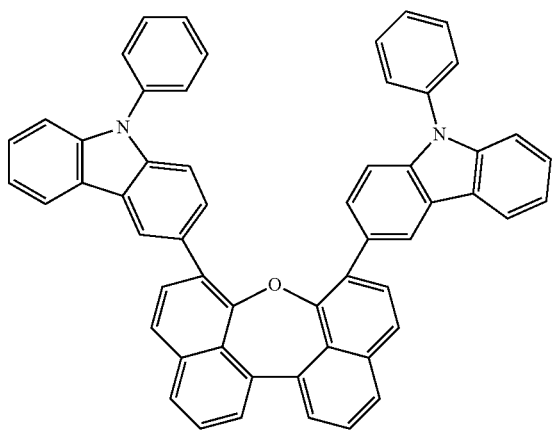
Formula (A-130)
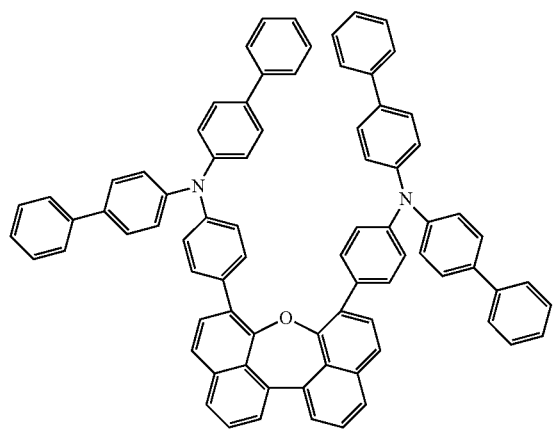
Formula (A-131)
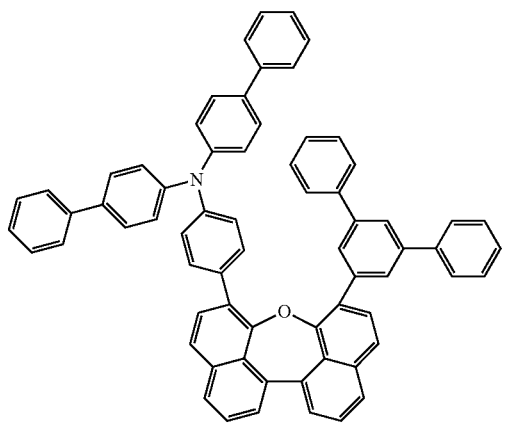
Formula (A-132)
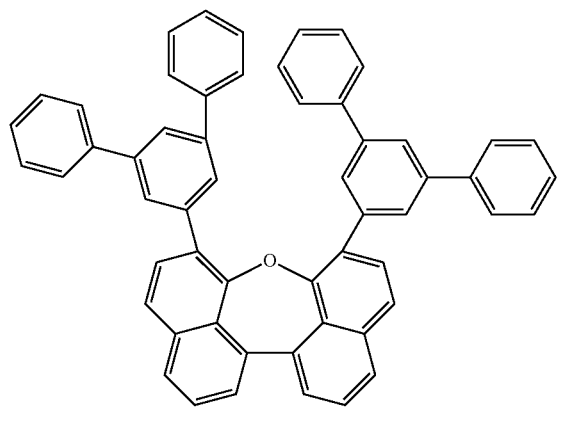
Formula (A-133)
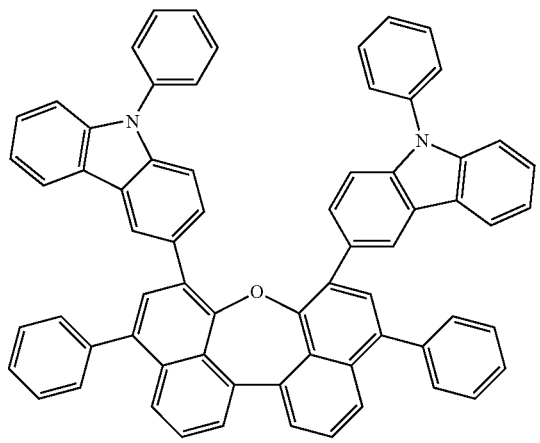

-continued
Formula (A-134)
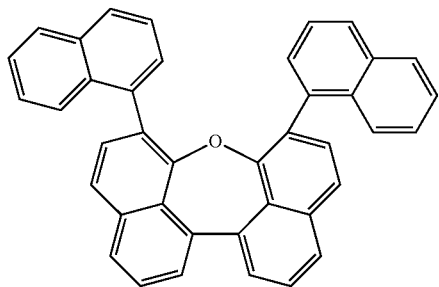
Formula (A-135)
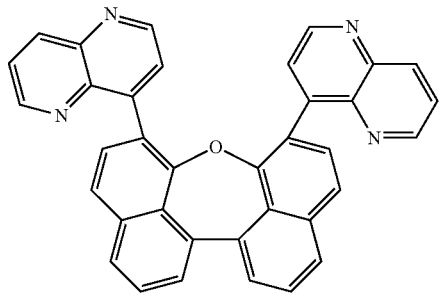
Formula (A-136)
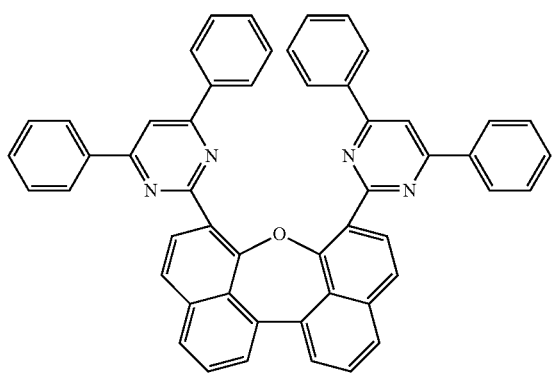
Formula (A-137)
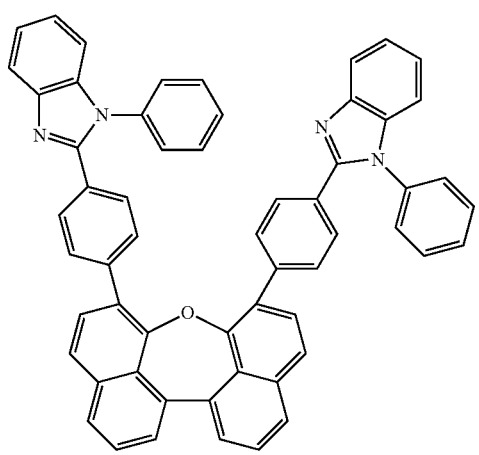
Formula (A-138)
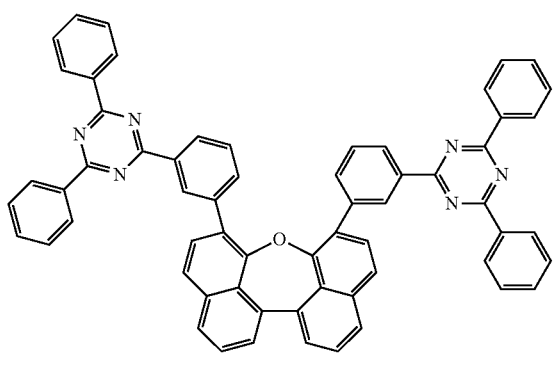
Formula (A-139)
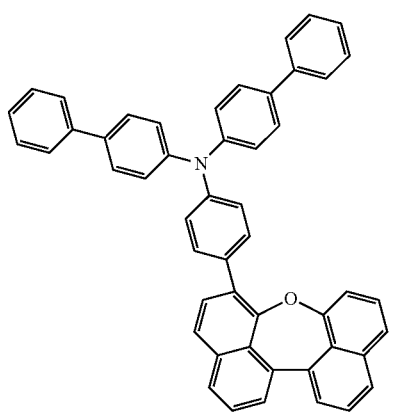

-continued
Formula (A-140)
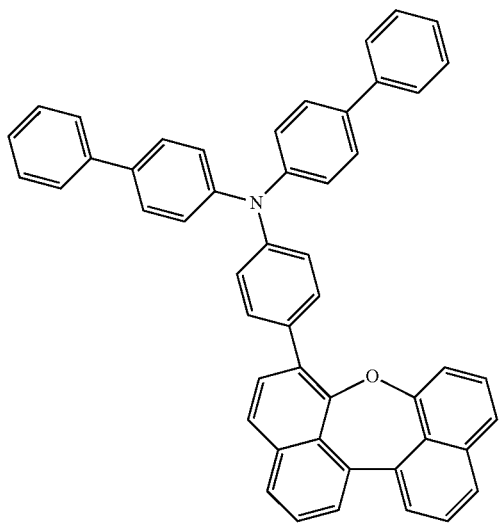
Formula (A-141)
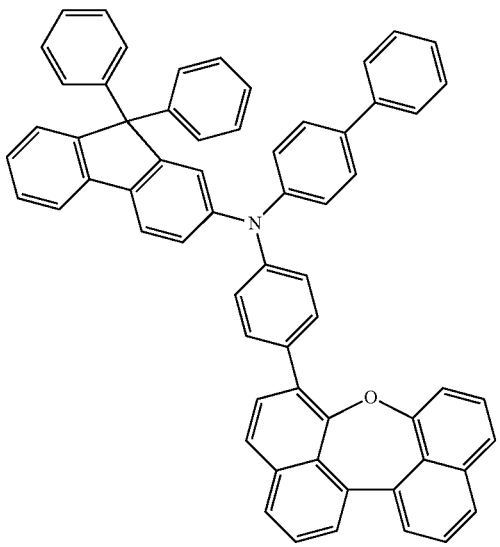
Formula (A-142)
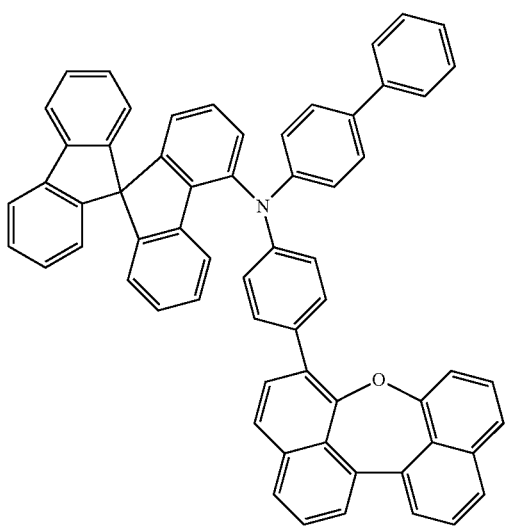
Formula (A-143)
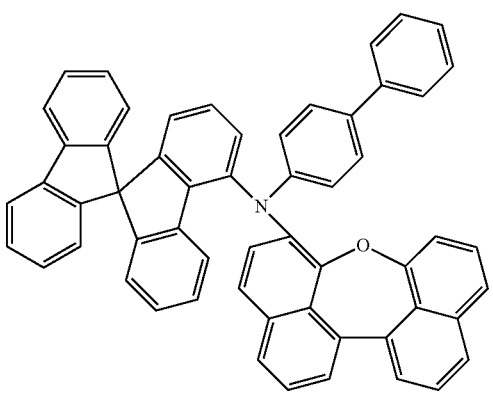
Formula (A-144)
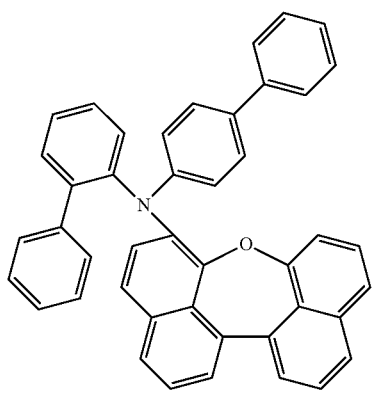
Formula (A-145)
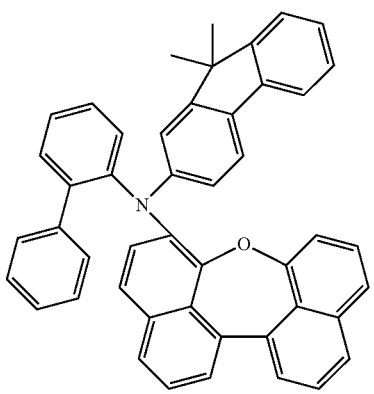

-continued
Formula (A-146)
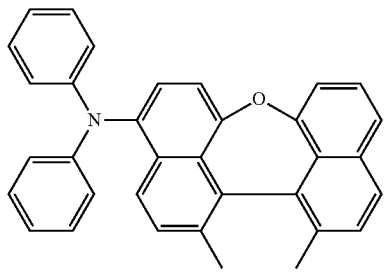
Formula (A-147)
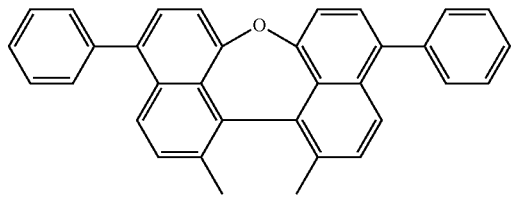
Formula (A-148)
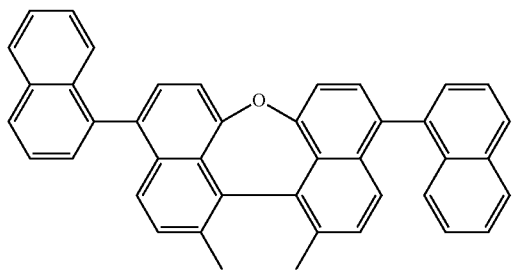
Formula (A-149)
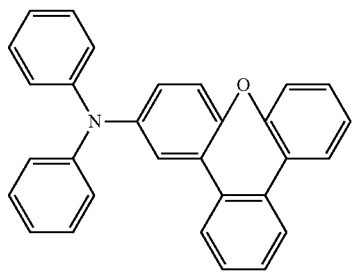
Formula (A-149)
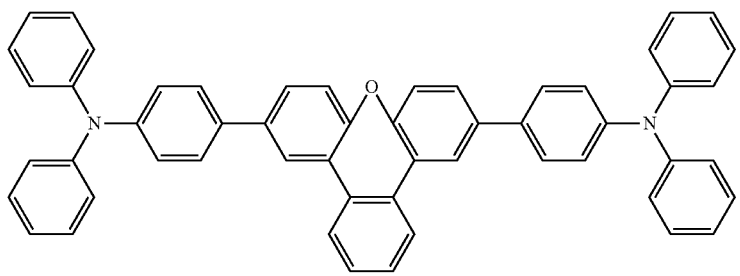
Formula (A-149)
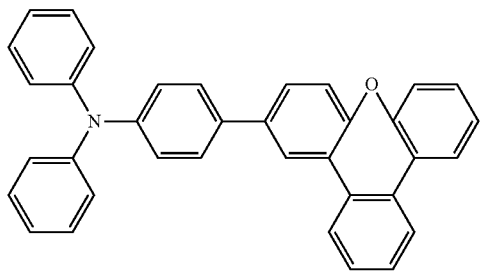
Formula (A-150)
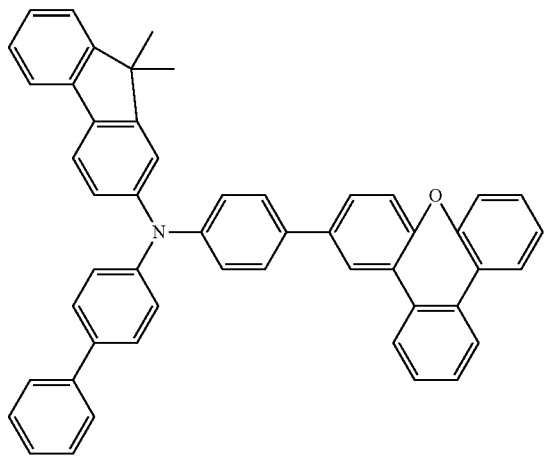

-continued
Formula (A-151)
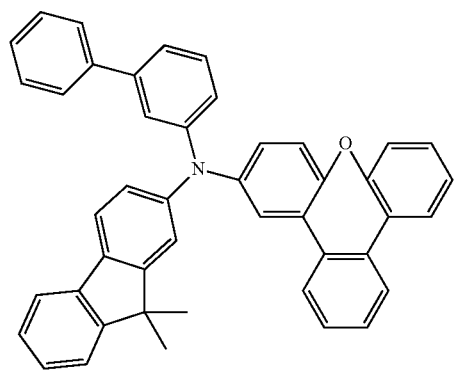
Formula (A-152)
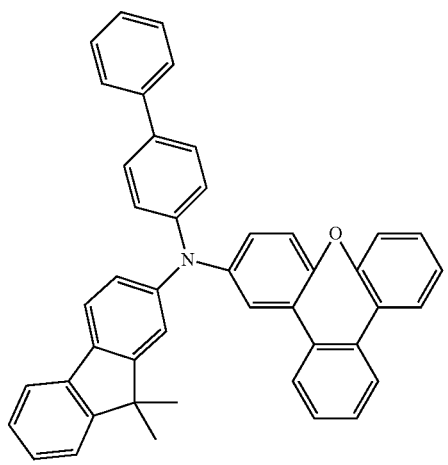
Formula (A-153)
Formula (A-154)
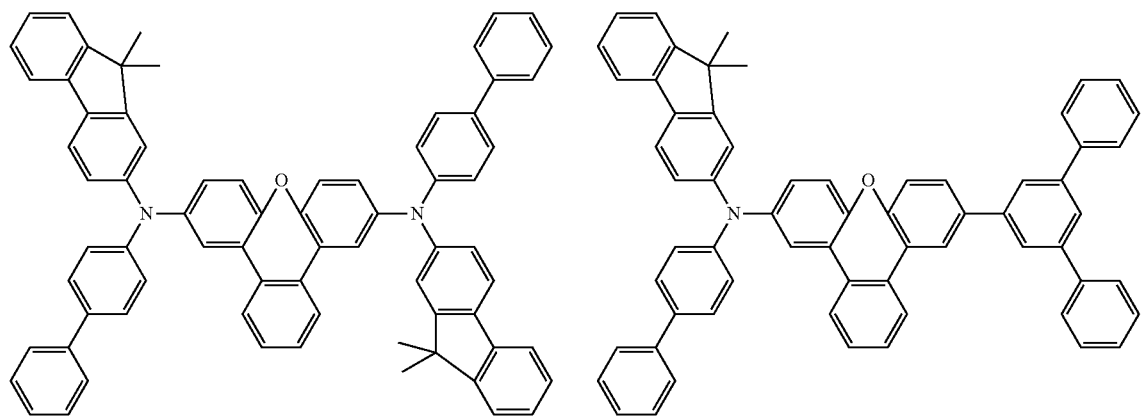
Formula (A-155)
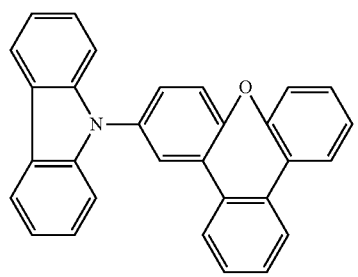
Formula (A-156)
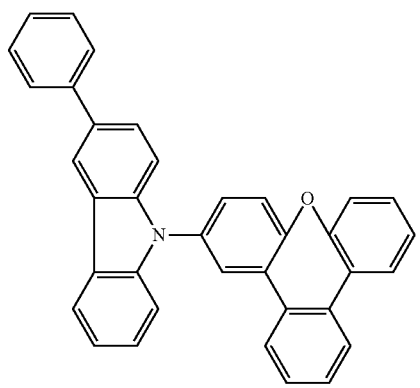

-continued
Formula (A-157)
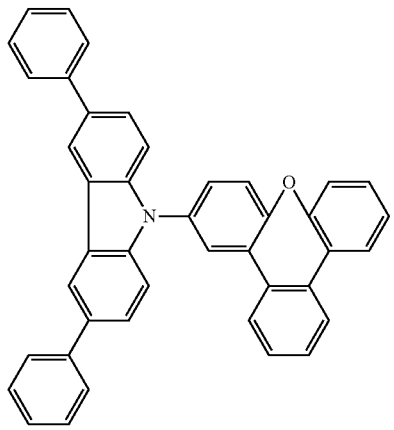
Formula (A-158)
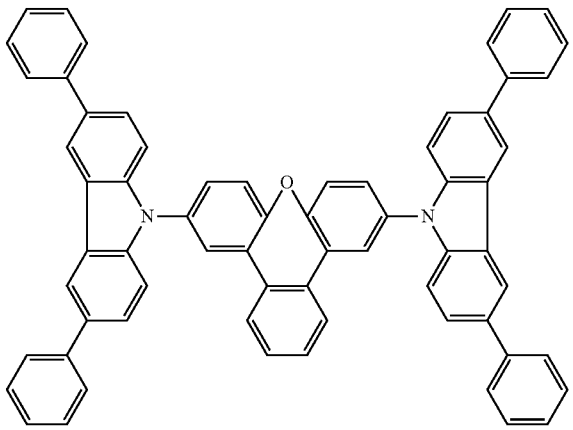
Formula (A-159)
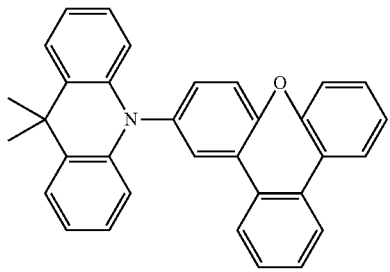
Formula (A-160)
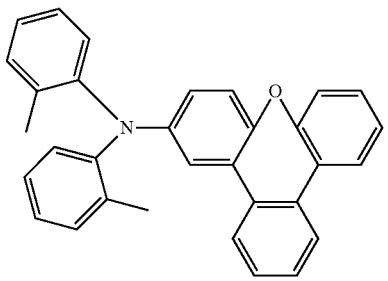
Formula (A-161)
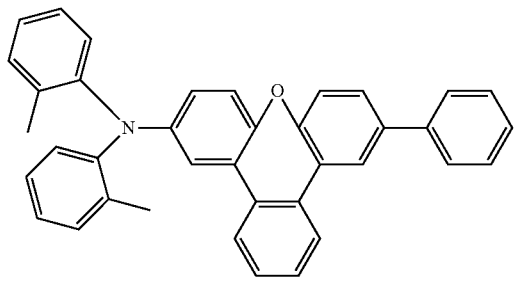
Formula (A-162)
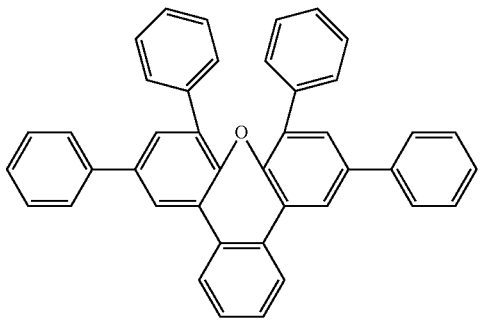
Formula (A-163)
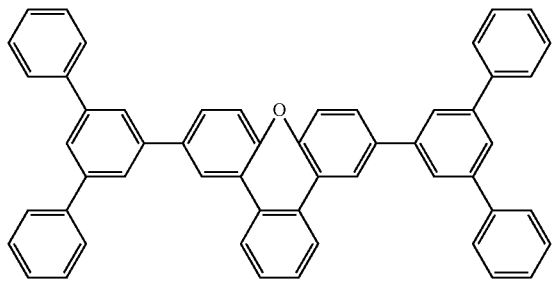
Formula (A-164)
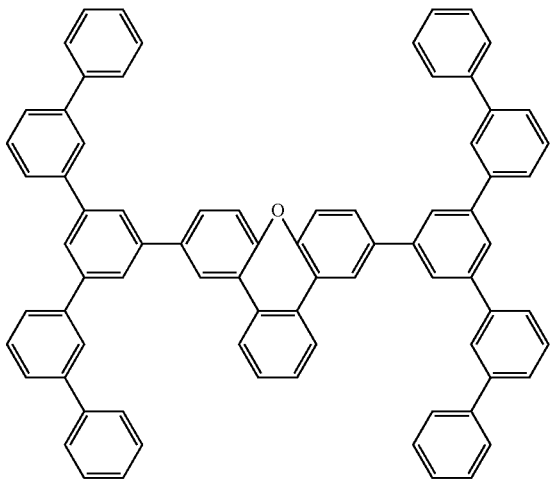

-continued
Formula (A-165)
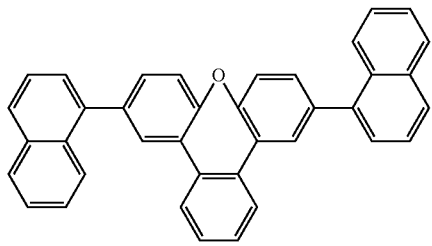
Formula (A-166)
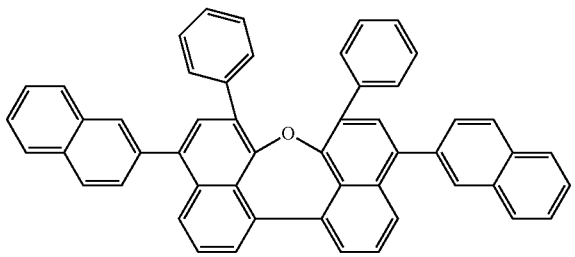
Formula (A-167)
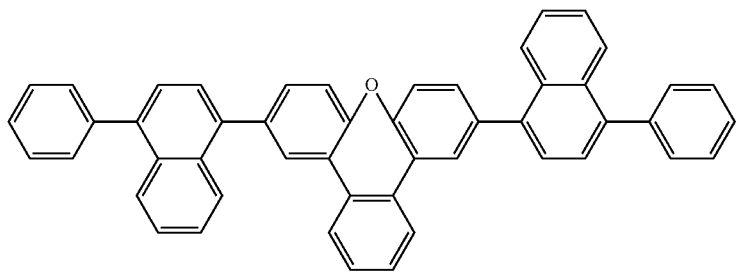
Formula (A-168)
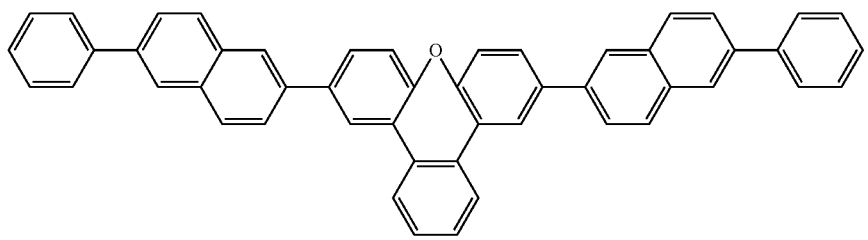
Formula (A-169)
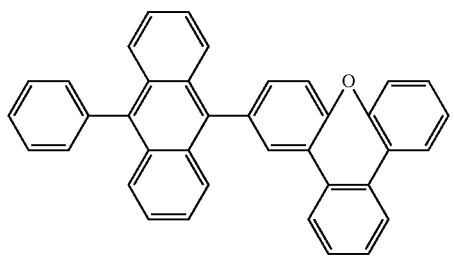
Formula (A-170)
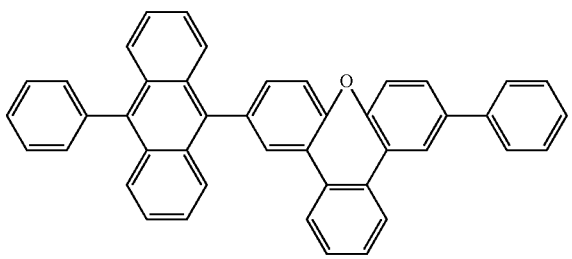
Formula (A-171)
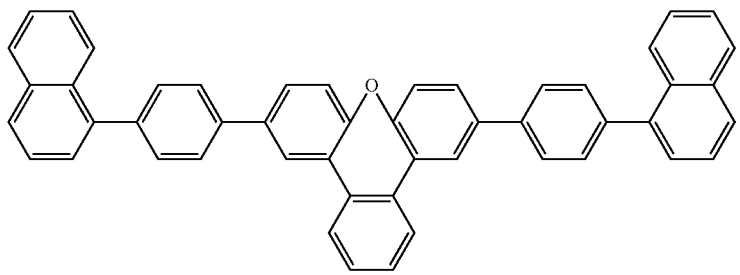
Formula (A-172)
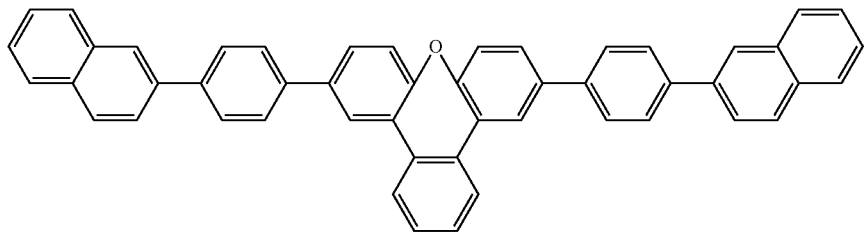

-continued
Formula (A-173)
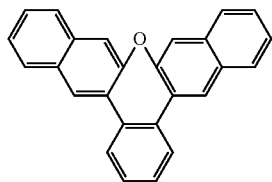
Formula (A-174)
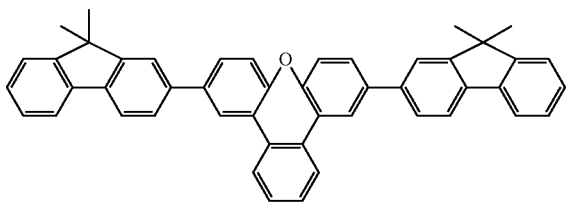
Formula (A-175)
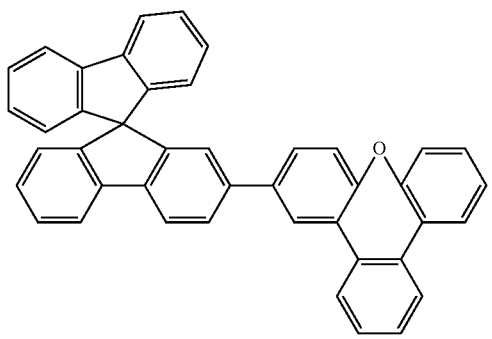
Formula (A-176)
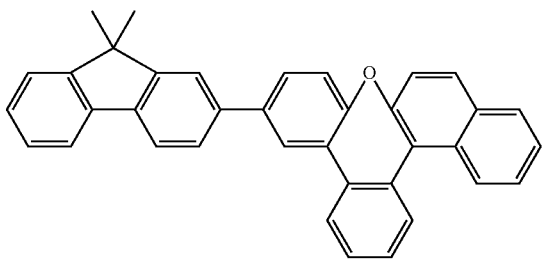
Formula (A-177)
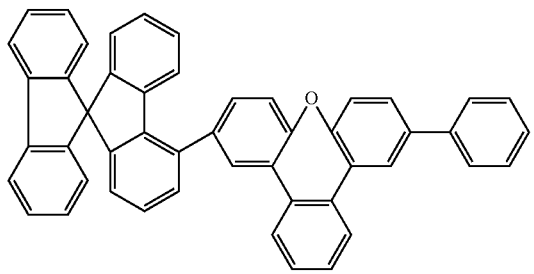
Formula (A-178)
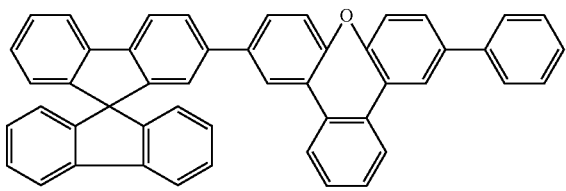
Formula (A-179)
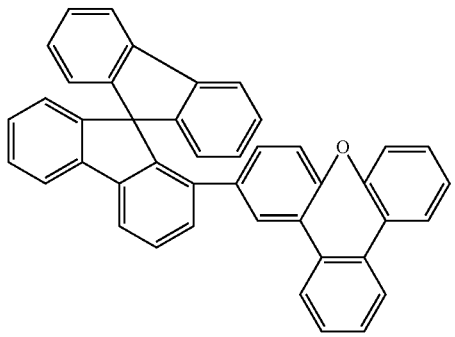
Formula (A-180)
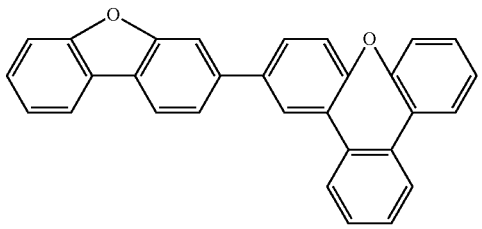
Formula (A-181)
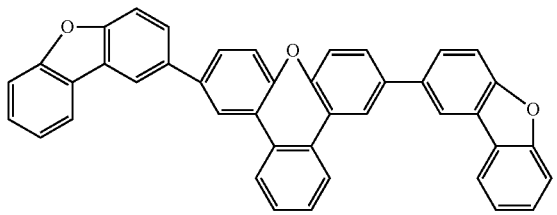
Formula (A-182)
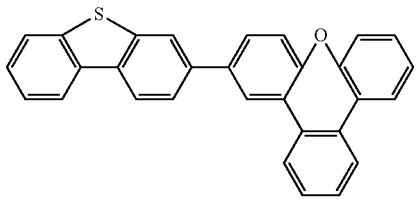

Formula (A-183)
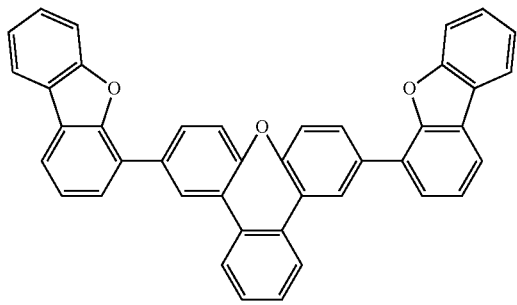
Formula (A-184)
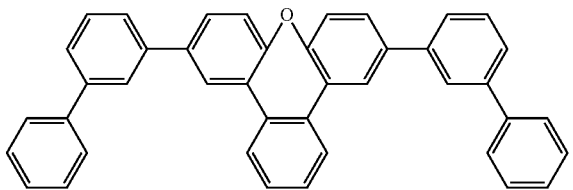
Formula (A-185)
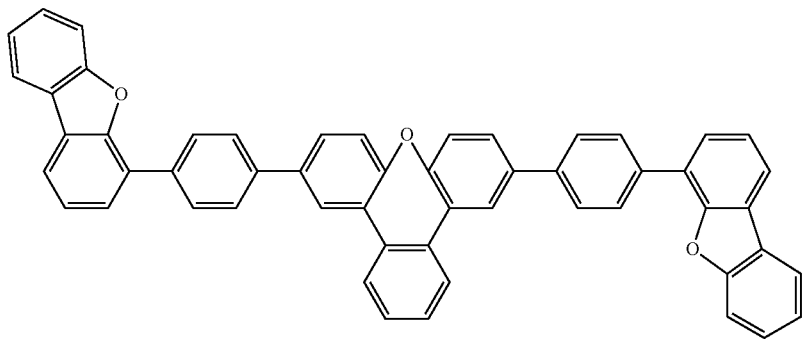
Formula (A-186)
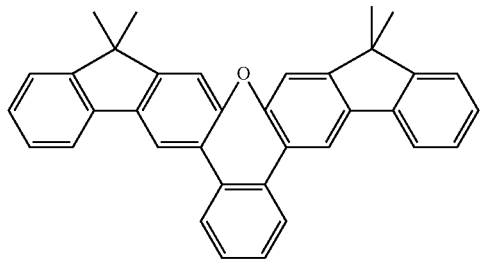
Formula (A-187)
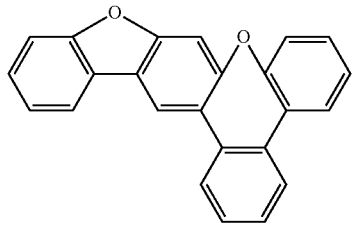
Formula (A-188)
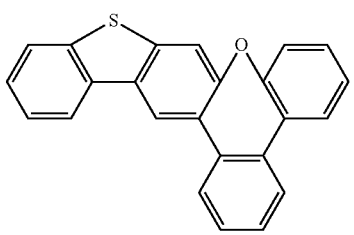
Formula (A-189)
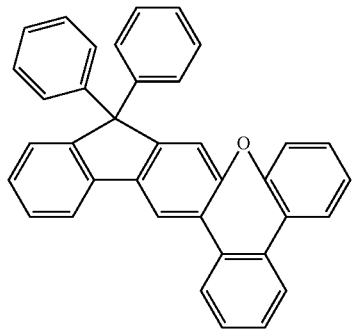
Formula (A-190)
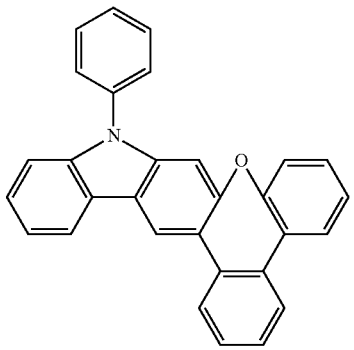

-continued
Formula (A-191)
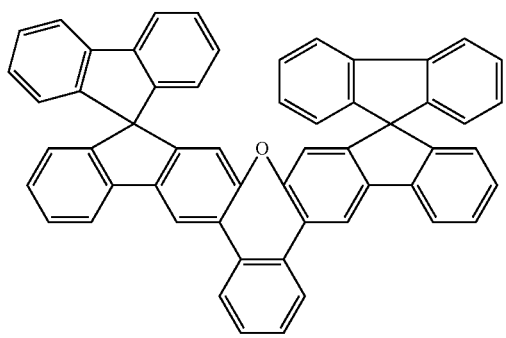
Formula (A-192)
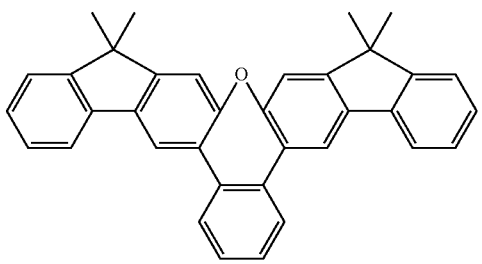
Formula (A-193)
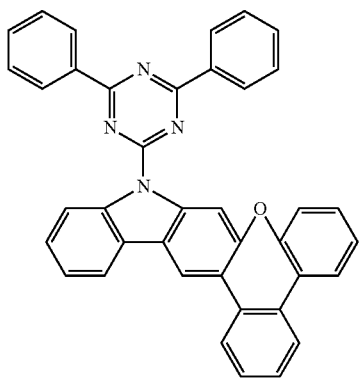
Formula (A-194)
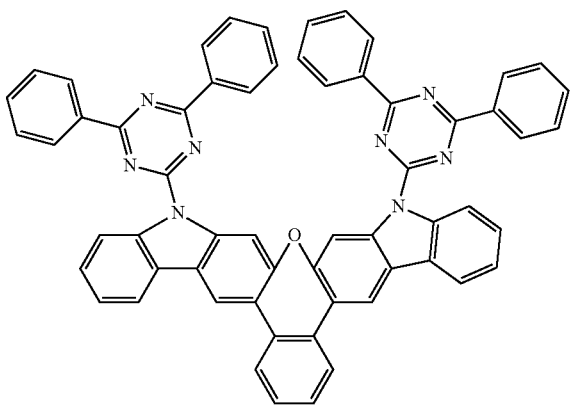
Formula (A-195)
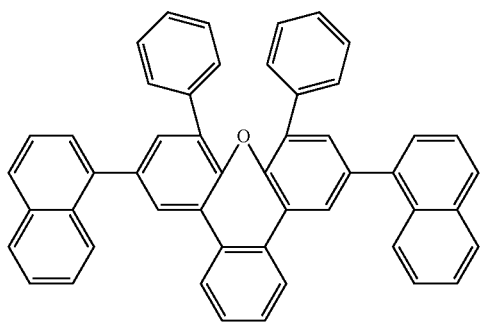
Formula (A-196)
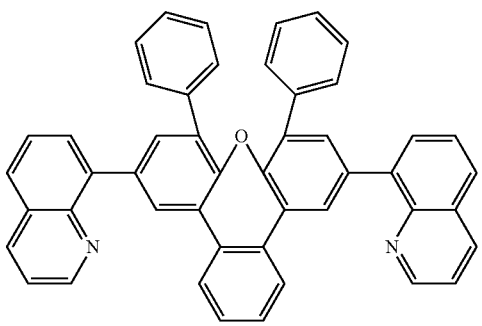
Formula (A-197)
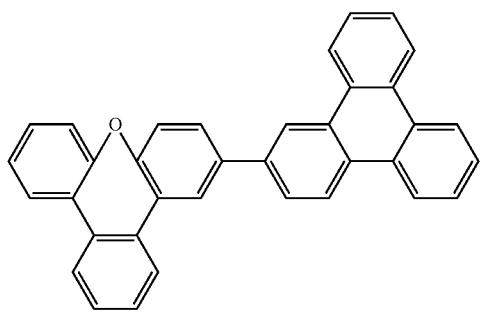
Formula (A-198)
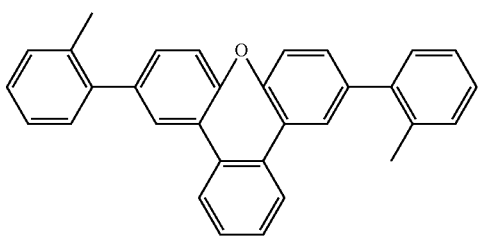

Formula (A-199)
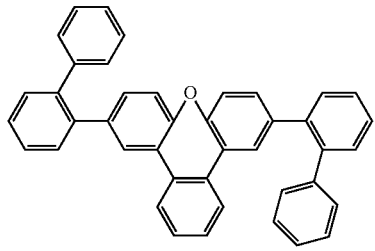
Formula (A-200)
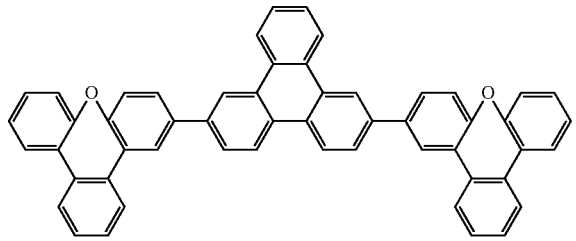
Formula (A-201)
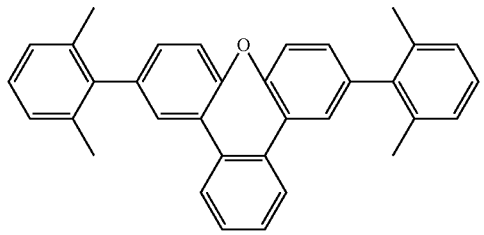
Formula (A-202)
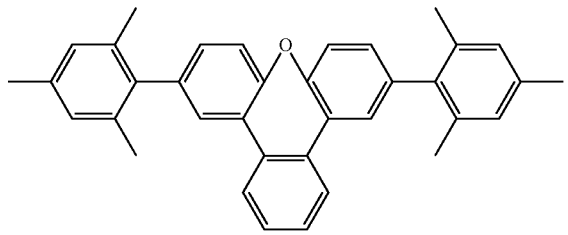
Formula (A-203)
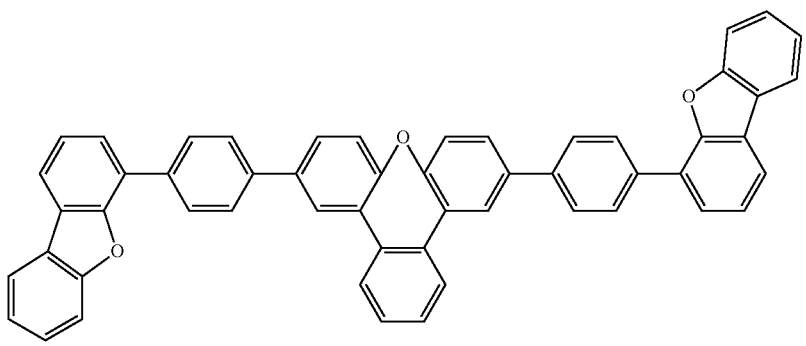
Formula (A-204)
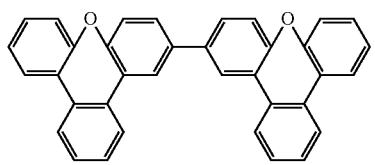
Formula (A-205)
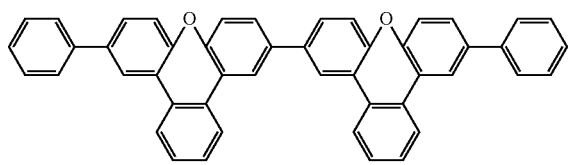
Formula (A-206)
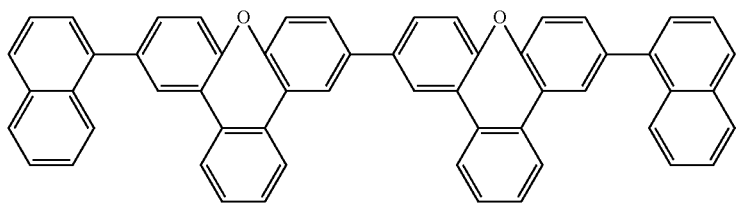
Formula (A-207)
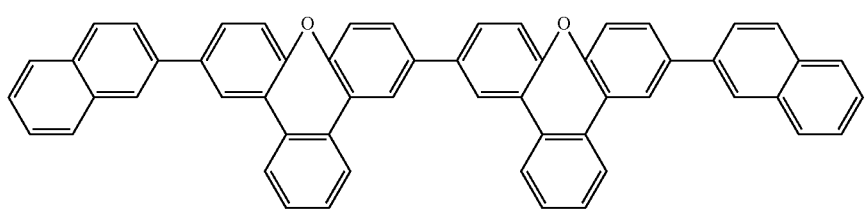

-continued
Formula (A-208)
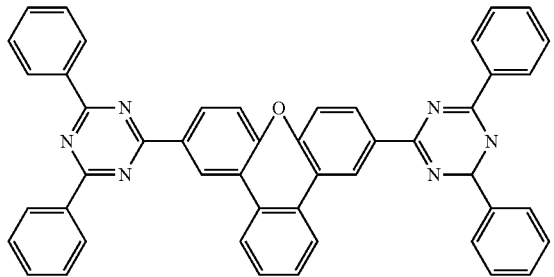
Formula (A-209)
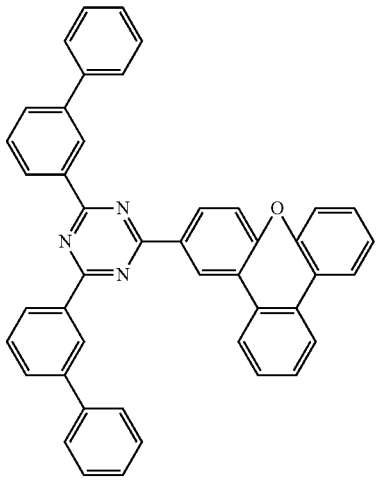
Formula (A-210)
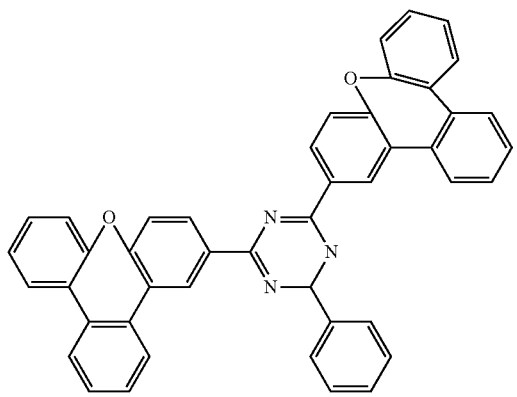
Formula (A-211)
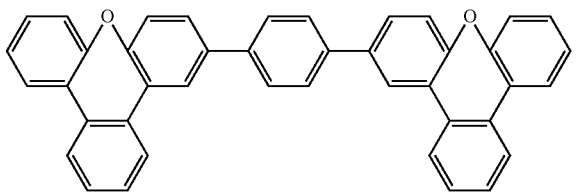
Formula (A-212)
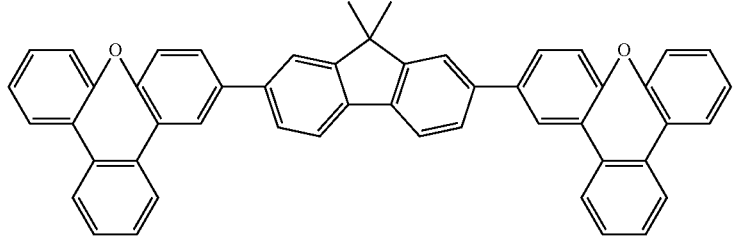
Formula (A-213)
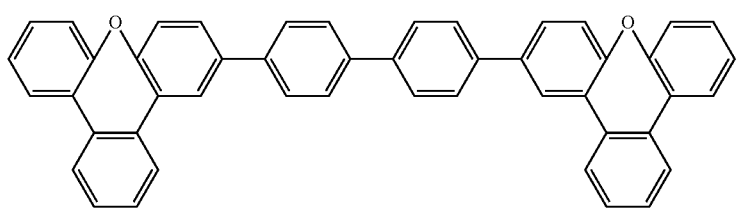
Formula (A-214)
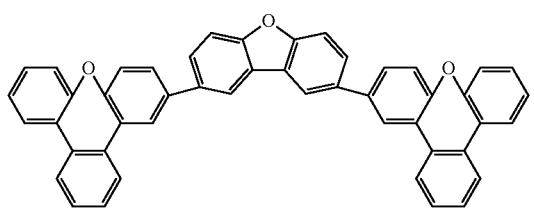
Formula (A-215)
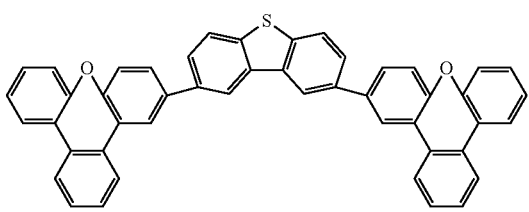

-continued
Formula (A-216)
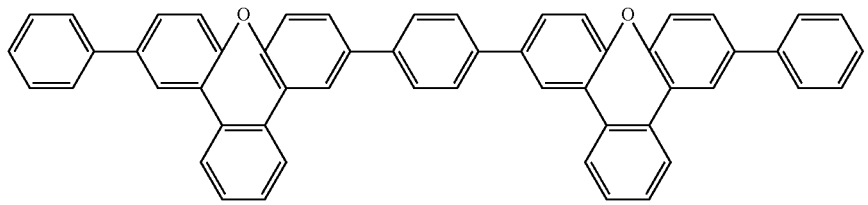
Formula (A-217)
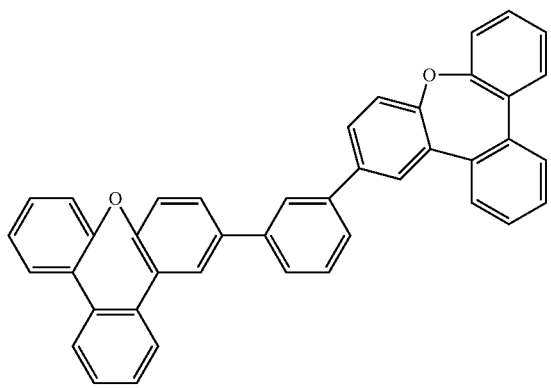
Formula (A-218)
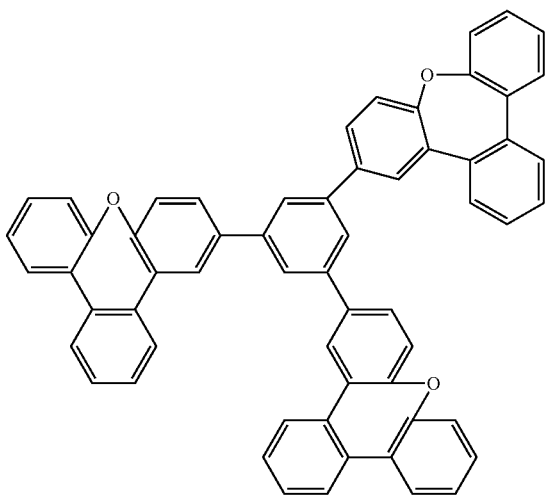
Formula (A-219)
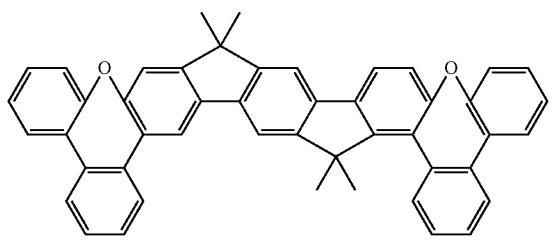
Formula (A-220)
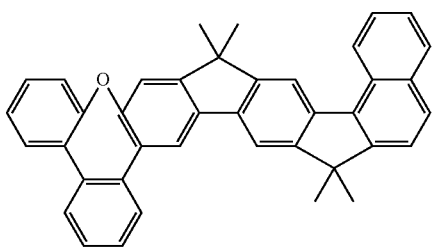
Formula (A-221)
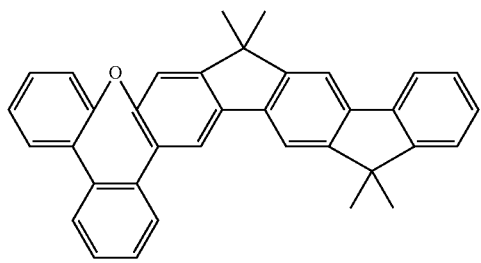
Formula (A-222)
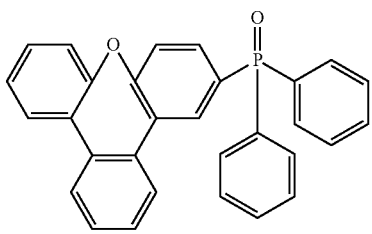
Formula (A-223)
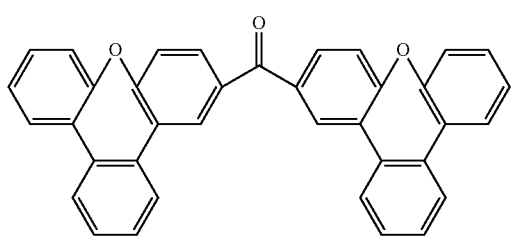

-continued
Formula (A-224)
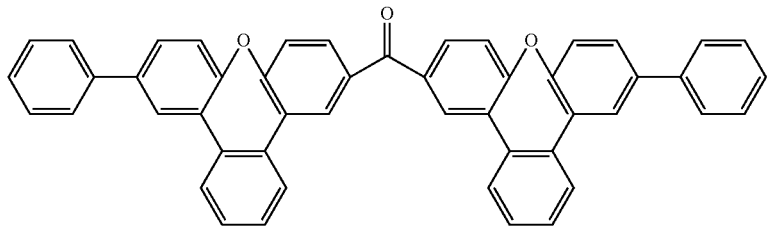
Formula (A-225)
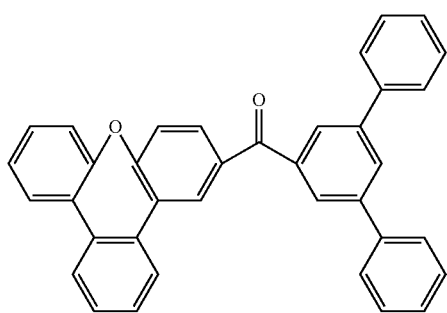
Formula (A-226)
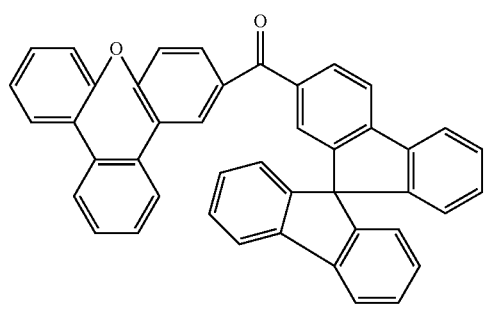
Formula (A-227)
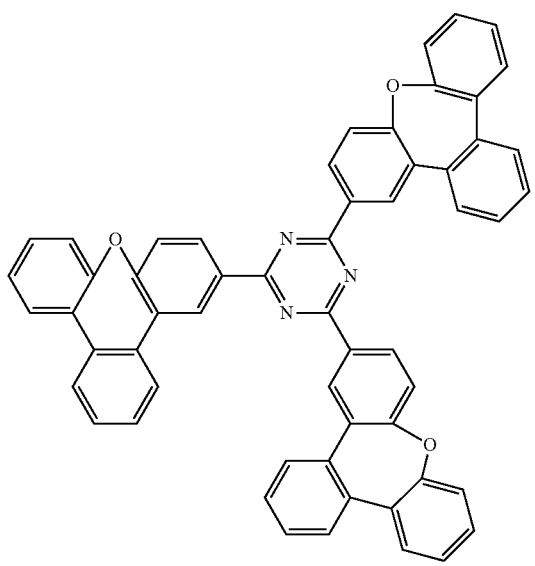
Formula (A-228)
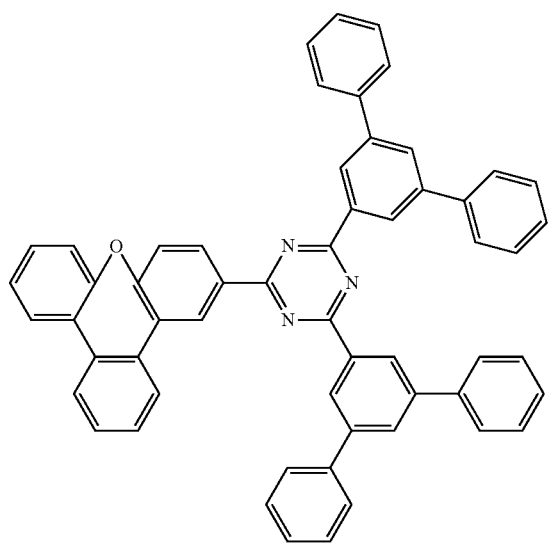
Formula (A-229)
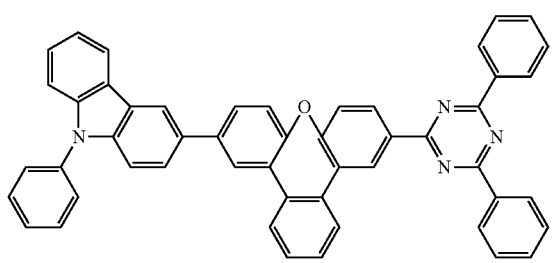
Formula (A-230)
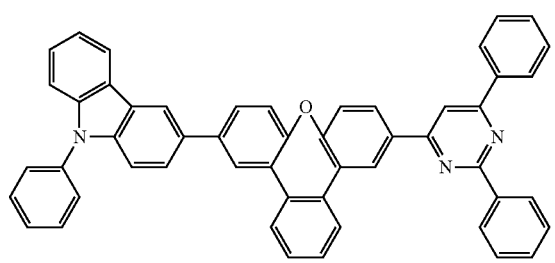

-continued
Formula (A-231)
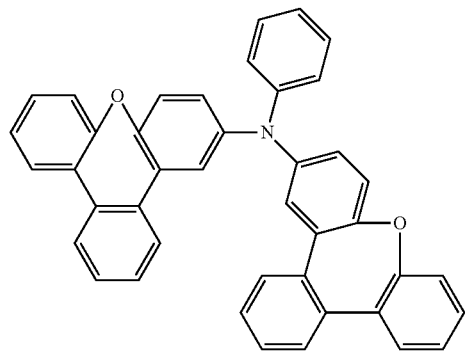
Formula (A-232)
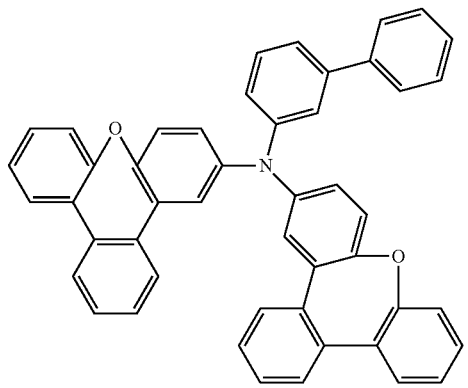
Formula (A-233)
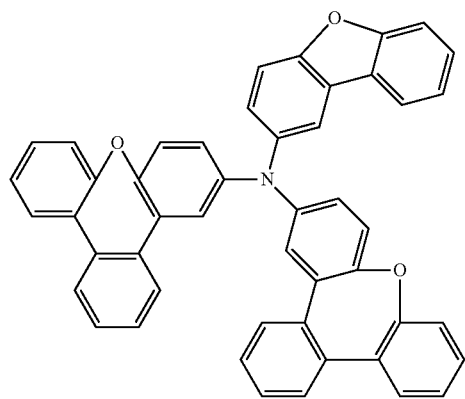
Formula (A-234)
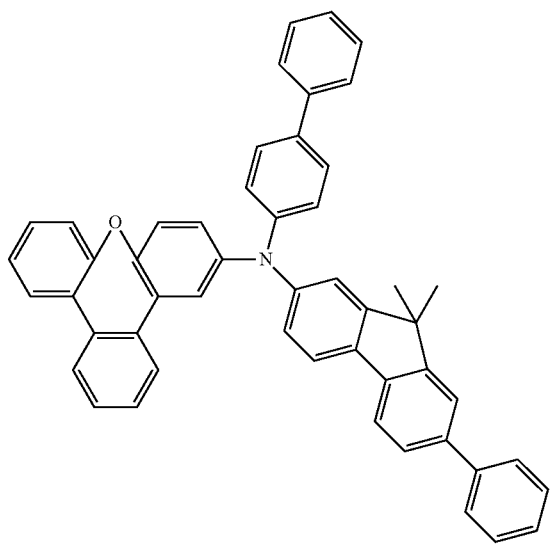
Formula (A-235)
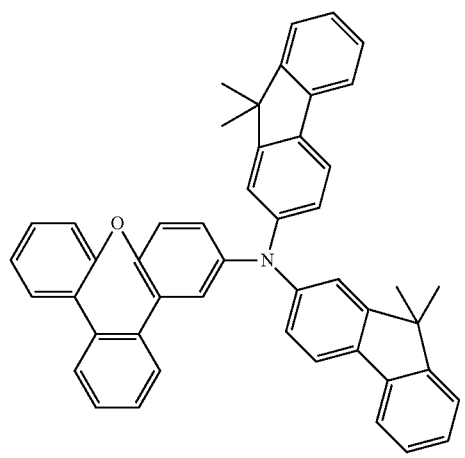
Formula (A-236)
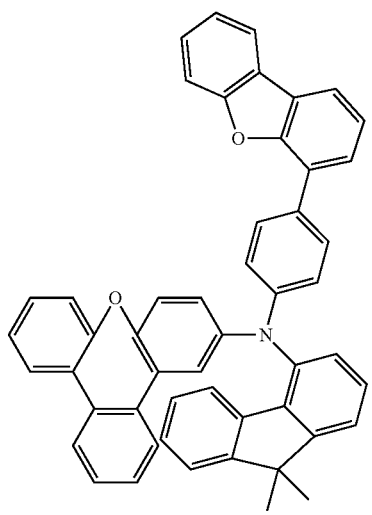

-continued
Formula (A-237)
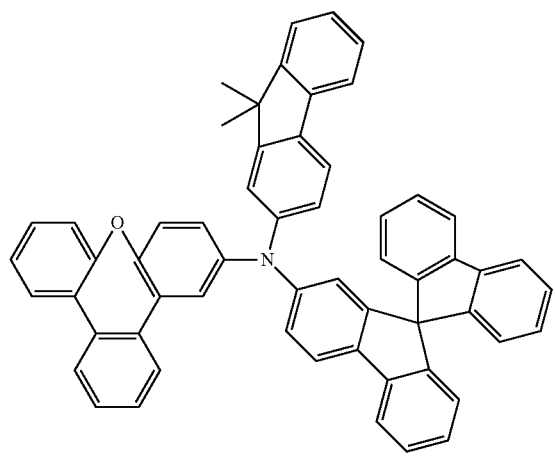
Formula (A-238)
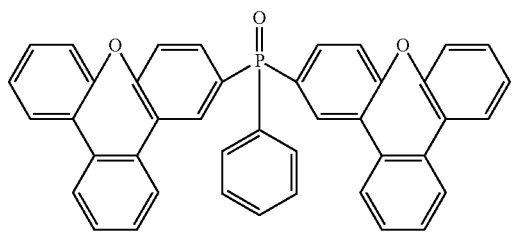
Formula (A-239)
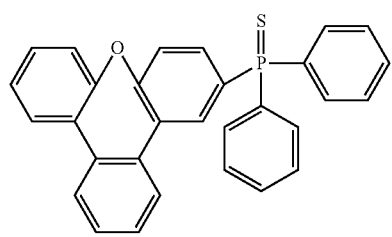
Formula (A-240)
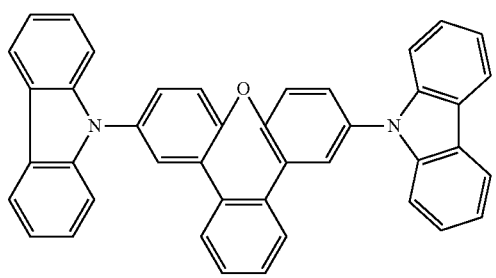
Formula (A-241)
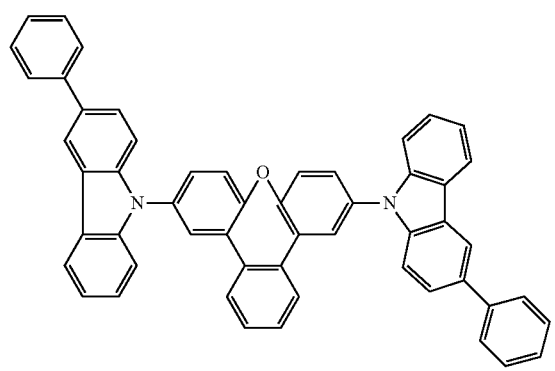
Formula (A-242)
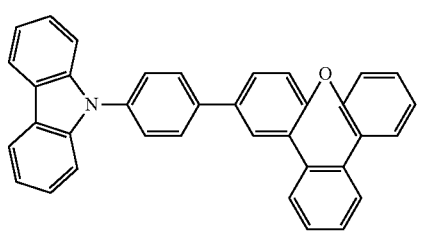
Formula (A-243)
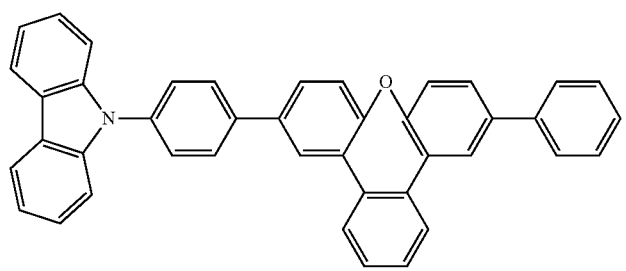

-continued
Formula (A-244)
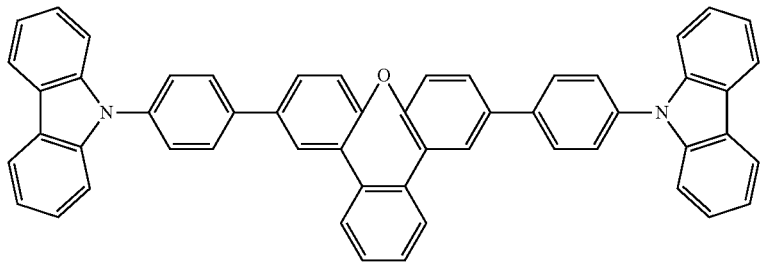
Formula (A-245)
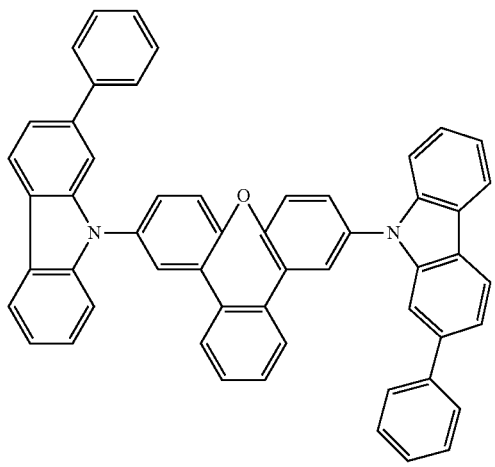
Formula (A-246)
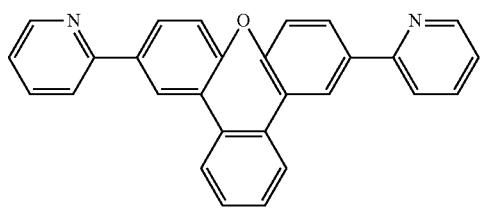
Formula (A-247)
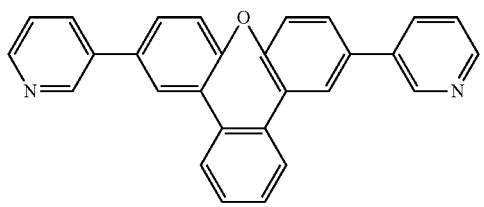
Formula (A-248)
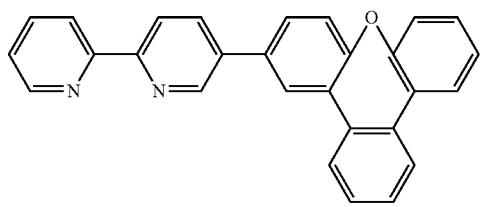
Formula (A-249)
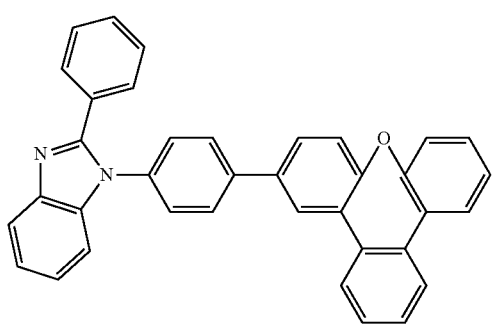
Formula (A-250)
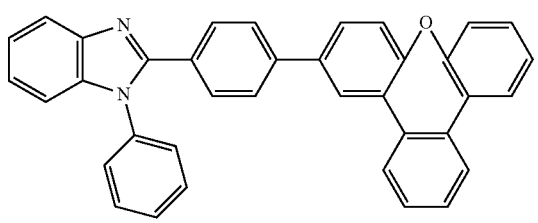
Formula (A-251)
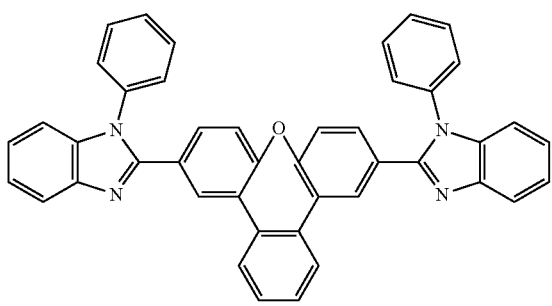
Formula (A-252)
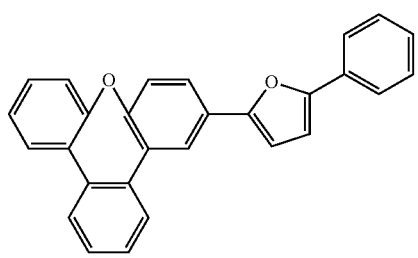

-continued
Formula (A-253)
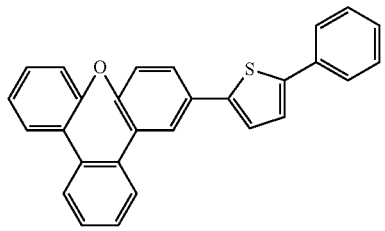
Formula (A-254)
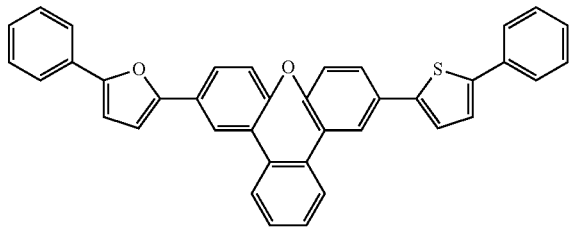
Formula (A-255)
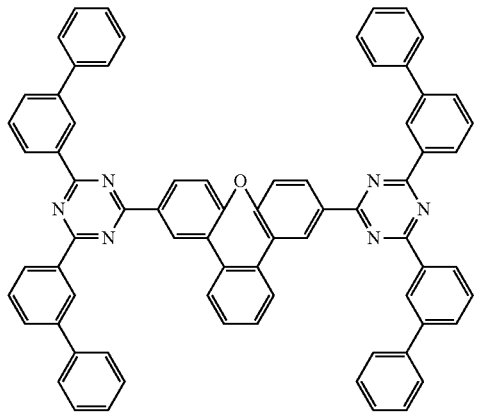
Formula (A-256)
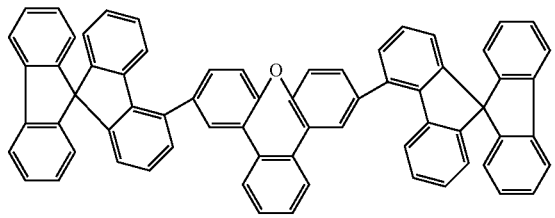
Formula (A-257)
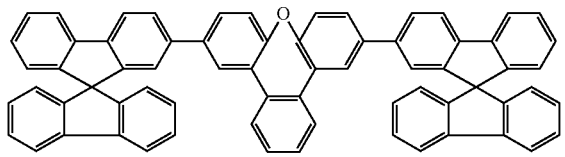
Formula (A-258)
Formula (A-259)
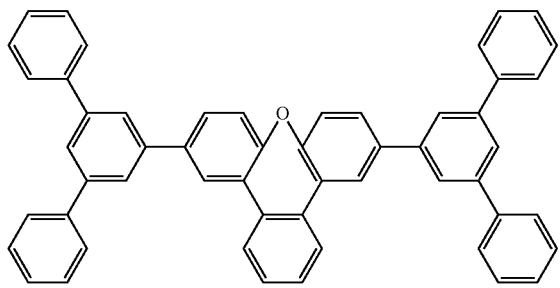
Formula (A-260)
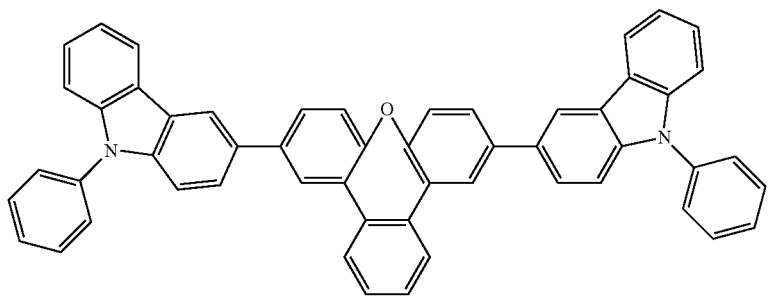

-continued
Formula (A-261)
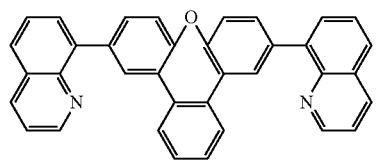
Formula (A-262)
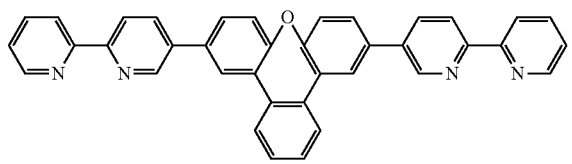
Formula (A-263)
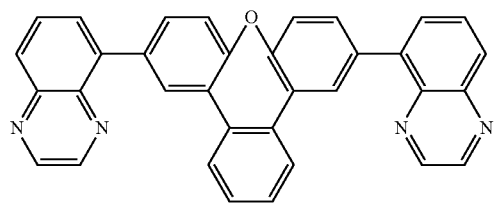
Formula (A-264)
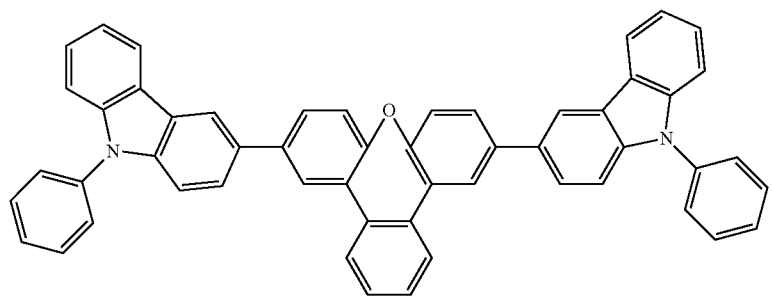
Formula (A-265)
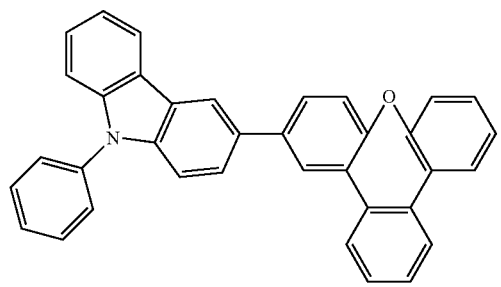
Formula (A-266)
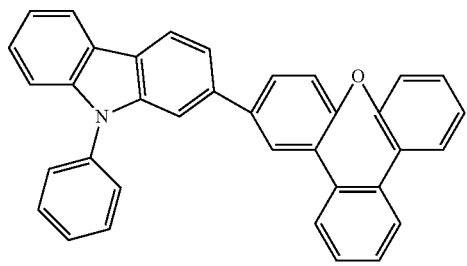
Formula (A-267)
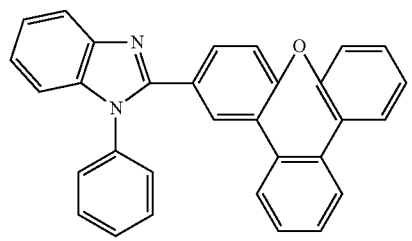
Formula (A-268)
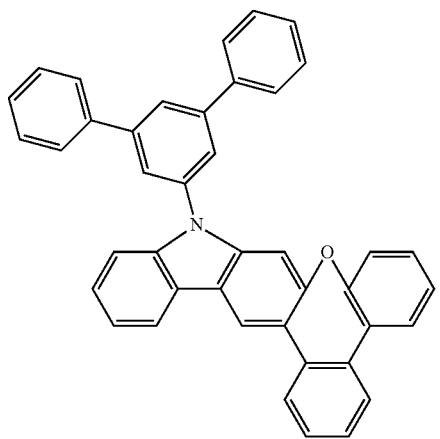

-continued
Formula (A-269)
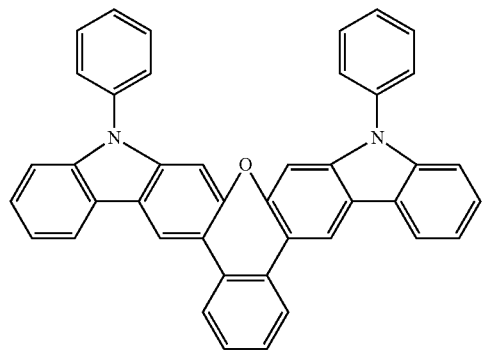
Formula (A-270)
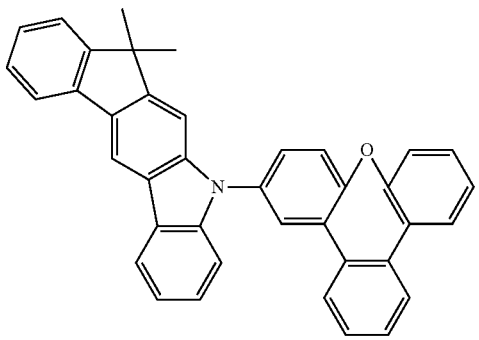
Formula (A-271)
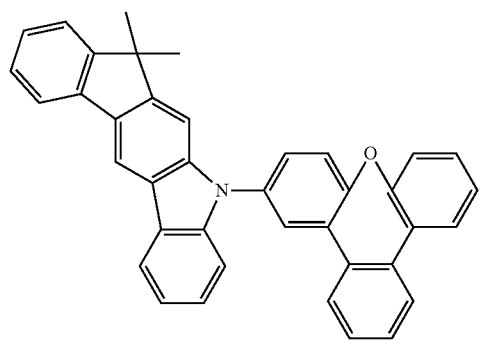
Formula (A-272)
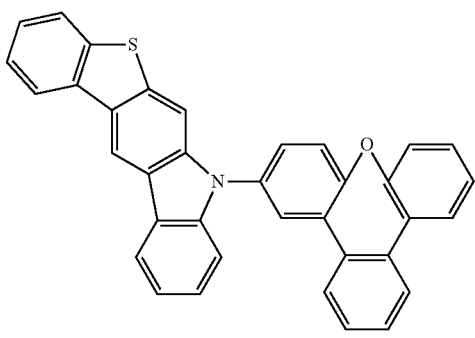
Formula (A-273)
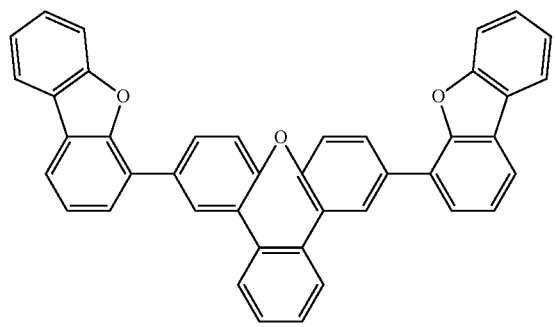
Formula (A-274)
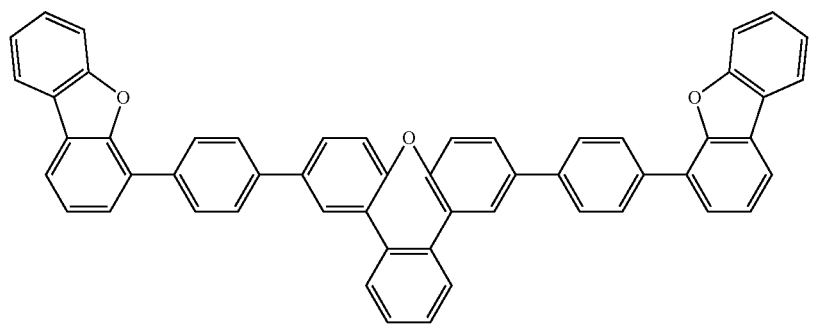

Formula (A-275)
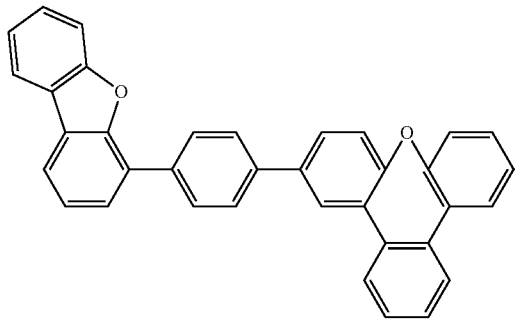
Formula (A-276)
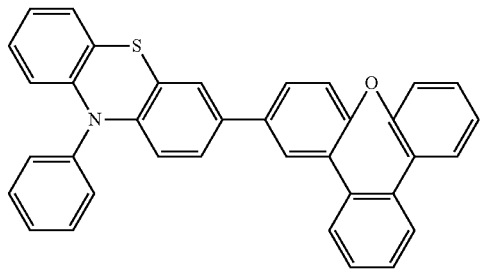
Formula (A-277)
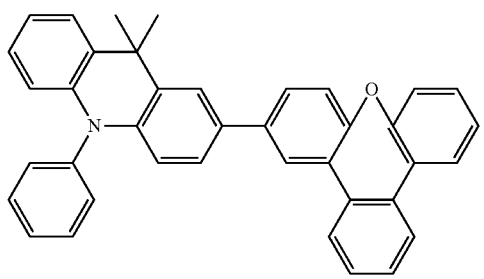
Formula (A-278)
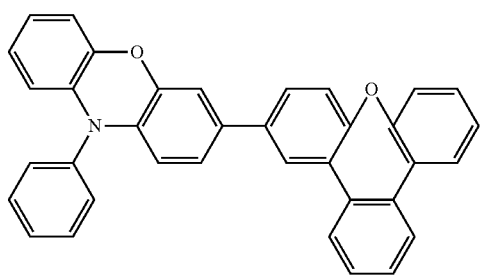
Formula (A-279)
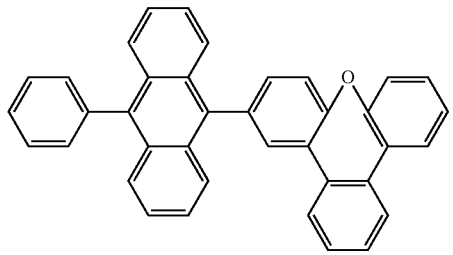
Formula (A-280)
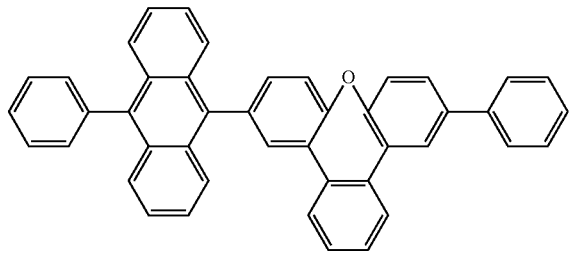
Formula (A-281)
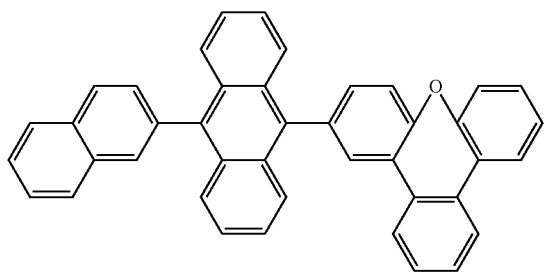
Formula (A-282)
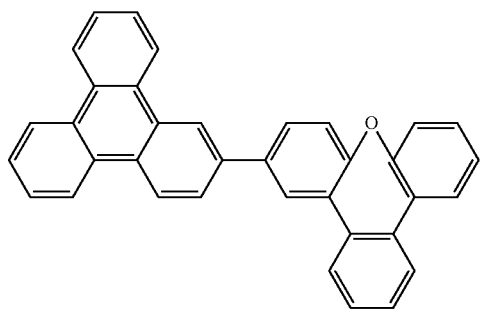
Formula (A-283)
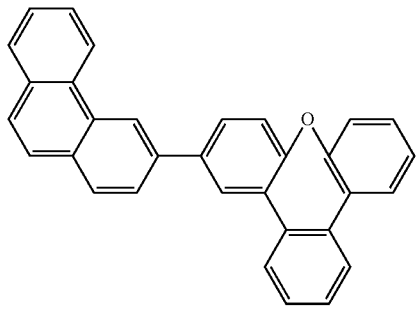
Formula (A-284)
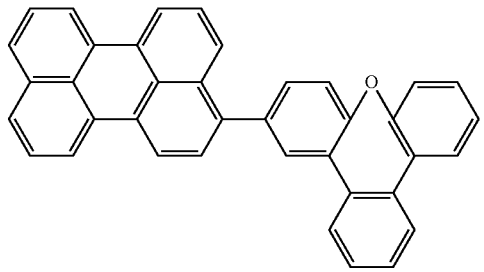

-continued
Formula (A-285)
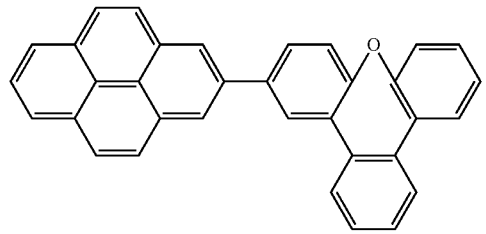
Formula (A-286)
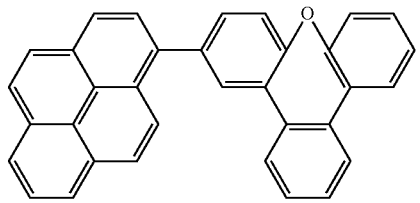
Formula (A-287)
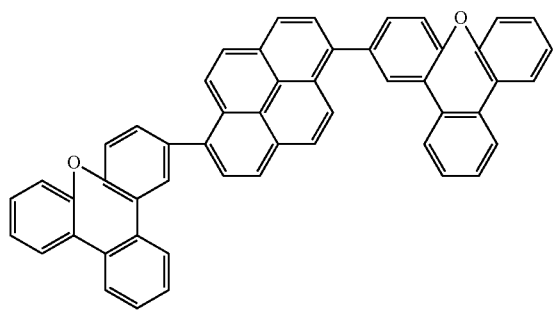
Formula (A-288)
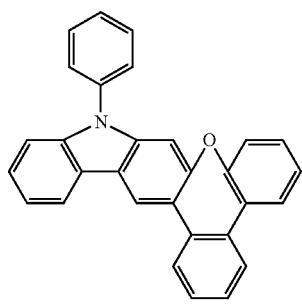
Formula (A-289)
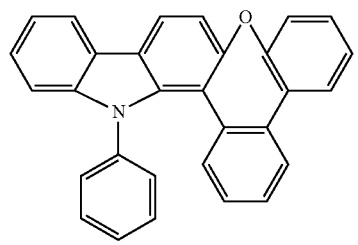
Formula (A-290)
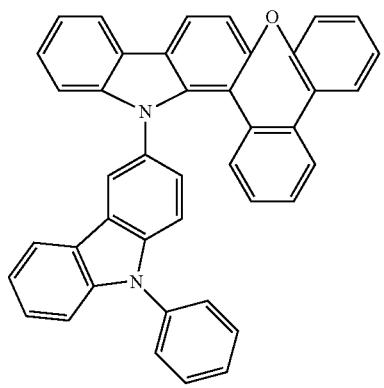
Formula (A-291)
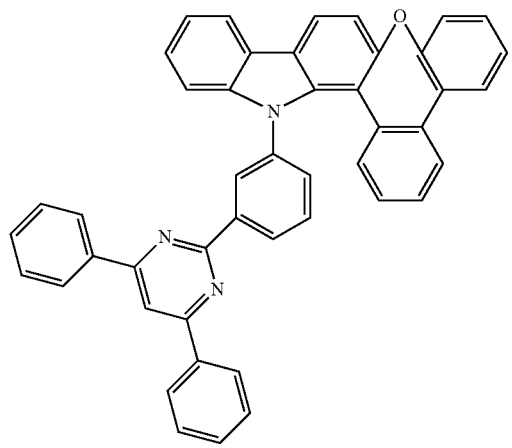
Formula (A-292)
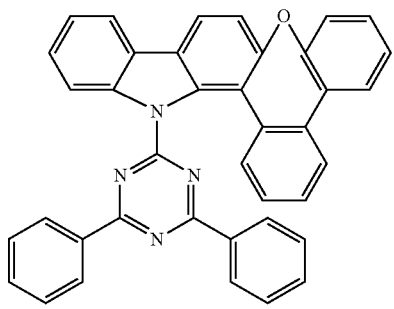

-continued

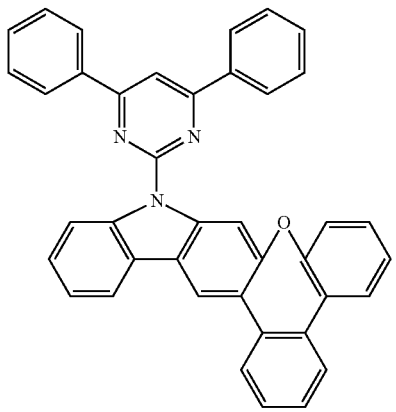

Formula (A-293)

The invention further provides for the use of a compound of the formula (1) in an organic electronic device, preferably in a charge-transporting layer and/or in an emitting layer.

The present invention therefore also relates to an organic electronic device comprising at least one compound of the general formula (1).

The electronic device of the invention is preferably selected from organic integrated circuits (OICs), organic field-effect transistors (OFETs), organic thin-film transistors (OTFTs), organic solar cells (OSCs), organic optical detectors, organic photoreceptors, organic field-quench devices (OFQDs), organic electroluminescent devices, the organic electroluminescent devices being very preferred.

The organic electroluminescent devices especially include the following, which are preferred herein: organic light-emitting transistors (OLETs), the organic light-emitting electrochemical cells (OLECs, LECs or LEECs), the organic laser diodes (O-lasers), the polymeric light-emitting diodes (PLEDs) and the organic light-emitting diodes (OLEDs), the OLECs, PLEDs and OLEDs being very preferred in the context of the present invention, the PLEDs and OLEDs being especially preferred and the OLEDs being very especially preferred.

The organic layer comprising the compound of the formula (1) is preferably a layer having a charge-transporting function. It is more preferably an electron injection layer, electron transport layer, a hole blocker and hole transport layer or an emitting layer.

A compound of the formula (1) can be used as emitter in an emission layer. The present invention therefore relates to an organic electronic device, preferably an organic electroluminescent device, comprising at least one compound of the general formula (1) in the emission layer as fluorescent emitter. The emission layer may comprise further materials. These are typically matrix or host materials or mixtures of host materials.

When the compound of the general formula (1) is used as emitter in an emitting layer, especially in a fluorescent layer, of an organic electroluminescent device, the proportion thereof in the overall layer is preferably between 0.1% and 50% by volume, very preferably between 0.5% and 20% by volume and especially preferably between 1.0% and 10% by volume. Correspondingly, the proportion of the matrix or the host is preferably between 50% and 99.9% by volume, very preferably between 80% and 99.5% by volume and especially preferably between 90% and 99% by volume.

In addition, the present invention also relates to an organic electroluminescent device comprising at least one compound of the formula (1) as matrix in an emission layer and at least one fluorescent emitter, also called fluorescent dopant.

When the compound of the general formula (1) is used as matrix or host in an emitting layer, especially in a fluorescent layer, of an organic electroluminescent device, the proportion thereof in the overall layer is preferably between 50% and 99.9% by volume, very preferably between 80% and 99.5% by volume and especially preferably between 90% and 99% by volume. Correspondingly, the proportion of the emitter (dopant) is preferably between 0.01% and 50% by volume, very preferably between 0.1% and 20% by volume, especially preferably between 0.5% and 15% by volume and very especially preferably between 1% and 10% by volume and In addition, the present invention also relates to an electronic device, especially an organic electroluminescent device, comprising at least one compound of the formula (1) in an electron transport layer (ETL).

The ETL may comprise further materials. Particular options here include further ETMs and n-dopants. n-Dopants are understood herein to mean reducing agents, i.e. electron donors. Preferred examples of n-dopants are W(hpp)$_4$ and further electron-rich metal complexes according to WO 2005/086251 A2, P=N compounds (e.g. WO 2012/175535 A1, WO 2012/175219 A1), naphthylenecarbodiimides (e.g. WO 2012/168358 A1), fluorenes (e.g. WO 2012/031735 A1), radicals and diradicals (e.g. EP 1837926 A1, WO 2007/107306 A1), pyridines (e.g. EP 2452946 A1, EP 2463927 A1), N-heterocyclic compounds (e.g. WO 2009/000237 A1) and acridines and phenazines (e.g. US 2007/145355 A1).

The present invention therefore also relates to an electronic device, especially an organic electroluminescent device, comprising at least one compound of the formula (1) in an electron transport layer (ETL) and at least one further compound preferably selected from the electron transport materials and n-dopants.

In addition, the present invention also relates to an electronic device, especially an organic electroluminescent device, comprising at least one compound of the formula (1) in a hole transport layer (HTL).

The HTL may comprise further materials. Particular options here include further HTMs and p-dopants.

p-Dopants are understood herein to mean oxidizing agents, i.e. electron acceptors. Preferred examples of p-dopants are $F_4$-TCNQ, $F_6$-TNAP, NDP-2 (from Novaled), NDP-9 (from Novaled), quinones (e.g. EP 1538684 A1, WO 2006/081780 A1, WO 2009/003455 A1, WO 2010/097433 A1), radialenes (e.g. EP 1988587 A1, US 2010/102709 A1, EP 2180029 A1, WO 2011/131185 A1, WO 2011134458 A1, US 2012/223296 A1), S-containing transition metal complexes (e.g. WO 2007/134873 A1, WO 2008/061517 A2, WO 2008/061518 A2, DE 102008051737 A1, WO 2009/089821 A1, US 2010/096600 A1), bisimidazoles (e.g. WO 2008/138580 A1), phthalocyanines (e.g. WO 2008/058525 A2), bora-tetraazapentalenes (e.g. WO 2007/115540 A1), fullerenes (e.g. DE 102010046040 A1) and main group halides (e.g. WO 2008/128519 A2).

A hole transport layer according to the present application is a layer having a hole-transporting function between the anode and emitting layer.

An electron transport layer according to the present application is a layer having an electron-transporting function between the cathode and emitting layer.

Hole injection layers and electron blacker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blacker layer, in the case of a plurality of hole transport layers between the anode and emitting layer, is that hole transport layer which directly adjoins the emitting layer on the anode side.

As already mentioned above, the compound of the formula (1), in a preferred embodiment, is used as matrix material in an emission layer of an organic electronic device, especially in an organic electroluminescent device, for example in an OLED, PLED or OLEC. In this case, the matrix material of the formula (1) is present in the electronic device in combination with one or more fluorescent or phosphorescent dopants.

It is particularly preferable when the compound of the formula (1) is a hole-transporting matrix and is used in combination with another matrix material as a mixed matrix for phosphorescent emitters in the emission layer. Hole-transporting compounds of the formula (1) have high $T_1$ energy levels that are particularly advantageous for the purpose.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

In addition, the present invention also relates to an organic electroluminescent device comprising at least one compound of the formula (1) as matrix in an emission layer and at least one further matrix or host material.

In addition, the present invention also relates to an organic electroluminescent device comprising at least one compound of the formula (1) as matrix in an emission layer, and also at least one fluorescent emitter and at least one further matrix or host material.

As already stated, an emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compounds of formula (1) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

Particularly suitable matrix materials which can be used in combination with the inventive compounds as matrix components of a mixed matrix system are selected from the preferred matrix materials specified below for phosphorescent dopants or the preferred matrix materials for fluorescent dopants, according to what type of dopant is used in the mixed matrix system.

The present invention further relates to a composition comprising at least one compound of formula (1) and at least one further organic semiconductor material selected from the group consisting of fluorescent emitters, phosphorescent emitters, host materials, matrix materials, electron transport materials, electron injection materials, hole conductor materials, hole injection materials, electron blocker materials and hole blocker materials, the n-dopants and the p-dopants.

n-Dopants are understood here to mean, as already defined above, reducing agents. Preferred n-dopants are the compounds listed further up.

p-Dopants are understood here to mean, as already defined above, oxidizing agents. Preferred p-dopants are the compounds listed further up.

The present invention also relates to a composition comprising at least one compound of formula (1) and at least one further matrix material.

The present invention also relates to a composition comprising at least one compound of formula (1) and at least one wide band gap material, a wide band gap material being understood to mean a material in the sense of the disclosure of U.S. Pat. No. 7,294,849. These systems exhibit particularly advantageous performance data in electroluminescent devices.

The present invention also relates to a composition comprising at least one compound of formula (1) and at least one further matrix material, and also at least one phosphorescent emitter.

The present invention also relates to a composition comprising at least one compound of formula (1) and at least one wide band gap material, and also at least one phosphorescent emitter.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices.

Explicit examples of phosphorescent dopants are adduced in the following table:

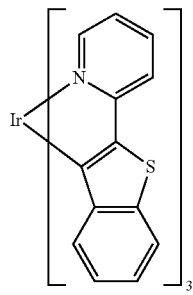
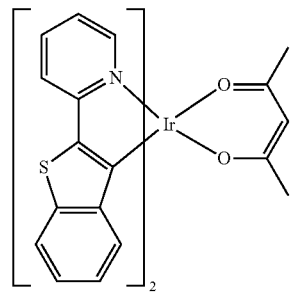
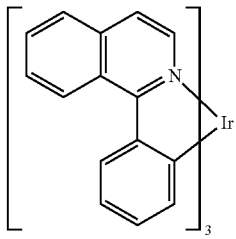
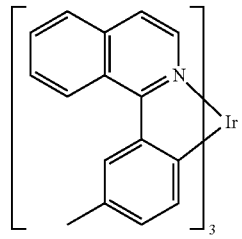
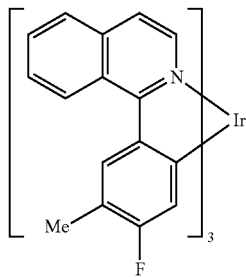
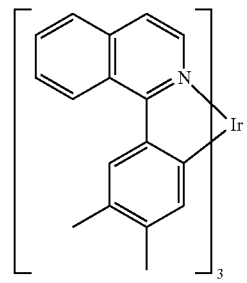
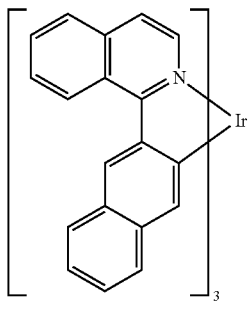
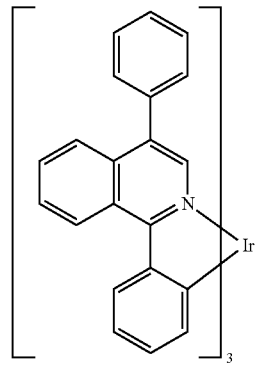

-continued
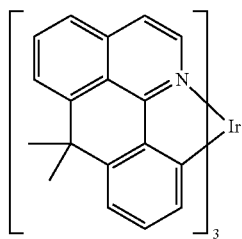 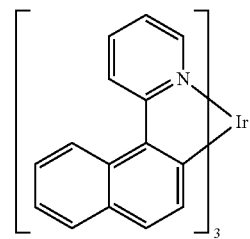
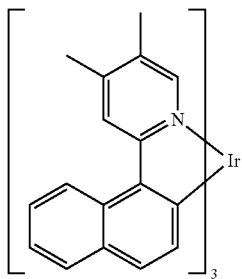 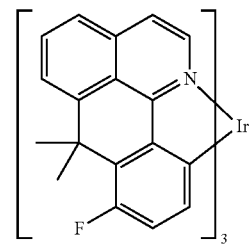
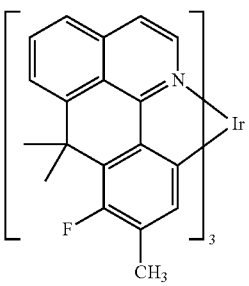 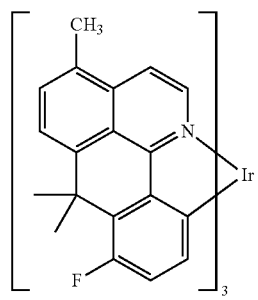
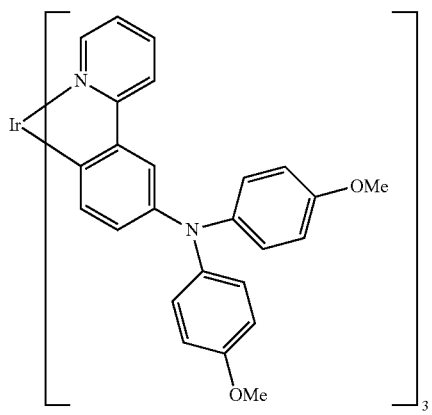 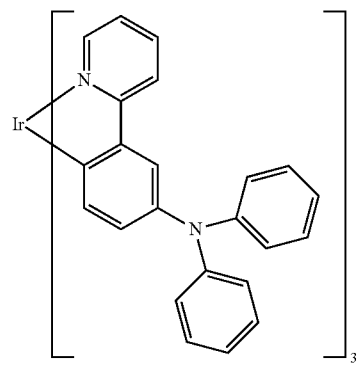
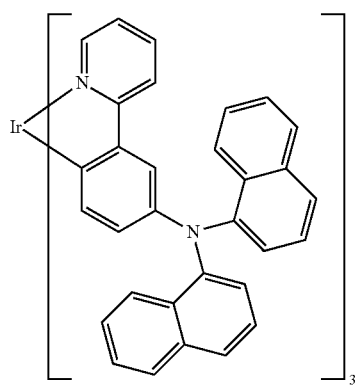 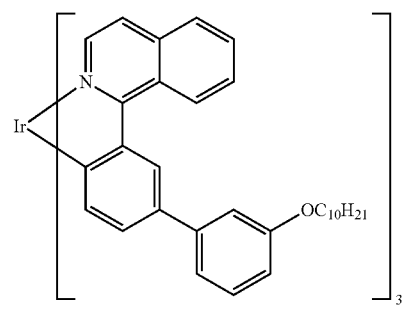

-continued
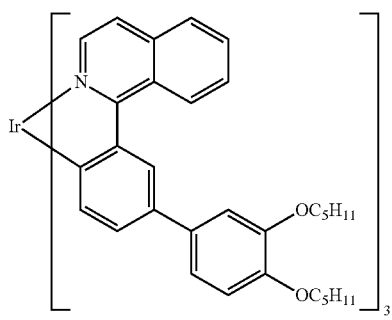
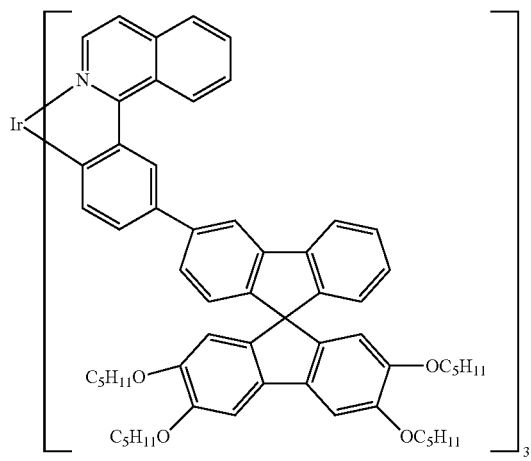
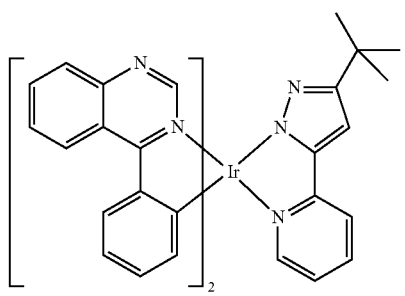
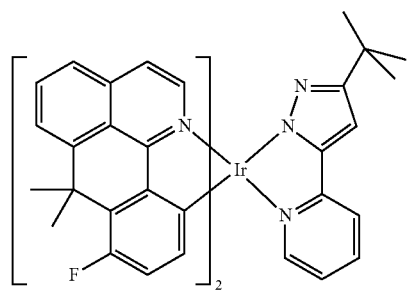
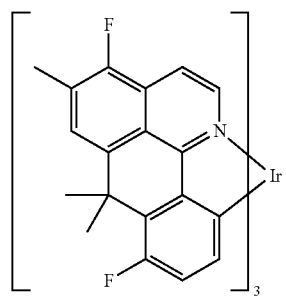
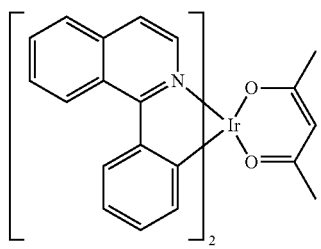
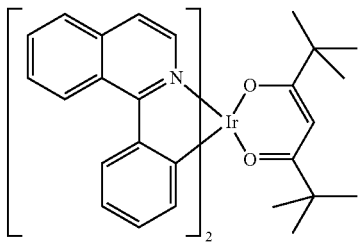
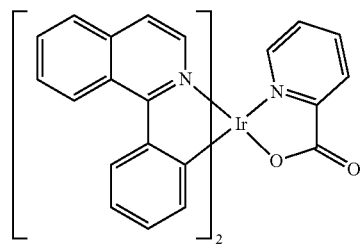
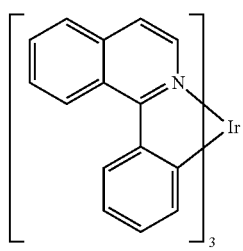
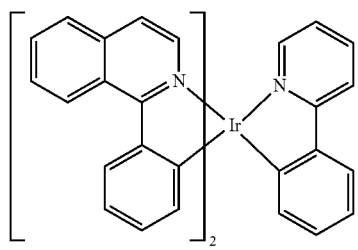

-continued
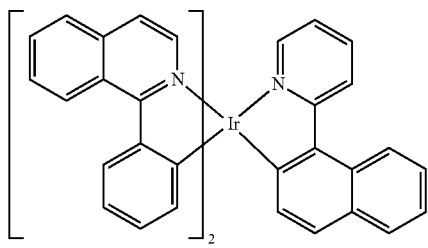
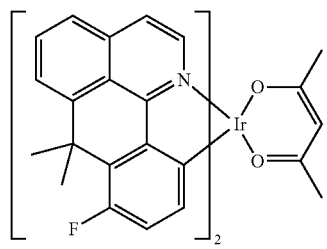
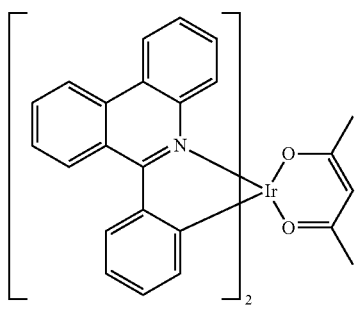
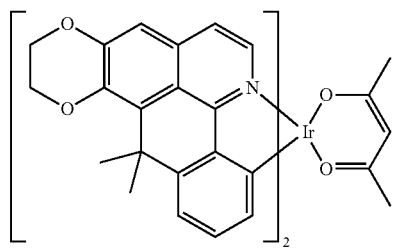
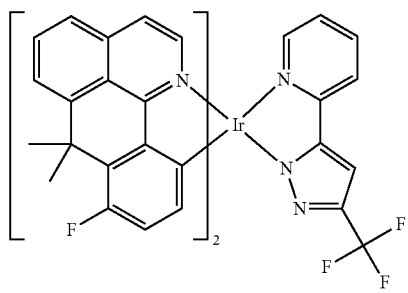
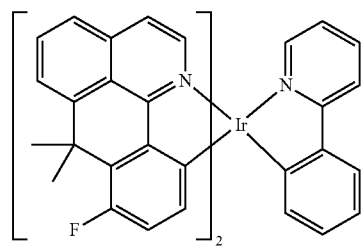
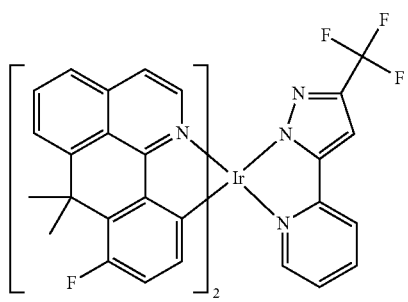
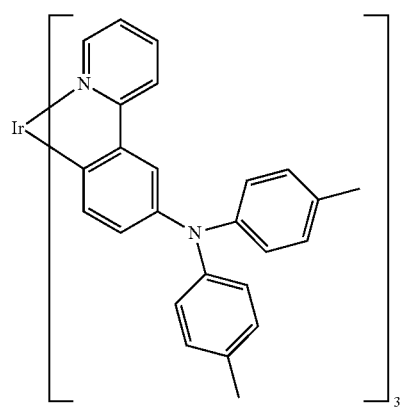
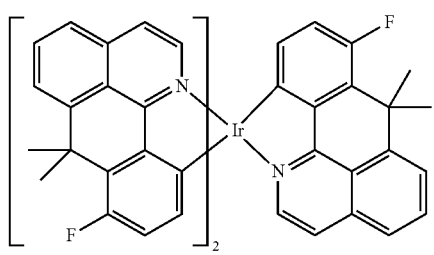
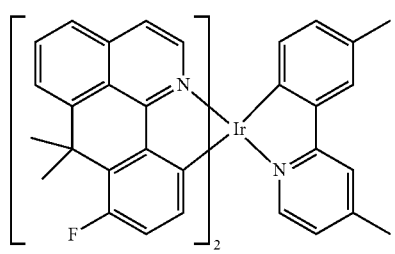

-continued
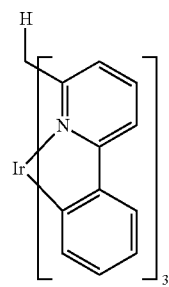 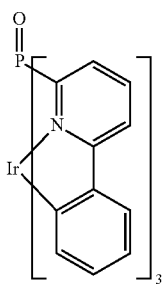
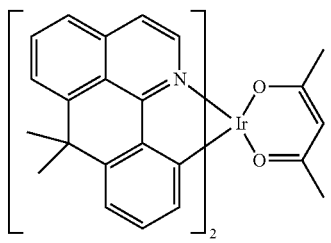 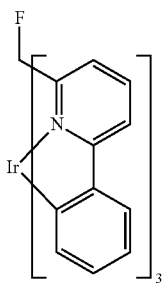
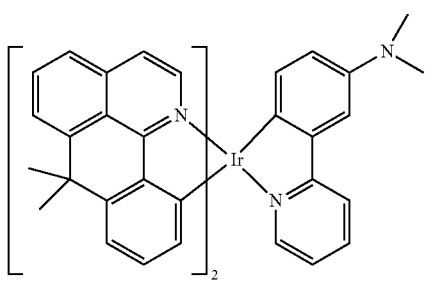 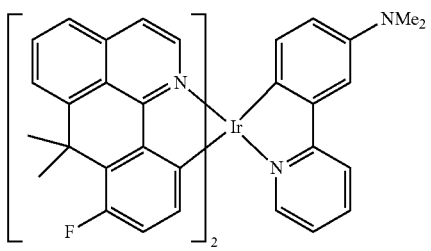
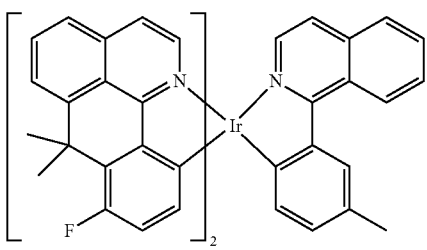 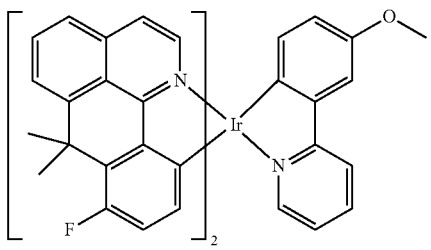
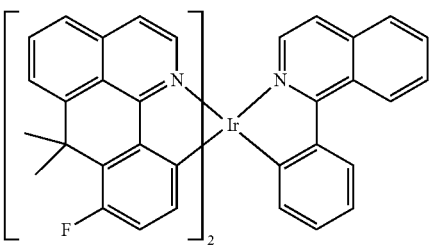 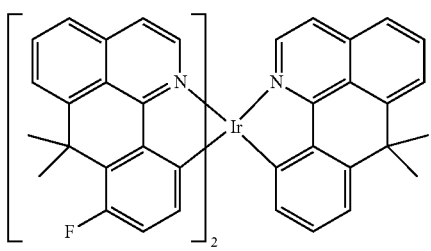

-continued
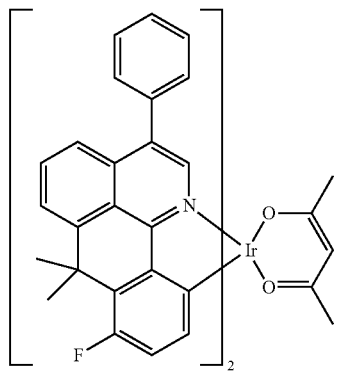
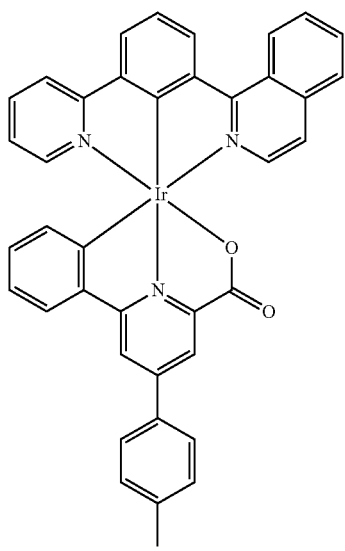
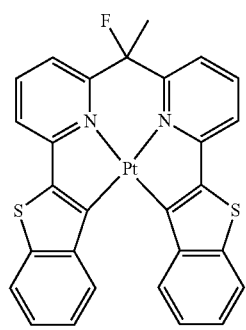
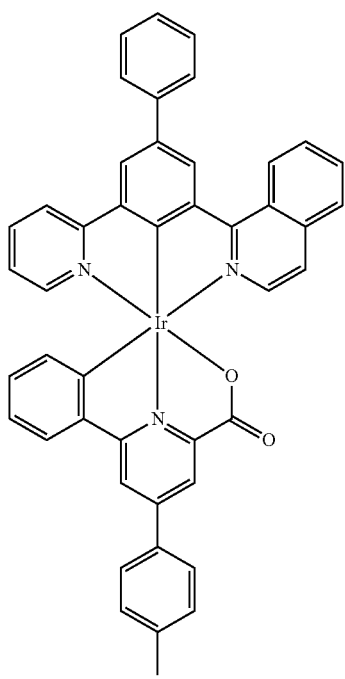
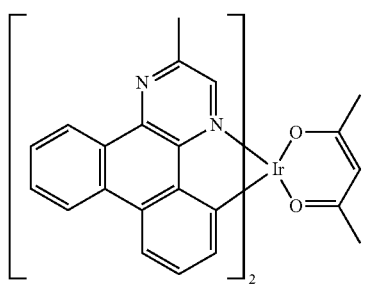
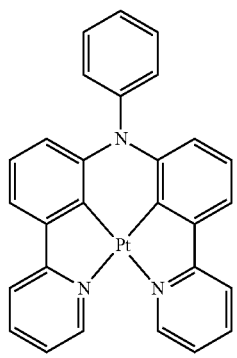

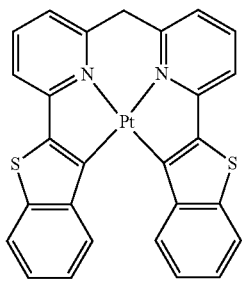
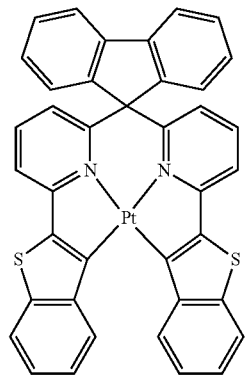
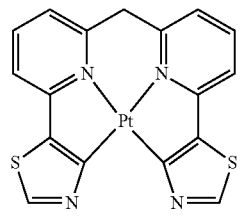
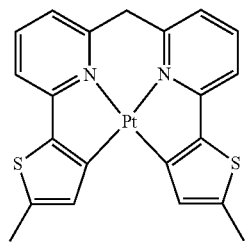
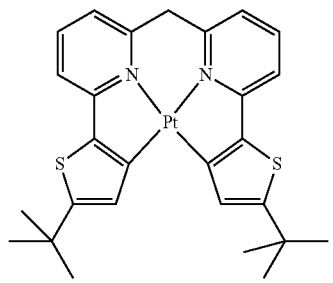
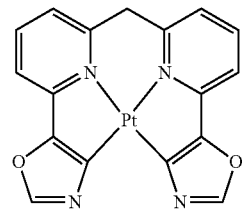
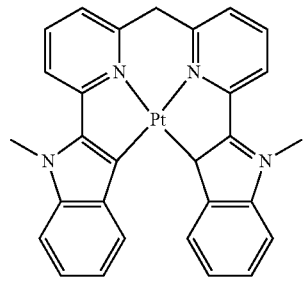
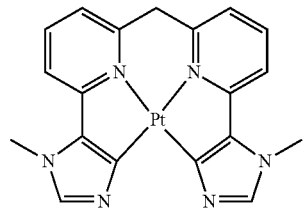
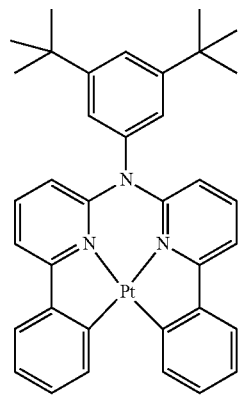
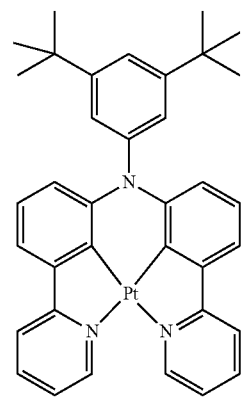

-continued
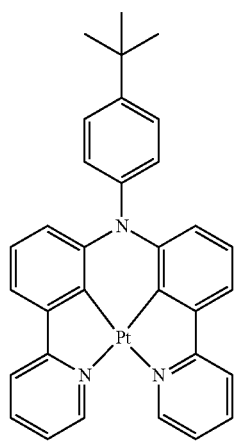
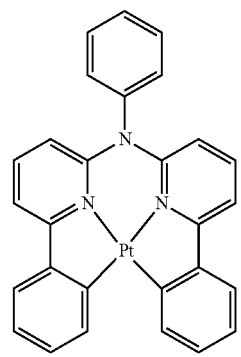
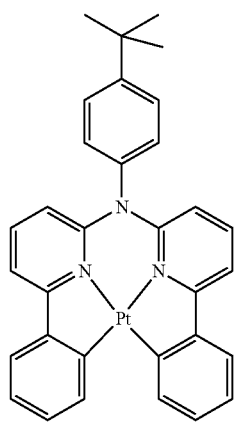
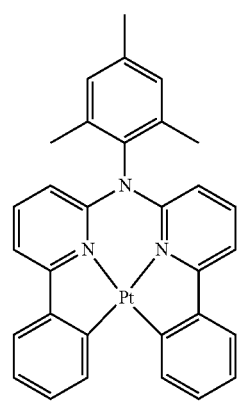
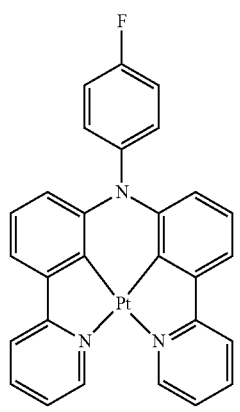
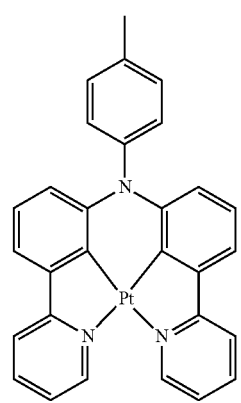

-continued
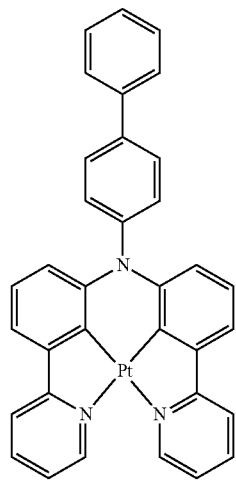
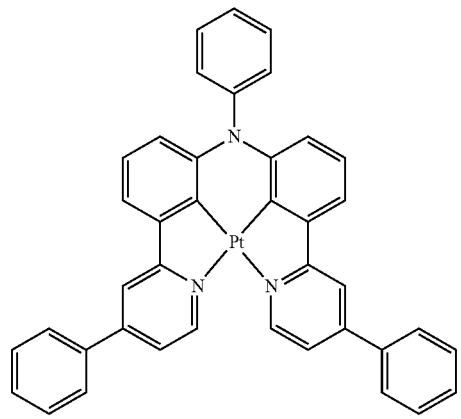
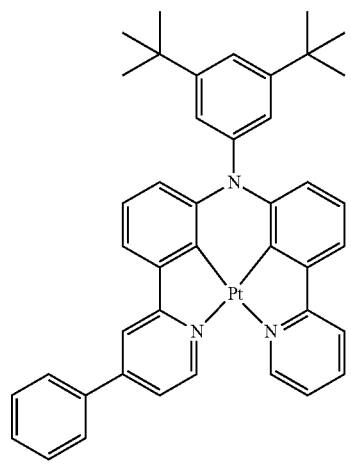
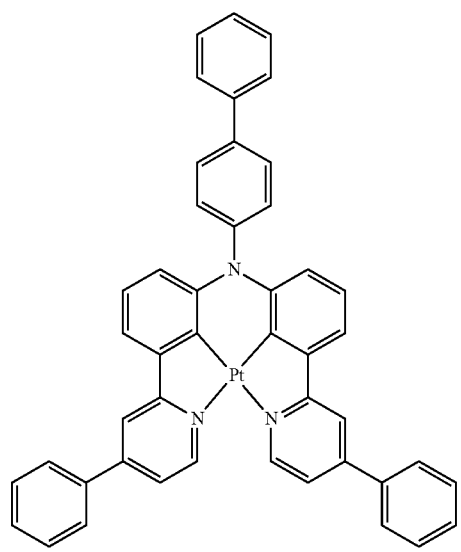
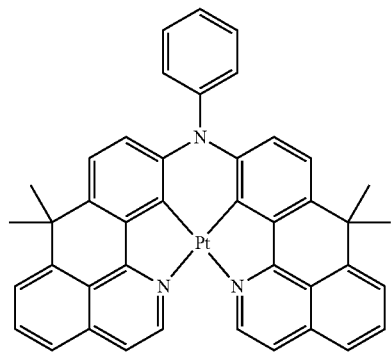
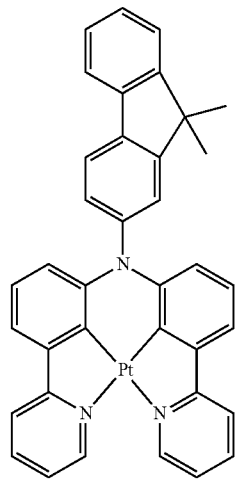

-continued
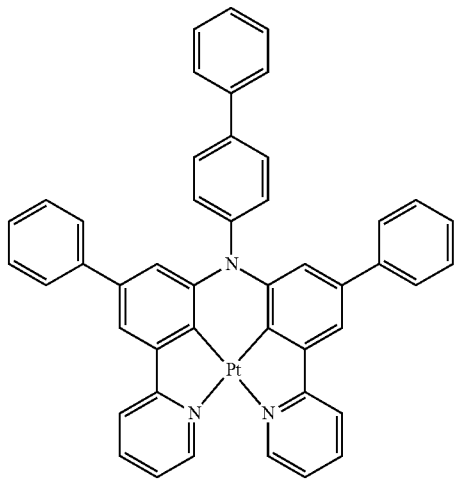
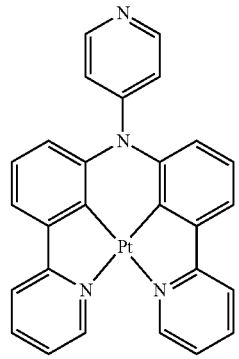
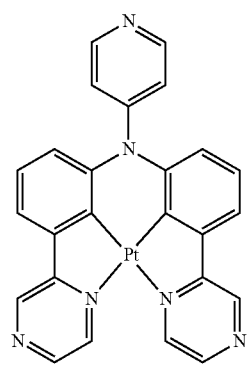
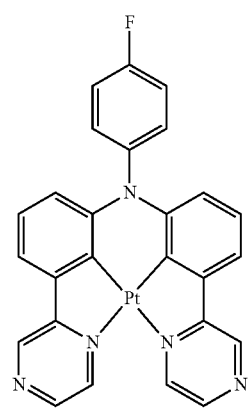
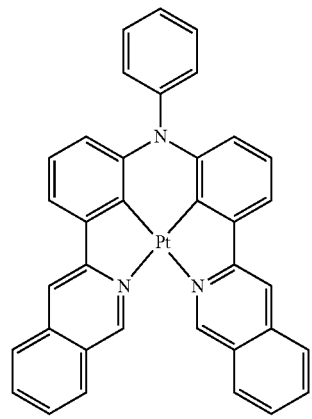
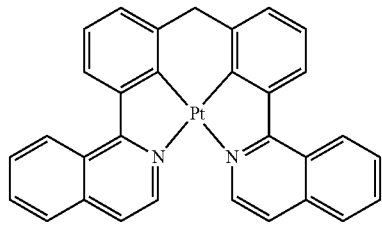
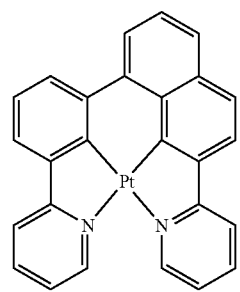
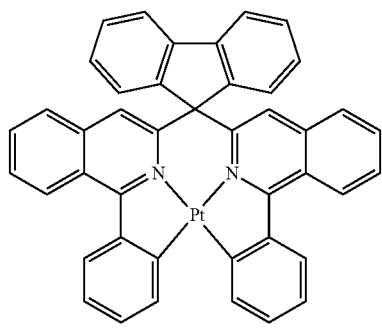

-continued
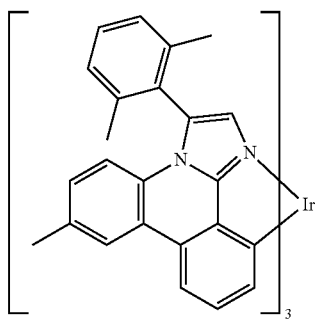
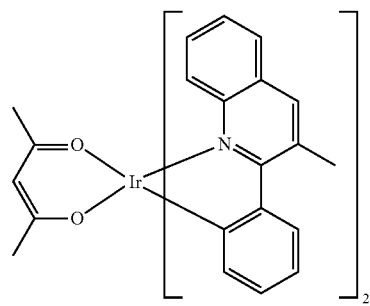
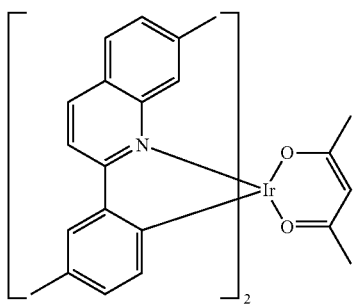
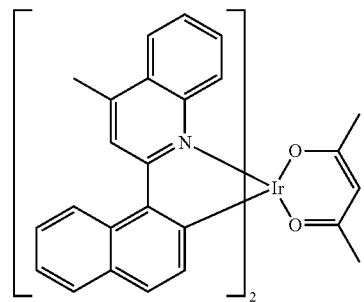
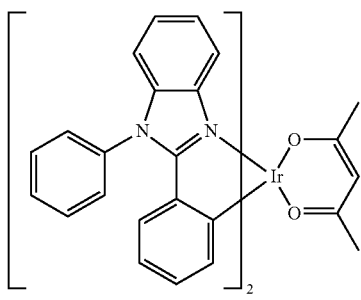
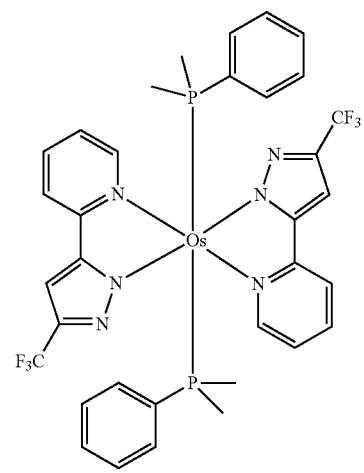
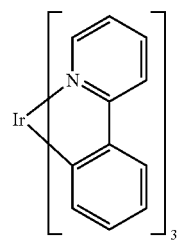
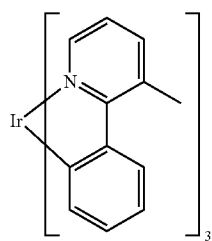
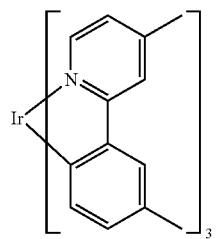

-continued
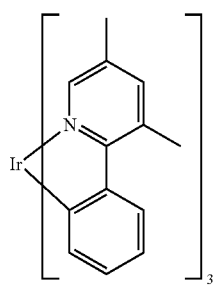
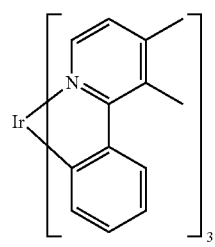
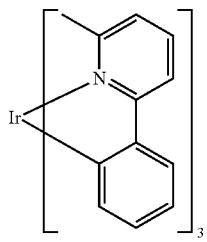
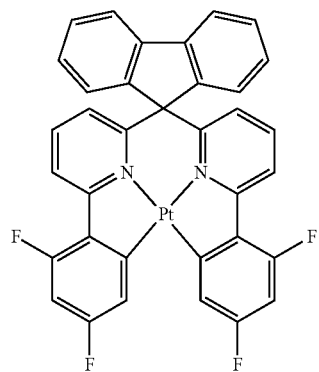
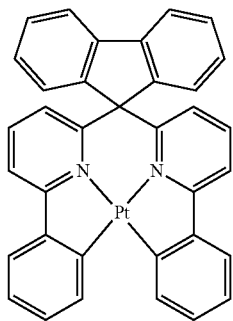
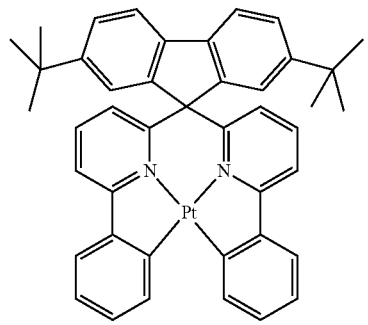
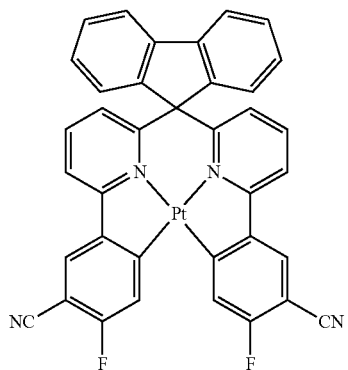
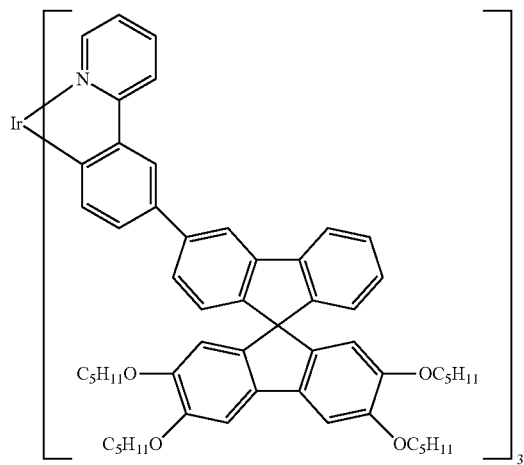

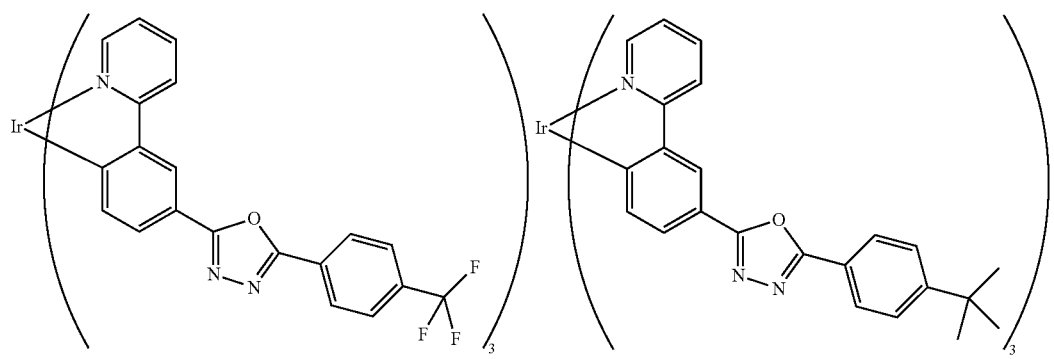
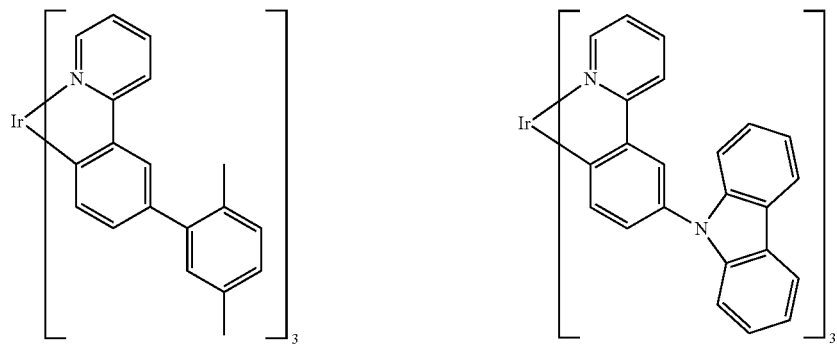
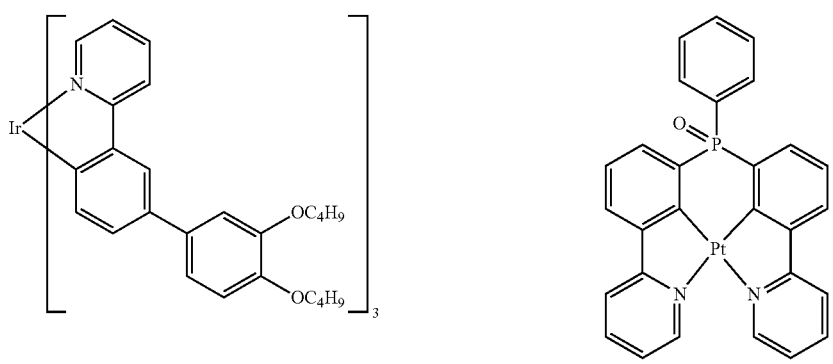
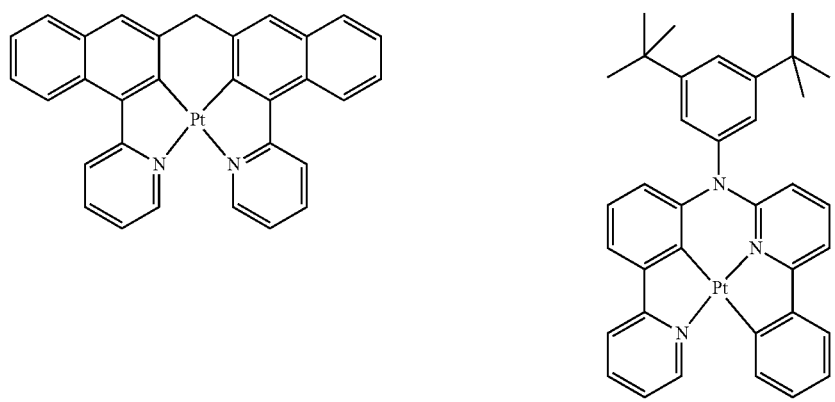

-continued
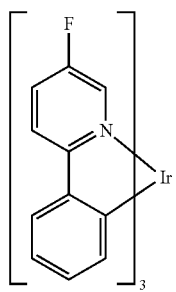
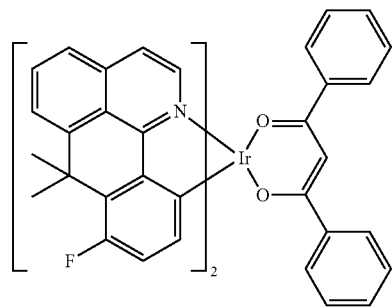
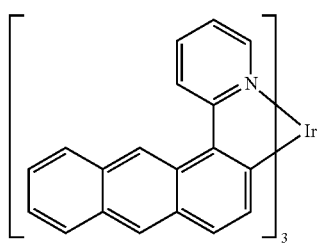
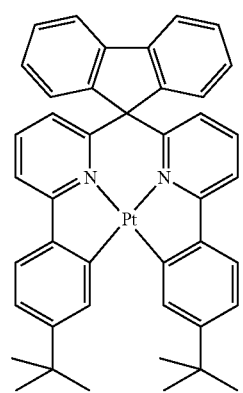
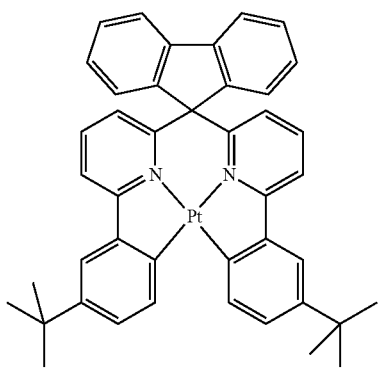
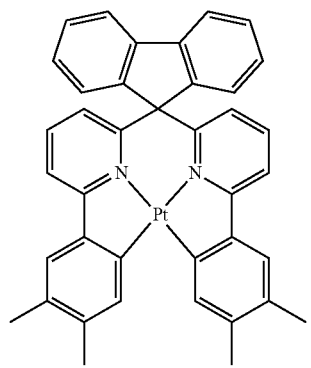
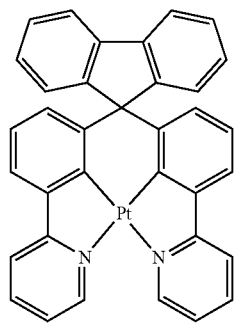
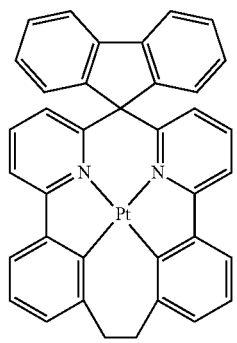

-continued
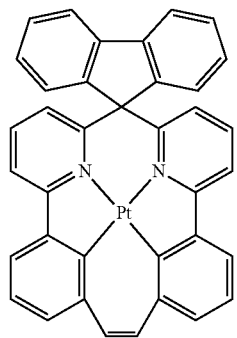
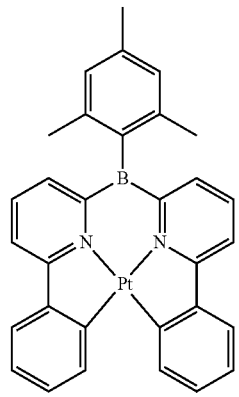
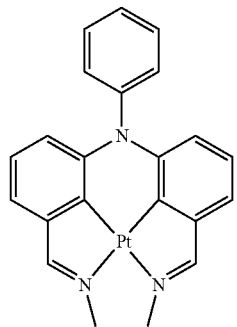
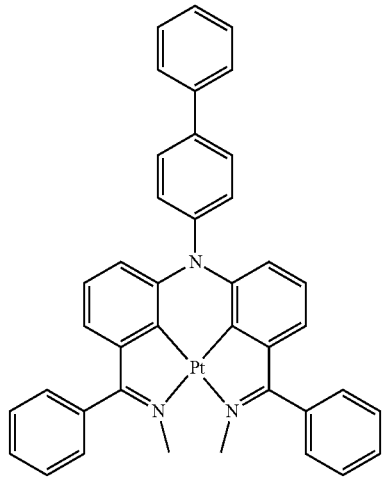
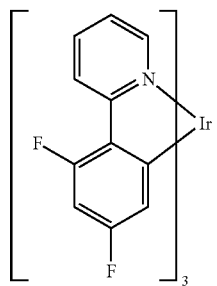
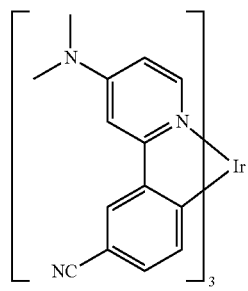
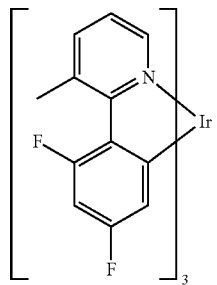
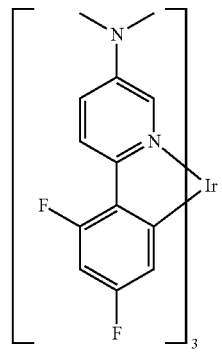

-continued
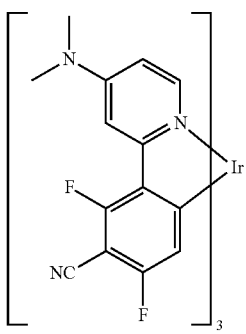
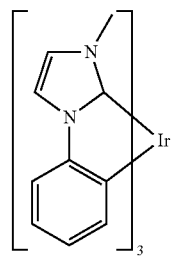
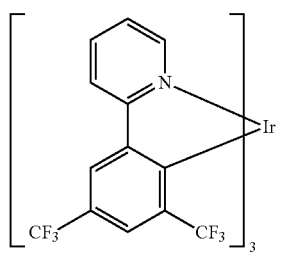
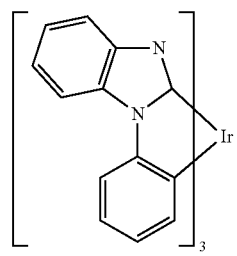
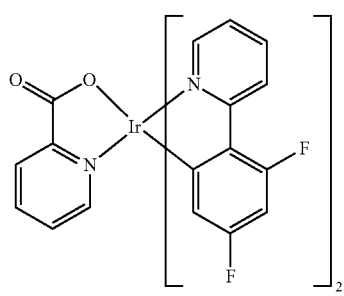
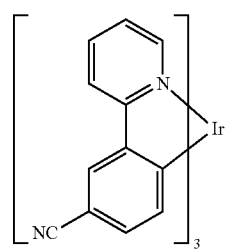
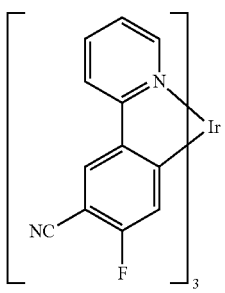
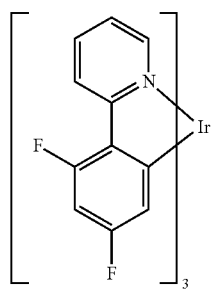
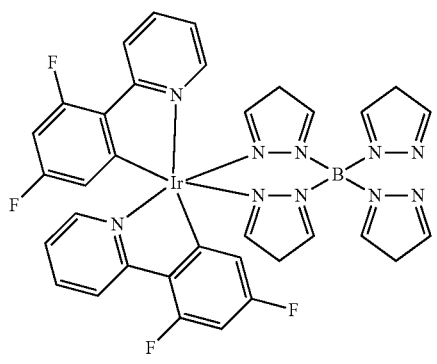
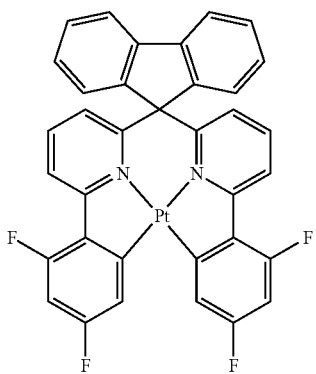

-continued
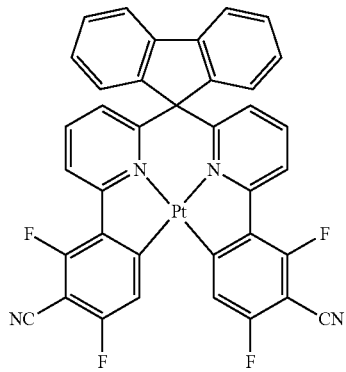
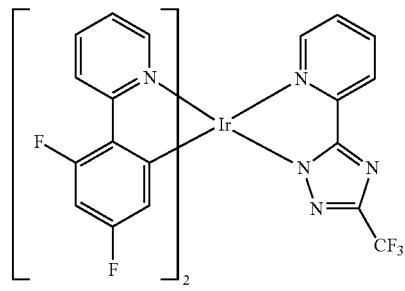
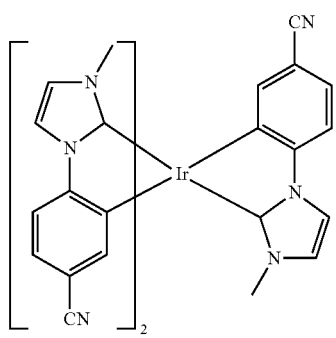
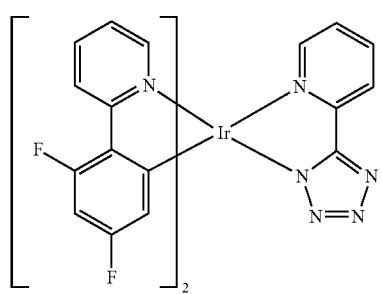
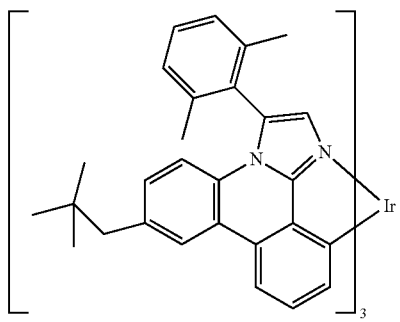
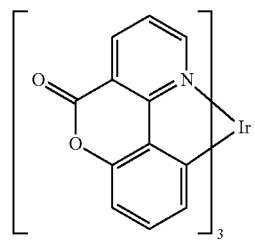
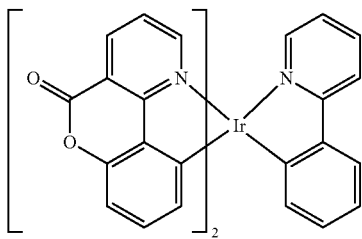
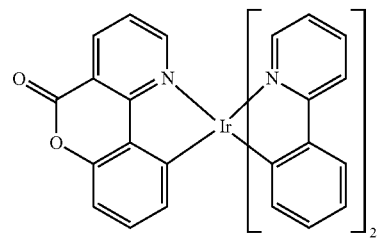
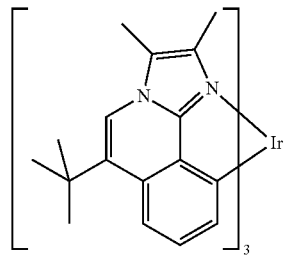
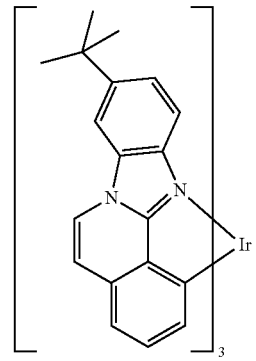

-continued

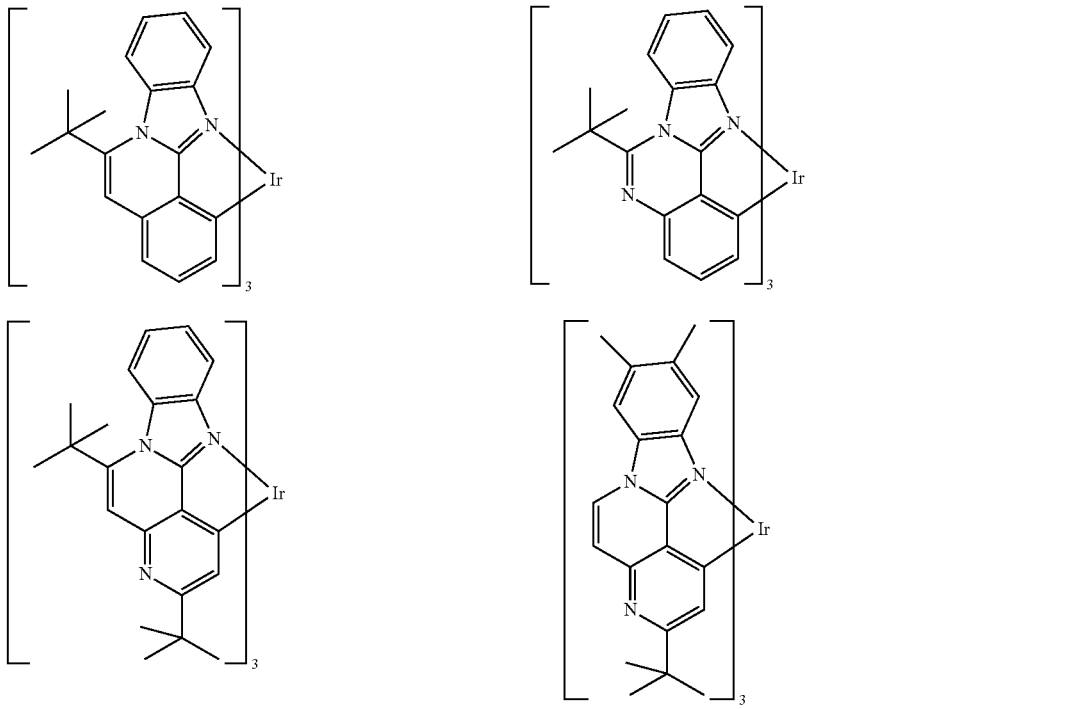

Preferred fluorescent dopants are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1 position or 1,6 positions. Further preferred dopants are indenofluorenamines or -fluorenediamines, for example according to WO 2006/108497 or WO 2006/122630, benzoindenofluorenamines or -fluorenediamines, for example according to WO 2008/006449, and dibenzoindenofluorenamines or -fluorenediamines, for example according to WO 2007/140847, and the indenofluorene derivatives having fused aryl groups disclosed in WO 2010/012328.

Useful matrix materials, preferably for fluorescent dopants, as well as the compounds of the formula (1), are materials from various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for phosphorescent dopants are, as well as the compounds of the formula (1), aromatic amines, especially triarylamines, for example according to US 2005/0069729, carbazole derivatives (e.g. CBP, N,N-biscarbazolylbiphenyl) or compounds according to WO 2005/039246, US 2005/0069729, JP 2004/288381, EP 1205527 or WO 2008/086851, bridged carbazole derivatives, for example according to WO 2011/088877 and WO 2011/128017, indenocarbazole derivatives, for example according to WO 2010/136109 and WO 2011/000455, azacarbazole derivatives, for example according to EP 1617710, EP 1617711, EP 1731584, JP 2005/347160, indolocarbazole derivatives, for example according to WO 2007/063754 or WO 2008/056746, ketones, for example according to WO 2004/093207 or WO 2010/006680, phosphine oxides, sulfoxides and sulfones, for example according to WO 2005/003253, oligophenylenes, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, aluminum complexes, e.g. BAlq, diazasilole derivatives and tetraazasilole derivatives, for example according to WO 2010/054729, diazaphosphole derivatives, for example according to WO 2010/054730, and aluminum complexes, e.g. BAIQ.

Apart from the cathode, anode and the layer comprising the compound of the formula (1), the electronic device may comprise further layers. These are selected, for example, from in each case one or more hole injection layers, hole transport layers, hole blacker layers, emitting layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that not necessarily every one of these layers need be present.

The sequence of layers in the organic electroluminescent device is preferably as follows: anode/hole injection layer/hole transport layer/emitting layer/electron transport layer/electron injection layer/cathode.

At the same time, it should be pointed out again that not all the layers mentioned need be present and/or that further layers may additionally be present.

The inventive organic electroluminescent device may contain two or more emitting layers. More preferably, these emission layers in this case have several emission maxima between 380 nm and 750 nm overall, such that the overall result is white emission; in other words, various emitting compounds which may fluoresce or phosphoresce and which emit blue or yellow or orange or red light are used in the emitting layers. Especially preferred are three-layer systems, i.e. systems having three emitting layers, where the three layers show blue, green and orange or red emission (for the basic construction see, for example, WO 2005/011013). It should be noted that, for the production of white light, rather than a plurality of color-emitting emitter compounds, an emitter compound used individually which emits over a broad wavelength range may also be suitable.

Suitable charge transport materials as usable in the hole injection or hole transport layer or electron blocker layer or in the electron transport layer of the organic electroluminescent device of the invention are, for example, the compounds disclosed in Y. Shirota et al., Chem. Rev. 2007, 107(4), 953-1010, or other materials as used in these layers according to the prior art.

Materials used for the electron transport layer may be any materials as used according to the prior art as electron transport materials in the electron transport layer. Especially suitable are aluminum complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the abovementioned compounds as disclosed in JP 2000/053957, WO 2003/060956, WO 2004/028217, WO 2004/080975 and WO 2010/072300.

As hole transport materials are especially preferably materials which can be used in a hole transport, hole injection or electron blocker layer, indenofluorenamine derivatives (for example according to WO 2006/122630 or WO 2006/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluorenamines (for example according to WO 08/006449), dibenzoindenofluorenamines (for example according to WO 2007/140847), spirobifluorenamines (for example according to WO 2012/034627 or the as yet unpublished EP 12000929.5), fluorenamines (for example according to the as yet unpublished applications EP 12005369.9, EP 12005370.7 and EP 12005371.5), spirodibenzopyranamines (for example according to the as yet unpublished application EP 11009127.9) and dihydroacridine derivatives (for example according to the as yet unpublished EP 11007067.9).

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LIQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiOx, Al/PtOx) may also be preferred. For some applications, at least one of the electrodes has to be transparent or partly transparent in order to enable the irradiation of the organic material (organic solar cell) or the emission of light (OLED, O-LASER), Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The electronic device, in the course of production, is appropriately (according to the application) structured, contact-connected and finally sealed, since the lifetime of the devices of the invention is shortened in the presence of water and/or air.

In a preferred embodiment, the electronic device of the invention is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (1) are needed. High solubility can be achieved by suitable substitution of the compounds. The compounds of the invention may additionally be applied from solution and be fixed in the respective layer by subsequent crosslinking or fixing in a polymer network.

It is further preferable that an organic electroluminescent device of the invention is produced by applying one or more layers from solution and one or more layers by a sublimation method.

The invention thus further provides a process for producing the electronic device of the invention, characterized in that at least one organic layer is applied by gas phase deposition or from solution.

According to the invention, the electronic devices comprising one or more compounds of formula (1) can be used in displays, as light sources in lighting applications and as light sources in medical and/or cosmetic applications (e.g. light therapy).

The present invention also relates to a formulation comprising at least one compound of formula (1) or at least one of the abovementioned compositions and at least one solvent.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

Devices comprising the compounds of formula (1) can be used in a wide variety of ways. For example, it is possible to use electroluminescent devices comprising one or more compounds of formula (1) in displays for televisions, mobile phones, computers and cameras. The devices may alternatively be used in lighting applications. In addition, electroluminescent devices can be utilized, for example, in OLEDs or OLECs comprising at least one of the compounds of formula (1) in medicine or cosmetics for phototherapy. It is thus possible to treat a multitude of disorders (psoriasis, atopic dermatitis, inflammation, acne, skin cancer etc.) or to avoid and reduce formation of skin wrinkles, skin reddening and skin aging. In addition, the light-emitting devices can be used to keep drinks or food fresh, or in order to sterilize devices (for example medical devices).

The present invention therefore provides an electronic device, preferably an organic electroluminescent device, very preferably an OLED or OLEC and most preferably an OLED, comprising at least one compound of formula (1) for use in medicine for phototherapy.

The present invention further preferably relates to an electronic device, preferably an organic electroluminescent device, very preferably an OLED or OLEC and most preferably an OLED, comprising at least one compound of formula (1) for use for phototherapeutic treatment of skin diseases.

The present invention further very preferably relates to an electronic device, preferably an organic electroluminescent device, very preferably an OLED or OLEC and most preferably an OLED, comprising at least one compound of formula (1) for use for phototherapeutic treatment of psoriasis, atopic dermatitis, inflammation disorders, vitiligo, wound healing and skin cancer.

The present invention further relates to the use of the electronic device, preferably an organic electroluminescent device, very preferably an OLED or OLEC and most preferably an OLED, comprising at least one compound of formula (1) in cosmetics, preferably for treatment of acne, skin aging and cellulite.

The compounds of the invention and the organic electroluminescent devices of the invention feature the following surprising advantages over the prior art:

1. The compounds of the invention are of very good suitability for use in an emission layer and exhibit improved performance data over compounds from the prior art.
2. The compounds of the invention have a relatively low sublimation temperature and high thermal stability, and can therefore be sublimed without decomposition or residue. In addition, they have high oxidation stability and a high glass transition temperature, which is advantageous for processibility, for example from solution or from the gas phase, and also for use in electronic devices.
3. The use of the compounds of the invention in electronic devices, especially used as matrix material, but also as electron transport, electron blocker or electron injection material, hole transport material or hole blacker material, leads to high efficiencies, low operating voltages and long lifetimes.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

EXAMPLES

The syntheses which follow, unless stated otherwise, are conducted under a protective gas atmosphere in dried solvents. The reactants can be sourced from Aldrich (p-toluenesulfonic acid, N-bromosuccinimide, benzeneboronic acid, tri(o-tolyl)phosphine, potassium phosphate, palladium (II) acetate). 8,8'-Dihydroxy-1,1'-binaphthyl can be prepared by a literature method [J. Org. Chem., 1985, 50, 1486-1496]. The figures in square brackets for chemical compounds known from the literature are the CAS number.

Example 1

Synthesis of dinaphth[1,8-bc:1',8'-ef]oxepine

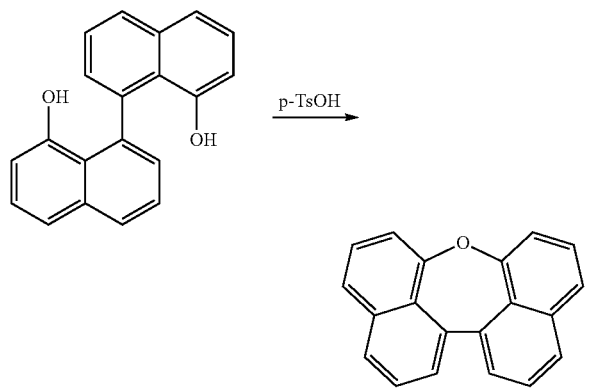

To a boiling solution of 24.4 g of 8,8'-dihydroxy-1,1'-binaphthyl (85.2 mmol) in 500 mL of toluene are added, in small portions over the course of 2 h, 17.8 g (190 mmol) of p-toluenesulfonic acid. The mixture is then stirred for 1 h. After the reaction mixture has been cooled down, a solution of 25.9 g (187.5 mmol) of $K_2CO_3$ in 25 mL of water is added and the mixture is stirred for 1 h. The organic phase is removed, washed with 100 mL of water, dried with $Mg_2SO_4$ and then concentrated. Yield: 19.8 g (73.8 mmol), 87% of theory.

In an analogous manner, it is possible to obtain the following compound:

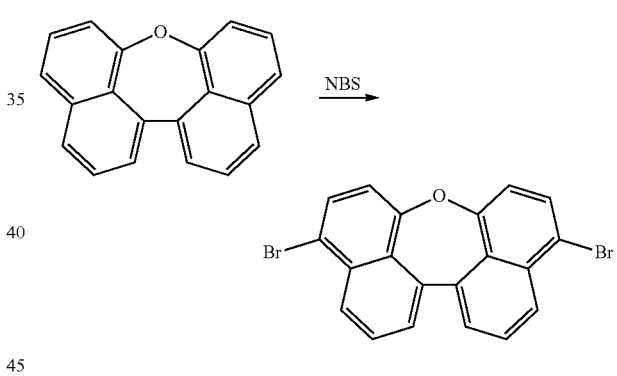

| Reactant 1 | Product | Yield |
|---|---|---|
| [250716-74-6] | | 49% |

Example 2

Synthesis of 4,4'-dibromodinaphth[1,8-bc:1',8'-ef]oxepine 19.6 g (73.0 mmol) of dinaphth[1,8-bc:1',8'-ef]oxepine are dissolved in 200 mL of dimethylformamide, 27.3 g (178.0 mmol) of N-bromosuccinimide are added thereto and the reaction mixture is heated to 40° C. After 30 min, the mixture is allowed to cool and the precipitated yellow solid is filtered off and washed twice with 40 mL of ethanol. Yield: 31.1 g (63.4 mmol), 87% of theory; purity about 99% by $^1$H NMR.

In an analogous manner, it is possible to obtain the following compound:

| Reactant 1 | Product | Yield |
|---|---|---|
| | | 78% |

Example 3

Synthesis of 4-bromodinaphth[1,8-bc:1'',8''-ef]ox-epine

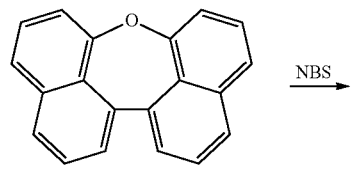 NBS → 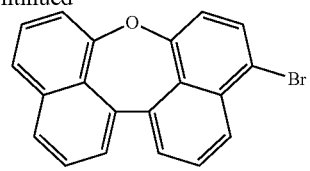

30 mg (0.11 mmol) of dinaphth[1,8-bc:1',8'-ef]oxepine are dissolved in 5 mL of chloroform, 40 mg (0.22 mmol) of N-bromosuccinimide are added thereto and the reaction mixture is stirred at room temperature for 6 h. Thereafter, the reaction mixture is extended with 5 mL of dichloromethane, water is added and the organic phase is separated off. The column chromatography purification gives a yield of 25.3 mg (0.07 mmol, 65.2% of theory).

In an analogous manner, it is possible to obtain the following compound:

| Reactant 1 | Product | Yield |
|---|---|---|
| | | 78% |

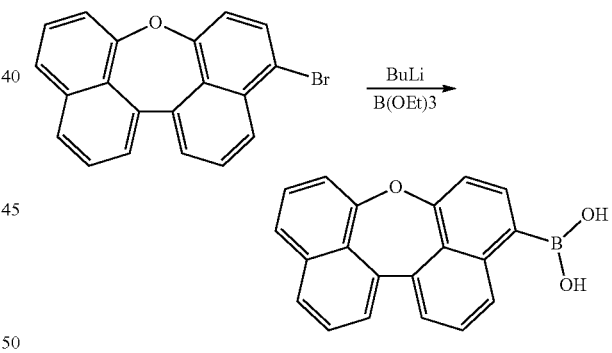

Example 4

Synthesis of dinaphth[1,8-bc:11',8'-ef]oxepine-4-boronic acid

To a solution, cooled to −78° C., of 93.6 g (270 mmol) of 4-bromodinaphth[1,8-bc:1',8'-ef]oxepine in 1500 mL of diethyl ether are added dropwise 110 mL (276 mmol) of n-butyllithium (2.5 M in hexane). The reaction mixture is stirred at −78° C. for 30 min. The mixture is allowed to come to room temperature and cooled again to −78° C., and then a mixture of 40 mL (351 mmol) of trimethyl borate in 50 mL of diethyl ether is added rapidly. After warming to −10° C., hydrolysis is effected with 135 mL of 2 N hydrochloric acid. The organic phase is removed, washed with water, dried over sodium sulfate and concentrated to dryness. The residue is taken up in 300 mL of n-heptane, and the colorless solid is filtered off with suction, washed with n-heptane and dried under reduced pressure. Yield: 77.6 g (248 mmol), 92% of theory.

In an analogous manner, 0.5 eq. of bromide can be used to obtain the following compound:

| Reactant 1 | Product | Yield |
|---|---|---|
| 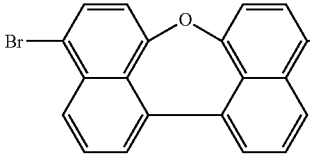 | 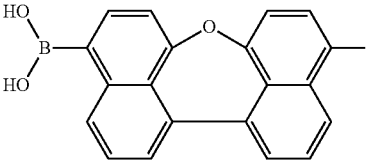 | 78% |

Example 5

Synthesis of 4,4'-diphenyldinaphth[1,8-bc:1',8'-ef]oxepine

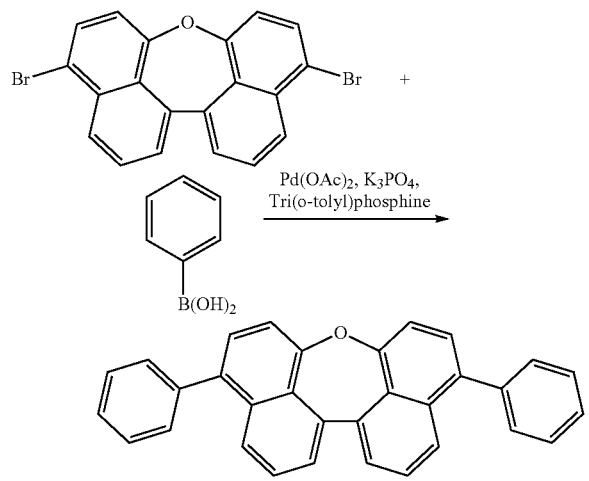

35 g (82.1 mmol) of 4,4'-dibromodinaphth[1,8-bc:1',8'-ef]oxepine, 22.0 g (180.7 mmol) of benzeneboronic acid and 38.3 g (180.7 mmol) of potassium phosphate are suspended in 500 mL of toluene, 250 mL of 1,4-dioxane and 120 mL of water. Added to the mixture are 1.3 g (4.1 mmol) of tri(o-tolyl)phosphine and then 461 mg (2 mmol) of palladium(II) acetate, and the reaction mixture is heated under reflux for 48 h. After cooling, the organic phase is removed, washed three times with 100 mL each time of water and concentrated. After purification by column chromatography ($SiO_2$, n-heptane/dichloromethane 3:1), the foam obtained is dissolved in dichloromethane and precipitated with ethanol. The residue is recrystallized from toluene and from dichloromethane and finally sublimed under high vacuum (p=5× $10^{-5}$ mbar). Yield: 18.2 g (43.2 mmol), 53% of theory. Purity: about 99.9% by HPLC.

In an analogous manner, it is possible to obtain the following compounds:

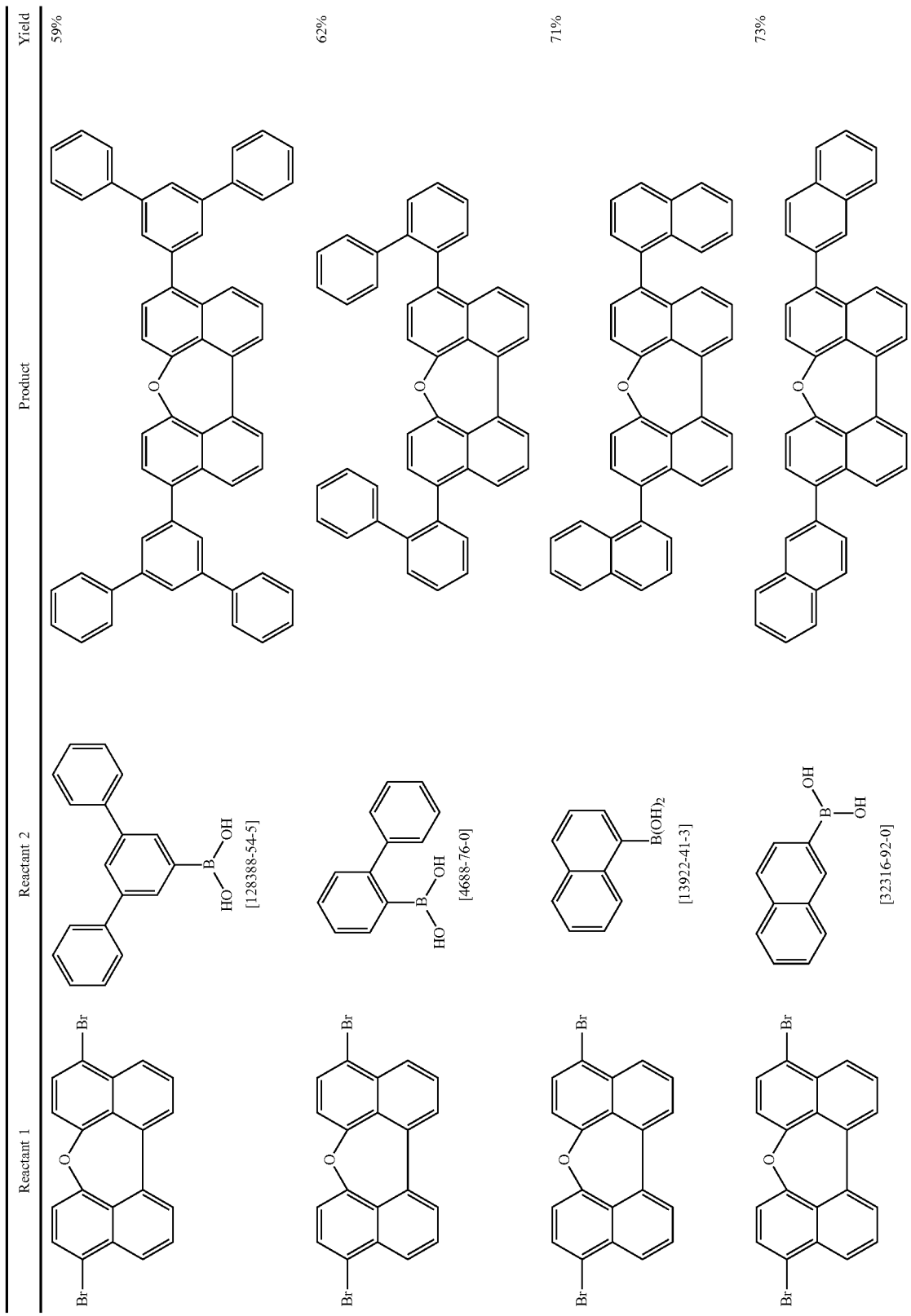

-continued
| Reactant 1 | Reactant 2 | Product | Yield |
|---|---|---|---|
| 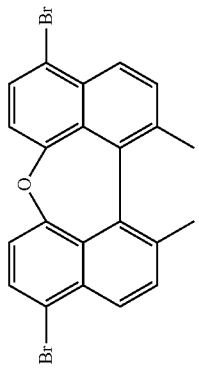 | 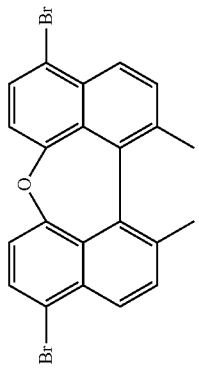 [13922-41-3] | 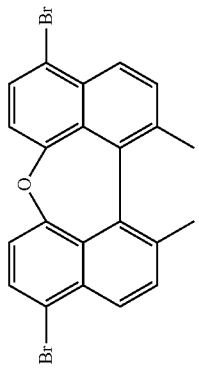 | 69% |
| 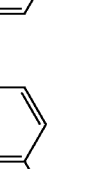 | 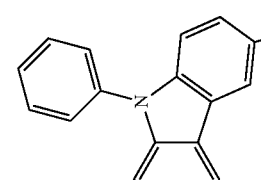 [854952-58-2] | 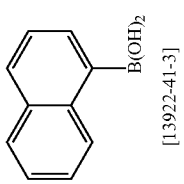 | 71% |
| 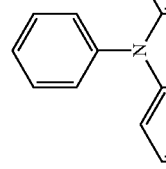 | 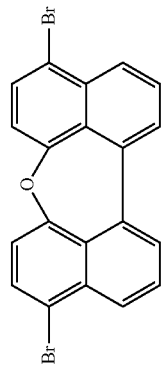 [201802-67-7] | 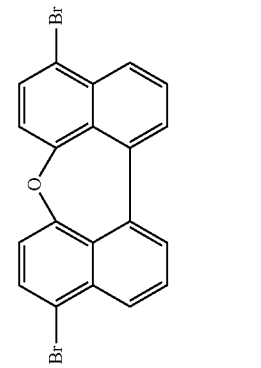 | 65% |

-continued
| Reactant 1 | Reactant 2 | Product | Yield |
|---|---|---|---|
| 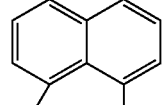 | 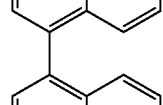 | 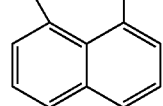 | 78% |
| 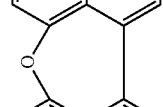 | 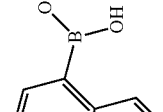 |  | 69% |

Example 6

Synthesis of 4 naphthalen-2-yldiphenyldinaphth[1,8-bc:1',8'-ef]oxepine

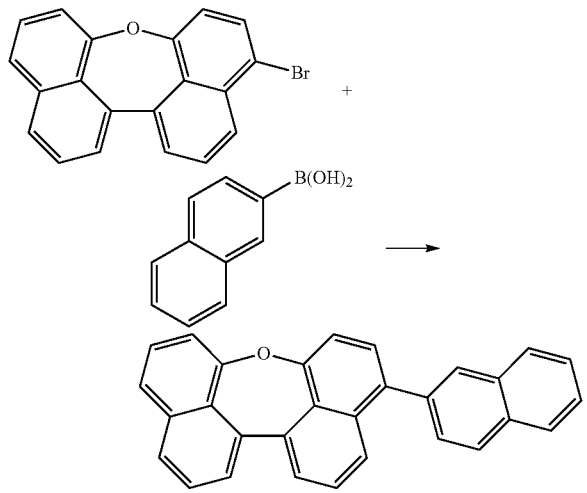

61 g (177 mmol) of 4-bromodinaphth[1,8-bc:1',8'-ef]oxepine, 25.5 g (180.7 mmol) of 2-naphthylboronic acid and 38.3 g (180.7 mmol) of potassium phosphate are suspended in 500 mL of toluene, 250 mL of 1,4-dioxane and 120 mL of water. Added to the mixture are 1.3 g (4.1 mmol) of tri(o-tolyl)phosphine and then 461 mg (2 mmol) of palladium(II) acetate, and the reaction mixture is heated under reflux for 48 h. After cooling, the organic phase is removed, washed three times with 100 mL each time of water and concentrated. After purification by column chromatography ($SiO_2$, n-heptane/dichloromethane 3:1), the foam obtained is dissolved in dichloromethane and precipitated with ethanol. The residue is recrystallized from toluene and from dichloromethane and finally sublimed under high vacuum (p=5× $10^{-5}$ mbar). Yield: 24 g (61.8 mmol), 59% of theory. Purity: about 99.9% by HPLC.

In an analogous manner, it is possible to obtain the following compounds:

| Reactant 1 | Reactant 2 | Product | Yield |
|---|---|---|---|
| (structure) | (structure) [13922-41-3] | (structure) | 58% |
| (structure) | (structure) [1161009-88-6] | (structure) | 63% |
| (structure) | (structure) [1001911-63-2] | (structure) | 62% |

-continued
| Reactant 1 | Reactant 2 | Product | Yield |
|---|---|---|---|
| 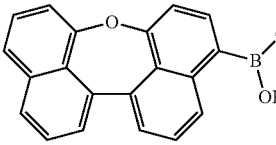 | 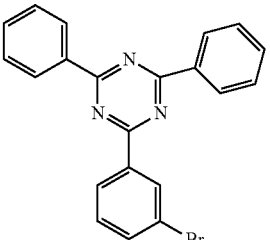\n[64377-31-1] | 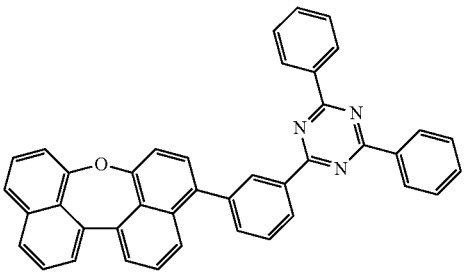 [SMILES: c1ccc(-c2nc(-c3ccccc3)nc(-c3cccc(-c4ccc5oc6cccc7cccc(c8cccc4c58)c76)c3)n2)cc1] | 64% |
| 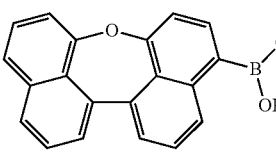 | 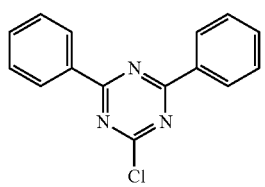 [SMILES: Clc1nc(-c2ccccc2)nc(-c2ccccc2)n1] | 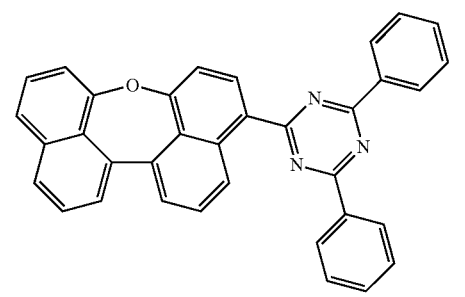 [SMILES: c1ccc(-c2nc(-c3ccccc3)nc(-c3ccc4oc5cccc6cccc(c7cccc3c47)c65)n2)cc1] | 59% |
| 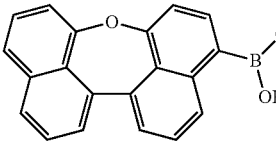 | 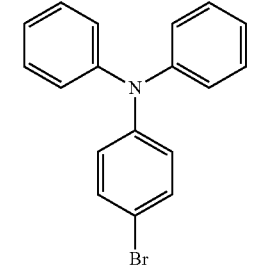\n[201802-67-7] | 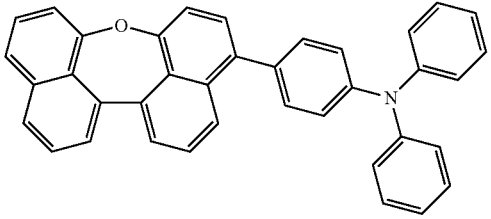 [SMILES: c1ccc(N(c2ccccc2)c2ccc(-c3ccc4oc5cccc6cccc(c7cccc3c47)c65)cc2)cc1] | 64% |
| 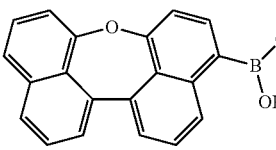 | 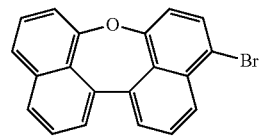 [SMILES: Brc1ccc2oc3cccc4cccc(c5cccc1c25)c43] | 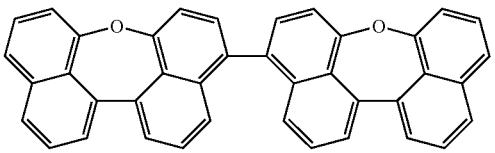 [SMILES: c1cc2cccc3c4cccc5c(-c6ccc7oc8cccc9cccc(c%10cccc6c7%10)c98)ccc(oc(c1)c23)c54] | 75% |
Example 7
Synthesis of 2,2'-dibromo-4,4'-diphenyldinaphth[1,8-bc:1',8'-ef]oxepine
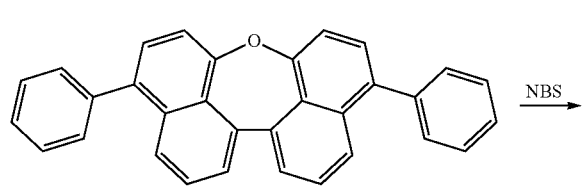 NBS →
-continued
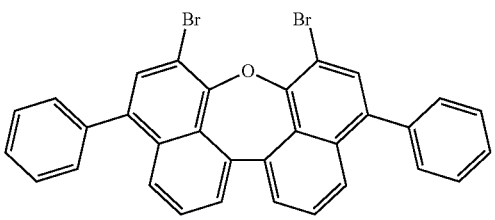
2 g (4.8 mmol) of 4,4'-diphenyldinaphth[1,8-bc:1',8'-ef] oxepine are dissolved in 20 mL of dimethylformamide, 1.8 g (10.0 mmol) of N-bromosuccinimide are added thereto and the reaction mixture is heated to 80° C. After 1 h, the mixture is allowed to cool and the precipitated green solid is filtered off and washed with 5 mL each of cold DMF and water. Yield: 1.2 g (2.1 mmol), 44% of theory; purity about 96% by $^1$H NMR.

Example 8

Synthesis of 2,2',4,4'-tetraphenyldinaphth[1,8-bc:1',8'-ef]oxepine

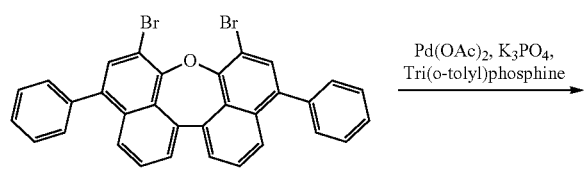

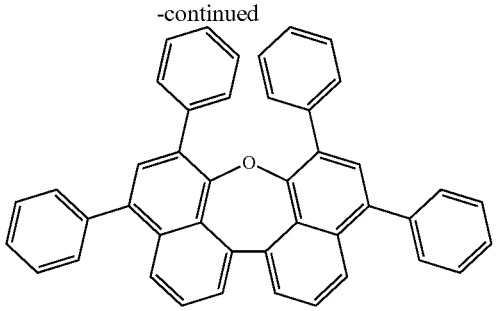

5 g (8.6 mmol) of 4,4'-dibromodinaphth[1,8-bc:1',8'-ef]oxepine, 2.3 g (19.0 mmol) of benzeneboronic acid and 4.0 g (19.0 mmol) of potassium phosphate are suspended in 55 mL of toluene, 26 mL of 1,4-dioxane and 12.5 mL of water. Added to the mixture are 130 mg (0.43 mmol) of tri(o-tolyl)phosphine and then 48 mg (0.21 mmol) of palladium(II) acetate, and the reaction mixture is heated under reflux for 48 h. After cooling, the organic phase is removed, washed three times with 50 mL each time of water and concentrated. After column chromatography purification (SiO$_2$, n-heptane/dichloromethane 3:1), the residue is recrystallized from toluene and from dichloromethane and then sublimed under high vacuum (p=5×10$^{-5}$ mbar). Yield: 3.2 g (5.6 mmol), 65% of theory. Purity: about 99.9% by HPLC.

In an analogous manner, it is possible to obtain the following compounds:

| Reactant 1 | Reactant 2 | Product | Yield |
|---|---|---|---|
| 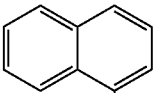 | 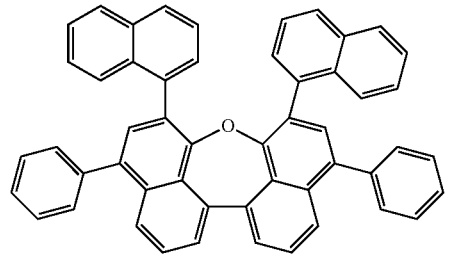 [SMILES: c1ccc(-c2cc(-c3cccc4ccccc34)c3oc4c(-c5cccc6ccccc56)cc(-c5ccccc5)c5cccc(c6cccc2c36)c54)cc1] [13922-41-3] | 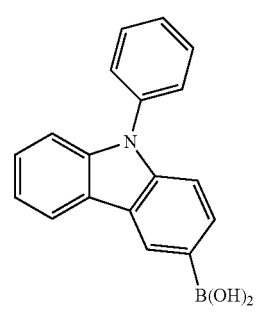 | 59% |
| 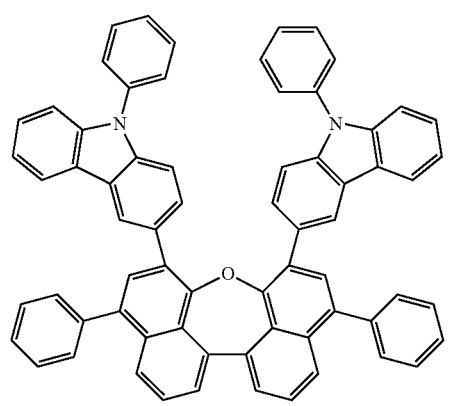 [SMILES: c1ccc(-c2cc(-c3ccc4c(c3)c3ccccc3n4-c3ccccc3)c3oc4c(-c5ccc6c(c5)c5ccccc5n6-c5ccccc5)cc(-c5ccccc5)c5cccc(c6cccc2c36)c54)cc1] | [854952-58-2] | | 76% |

Example 9

Synthesis of N,N,N',N'-tetrakis(biphenyl-4-yl)dinaphth[1,8-bc:1,8"-ef]oxepine-4,4'-diamine

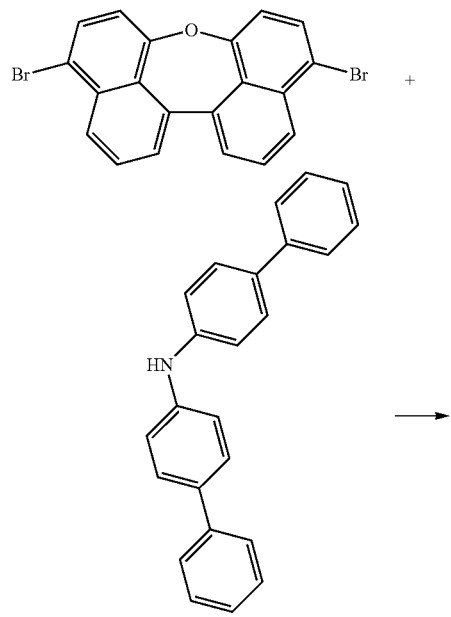

[102113-98-4]

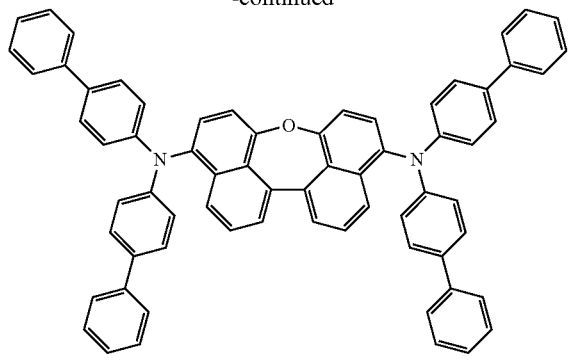

A mixture of 12.3 g (50 mmol) of 4,4'-dibromodinaphth[1,8-bc:1',8'-ef]oxepine, 19.2 g (60 mmol) of bis(biphenyl-4-yl)amine, 7.7 g (80 mmol) of sodium tert-butoxide, 1.4 g (5 mmol) of tricyclohexylamine, 561 mg (2.5 mmol) of palladium(II) acetate and 300 mL of mesitylene is heated under reflux for 24 h. After cooling, 200 mL of water are added, the mixture is stirred for a further 30 min, the organic phase is removed and the latter is filtered through a short Celite bed and then the solvent is removed under reduced pressure. The residue is recrystallized five times from DMF and finally fractionally sublimed twice (p about $10^{-6}$ mbar). Yield: 20.9 g (23 mmol), 80% of theory; purity: 99.9% by HPLC.

In an analogous manner, it is possible to obtain the following compounds:

| Reactant 1 | Reactant 2 | Product | Yield |
|---|---|---|---|
| [1290039-85-8] | | | 63% |
| [1198395-24-2] | | | 76 |

| Reactant 1 | Reactant 2 | Product | Yield |
|---|---|---|---|
| 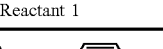 | 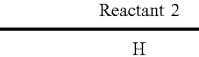 [86-74-8] | 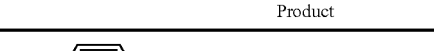 | 75% |

Example 10

Synthesis of 8-trimethylsilyltribenz[a,c,e]oxepine

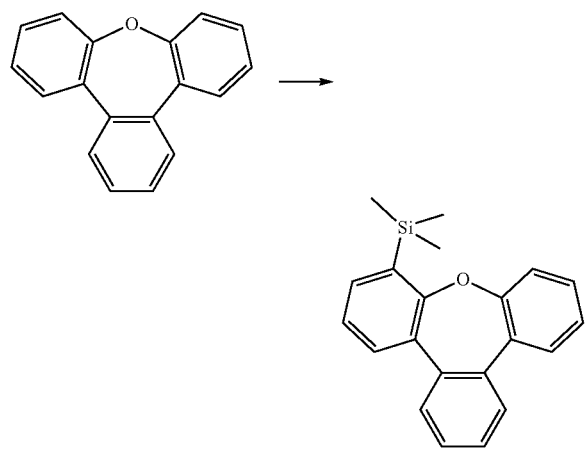

4.73 g (19.4 mmol) of tribenz[a,c,e]oxepine [2688-95-1] and 5.86 mL (4.57 g, 39.3 mmol, 2 mol %) of tetramethylethylenediamine (TMEDA) are dissolved in 60 mL of dry diethyl ether. Then 18.7 mL of n-butyllithium (2.5 M in hexane, 46.9 mmol, 2.4 mol %) are added and the reaction mixture is then heated to reflux for 2 h. Then the reaction mixture is cooled down 0° C., chlorotrimethylsilane (6.0 mL, 47.4 mmol) is added and the mixture is stirred overnight, in the course of which it is allowed to warm up to room temperature. 60 mL of water are added to the reaction mixture and the organic phase is separated off. The aqueous phase is extracted twice with 30 mL each time of diethyl ether and the combined organic phases are dried with MgSO$_4$ and concentrated on a rotary evaporator. The oily crude product obtained is purified by column chromatography (SiO$_2$, heptane) and gives 8-trimethylsilyltribenz[a,c,e]oxepine in 94% yield (5.76 g, 18.2 mmol) in the form of a colorless oil.

Example 11

Synthesis of tribenz[a,c,e]oxepine-1-boronic acid (Int-4)

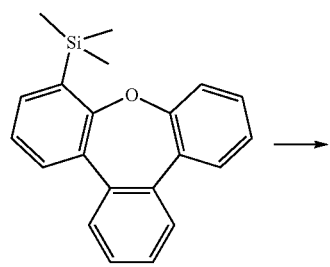

-continued

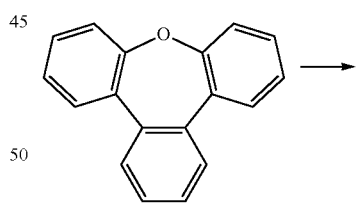

To an initial charge of 9.82 g (31.03 mmol) of 8-trimethylsilyltribenz[a,c,e]oxepine in 50 mL of dry dichloromethane are then gradually added 37.2 mL of boron tribromide (1 M in dichloromethane (37.2 mmol, 1.2 mol %)). The reaction mixture is stirred for 15 h and then added to ice. The yellow organic phase is separated off, and the aqueous phase is extracted twice with 30 mL each time of ethyl acetate. The combined organic phases are washed with 30 mL each of water and saturated NaCl solution and then dried with Na$_2$SO$_4$, filtered and concentrated. The resultant yellow oil of Int-4 (8.4 g, 29.2 mmol, 94%) is converted further without further purification.

Example 12

Synthesis of 6-bromotribenz[a,c,e]oxepine (Int-5)

10 g (41 mmol) of tribenz[a,c,e]oxepine are initially charged together with 8 mg of N-bromosuccinimide (45 mmol, 1.1 mol %) in 100 mL of dry dimethylformamide (DMF). The reaction mixture is heated to 120° C. for 24 h and then the solvent is removed under reduced pressure. The residue is purified by column chromatography on silica gel with heptane/DCM (2/1) as eluent. Int-5 is obtained as a pale yellowish solid in 76% yield (10 g, 31 mmol).

Example 13

Synthesis of 6,12-dibromotribenz[a,c,e]oxepine (Int-6)

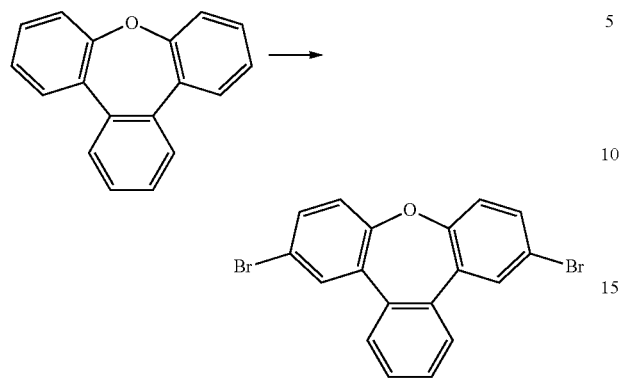

10 g (41 mmol) of tribenz[a,c,e]oxepine are initially charged together with 16 g of N-bromosuccinimide (90 mmol, 22 mol %) in 150 mL of dry dimethylformamide (DMF). The reaction mixture is heated to 120° C. for 24 h and then the solvent is removed under reduced pressure. The residue is purified by column chromatography on silica gel with heptane/DCM (2/1) as eluent. Int-6 is obtained as a yellow solid in 91% yield (15 g, 37 mmol).

Example 14

Synthesis of 2-(tribenz[a,c,e]oxepin-8-yl)-4,6-diphenyl-[1,3,5]triazine

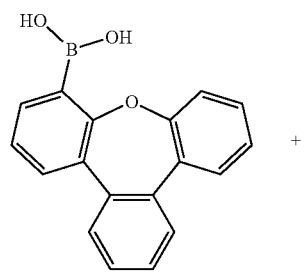

+

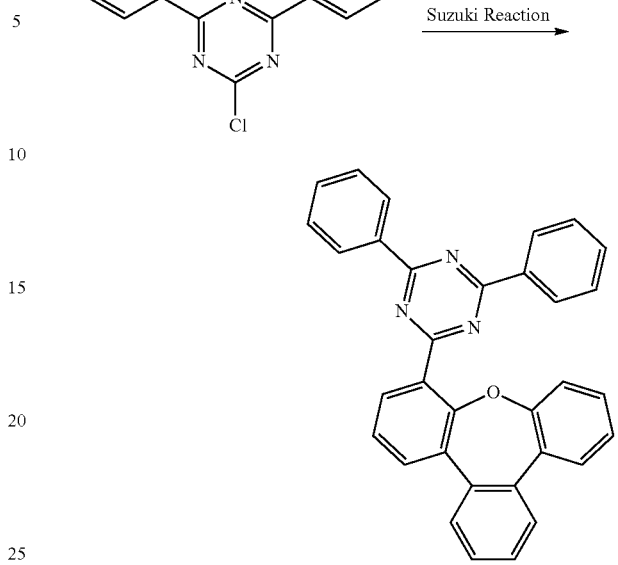

8.4 g (29.2 mmol) of tribenz[a,c,e]oxepine-1-boronic acid, 10.2 g of 2-chloro-4,6-diphenyl-[1,3,5]triazine (37.9 mmol, 1.3 mol %) and 6.8 g of $Na_2CO_3$ (64.1 mmol, 2.2 mol %) are initially charged in a mixture of 122 mL of toluene, 60 mL of 1,4-dioxane and 30 mL of water. Then 1.68 g of $Pd(PPh_3)_4$ (1.46 mmol, 0.05 mol %) are added and the reaction mixture is heated to 80° C. for 15 h. The organic phase is separated off, extracted three times with 100 mL each time of water, dried with $Na_2SO_4$ and concentrated to dryness under reduced pressure. The crude product was purified by column chromatography ($SiO_2$, heptane/$CH_2Cl_2$ 2/1). The oxepine is obtained in 63% yield (8.74 g, 18.4 mmol) in the form of very fine pale yellowish crystals.

In an analogous manner, it is possible to obtain the following compounds:

| Reactant 1 | Reactant 2 | Product | Yield |
|---|---|---|---|
| (boronic acid tribenzoxepine) | (3-bromo-9-phenylcarbazole) [1153-85-1] | (coupled product) | 78% |

213                                                                                             214
-continued
| Reactant 1 | Reactant 2 | Product | Yield |
|---|---|---|---|
| 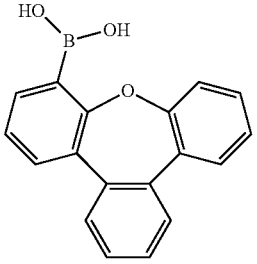 [SMILES: OB(O)c1cccc2c1Oc1ccccc1-c1ccccc1-2] | 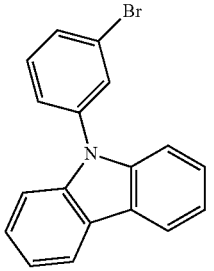  [185112-61-2] | 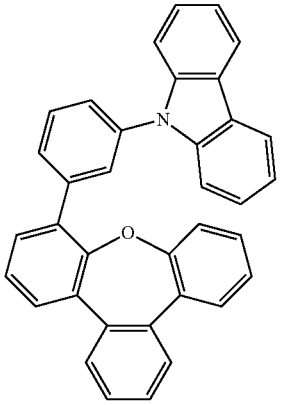 [SMILES: c1cc(-c2cccc3c2Oc2ccccc2-c2ccccc2-3)cc(-n2c3ccccc3c3ccccc32)c1] | 79% |
| 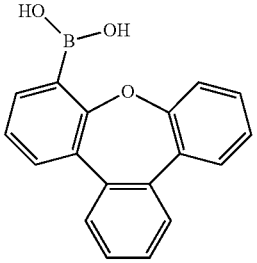 [SMILES: OB(O)c1cccc2c1Oc1ccccc1-c1ccccc1-2] | 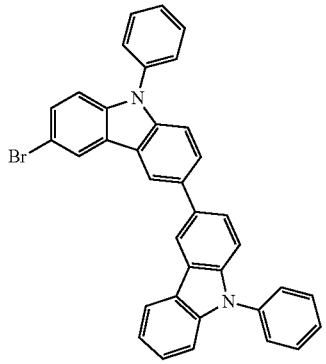  [918137-64-5] | 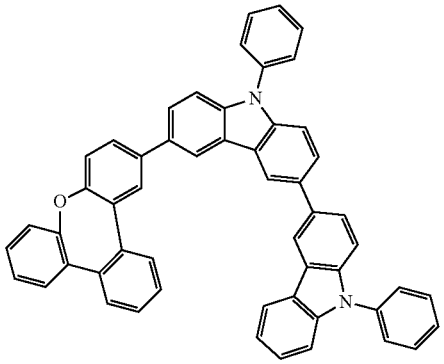 [SMILES: c1ccc(-n2c3ccccc3c3cc(-c4ccc5c(c4)c4cc(-c6ccc7c(c6)-c6ccccc6-c6ccccc6O7)ccc4n5-c4ccccc4)ccc32)cc1] | 88% |
| 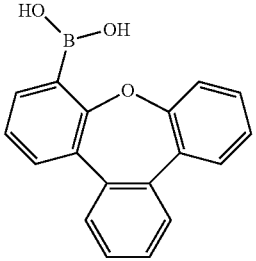 [SMILES: OB(O)c1cccc2c1Oc1ccccc1-c1ccccc1-2] | 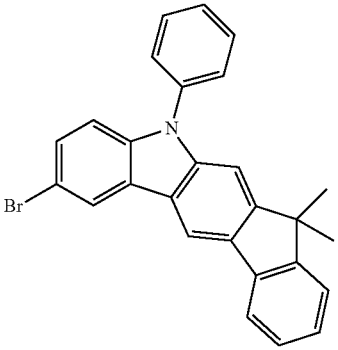 [SMILES: CC1(C)c2ccccc2-c2cc3c4cc(Br)ccc4n(-c4ccccc4)c3cc21] | 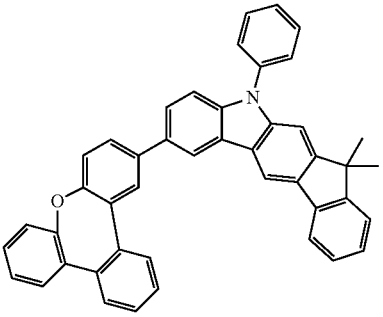 [SMILES: CC1(C)c2ccccc2-c2cc3c4cc(-c5ccc6c(c5)-c5ccccc5-c5ccccc5O6)ccc4n(-c4ccccc4)c3cc21] | 83 % |
| 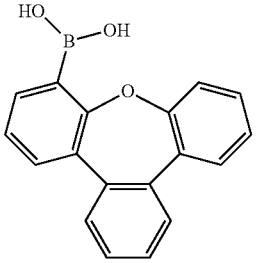 [SMILES: OB(O)c1cccc2c1Oc1ccccc1-c1ccccc1-2] | 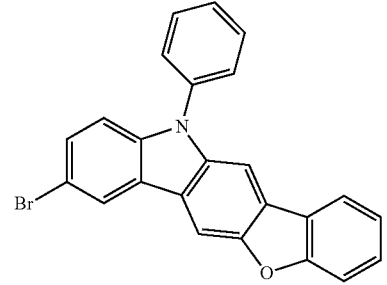  [1377576-51-6] | 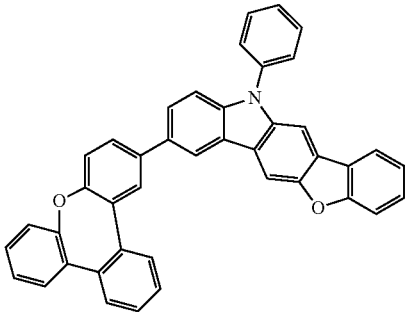 [SMILES: c1ccc(-n2c3ccc(-c4ccc5c(c4)-c4ccccc4-c4ccccc4O5)cc3c3cc4oc5ccccc5c4cc32)cc1] | 84% |

-continued
| Reactant 1 | Reactant 2 | Product | Yield |
|---|---|---|---|
| 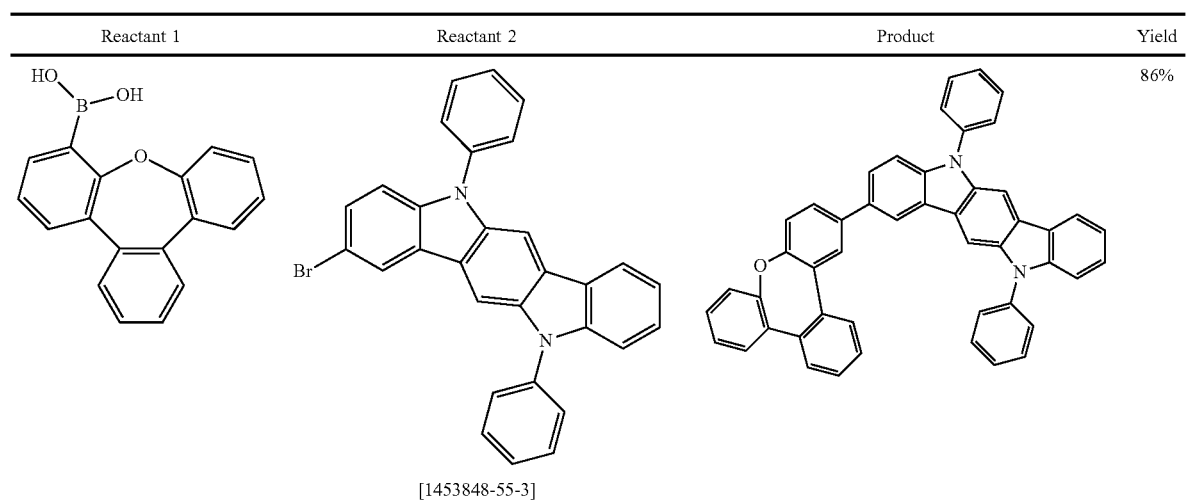 | | | 86% / 82% |
[1453848-55-3]
[499128-71-1]
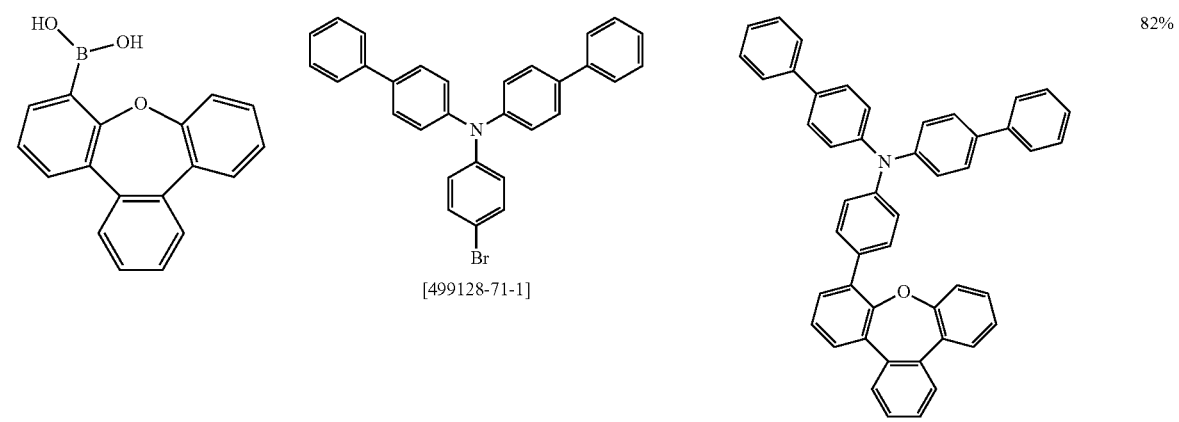
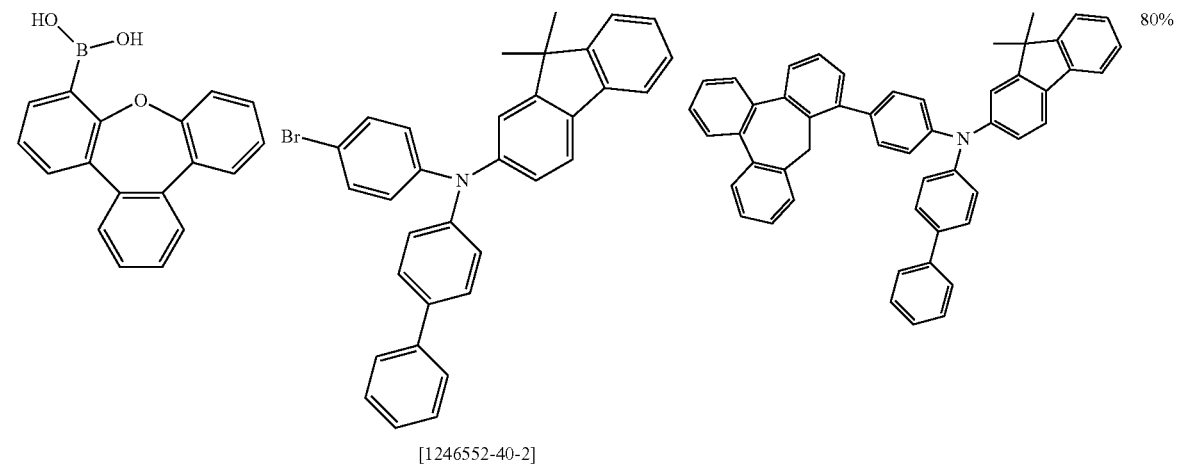
[1246552-40-2]

-continued
| Reactant 1 | Reactant 2 | Product | Yield |
|---|---|---|---|
| 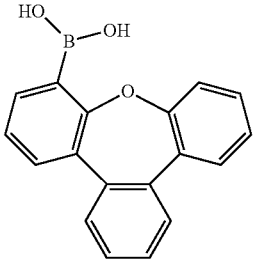 [SMILES: OB(O)c1cccc2c1Oc1ccccc1-c1ccccc1-2] | 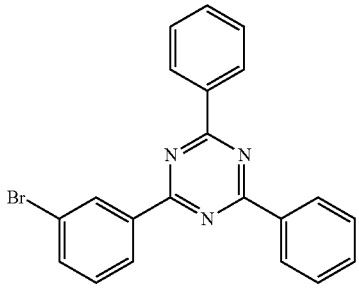<br>[864377-31-1] | 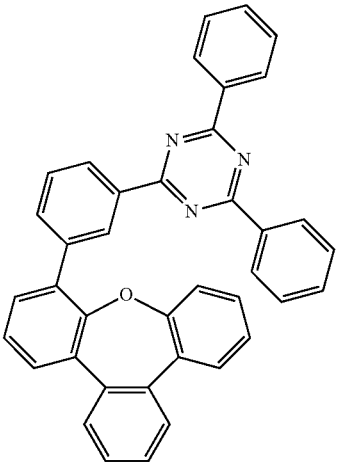 | 85% |
| 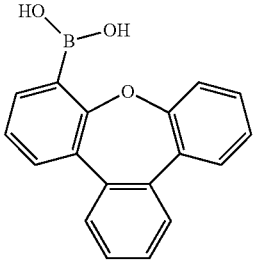 [SMILES: OB(O)c1cccc2c1Oc1ccccc1-c1ccccc1-2] | 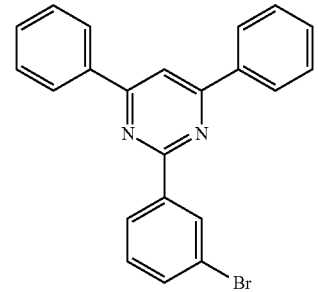<br>[864377-22-0] | 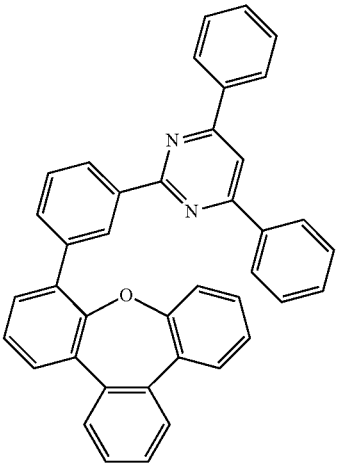 [SMILES: c1ccc(-c2nc(-c3ccccc3)nc(-c3cccc(-c4cccc5c4Oc4ccccc4-c4ccccc4-5)c3)n2)cc1] | 87% |
| 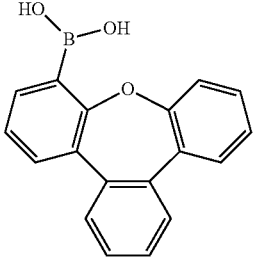 [SMILES: OB(O)c1cccc2c1Oc1ccccc1-c1ccccc1-2] | 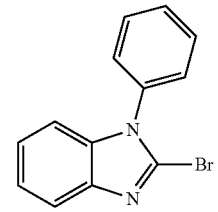<br>[1418123-78-0] | 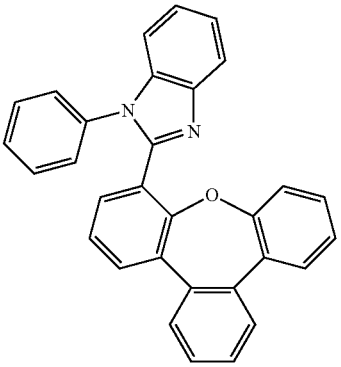 [SMILES: c1ccc(-n2c(-c3cccc4c3Oc3ccccc3-c3ccccc3-4)nc3ccccc32)cc1] | 82% |

-continued
| Reactant 1 | Reactant 2 | Product | Yield |
|---|---|---|---|
| 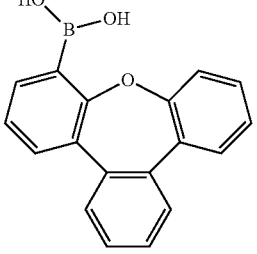 | 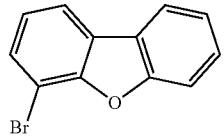 [SMILES: Brc1cccc2c1oc1ccccc12] | 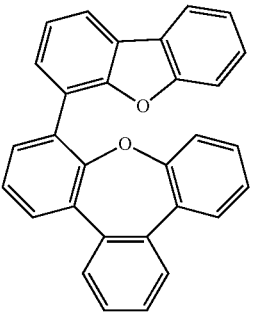 [SMILES: c1ccc2c(c1)Oc1c(cccc1-c1cccc3c1oc1ccccc13)-c1ccccc1-2] | 91% |
| 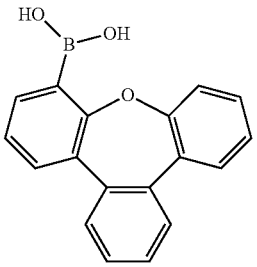 [SMILES: OB(O)c1cccc2c1Oc1ccccc1-c1ccccc1-2] | 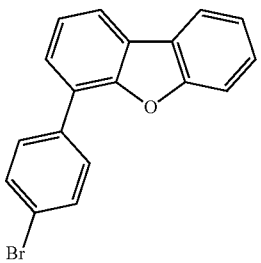 [SMILES: Brc1ccc(-c2cccc3c2oc2ccccc23)cc1] | 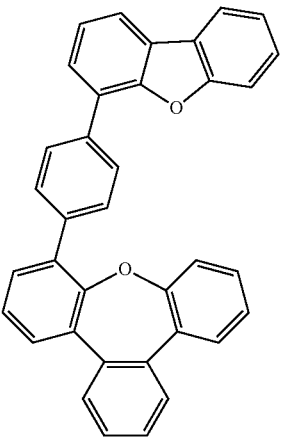 [SMILES: c1ccc2c(c1)Oc1c(-c3ccc(-c4cccc5c4oc4ccccc45)cc3)cccc1-c1ccccc1-2] | 90% |
| 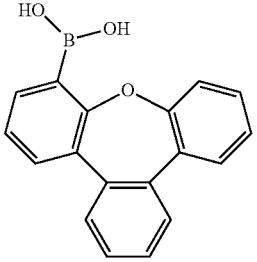 [SMILES: OB(O)c1cccc2c1Oc1ccccc1-c1ccccc1-2] | 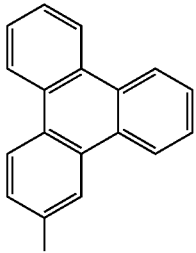 | 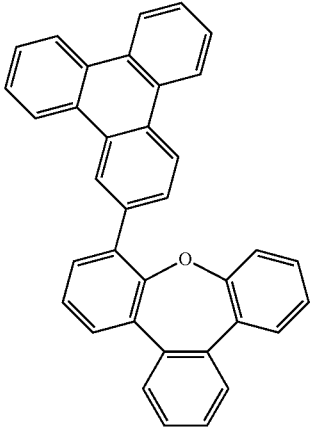 [SMILES: c1ccc2c(c1)Oc1c(-c3ccc4c5ccccc5c5ccccc5c4c3)cccc1-c1ccccc1-2] | 89% |
| 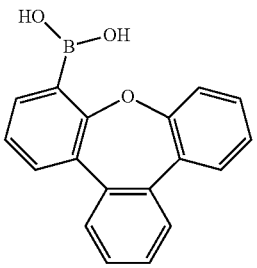 [SMILES: OB(O)c1cccc2c1Oc1ccccc1-c1ccccc1-2] | 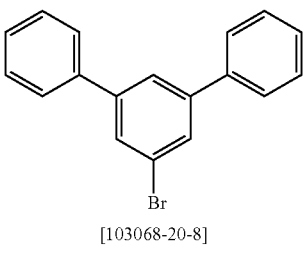 [SMILES: Brc1cc(-c2ccccc2)cc(-c2ccccc2)c1] [103068-20-8] | 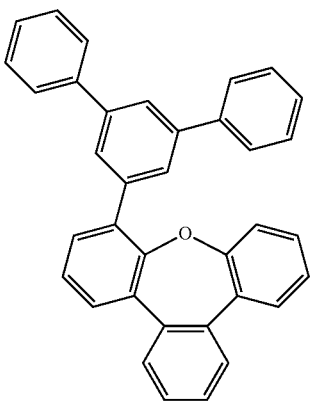 [SMILES: c1ccc(-c2cc(-c3ccccc3)cc(-c3cccc4c3Oc3ccccc3-c3ccccc3-4)c2)cc1] | 93% |

-continued
| Reactant 1 | Reactant 2 | Product | Yield |
|---|---|---|---|
| 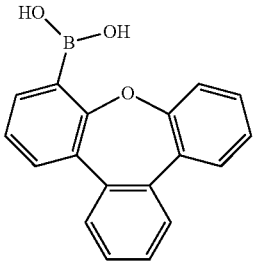 [SMILES: OB(O)c1cccc2c1Oc1ccccc1-c1ccccc1-2] | 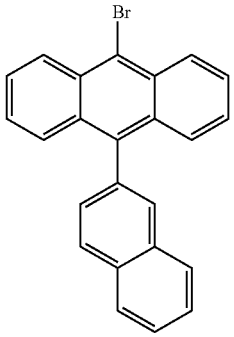
[474688-73-8] | 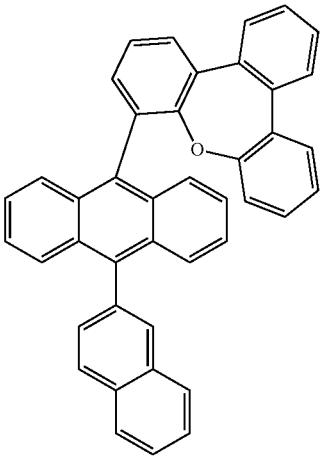 [SMILES: c1ccc2c(c1)Oc1c(cccc1-c1c3ccccc3c(-c3ccc4ccccc4c3)c3ccccc13)-c1ccccc1-2] | 79 % |
In an analogous manner, it is possible to obtain the following compounds with 0.5 eq. of corresponding boronic acid:
| Reactant 1 | Reactant 2 | Product | Yield |
|---|---|---|---|
| 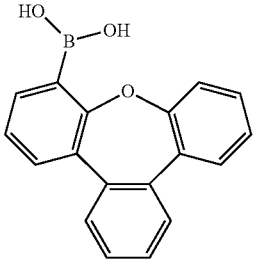 [SMILES: OB(O)c1cccc2c1Oc1ccccc1-c1ccccc1-2] | 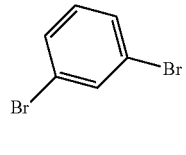 | 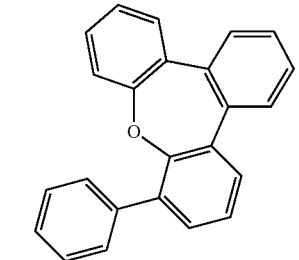 | 79% |
| 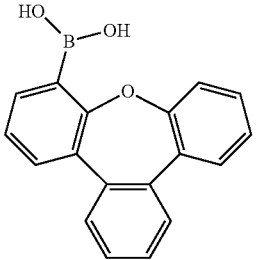 [SMILES: OB(O)c1cccc2c1Oc1ccccc1-c1ccccc1-2] | 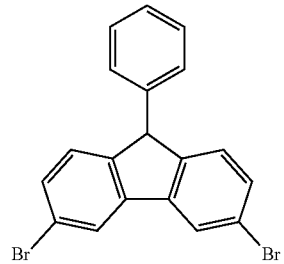
[57103-20-5] | 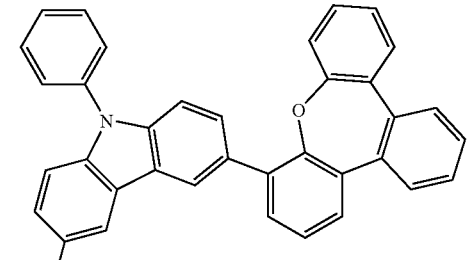 | 75% |

223
224
-continued
| Reactant 1 | Reactant 2 | Product | Yield |
|---|---|---|---|
| 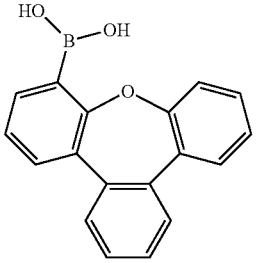 [SMILES: OB(O)c1cccc2c1Oc1ccccc1-c1ccccc1-2] | 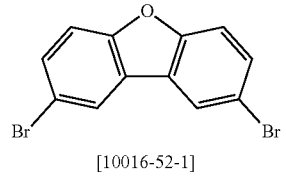 [SMILES: Brc1ccc2oc3ccc(Br)cc3c2c1] [10016-52-1] | 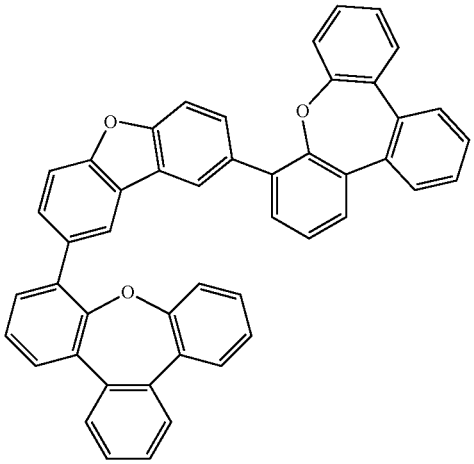 [SMILES: c1ccc2c(c1)Oc1c(-c3ccc4oc5ccc(-c6cccc7c6Oc6ccccc6-c6ccccc6-7)cc5c4c3)cccc1-c1ccccc1-2] | 76% |
| 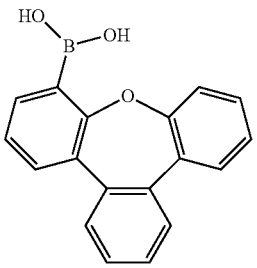 [SMILES: OB(O)c1cccc2c1Oc1ccccc1-c1ccccc1-2] | 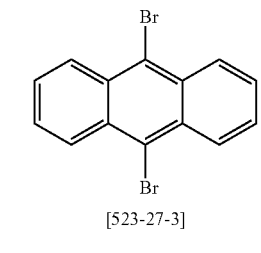 [SMILES: Brc1c2ccccc2c(Br)c2ccccc12] [523-27-3] | 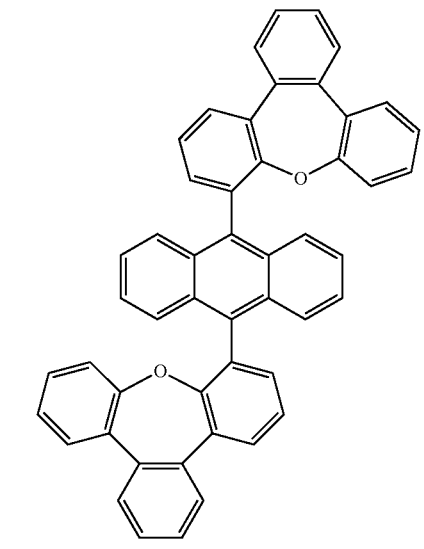 [SMILES: c1ccc2c(c1)Oc1c(cccc1-c1c3ccccc3c(-c3cccc4c3Oc3ccccc3-c3ccccc3-4)c3ccccc13)-c1ccccc1-2] | 79% |
Example 15
Synthesis of 3-(tribenz[a,c,e]oxepin-6-yl)-9-phenyl-9H-carbazole
-continued
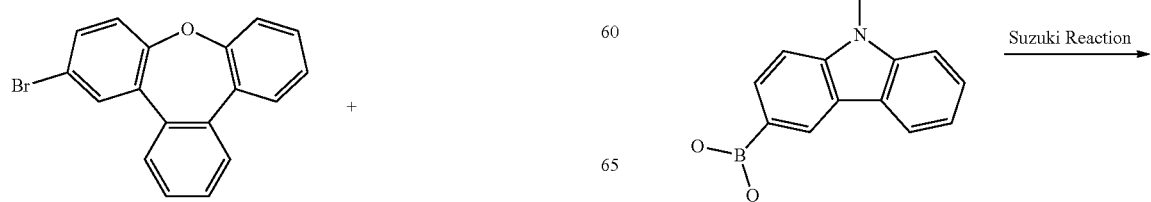
Suzuki Reaction →

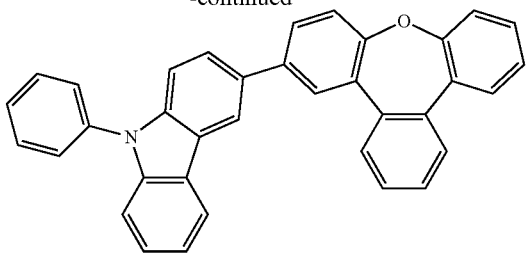

6-Bromotribenz[a,c,e]oxepine (Int-5) (132.3 mg; 0.41 mmol) and N-phenylcarbazole-3-boronic acid (129.3 mg; 0.45 mmol; 1.1 mol %) are initially charged together with potassium carbonate (124.5 mg; 0.90 mmol; 2.2 mol %) in a mixture of 3.5 mL of ethylene glycol dimethyl ether, 3.5 mL of toluene and 2.5 mL of demineralized water. Argon is passed through the mixture for 30 min. Added to the mixture thereafter are tri(o-tolyl)phosphine (3.37 mg; 0.011 mmol; 4 mol %) and Pd(OAc)$_2$ (1.24 mg; 0.006 mmol; 2 mol %). The reaction mixture is heated to 85° C. overnight. After cooling, the organic phase is separated off and the aqueous phase is extracted with 50 mL of CH$_2$Cl$_2$. The combined organic phases are extracted with 50 mL of water and dried with MgSO$_4$. The solvent is removed under reduced pressure and the oily residue is purified by column chromatography on silica gel with heptane/DCM (2/1) as eluent. The target product is obtained as a pale yellowish solid in 72% yield (100.5 mg, 0.31 mmol).

In an analogous manner, it is possible to obtain the following compounds:

| Reactant 1 | Reactant 2 | Product | Yield |
|---|---|---|---|
| ![Br-tribenzoxepine] | ![diphenyltriazine boronic acid] [1251825-65-6] | ![product1] | 56% |
| ![Br-tribenzoxepine] | ![triazine-phenyl boronic acid] [1269508-31-7] | ![product2] | 92% |
| ![Br-tribenzoxepine] | ![N-phenylbenzimidazole boronic acid] [1214723-25-7] | ![product3] | 75% |

-continued
| Reactant 1 | Reactant 2 | Product | Yield |
|---|---|---|---|
| 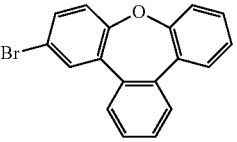 [SMILES: Brc1ccc2c(c1)-c1ccccc1-c1ccccc1O2] | 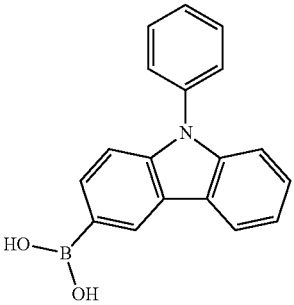
[854952-58-2] | 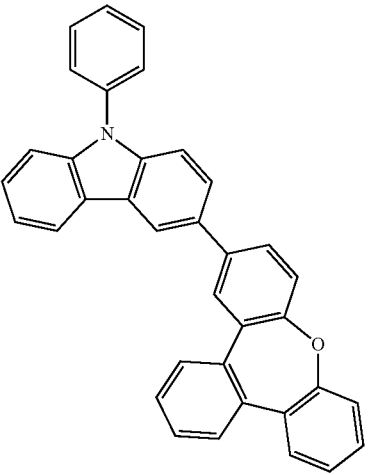 [SMILES: c1ccc(-n2c3ccccc3c3cc(-c4ccc5c(c4)-c4ccccc4-c4ccccc4O5)ccc32)cc1] | 76% |
| 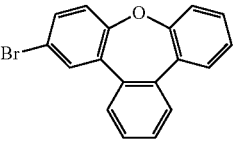 [SMILES: Brc1ccc2c(c1)-c1ccccc1-c1ccccc1O2] | 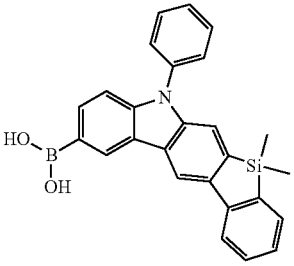
[1377576-48-1] | 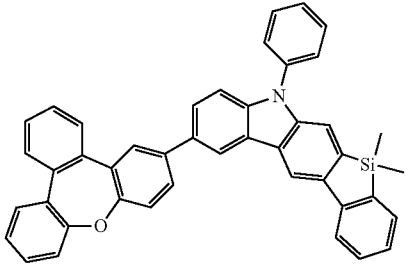 [SMILES: C[Si]1(C)c2ccccc2-c2cc3c4cc(-c5ccc6c(c5)-c5ccccc5-c5ccccc5O6)ccc4n(-c4ccccc4)c3cc21] | 84% |
| 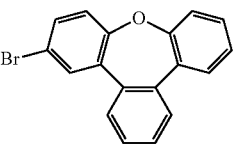 [SMILES: Brc1ccc2c(c1)-c1ccccc1-c1ccccc1O2] | 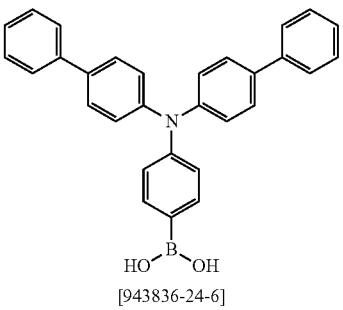 [SMILES: OB(O)c1ccc(N(c2ccc(-c3ccccc3)cc2)c2ccc(-c3ccccc3)cc2)cc1]
[943836-24-6] | 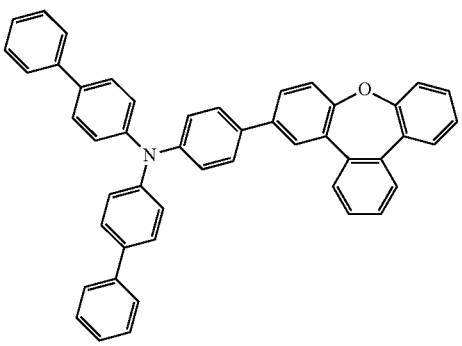 [SMILES: c1ccc(-c2ccc(N(c3ccc(-c4ccccc4)cc3)c3ccc(-c4ccc5c(c4)-c4ccccc4-c4ccccc4O5)cc3)cc2)cc1] | 89% |
In an analogous manner, it is possible to obtain the following compounds when 0.5 eq. of the boronic acid is used:
| Reactant 1 | Reactant 2 | Product | Yield |
|---|---|---|---|
| 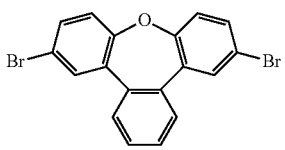 [SMILES: Brc1ccc2c(c1)-c1ccccc1-c1cc(Br)ccc1O2] | 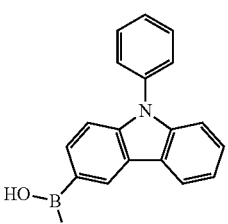
[854952-58-2] | 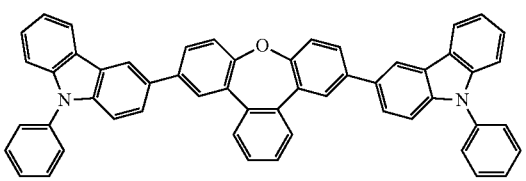 [SMILES: c1ccc(-n2c3ccccc3c3cc(-c4ccc5c(c4)-c4ccccc4-c4cc(-c6ccc7c(c6)c6ccccc6n7-c6ccccc6)ccc4O5)ccc32)cc1] | 72% |

| Reactant 1 | Reactant 2 | Product | Yield |
|---|---|---|---|
| | [1214723-25-7] | | 74% |
| | [1251825-65-6] | | 63% |
| | [100124-06-9] | | 72% |
| | [128388-54-5] | | 76% |

Example 16

Synthesis of 2-(12-bromotribenz[a,c,e]oxepin-8-yl)-4,6-diphenyl-[1,3,5]triazine

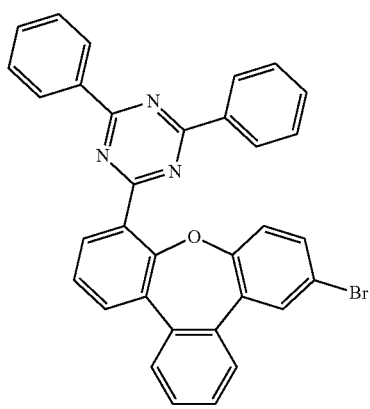

5 g (10.5 mmol) of 2-(tribenz[a,c,e]oxepin-8-yl)-4,6-diphenyl-[1,3,5]triazine are initially charged together with 2.06 g of N-bromosuccinimide (11.6 mmol, 110 mol %) in 100 mL of dry dimethylformamide (DMF). The reaction mixture is heated to 60° C. for 48 h and then the solvent is removed under reduced pressure. The residue is purified by column chromatography on silica gel with heptane/DCM (2/1) as eluent. The bromide is obtained as a colorless solid in 74% yield (4.31 g; 7.78 mmol).

In an analogous manner, it is possible to obtain the following with 2 eq. of NBS corresponding dibromides:

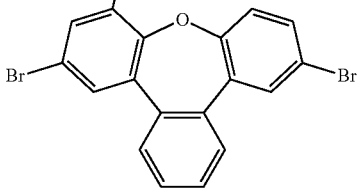

Example 17

Synthesis of 3-[10-(4,6-diphenyl-[1,3,5]triazine-2-yl)-tribenz[a,c,e]oxepin-6-yl]-9-phenyl-9H-carbazole

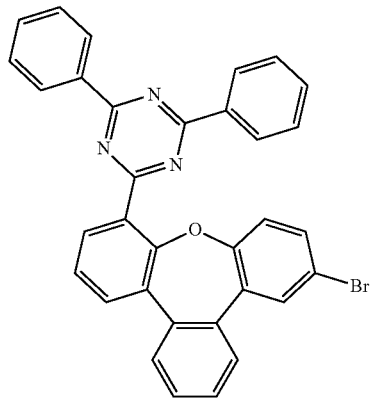 [SMILES: Brc1ccc2c(c1)-c1ccccc1-c1cccc(-c3nc(-c4ccccc4)nc(-c4ccccc4)n3)c1O2]

+

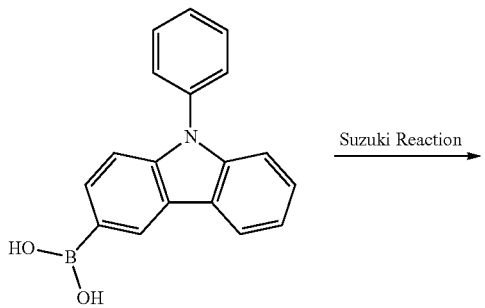

→ Suzuki Reaction →

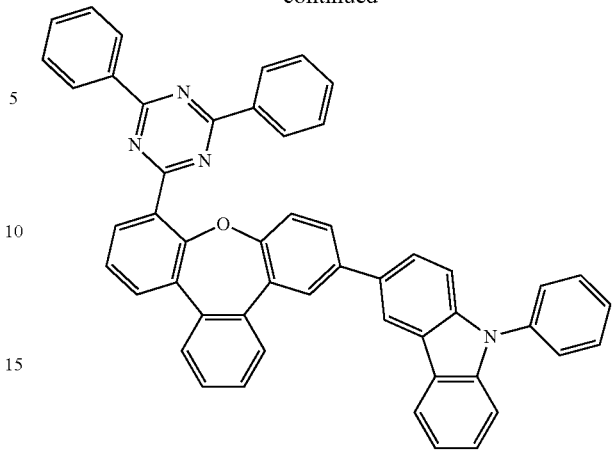

5 g (9 mmol) of 2-(12-bromotribenz[a,c,e]oxepin-8-yl)-4,6-diphenyl-[1,3,5]triazine and N-phenylcarbazole-3-boronic acid (2.85 g; 9.9 mmol; 110 mol %) are initially charged together with potassium carbonate (2.74 g; 19.8 mmol; 220 mol %) in a mixture of 200 mL of ethylene glycol dimethyl ether, 200 mL of toluene and 150 mL of demineralized water. Argon is passed through the mixture for 30 min. Added to the mixture thereafter are tri(o-tolyl)phosphine (274 mg; 0.90 mmol; 10 mol %) and Pd(OAc)$_2$ (101 mg; 0.45 mmol; 5 mol %). The reaction mixture is heated to 85° C. overnight. After cooling, the organic phase is separated off and the aqueous phase is extracted with 50 mL of CH$_2$Cl$_2$. The combined organic phases are extracted with 50 mL of water and dried with MgSO$_4$. The solvent is removed under reduced pressure and the oily residue is purified by column chromatography on silica gel with heptane/DCM (2/1) as eluent. The residue is recrystallized from toluene and finally sublimed under high vacuum (p=5×10$^{-6}$ mbar). Yield: 5.62 g (7.85 mmol), 87%; purity: 99.9% by HPLC.

In an analogous manner, it is possible to obtain the following compounds:

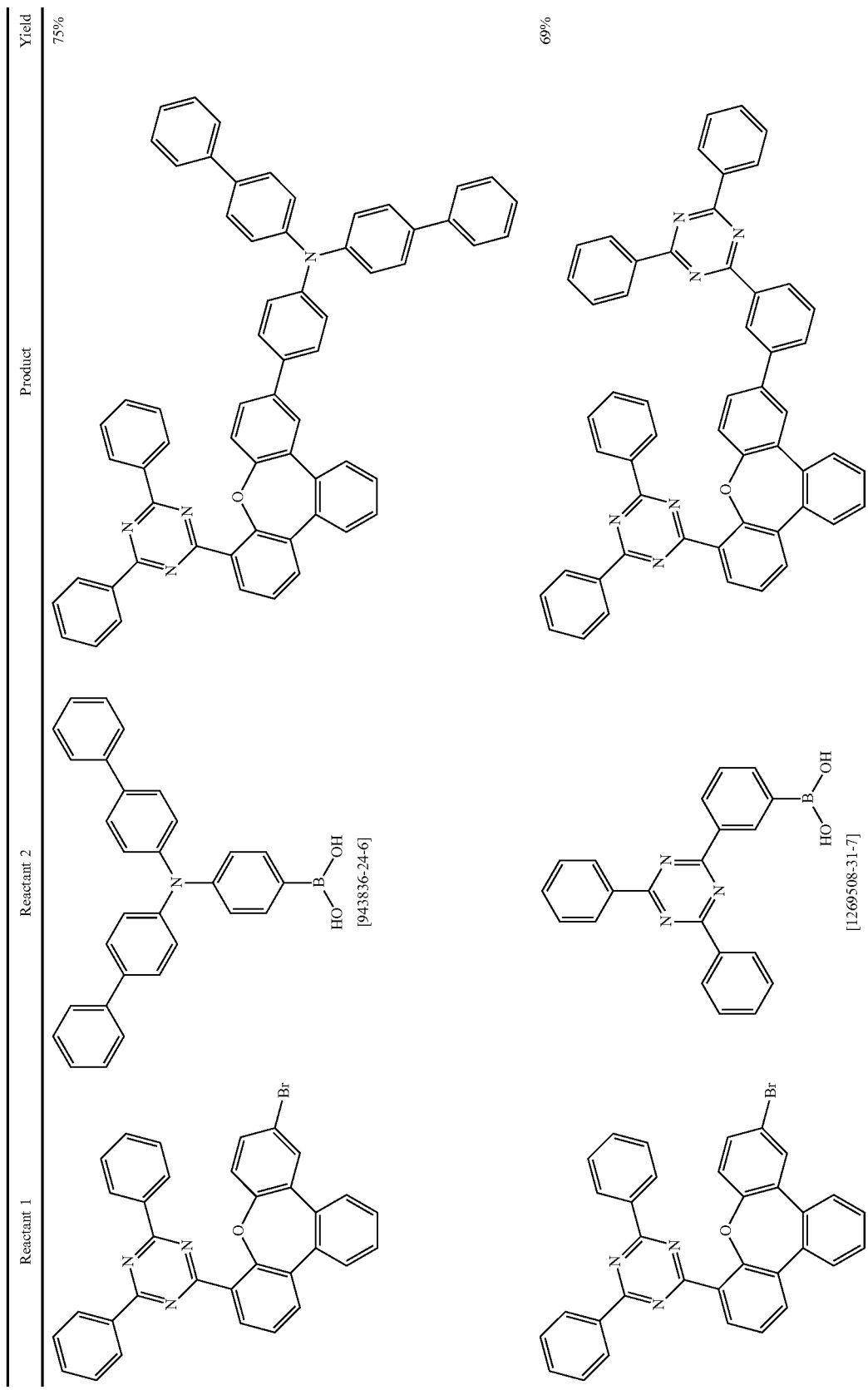

-continued
| Reactant 1 | Reactant 2 | Product | Yield |
|---|---|---|---|
| 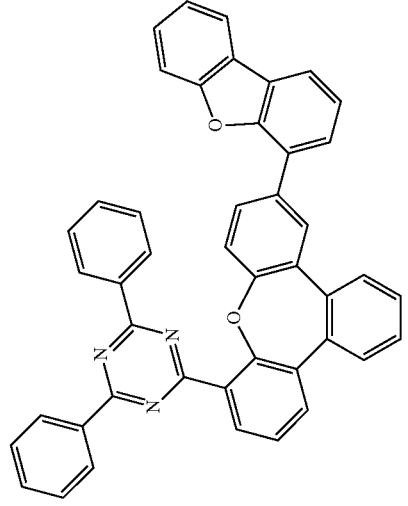 | 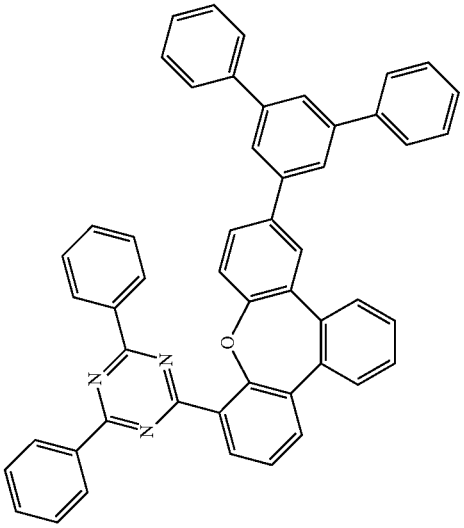 [100124-06-9] | 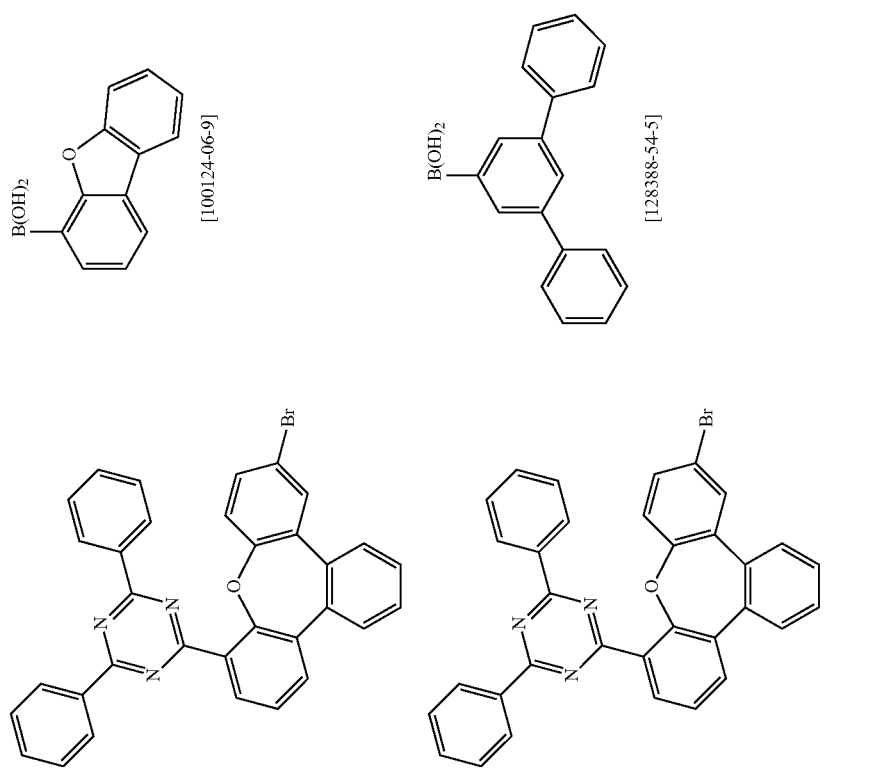 | 76% |
| 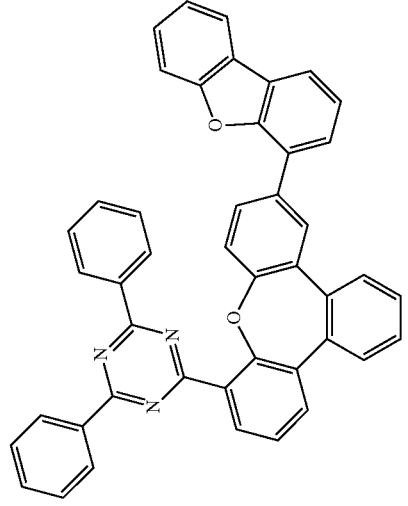 | 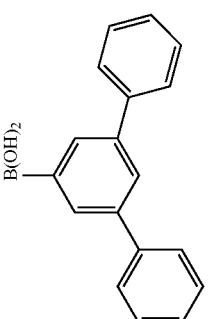 [128388-54-5] | 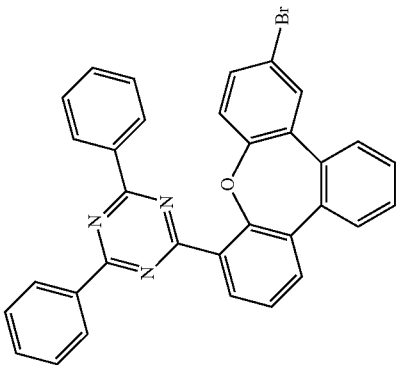 | 79% |

| Reactant 1 | Reactant 2 | Product | Yield |
|---|---|---|---|
| 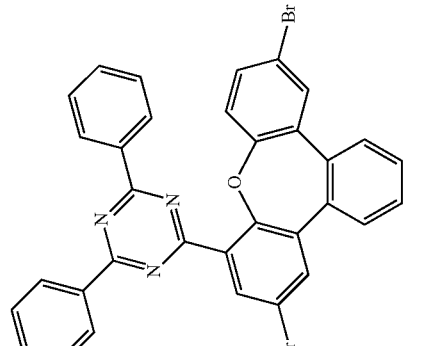 | 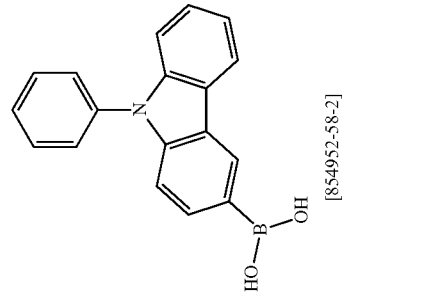 [854952-58-2] | 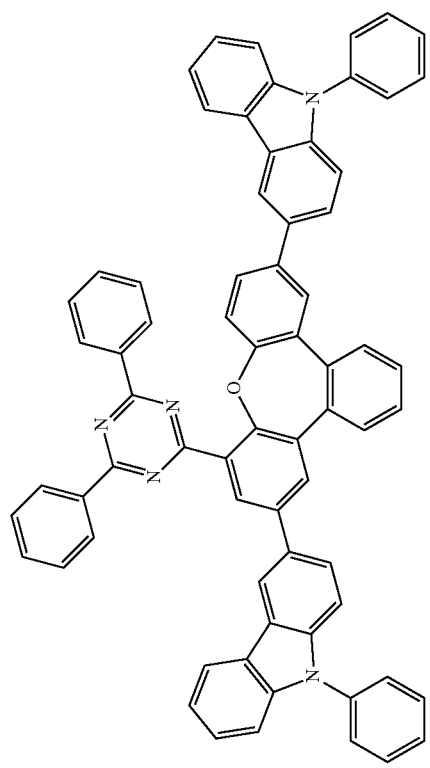 | 62% |

Example 18

Synthesis of biphenyl-4-yl-(9,9-dimethyl-9H-fluoren-2-yl)-(9-oxatribenzo[a,c,e]cyclohepten-6-yl)-amine

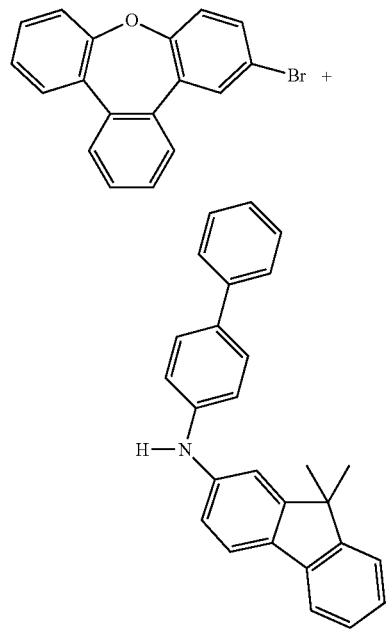

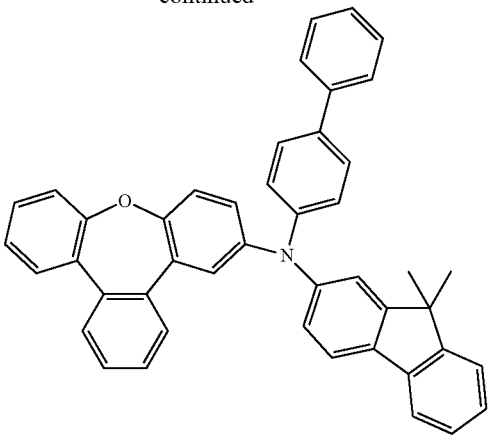

A mixture of 16 g (50 mmol) of 6-bromotribenz[a,c,e]oxepine, 21.7 g (60 mmol) of 4-biphenyl-2-(9,9'-dimethylfluorenyl)amine [897671-69-1], 7.7 g (80 mmol) of sodium tert-butoxide, 1.4 g (5 mmol) of tricyclohexylamine, 561 mg (2.5 mmol) of palladium(II) acetate and 300 mL of mesitylene is heated under reflux for 24 h. After cooling, 200 mL of water are added, the mixture is stirred for a further 30 min, the organic phase is removed and the latter is filtered through a short Celite bed and then the solvent is removed under reduced pressure. The residue is recrystallized five times from DMF and finally fractionally sublimed twice (p about $10^{-6}$ mbar, T=330-340° C.). Yield: 21.7 g (34 mmol), 72%; purity: 99.9% by HPLC.

In an analogous manner, it is possible to obtain the following compounds:

| Reactant 1 | Reactant 2 | Product | Yield |
|---|---|---|---|
| | [102113-98-4] | | 43% |
| | 1198395-24-2 | | 72% |

-continued
| Reactant 1 | Reactant 2 | Product | Yield |
|---|---|---|---|
| 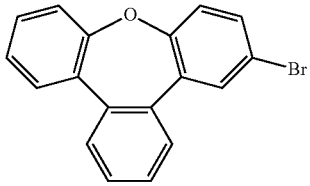 [SMILES: Brc1ccc2c(c1)-c1ccccc1-c1ccccc1O2] | 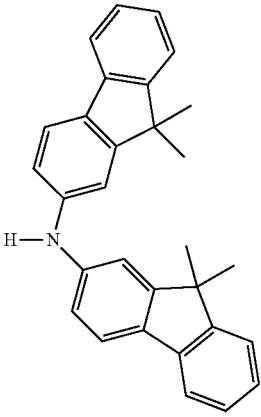 500717-23-7 | 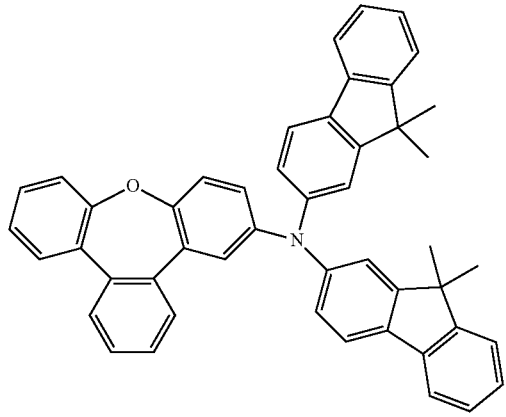 [SMILES: CC1(C)c2ccccc2-c2ccc(N(c3ccc4c(c3)-c3ccccc3-c3ccccc3O4)c3ccc4c(c3)C(C)(C)c3ccccc3-4)cc21] | 61% |
| 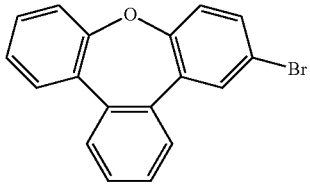 [SMILES: Brc1ccc2c(c1)-c1ccccc1-c1ccccc1O2] | 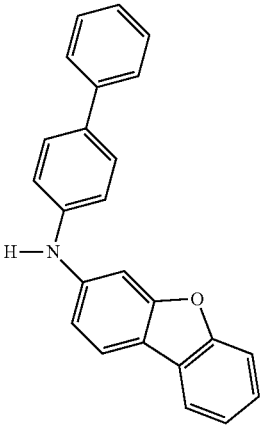 1290039-85-8 | 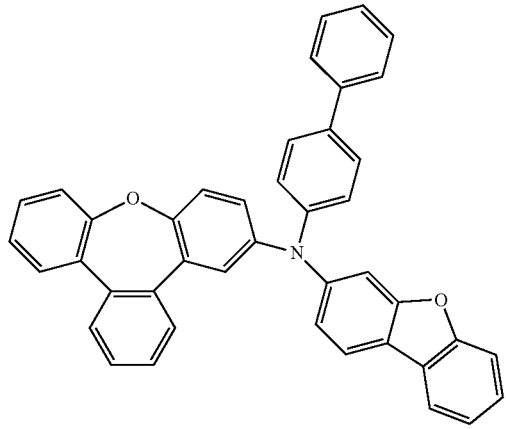 [SMILES: c1ccc(-c2ccc(N(c3ccc4c(c3)-c3ccccc3-c3ccccc3O4)c3ccc4c(c3)oc3ccccc34)cc2)cc1] | 73% |
| 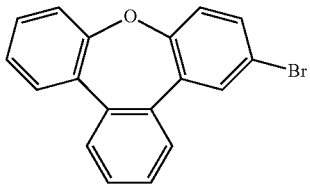 [SMILES: Brc1ccc2c(c1)-c1ccccc1-c1ccccc1O2] | 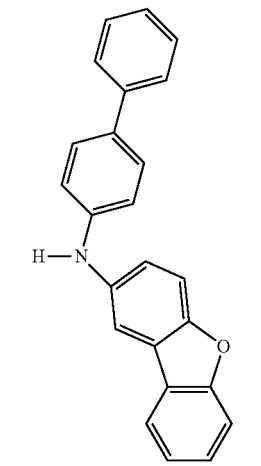 1300028-94-7 | 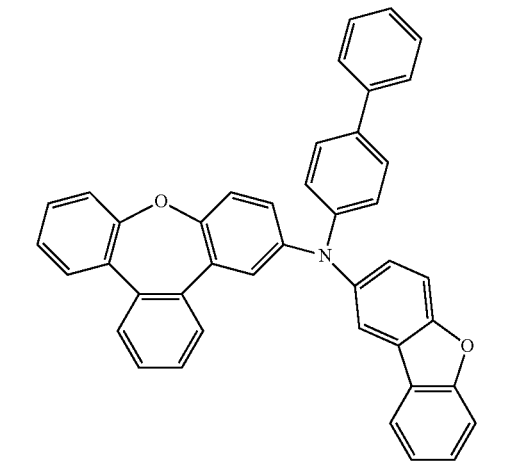 [SMILES: c1ccc(-c2ccc(N(c3ccc4c(c3)-c3ccccc3-c3ccccc3O4)c3ccc4oc5ccccc5c4c3)cc2)cc1] | 67% |

-continued
| Reactant 1 | Reactant 2 | Product | Yield |
|---|---|---|---|
| 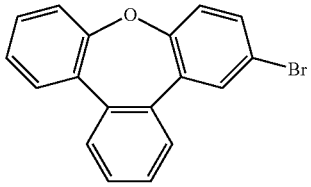 [SMILES: Brc1ccc2c(c1)-c1ccccc1-c1ccccc1O2] | 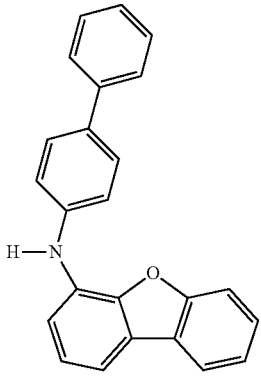<br>1318338-47-4 | 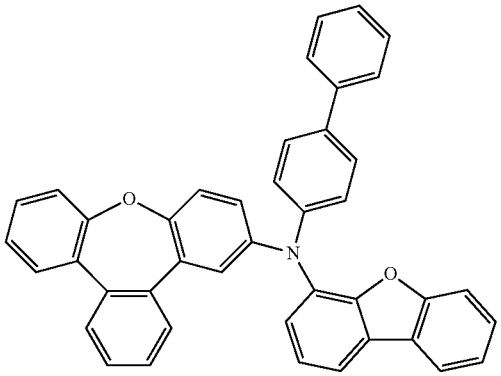 [SMILES: c1ccc(-c2ccc(N(c3ccc4c(c3)-c3ccccc3-c3ccccc3O4)c3cccc4c3oc3ccccc34)cc2)cc1] | 60% |
| 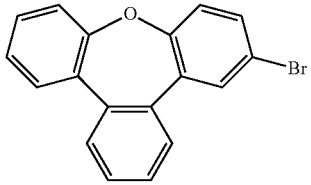 [SMILES: Brc1ccc2c(c1)-c1ccccc1-c1ccccc1O2] | 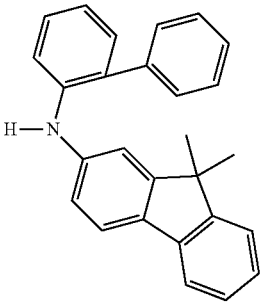<br>1198395-24-2 | 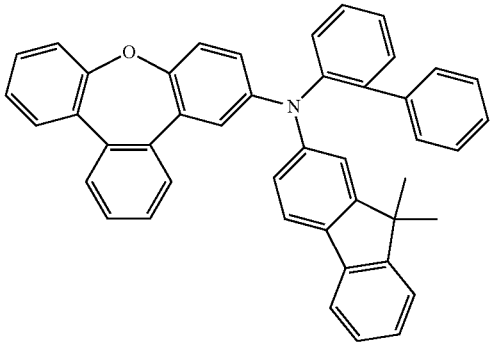 [SMILES: CC1(C)c2ccccc2-c2ccc(N(c3ccc4c(c3)-c3ccccc3-c3ccccc3O4)c3ccccc3-c3ccccc3)cc21] | 64% |
| 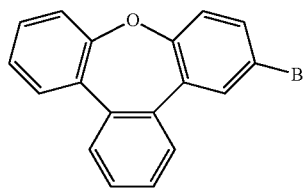 | 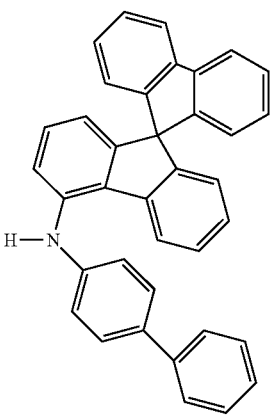<br>[1421789-18-5] | 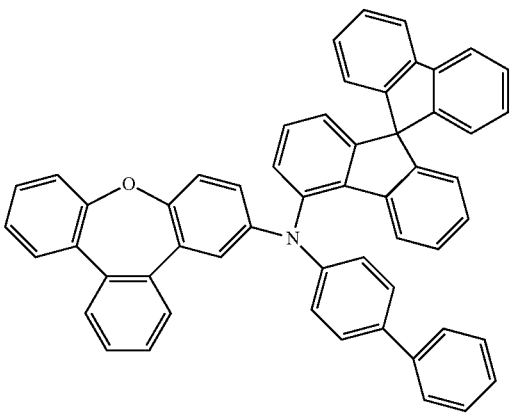 [SMILES: c1ccc(-c2ccc(N(c3ccc4c(c3)-c3ccccc3-c3ccccc3O4)c3cccc4c3-c3ccccc3C43c4ccccc4-c4ccccc43)cc2)cc1] | 72% |

In an analogous manner, 0.5 eq. of dibromides can be used to obtain the following compounds:
| Reactant 1 | Reactant 2 | Product | Yield |
|---|---|---|---|
| 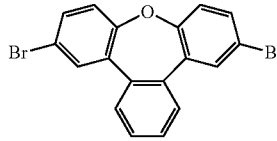 | 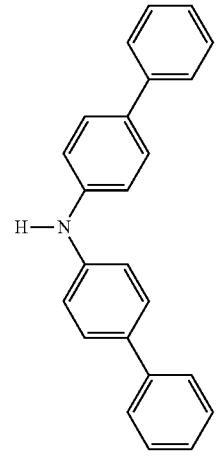  102113-98-4 | 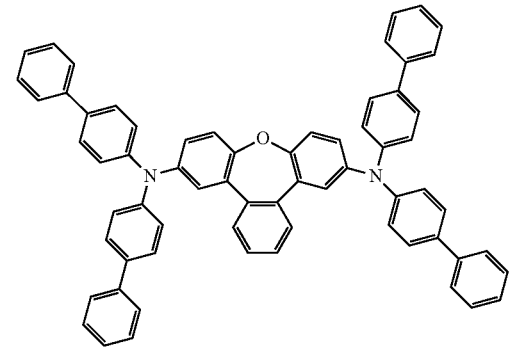 [SMILES: c1ccc(-c2ccc(N(c3ccc(-c4ccccc4)cc3)c3ccc4c(c3)-c3ccccc3-c3cc(N(c5ccc(-c6ccccc6)cc5)c5ccc(-c6ccccc6)cc5)ccc3O4)cc2)cc1] | 58% |
| 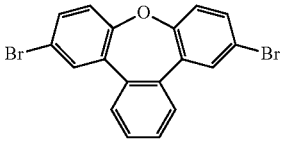 | 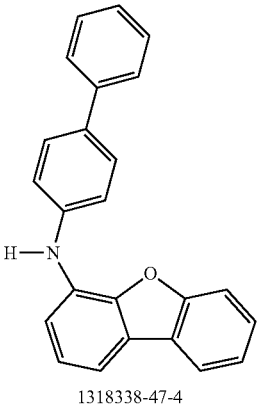 [SMILES: c1ccc(-c2ccc(Nc3cccc4c3oc3ccccc34)cc2)cc1]  1318338-47-4 | 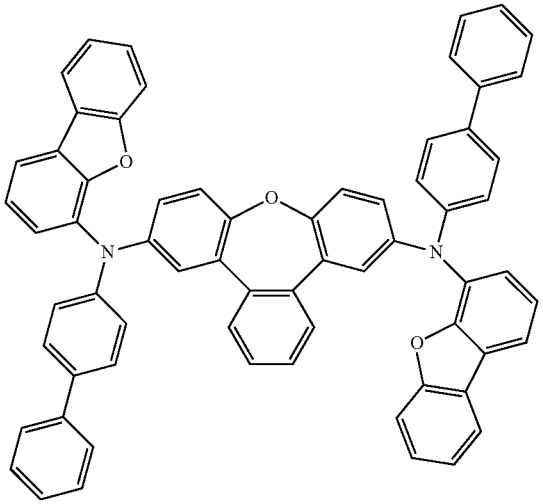 [SMILES: c1ccc(-c2ccc(N(c3ccc4c(c3)-c3ccccc3-c3cc(N(c5ccc(-c6ccccc6)cc5)c5cccc6c5oc5ccccc56)ccc3O4)c3cccc4c3oc3ccccc34)cc2)cc1] | 69% |
Example 19
Synthesis of 9-(9-oxatribenzo[a,c,e]cyclohepten-6-yl)-9'-phenyl-9H,9'H-[3,3']bicarbazolyl
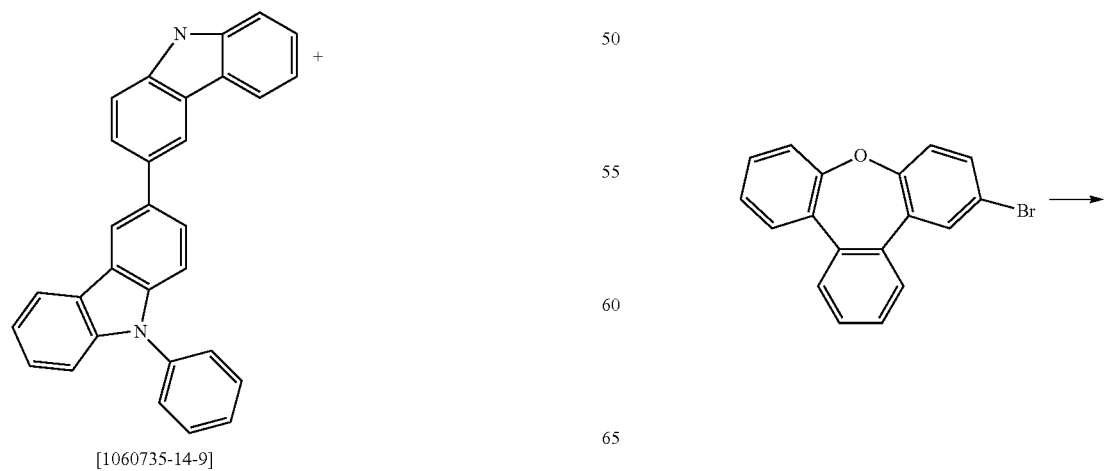
[1060735-14-9]
-continued

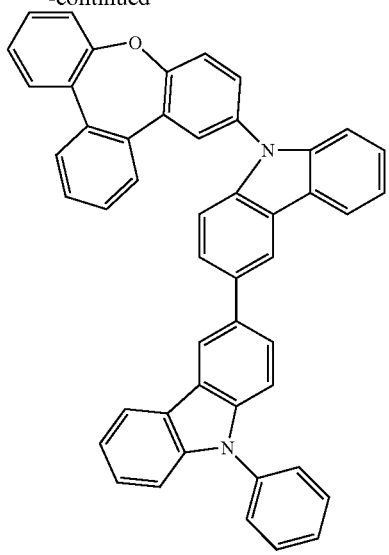

18.7 g (46 mmol) of 9-phenyl-3,3'-bicarbazole and 14.8 g (46 mmol) of 6-bromotribenz[a,c,e]oxepine are dissolved in 450 mL of toluene and degassed by means of introduction of protective gas. This is followed by addition of 7 mL (7 mmol, 1 M solution in toluene) of tri-tert-butylphosphine, 633.8 mg (2.82 mmol) of Pd(OAc)$_2$ and 7 g (76 mmol) of NaOtBu. The solids are degassed beforehand, and the reaction mixture is post-degassed and then stirred under reflux for 3 h. The warm reaction solution is filtered through Alox B (activity level 1), washed with water, dried and concentrated. The residue is recrystallized from toluene and finally sublimed under high vacuum (p=5×10$^{-6}$ mbar). Yield: 24 g (38 mmol), 83%; purity: 99.9% by HPLC.

In an analogous manner, it is possible to obtain the following compounds:

| Reactant 1 | Reactant 2 | Product | Yield |
|---|---|---|---|
| (structure) | (structure) [103012-26-6] | (structure) | 68% |
| (structure) | (structure) [1439927-96-4] | (structure) | 65% |

-continued
| Reactant 1 | Reactant 2 | Product | Yield |
|---|---|---|---|
| 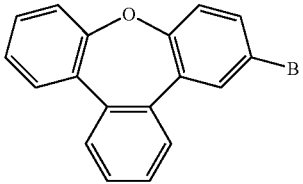 | 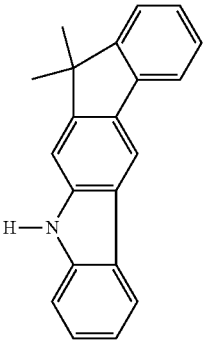<br>[1257220-47-5]] | 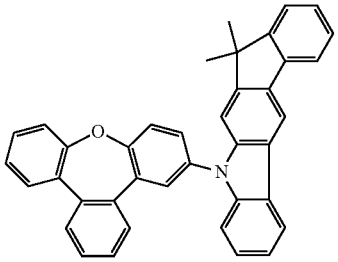 [SMILES: CC1(C)c2ccccc2-c2cc3c4ccccc4n(-c4ccc5c(c4)-c4ccccc4-c4ccccc4O5)c3cc21] | 64% |
| 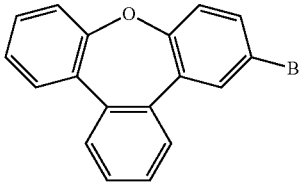 | 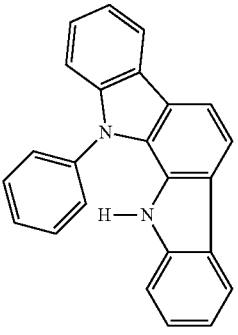<br>[1024598-06-8] | 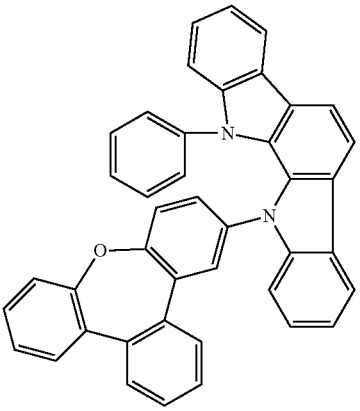 [SMILES: c1ccc(-n2c3ccccc3c3ccc4c5ccccc5n(-c5ccc6c(c5)-c5ccccc5-c5ccccc5O6)c4c32)cc1] | 61% |
In an analogous manner, 0.5 eq. of the corresponding dibromides can be used to obtain the following compound:
| Reactant 1 | Reactant 2 | Product | Yield |
|---|---|---|---|
| 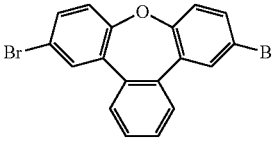 | 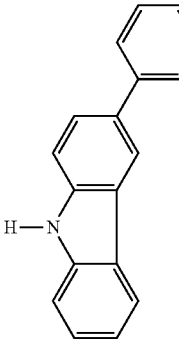<br>[103012-26-6]<br>102113-98-4 | 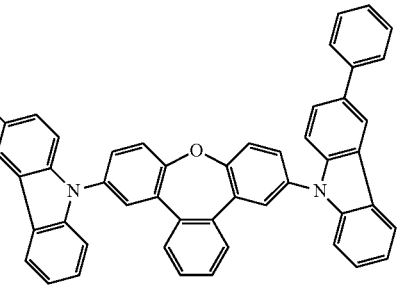 | 68% |

Example 20

Synthesis of (2-chlorophenyl)-(9-oxatribenzo[a,c,e]cyclohepten-6-yl)amine

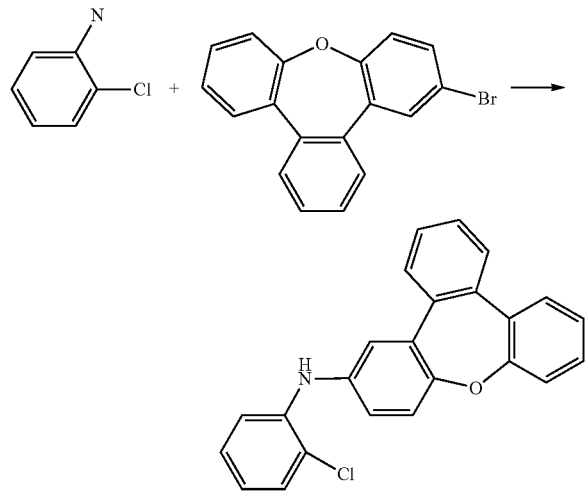

25.5 g (79 mmol) of 6-bromotribenz[a,c,e]oxepine, 10 mL (95 mmol) of 2-chloroaniline, 36.3 g (111 mmol) of cesium carbonate, 0.89 g (3.9 mmol) of palladium(II) acetate and 3.9 g (6 mmol) of 2,2'-bis(diphenylphosphanyl)-[1,1']binaphthalene are dissolved in 500 mL of toluene and stirred under reflux for 5 h. The reaction mixture is cooled down to room temperature, extended with toluene and filtered through Celite. The filtrate is concentrated under reduced pressure and the residue is crystallized from toluene/heptane. The product is isolated as a colorless solid. Yield: 22 g (61 mmol), 78% of theory.

Example 21

Cyclization

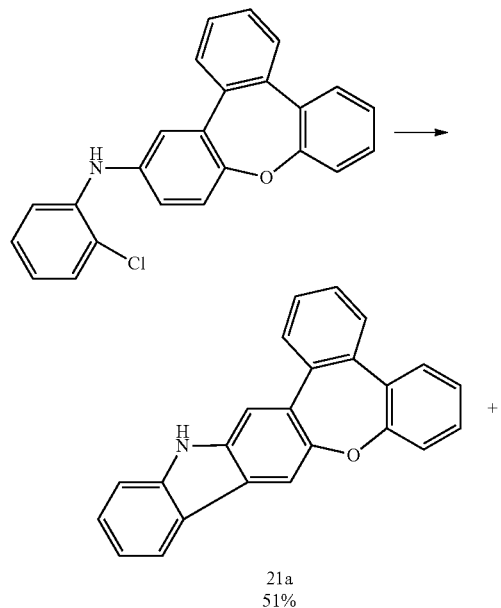

21a
51%

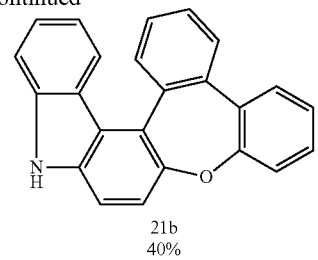

21b
40%

36.7 g (102 mmol) of (2-chlorophenyl)-(9-oxatribenzo[a,c,e]cyclohepten-6-yl)-amine, 32 g (268 mmol) of potassium carbonate, 0.6 g (2.7 mmol) of palladium(II) acetate and 4.2 mL (4.2 mmol) of tri-tert-butylphosphine are suspended in 350 mL of dimethylacetamide and stirred under reflux for 6 h. After the reaction mixture has cooled, 300 mL of water and 400 mL of ethyl acetate are added. The mixture is stirred for a further 30 min, the organic phase is separated off and filtered through a short Celite bed, and then the solvent is removed under reduced pressure. The crude product is subjected to hot extraction with toluene and recrystallized from toluene. The isomers are separated by chromatography. Yield: 30 g (91 mmol), 92% of theory.

Example 22

Arylation

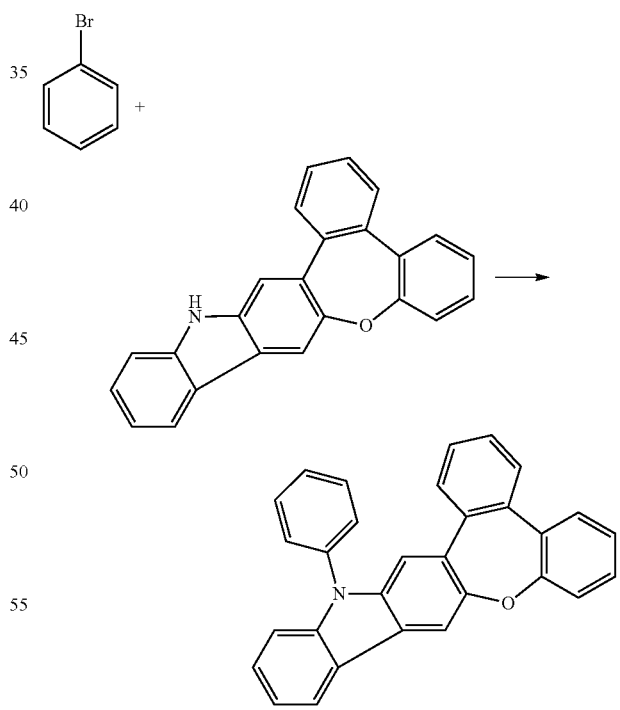

35 g (106 mmol) of compound 21a, 17.9 g (114 mmol) of bromobenzene and 30.5 g of NaOtBu are suspended in 1.5 L of p-xylene. To this suspension are added 0.5 g (2.11 mmol) of Pd(OAc)$_2$ and 6 mL of a 1M tri-tert-butylphosphine (1 M solution in toluene). The reaction mixture is heated under reflux for 16 h. After cooling, the organic phase is removed, washed three times with 200 mL each time of water and then concentrated to dryness. The residue is hot-extracted with toluene, recrystallized from toluene and finally sublimed under high vacuum; purity is 99.9% at a yield of 29 g (73 mmol; 69%).

In an analogous manner, it is possible to prepare the following compound:

Example 23

Production of OLEDs

OLEDs of the invention and OLEDs according to the prior art are produced by a general method according to WO

| Reactant 1 | Reactant 2 | Product | Yield |
|---|---|---|---|
| | [19111-87-6] | | 78% |
| | [955959-84-9] | | 79% |
| | [1153-85-1] | | 88% |
| | [56181-49-6] | | 83% |

04/058911, which is adapted to the circumstances described here (variation in layer thickness, materials).

In the examples which follow (see tables 1 and 2), the data of various OLEDs are presented. Substrates used are glass plates coated with structured ITO (indium tin oxide) of thickness 50 nm, The OLEDs basically have the following layer structure: substrate/interlayer (IL)/hole injection layer (HIL)/electron blocker layer (EBL)/emission layer (EML)/electron transport layer (ETL)/electron injection layer (EIL) and finally a cathode. The EIL is obtained by vapor deposition of a 2 nm-thick layer consisting of Liq. The cathode is formed by an aluminum layer of thickness 100 nm. The exact structure of the OLEDs can be found in Table 1. The materials required for production of the OLEDs are shown in Table 3.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as H1:D1 (95%: 5%) mean here that the material H1 is present in the layer in a proportion by volume of 95% and SEB1 in a proportion of 5%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian radiation characteristics, and also the lifetime are determined. The electroluminescence spectra are determined at a luminance of 1000 cd/m$^2$, and the CIE 1931 x and y color coordinates are calculated therefrom. The parameter EQE @ 1000 cd/m$^2$ refers to the external quantum efficiency at an operating luminance of 1000 cd/m$^2$. LD80 @ 100 mA/cm$^2$ or 60 mA/cm$^2$ is the lifetime by which the OLED has dropped to 80% of the starting intensity when the OLED is being operated at a current of 100 mA/cm$^2$ or 60 mA/cm$^2$. For green-emitting OLEDs a starting brightness of 100 mA/cm$^2$ is chosen, and for blue-emitting OLEDs a starting brightness of 60 mA/cm$^2$. The data for the various OLEDs are collated in Table 2.

Use of Inventive Compounds as Matrix Materials, as Emitter and as Electron Transport Material in Green- or Blue-Fluorescing OLEDs The inventive compounds are especially suitable as matrix material, dopant or else as electron transport material in OLEDs. They are suitable as an individual layer, but also as a mixed component within the EML or ETL. Compared to reference components (C1 or C4), all samples comprising the inventive compounds exhibit higher efficiencies, lower operating voltage and/or distinctly improved lifetimes in green- or blue- or green-fluorescing OLEDs. Component C5 comprising the inventive compound INV-3 exhibits a much deeper color than the reference component C4.

TABLE 1

Structure of the OLEDs

| Ex. | IL Thickness/nm | HIL Thickness/nm | EBL Thickness/nm | EML Thickness/nm | ETL Thickness/nm |
|---|---|---|---|---|---|
| C1 | HIL1 5 nm | HIL2 140 nm | NPB 20 nm | H1(95%):G1(5%) 20 nm | ETM1(50%):LiQ(50%) 30 nm |
| C2 | HIL1 5 nm | HIL2 140 nm | NPB 20 nm | INV-1(95%):G1(5%) 20 nm | ETM1(50%):LiQ(50%) 30 nm |
| C3 | HIL1 5 nm | HIL2 140 nm | NPB 20 nm | INV-2(95%):G1(5%) 20 nm | ETM1(50%):LiQ(50%) 30 nm |
| C4 | HIL1 5 nm | HIL2 140 nm | NPB 20 nm | H1(95%):B1(5%) 20 nm | ETM1(50%):LiQ(50%) 30 nm |
| C5 | HIL1 5 nm | HIL2 140 nm | NPB 20 nm | H1(95%):INV-3(5%) 20 nm | ETM1(50%):LiQ(50%) 30 nm |
| C6 | HIL1 5 nm | HIL2 140 nm | NPB 20 nm | H1(95%):B1(5%) 20 nm | INV-6(50%):LiQ(50%) 30 nm |

TABLE 2

Data of the OLEDs

| Ex. | EQE @ 1000 cd/m2 % | U @ 1000 cd/m2 V | LD80 @ 100 mA/cm$^2$ or 60 mA/cm$^2$ [h] | CIE x | CIE y |
|---|---|---|---|---|---|
| C1 | 7.0 | 4.2 | 190 | 0.27 | 0.66 |
| C2 | 7.5 | 4.4 | 190 | 0.27 | 0.67 |
| C3 | 6.8 | 4.0 | 270 | 0.27 | 0.67 |
| C4 | 6.3 | 5.0 | 210 | 0.14 | 0.16 |
| C5 | 6.7 | 4.7 | 200 | 0.13 | 0.14 |
| C6 | 6.3 | 4.8 | 250 | 0.14 | 0.16 |

TABLE 3
Materials used
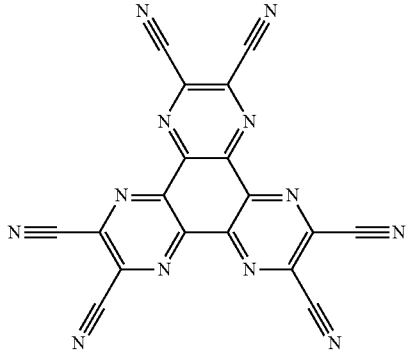 [SMILES: N#Cc1nc2c3nc(C#N)c(C#N)nc3c3nc(C#N)c(C#N)nc3c2nc1C#N]
HIL1
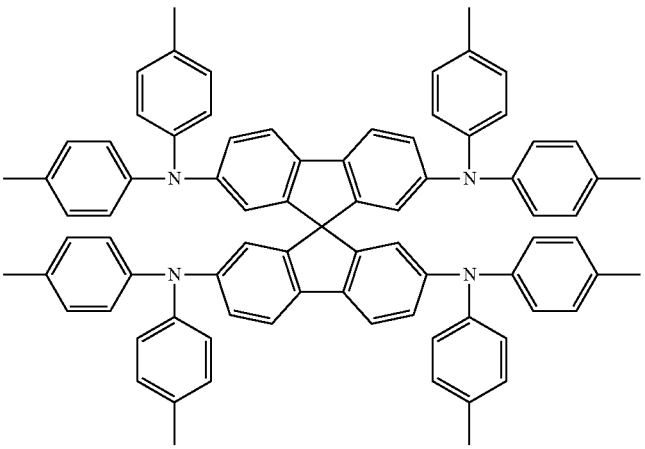
HIL2
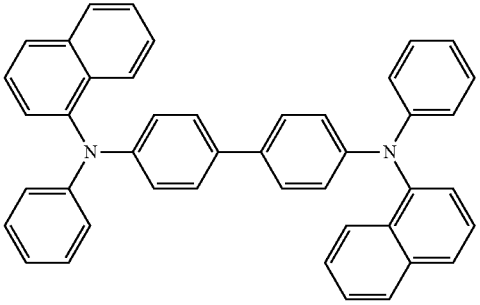 [SMILES: c1ccc(N(c2ccc(-c3ccc(N(c4ccccc4)c4cccc5ccccc45)cc3)cc2)c2cccc3ccccc23)cc1]
NPB
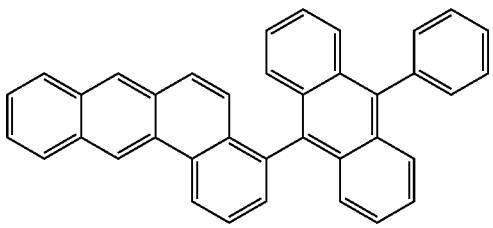 [SMILES: c1ccc(-c2c3ccccc3c(-c3cccc4c3ccc3cc5ccccc5cc34)c3ccccc23)cc1]
H1
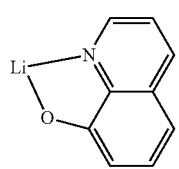
LiQ TABLE 3-continued
Materials used
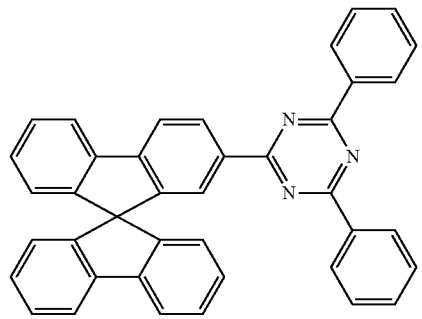 [SMILES: c1ccc(-c2nc(-c3ccccc3)nc(-c3ccc4c(c3)C3(c5ccccc5-c5ccccc53)c3ccccc3-4)n2)cc1]
ETM1
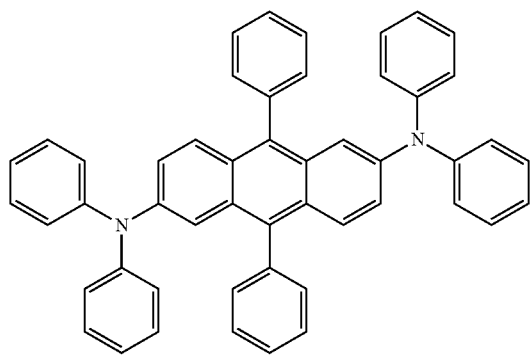 [SMILES: c1ccc(-c2c3ccc(N(c4ccccc4)c4ccccc4)cc3c(-c3ccccc3)c3ccc(N(c4ccccc4)c4ccccc4)cc23)cc1]
G1
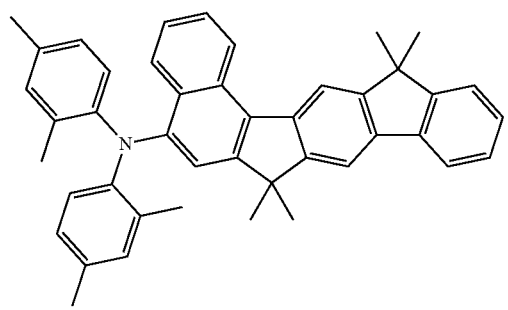 [SMILES: Cc1ccc(N(c2ccc(C)cc2C)c2cc3c(c4ccccc24)-c2cc4c(cc2C3(C)C)-c2ccccc2C4(C)C)c(C)c1]
B1
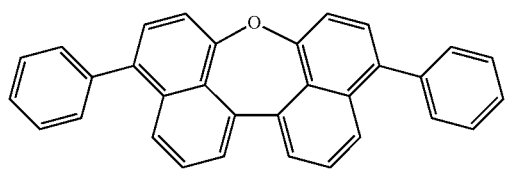 [SMILES: c1ccc(-c2ccc3oc4ccc(-c5ccccc5)c5cccc(c6cccc2c36)c45)cc1]
INV-1
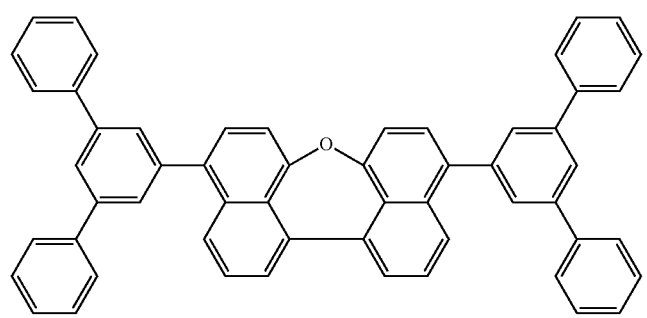 [SMILES: c1ccc(-c2cc(-c3ccccc3)cc(-c3ccc4oc5ccc(-c6cc(-c7ccccc7)cc(-c7ccccc7)c6)c6cccc(c7cccc3c47)c56)c2)cc1]
INV-2

TABLE 3-continued

Materials used

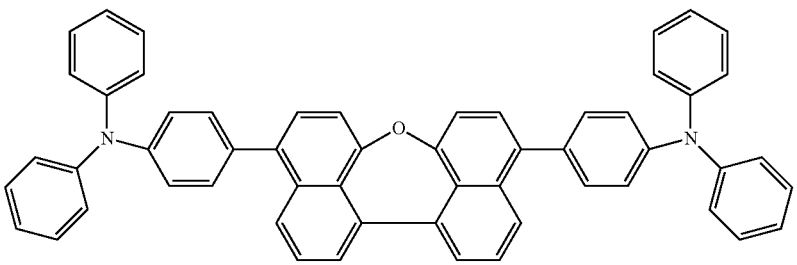 [SMILES: c1ccc(N(c2ccccc2)c2ccc(-c3ccc4oc5ccc(-c6ccc(N(c7ccccc7)c7ccccc7)cc6)c6cccc(c7cccc3c47)c56)cc2)cc1]

INV-3

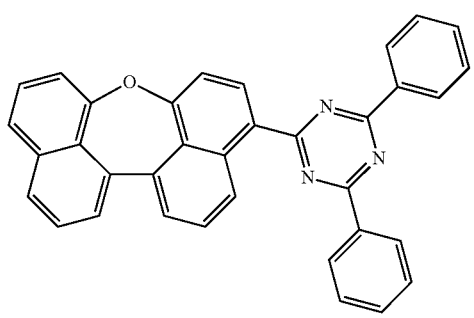 [SMILES: c1ccc(-c2nc(-c3ccccc3)nc(-c3ccc4oc5cccc6cccc(c7cccc3c47)c65)n2)cc1]

INV-4

Example 24

Production of OLEDs

In examples I1 to I27 which follow (tables 4 and 5), the data of various OLEDs are presented. Cleaned glass plates (cleaning in laboratory washer, Merck Extran detergent) coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution) and baked at 180° C. for 10 min. These coated glass plates form the substrates to which the OLEDs are applied.

The OLEDs basically have the following layer structure: substrate/hole transport layer (HTL)/interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 4. A designation such as "INV-10" in the table relates to the inventive materials, the structure of which is shown in table 6.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:INV-7: TEG2 (59%:29%:12%) mean here that the material IC1 is present in the layer in a proportion by volume of 59%, INV-7 in a proportion of 29% and TEG2 in a proportion of 12%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are determined as a function of luminance, calculated from current-voltage-luminance characteristics (IUL characteristics) assuming Lambertian radiation characteristics. The electroluminescence spectra are determined at a luminance of 1000 cd/m$^2$, and the CIE 1931 x and y color coordinates are calculated therefrom. The parameter U1000 in Table 5 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$. The data for the various OLEDs are collated in Table 5. It is observed that excellent performance data can be achieved with inventive materials when they are used as hole transport material, as matrix material for phosphorescent emitters, and when they are used as electron transport material.

TABLE 4

| | | | | Structure of the OLEDs | | | |
|---|---|---|---|---|---|---|---|
| Ex. | HTL thickness | IL thickness | EBL thickness | EML thickness | HBL thickness | ETL thickness | EIL thickness |
| I1 | HATCN 5 nm | SpMA1 50 nm | SpMA2 10 nm | INV-5:TEG2 (83%:17%) 30 nm | ST2 10 nm | ST2:LiQ (50%:50%) 30 nm | — |
| I2 | HATCN 5 nm | SpMA1 50 nm | SpMA2 10 nm | IC1:INV-6:TEG2 (44%:44%:12%) 30 nm | ST2 10 nm | ST2:LiQ (50%:50%) 30 nm | — |

TABLE 4-continued

Structure of the OLEDs

| Ex. | HTL thickness | IL thickness | EBL thickness | EML thickness | HBL thickness | ETL thickness | EIL thickness |
|---|---|---|---|---|---|---|---|
| I3 | HATCN 5 nm | SpMA1 50 nm | SpMA2 10 nm | IC1:INV-7:TEG2 (59%:29%:12%) 30 nm | ST2 10 nm | ST2:LiQ (50%:50%) 30 nm | — |
| I4 | HATCN 5 nm | SpMA1 50 nm | SpMA2 10 nm | INV-5:INV-8:TEG2 (44%:44%:12) 30 nm | ST2 10 nm | ST2:LiQ (50%:50%) 30 nm | — |
| I5 | HATCN 5 nm | SpMA1 50 nm | SpMA2 10 nm | IC3:INV-9:TEG2 (55%:35%:10%) 30 nm | ST2 10 nm | ST2:LiQ (50%:50%) 30 nm | — |
| I6 | HATCN 5 nm | SpMA1 50 nm | INV-10 10 nm | IC3:TEG2 (83%:17%) 30 nm | ST2 10 nm | ST2:LiQ (50%:50%) 30 nm | — |
| I7 | HATCN 5 nm | — | SpMA1 60 nm | INV-11:TEG1 (83%:17%) 30 nm | ST2 10 nm | ST2:LiQ (50%:50%) 30 nm | — |
| I8 | HATCN 5 nm | SpMA1 50 nm | SpMA2 10 nm | ST1:INV-12:TEG2 (28%:55%:17%) 30 nm | ST2 10 nm | ST2:LiQ (50%:50%) 30 nm | — |
| I9 | HATCN 5 nm | SpMA1 50 nm | SpMA2 10 nm | L1:INV-13:TEG2 (33%:50%:17%) 30 nm | ST2 10 nm | ST2:LiQ (50%:50%) 30 nm | — |
| I10 | HATCN 5 nm | SpMA1 50 nm | SpMA2 10 nm | IC1:INV-14:TEG2 (44%:44%:12%) 30 nm | ST2 10 nm | ST2:LiQ (50%:50%) 30 nm | — |
| I11 | HATCN 5 nm | SpMA1 50 nm | SpMA2 10 nm | L2:INV-15:TEG2 (42%:41%:17%) 30 nm | — | ST2:LiQ (50%:50%) 40 nm | — |
| I12 | HATCN 5 nm | SpMA1 50 nm | SpMA2 10 nm | IC1:INV-16:TEG2 (44%:44%:12%) 30 nm | ST2 10 nm | ST2:LiQ (50%:50%) 30 nm | — |
| I13 | HATCN 5 nm | SpMA1 50 nm | SpMA2 10 nm | IC1:TEG2 (83%:17%) 30 nm | ST2 10 nm | INV-17 30 nm | LiQ 3 nm |
| I14 | HATCN 5 nm | SpMA1 50 nm | SpMA2 10 nm | IC1:INV-18:TEG2 (44%:44%:12%) 30 nm | ST2 10 nm | ST2:LiQ (50%:50%) 30 nm | — |
| I15 | HATCN 5 nm | SpMA1 50 nm | SpMA2 10 nm | INV-19:TEG2 (83%:17%) 30 nm | — | ST2:LiQ (50%:50%) 40 nm | — |
| I16 | HATCN 5 nm | SpMA1 50 nm | SpMA2 10 nm | INV-20:TEG2 (83%:17%) 30 nm | ST2 10 nm | ST2:LiQ (50%:50%) 30 nm | — |
| I17 | HATCN 5 nm | SpMA1 50 nm | SpMA2 10 nm | IC1:TEG2 (83%:17%) 30 nm | ST2 10 nm | INV-20:LiQ (50%:50%) 30 nm | — |
| I18 | SpA1 90 nm | HATCN 5 nm | SpMA1 130 nm | 9a:IC2:TER3 (40%:50%:10%) 40 nm | IC3 5 nm | ST2:LiQ (50%:50%) 35 nm | — |
| I19 | HATCN 5 nm | SpMA1 50 nm | INV-21 10 nm | IC3:TEG1 (90%:10%) 30 nm | ST2 10 nm | ST2:LiQ (50%:50%) 30 nm | — |
| I20 | HATCN 5 nm | SpMA1 f50 nm | INV-22 10 nm | IC1:TEG2 (83%:17%) 30 nm | ST2 10 nm | ST2:LiQ (50%:50%) 30 nm | — |
| I21 | HATCN 5 nm | SpMA1 50 nm | INV-23 10 nm | IC1:TEG2 (83%:17%) 30 nm | ST2 10 nm | ST2:LiQ (50%:50%) 30 nm | — |
| I22 | HATCN 5 nm | INV-24 50 nm | SpMA1 10 nm | IC3:TEG1 (90%:10%) 30 nm | IC3 10 nm | ST2:LiQ (50%:50%) 30 nm | — |
| I23 | HATCN 5 nm | SpMA1 50 nm | SpMA2 10 nm | L1:INV-25:TEG2 (29%:59%:12%) 30 nm | ST2 10 nm | ST2:LiQ (50%:50%) 30 nm | — |
| I24 | HATCN 5 nm | SpMA1 50 nm | SpMA2 10 nm | L1:INV-26:TEG2 (29%:59%:12%) 30 nm | ST2 10 nm | ST2:LiQ (50%:50%) 30 nm | — |
| I25 | HATCN 5 nm | SpMA1 50 nm | SpMA2 10 nm | IC1:INV-27:TEG2 (44%:44%:12%) 30 nm | ST2 10 nm | ST2:LiQ (50%:50%) 30 nm | — |
| I26 | HATCN 5 nm | SpMA1 50 nm | SpMA2 10 nm | IC1:INV-28:TEG2 (40%:48%:12%) 30 nm | ST2 10 nm | ST2:LiQ (50%:50%) 30 nm | — |
| I27 | HATCN 5 nm | SpMA1 50 nm | SpMA2 10 nm | INV-29:TEG2 (83%:17%) 30 nm | ST2 10 nm | ST2:LiQ (50%:50%) 30 nm | — |

TABLE 5

Data of the OLEDs

| Ex. | U1000 (V) | CE1000 (cd/A) | PE1000 (lm/W) | EQE 1000 | CIE x/y at 1000 cd/m² |
|---|---|---|---|---|---|
| I1 | 3.4 | 62 | 58 | 16.6% | 0.34/0.62 |
| I2 | 3.2 | 67 | 70 | 18.1% | 0.34/0.62 |
| I3 | 3.4 | 57 | 52 | 15.4% | 0.34/0.62 |
| I4 | 3.4 | 68 | 63 | 18.4% | 0.34/0.62 |
| I5 | 3.2 | 75 | 73 | 20.2% | 0.34/0.62 |
| I6 | 3.2 | 76 | 75 | 20.7% | 0.34/0.62 |
| I7 | 3.5 | 74 | 67 | 20.0% | 0.33/0.63 |
| I8 | 3.3 | 68 | 64 | 18.3% | 0.34/0.62 |
| I9 | 3.1 | 72 | 72 | 19.5% | 0.34/0.62 |
| I10 | 3.3 | 62 | 59 | 16.8% | 0.34/0.62 |
| I11 | 3.1 | 72 | 73 | 19.4% | 0.33/0.63 |
| I12 | 3.2 | 72 | 71 | 19.3% | 0.34/0.62 |
| I13 | 3.5 | 65 | 59 | 17.5% | 0.35/0.62 |
| I14 | 3.2 | 68 | 68 | 18.6% | 0.35/0.62 |
| I15 | 3.1 | 77 | 79 | 20.8% | 0.34/0.62 |
| I16 | 3.8 | 62 | 52 | 16.7% | 0.33/0.63 |
| I17 | 4.4 | 65 | 47 | 17.7% | 0.35/0.62 |
| I18 | 4.6 | 11.2 | 8.2 | 12.2% | 0.67/0.33 |
| I19 | 3.3 | 72 | 69 | 19.8% | 0.36/0.61 |
| I20 | 3.2 | 62 | 62 | 17.0% | 0.35/0.61 |
| I21 | 3.2 | 64 | 63 | 17.3% | 0.35/0.62 |
| I22 | 3.4 | 73 | 67 | 20.0% | 0.34/0.62 |
| I23 | 3.3 | 59 | 56 | 16.0% | 0.35/0.61 |
| I24 | 3.2 | 61 | 60 | 16.7% | 0.35/0.62 |
| I25 | 3.2 | 71 | 70 | 19.1% | 0.33/0.63 |
| I26 | 3.5 | 63 | 58 | 17.2% | 0.36/0.61 |
| I27 | 4.1 | 72 | 55 | 19.4% | 0.35/0.62 |

TABLE 6
Structural formulae of the materials for the OLEDs
SpA1
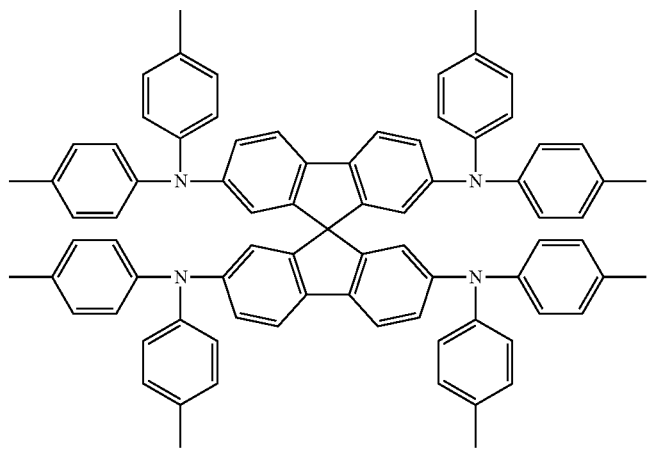
TEG1
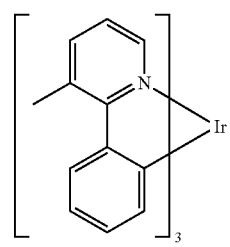
SpMA1
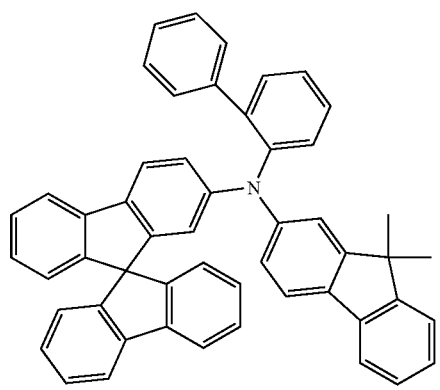 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA2
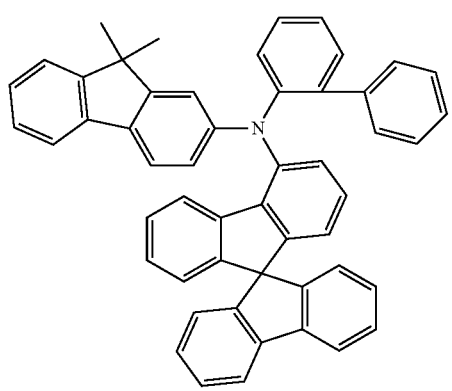 [SMILES: CC1(C)c2ccccc2-c2ccc(N(c3ccccc3-c3ccccc3)c3cccc4c3-c3ccccc3C43c4ccccc4-c4ccccc43)cc21]

TABLE 6-continued
Structural formulae of the materials for the OLEDs
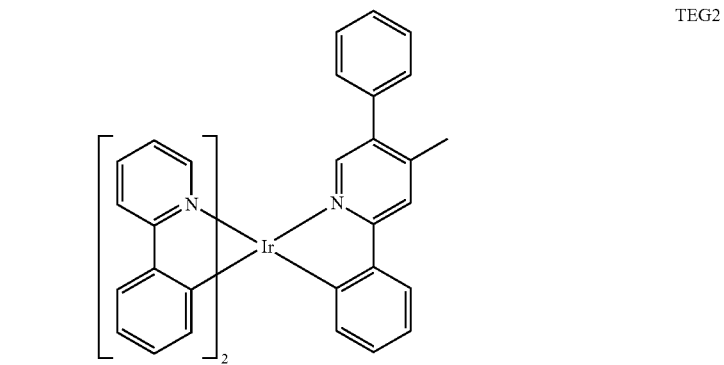
TEG2
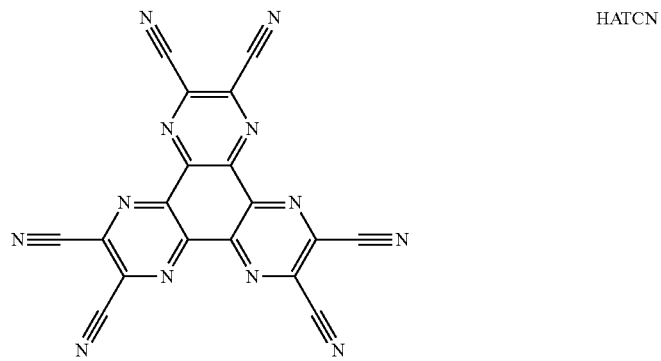
HATCN
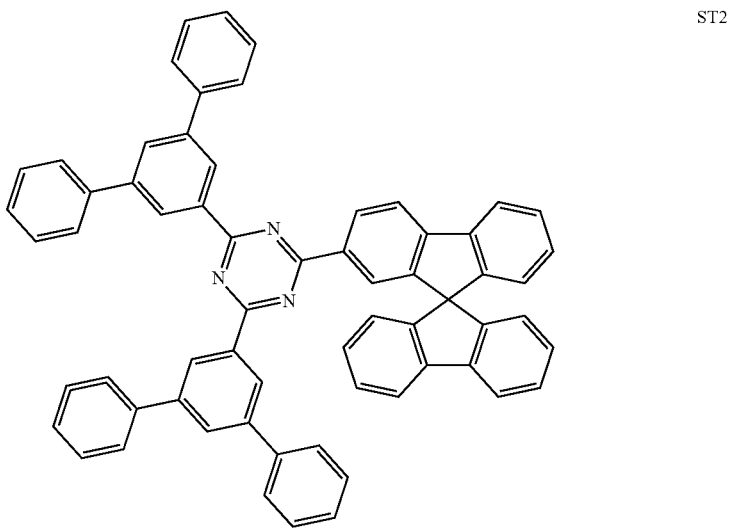
ST2
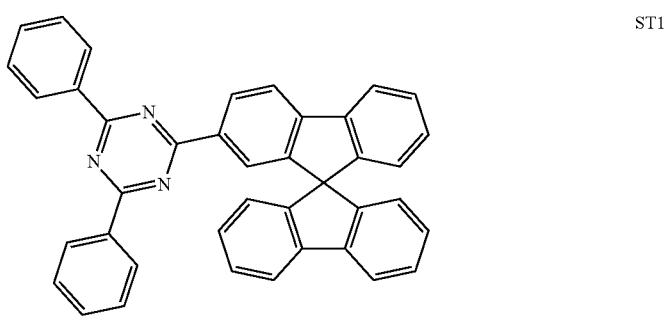
ST1

TABLE 6-continued
Structural formulae of the materials for the OLEDs
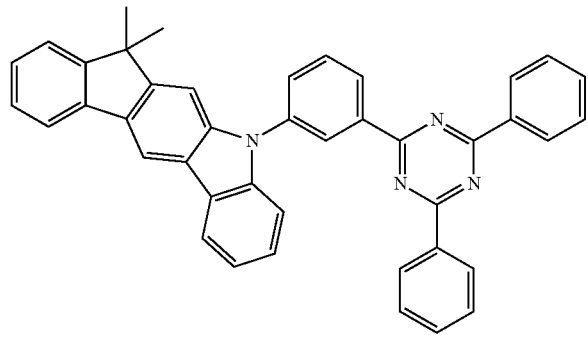 [SMILES: CC1(C)c2ccccc2-c2cc3c4ccccc4n(-c4cccc(-c5nc(-c6ccccc6)nc(-c6ccccc6)n5)c4)c3cc21]
IC1
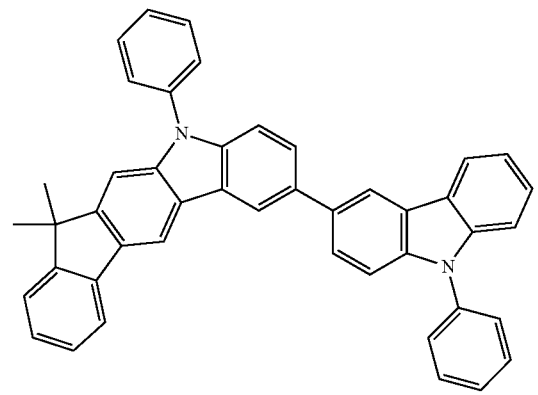 [SMILES: CC1(C)c2ccccc2-c2cc3c4cc(-c5ccc6c(c5)c5ccccc5n6-c5ccccc5)ccc4n(-c4ccccc4)c3cc21]
IC2
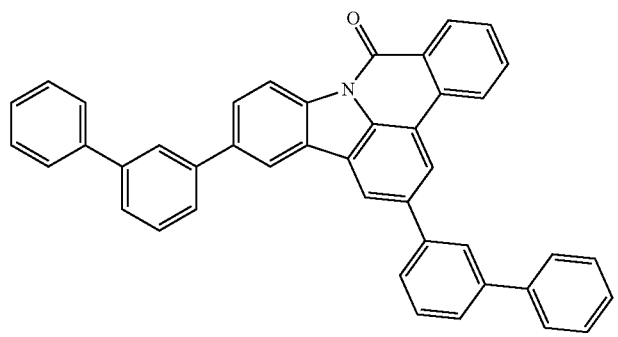 [SMILES: O=c1c2ccccc2c2cc(-c3cccc(-c4ccccc4)c3)cc3c4cc(-c5cccc(-c6ccccc6)c5)ccc4n1c23]
L1
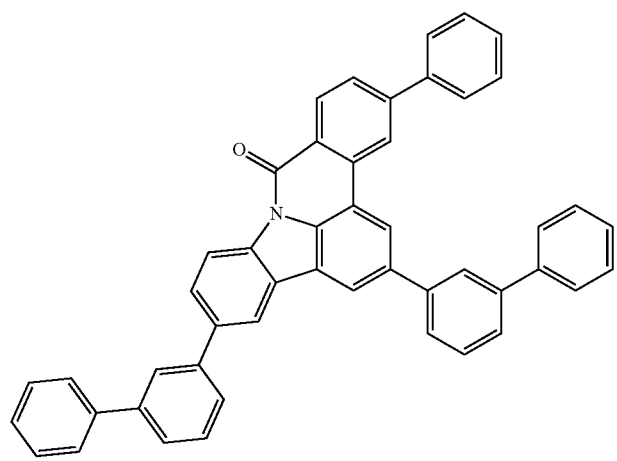 [SMILES: O=c1c2ccc(-c3ccccc3)cc2c2cc(-c3cccc(-c4ccccc4)c3)cc3c4cc(-c5cccc(-c6ccccc6)c5)ccc4n1c23]
L2

TABLE 6-continued
Structural formulae of the materials for the OLEDs
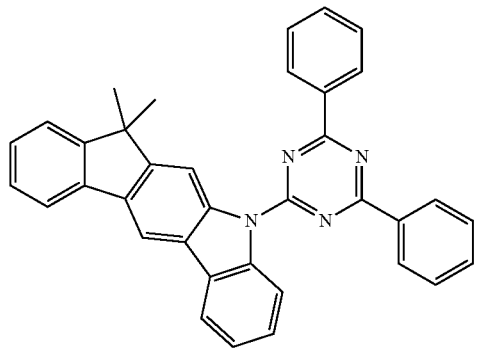 [SMILES: CC1(C)c2ccccc2-c2cc3c4ccccc4n(-c4nc(-c5ccccc5)nc(-c5ccccc5)n4)c3cc21]
IC3
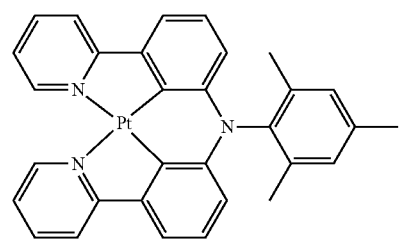
TER3
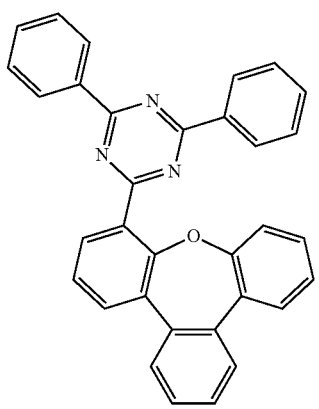 [SMILES: c1ccc(-c2nc(-c3ccccc3)nc(-c3cccc4c3Oc3ccccc3-c3ccccc3-4)n2)cc1]
INV-5
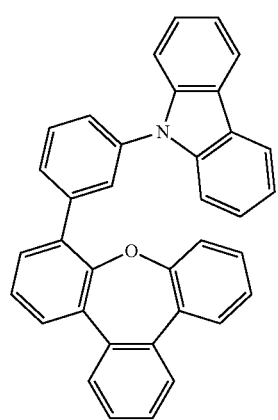 [SMILES: c1cc(-c2cccc3c2Oc2ccccc2-c2ccccc2-3)cc(-n2c3ccccc3c3ccccc32)c1]
INV-6

TABLE 6-continued
Structural formulae of the materials for the OLEDs
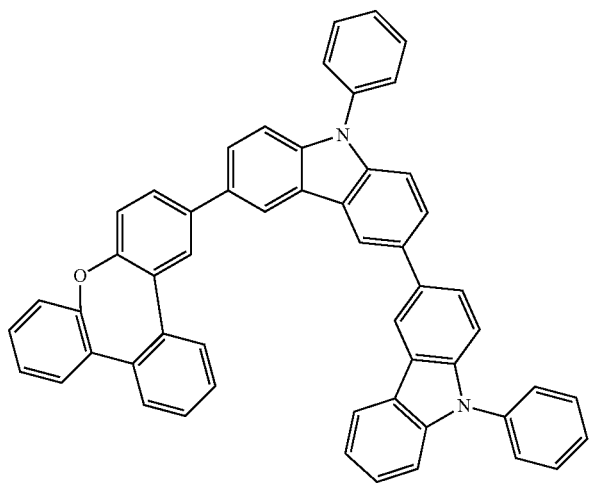 [SMILES: c1ccc(-n2c3ccccc3c3cc(-c4ccc5c(c4)c4cc(-c6ccc7c(c6)-c6ccccc6-c6ccccc6O7)ccc4n5-c4ccccc4)ccc32)cc1]
INV-7
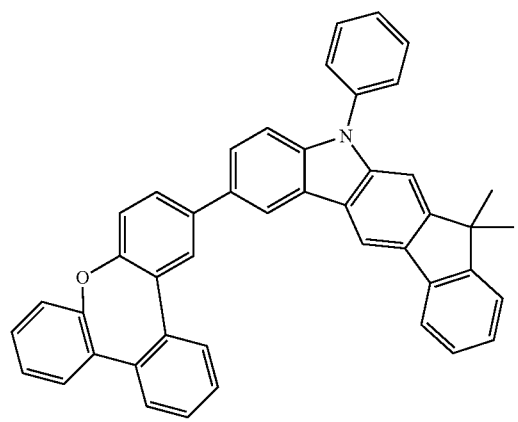 [SMILES: CC1(C)c2ccccc2-c2cc3c4cc(-c5ccc6c(c5)-c5ccccc5-c5ccccc5O6)ccc4n(-c4ccccc4)c3cc21]
INV-8
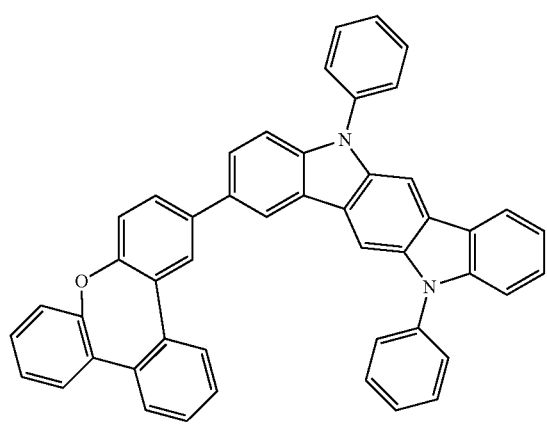 [SMILES: c1ccc(-n2c3ccccc3c3cc4c(cc32)c2cc(-c3ccc5c(c3)-c3ccccc3-c3ccccc3O5)ccc2n4-c2ccccc2)cc1]
INV-9

TABLE 6-continued
Structural formulae of the materials for the OLEDs
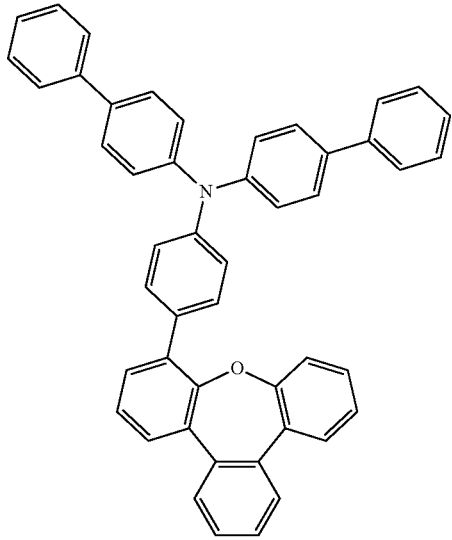 [SMILES: c1ccc(-c2ccc(N(c3ccc(-c4ccccc4)cc3)c3ccc(-c4cccc5c4Oc4ccccc4-c4ccccc4-5)cc3)cc2)cc1]
INV-10
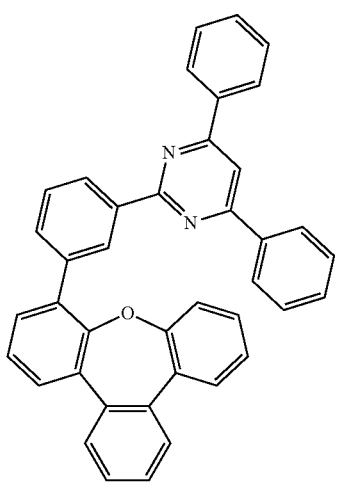 [SMILES: c1ccc(-c2cc(-c3ccccc3)nc(-c3cccc(-c4cccc5c4Oc4ccccc4-c4ccccc4-5)c3)n2)cc1]
INV-11
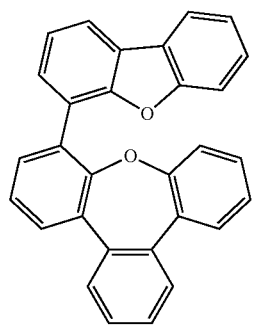 [SMILES: c1ccc2c(c1)Oc1c(cccc1-c1cccc3c1oc1ccccc13)-c1ccccc1-2]
INV-12

TABLE 6-continued
Structural formulae of the materials for the OLEDs
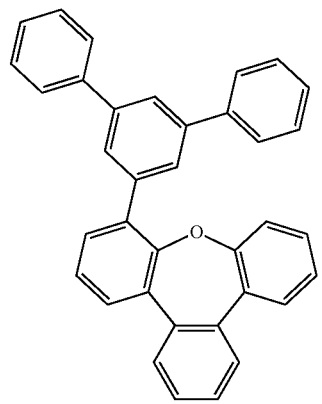 [SMILES: c1ccc(-c2cc(-c3ccccc3)cc(-c3cccc4c3Oc3ccccc3-c3ccccc3-4)c2)cc1]
INV-13
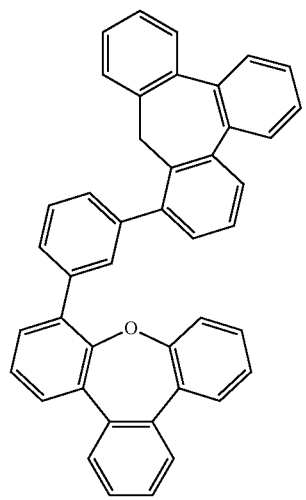 [SMILES: c1cc(-c2cccc3c2Cc2ccccc2-c2ccccc2-3)cc(-c2cccc3c2Oc2ccccc2-c2ccccc2-3)c1]
INV-14
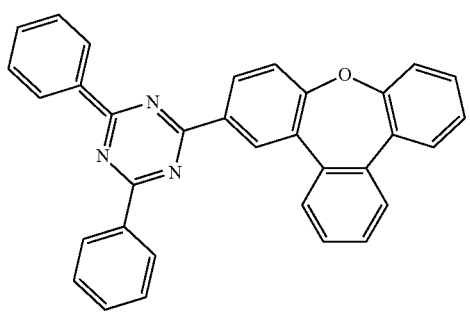
INV-15
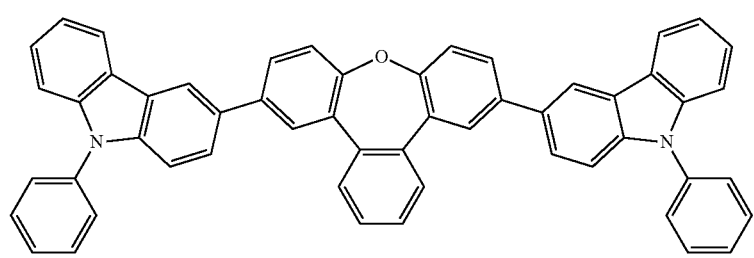 [SMILES: c1ccc(-n2c3ccccc3c3cc(-c4ccc5c(c4)-c4ccccc4-c4cc(-c6ccc7c(c6)c6ccccc6n7-c6ccccc6)ccc4O5)ccc32)cc1]
INV-16

279
TABLE 6-continued
Structural formulae of the materials for the OLEDs
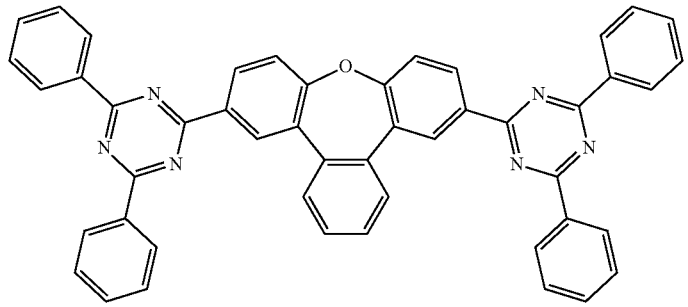 [SMILES: c1ccc(-c2nc(-c3ccccc3)nc(-c3ccc4c(c3)-c3ccccc3-c3cc(-c5nc(-c6ccccc6)nc(-c6ccccc6)n5)ccc3O4)n2)cc1]
INV-17
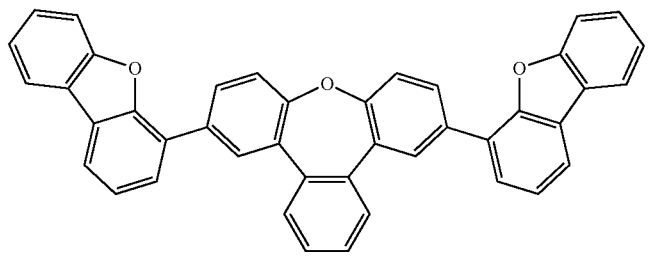 [SMILES: c1ccc2c(c1)-c1cc(-c3cccc4c3oc3ccccc34)ccc1Oc1ccc(-c3cccc4c3oc3ccccc34)cc1-2]
INV-18
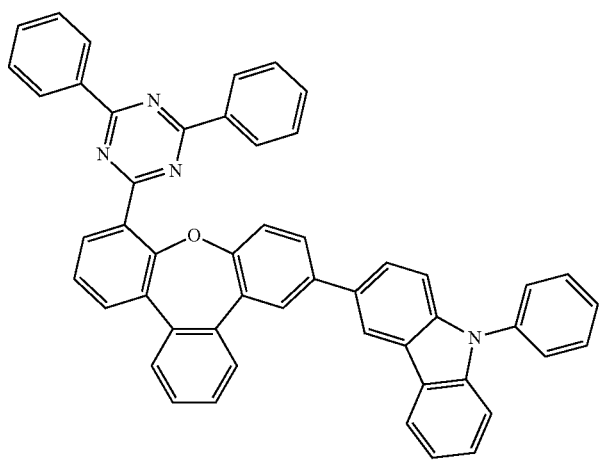 [SMILES: c1ccc(-c2nc(-c3ccccc3)nc(-c3cccc4c3Oc3ccc(-c5ccc6c(c5)c5ccccc5n6-c5ccccc5)cc3-c3ccccc3-4)n2)cc1]
INV-19
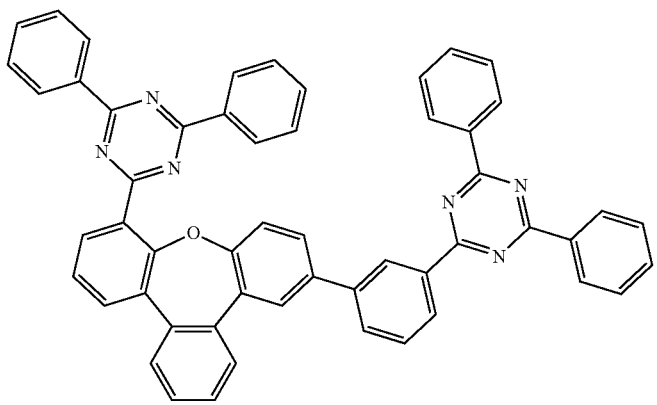 [SMILES: c1ccc(-c2nc(-c3ccccc3)nc(-c3cccc(-c4ccc5c(c4)-c4ccccc4-c4cccc(-c6nc(-c7ccccc7)nc(-c7ccccc7)n6)c4O5)c3)n2)cc1]
INV-20

TABLE 6-continued
Structural formulae of the materials for the OLEDs
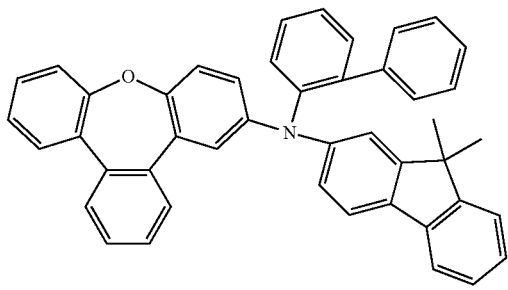 [SMILES: CC1(C)c2ccccc2-c2ccc(N(c3ccc4c(c3)-c3ccccc3-c3ccccc3O4)c3ccccc3-c3ccccc3)cc21]
INV-21
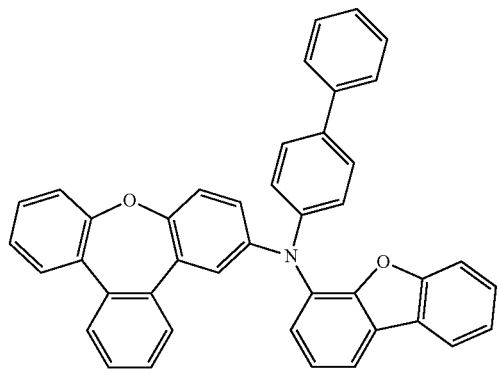 [SMILES: c1ccc(-c2ccc(N(c3ccc4c(c3)-c3ccccc3-c3ccccc3O4)c3cccc4c3oc3ccccc34)cc2)cc1]
INV-22
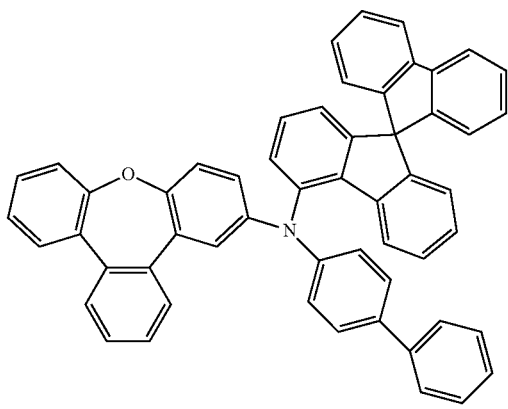 [SMILES: c1ccc(-c2ccc(N(c3ccc4c(c3)-c3ccccc3-c3ccccc3O4)c3cccc4c3-c3ccccc3C43c4ccccc4-c4ccccc43)cc2)cc1]
INV-23
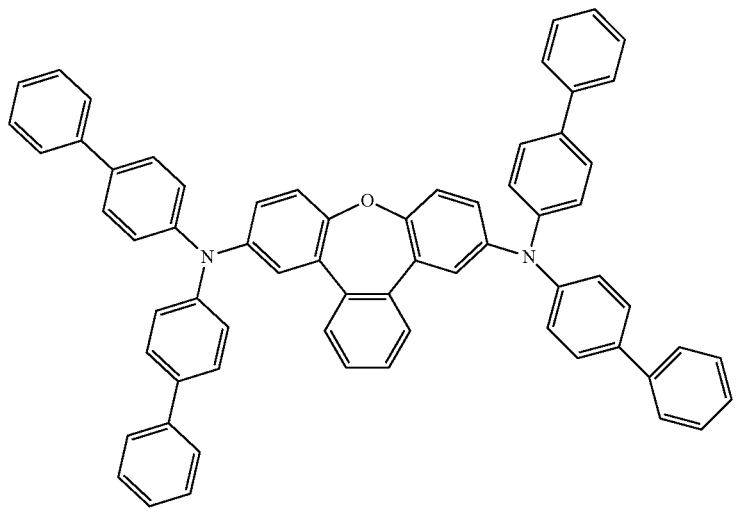 [SMILES: c1ccc(-c2ccc(N(c3ccc(-c4ccccc4)cc3)c3ccc4c(c3)-c3ccccc3-c3cc(N(c5ccc(-c6ccccc6)cc5)c5ccc(-c6ccccc6)cc5)ccc3O4)cc2)cc1]
INV-24

TABLE 6-continued
Structural formulae of the materials for the OLEDs
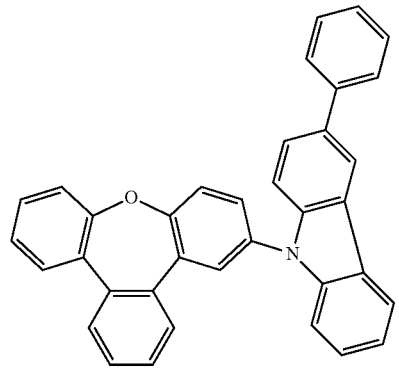 [SMILES: c1ccc(-c2ccc3c(c2)c2ccccc2n3-c2ccc3c(c2)-c2ccccc2-c2ccccc2O3)cc1]
INV-25
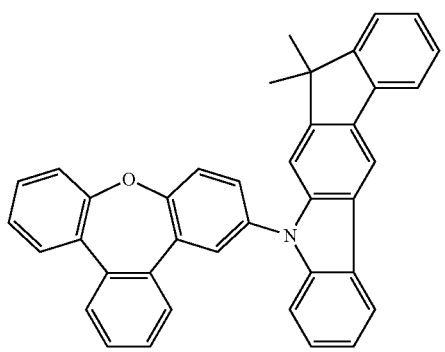 [SMILES: CC1(C)c2ccccc2-c2cc3c4ccccc4n(-c4ccc5c(c4)-c4ccccc4-c4ccccc4O5)c3cc21]
INV-26
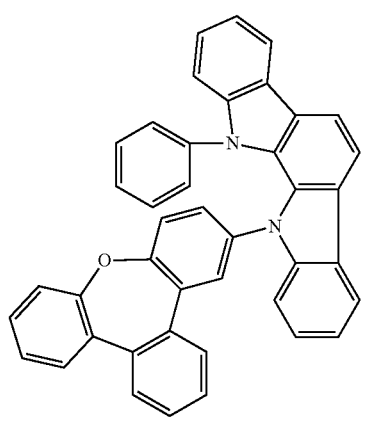 [SMILES: c1ccc(-n2c3ccccc3c3ccc4c5ccccc5n(-c5ccc6c(c5)-c5ccccc5-c5ccccc5O6)c4c32)cc1]
INV-27
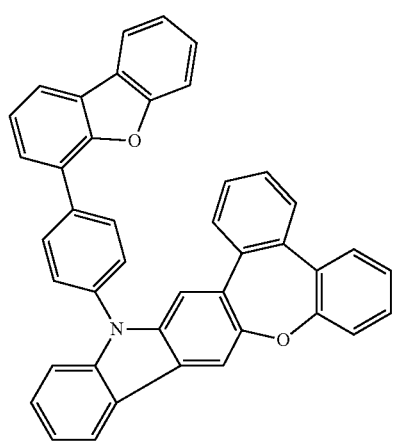 [SMILES: c1ccc2c(c1)Oc1cc3c4ccccc4n(-c4ccc(-c5cccc6c5oc5ccccc56)cc4)c3cc1-c1ccccc1-2]
INV-28

TABLE 6-continued

Structural formulae of the materials for the OLEDs

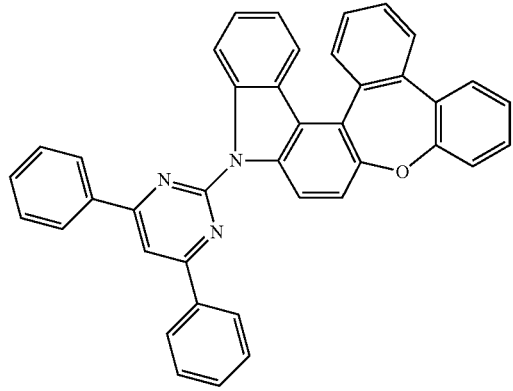 [SMILES: c1ccc(-c2cc(-c3ccccc3)nc(-n3c4ccccc4c4c5c(ccc43)Oc3ccccc3-c3ccccc3-5)n2)cc1]

INV-29

The invention claimed is:

1. A compound of the formula (4a) or (6a)

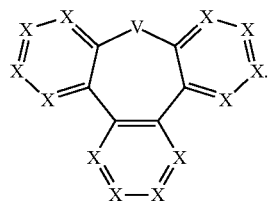

Formula (4a)

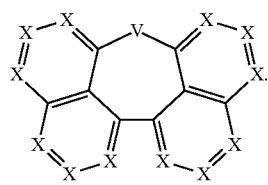

Formula (6a)

V is either O or S,

X is the same or different at each instance and is N or $CR^1$, $R^1$ is the same or different at each instance and is H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which is optionally substituted by one or more $R^2$ radicals, where one or more nonadjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more hydrogen atoms is optionally replaced by D, F, Cl, Br, I, CN or $NO_2$, or an aromatic or heteroaromatic ring system which has 5 to 60 aromatic ring atoms and is optionally substituted in each case by one or more $R^2$ radicals, or an aryloxy, arylalkoxy or heteroaryloxy group which has 5 to 60 aromatic ring atoms and is optionally substituted by one or more $R^2$ radicals, or a diarylamino group, diheteroarylamino group or arylheteroarylamino group which has 10 to 40 aromatic ring atoms and is optionally substituted by one or more $R^2$ radicals, or a combination of two or more of these groups or a crosslinkable Q group; at the same time, two or more adjacent $R^1$ radicals together may form a mono- or polycyclic, aliphatic or aromatic or heteroaromatic ring system which is optionally substituted by one or more $R^2$ radicals;

$R^2$ is the same or different at each instance and is H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which is optionally substituted by one or more $R^3$ radicals, where one or more nonadjacent $CH_2$ groups is optionally replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more hydrogen atoms is optionally replaced by D, F, Cl, Br, I, CN or $NO_2$, or an aromatic or heteroaromatic ring system which has 5 to 60 aromatic ring atoms and is optionally substituted in each case by one or more $R^3$ radicals, or an aryloxy, arylalkoxy or heteroaryloxy group which has 5 to 60 aromatic ring atoms and is optionally substituted by one or more $R^3$ radicals, or a diarylamino group, diheteroarylamino group or arylheteroarylamino group which has 10 to 40 aromatic ring atoms and is optionally substituted by one or more $R^3$ radicals, or a combination of two or more of these groups; at the same time, two or more adjacent $R^2$ radicals together may form a mono- or polycyclic, aliphatic or aromatic or heteroaromatic ring system;

$R^3$ is the same or different at each instance and is H, D, F or an aliphatic, aromatic and/or heteroaromatic hydrocarbyl radical having 1 to 40 carbon atoms, in which one or more hydrogen atoms may also be replaced by F; at the same time, two or more $R^3$ substituents together may also form a mono- or polycyclic, aliphatic or aromatic or heteroaromatic ring system;

and with the proviso that at least one of the $R^1$ radicals is not H.

2. An electronic device comprising at least one compound as claimed in claim 1.

3. The electronic device as claimed in claim 2, wherein is selected from organic integrated circuits (OICs), organic field-effect transistors (OFETs), organic thin-film transistors (OTFTs), organic electroluminescent devices, organic solar cells (OSCs), organic optical detectors, organic photoreceptors.

4. The electronic device as claimed in claim 3, wherein the device is an organic electroluminescent device also selected from the group consisting of organic light-emitting transistors (OLETs), organic field quench devices (OFQDs), organic light-emitting electrochemical cells (OLECs, LECs, LEECs), organic laser diodes (O-lasers) and organic light-emitting diodes (OLEDs).

5. A process for producing the electronic device as claimed in claim 2, wherein at least one organic layer is applied by gas phase deposition or from solution.

6. A process for phototherapy of the skin which comprises treating the skin with the device as claimed in claim 2.

7. A process for the reduction or prevention of skin ageing, skin wrinkles, crows' feet, acne, comedones and cellulite which comprises treating the skin with the device according to claim 2.

8. A display or for lighting which comprises the device as claimed in claim 2.

9. A composition comprising at least one compound as claimed in claim 1 and at least one additional compound selected from the group consisting of fluorescent emitters, phosphorescent emitters, host materials, matrix materials, electron transport materials, electron injection materials, hole conductor materials, hole injection materials, electron blocker materials, hole blocker materials, n-dopants and p-dopants.

10. The composition as claimed in claim 9, wherein the additional compound is a phosphorescent emitter.

11. The composition as claimed in claim 9, wherein the additional compound is a host or matrix material.

12. The composition as claimed in claim 9, wherein the additional compound has a band gap of 2.5 eV or more.

13. The compound as claimed in claim 1, wherein the compound has the following formula (4a):

Formula (4a)

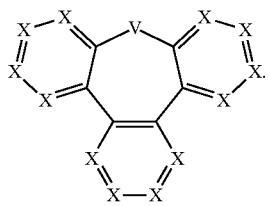

14. The compound as claimed in claim 1, wherein the compound has the following formula (10a):

Formula (10a)

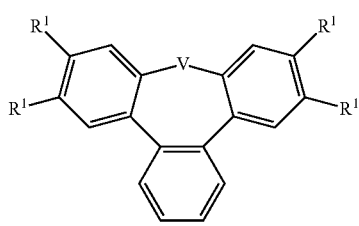

15. The compound as claimed in claim 1, wherein the compound has the following formula (6a):

Formula (6a)

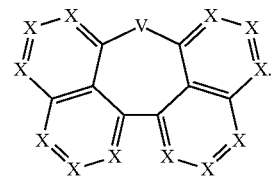

16. The compound as claimed in claim 1, wherein the compound has the following formula (17):

Formula (17)

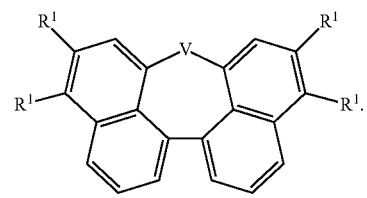

17. The compound as claimed in claim 1, wherein the compound has the following formula (18):

Formula (18)

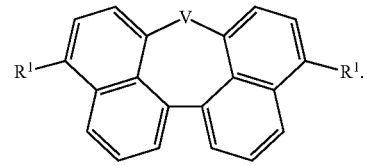

18. A process for preparing the compound as claimed in claim 1 with the aid of Suzuki coupling, Buchwald or Ullmann coupling.

19. A formulation comprising at least one compound as claimed in claim 1 and at least one solvent.

20. The compound as claimed in claim 1, wherein V is O.

21. The compound as claimed in claim 1, wherein the compound is of the Formula (10d)

Formula (10d)

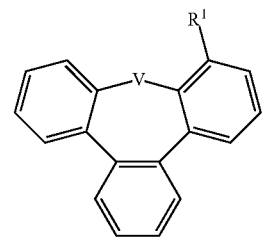

22. A compound of the following formula (A-1)-(A-69), (A-50a)-(A-69a), (A-70)-(A293) and (INV-5)-(INV-29):

Formula (A-1)
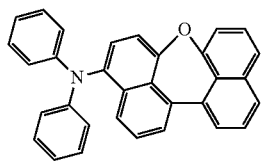
Formula (A-2)
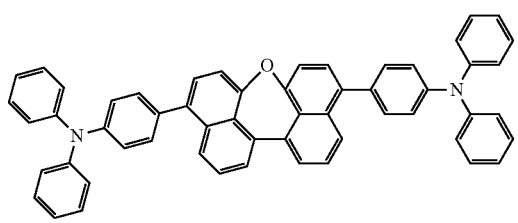
Formula (A-3)
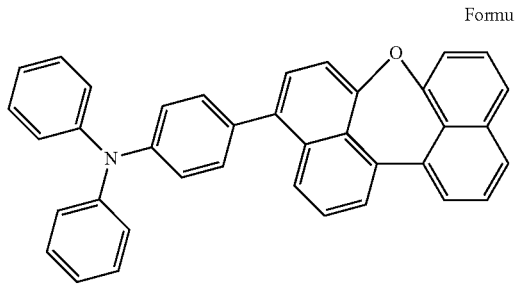
Formula (A-4)
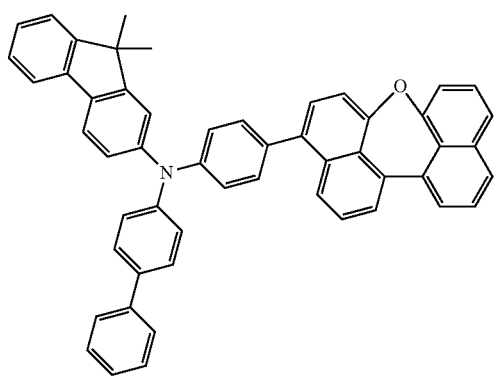
Formula (A-5)
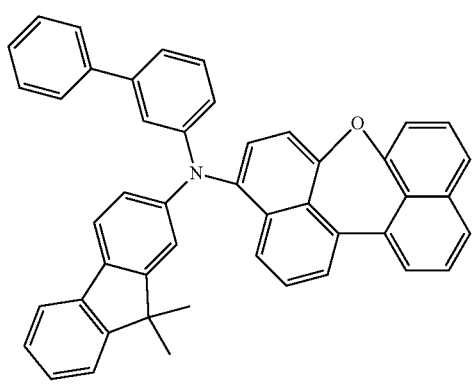
Formula (A-6)
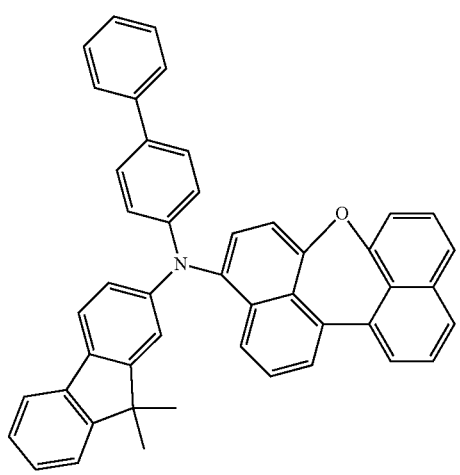
Formula (A-7)
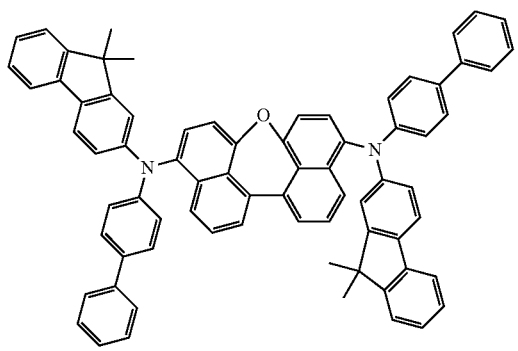
Formula (A-8)
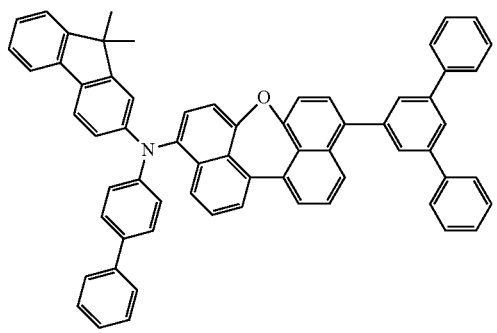

-continued
Formula (A-9)
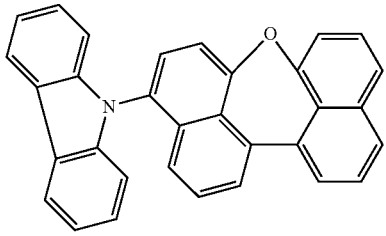
Formula (A-10)
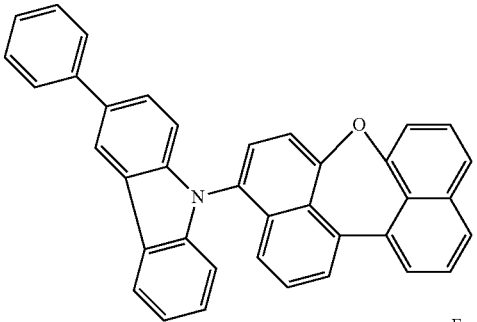
Formula (A-11)
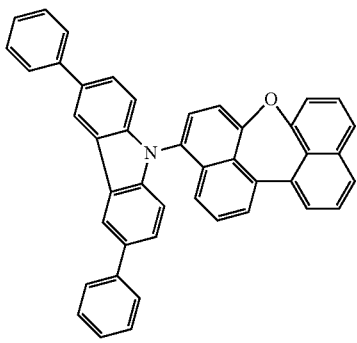
Formula (A-12)
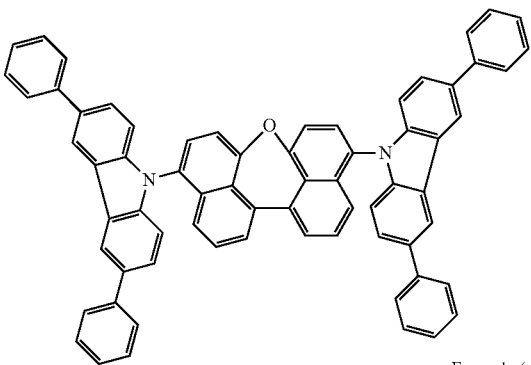
Formula (A-13)
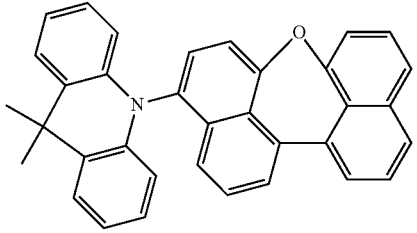
Formula (A-14)
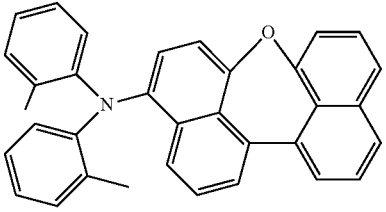
Formula (A-15)
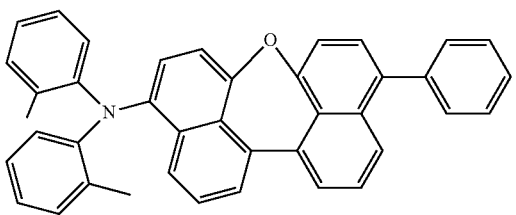
Formula (A-16)
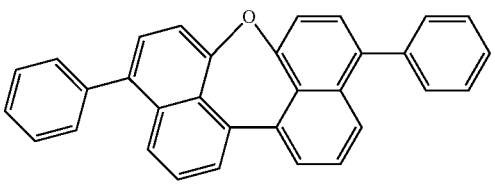
Formula (A-17)
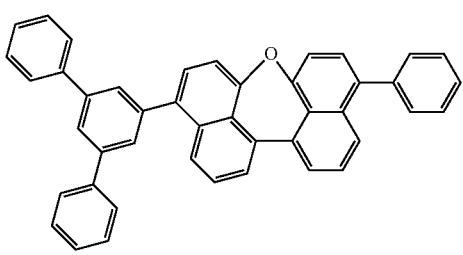
Formula (A-18)
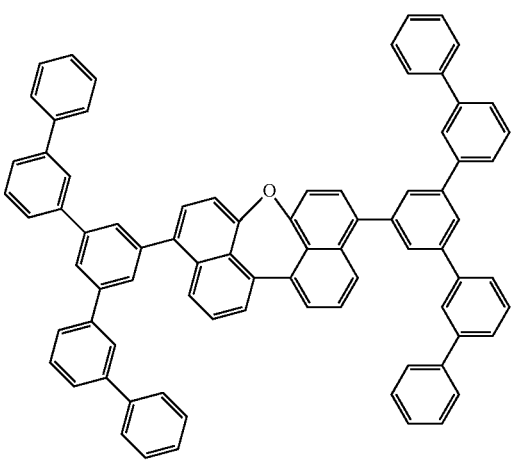

-continued
Formula (A-19)
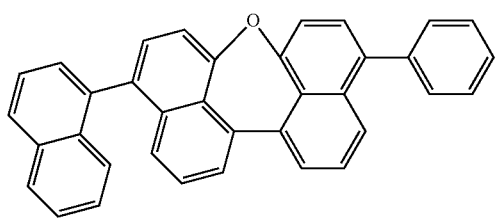
Formula (A-20)
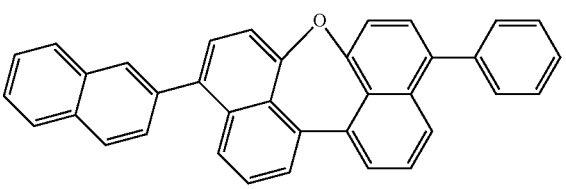
Formula (A-21)
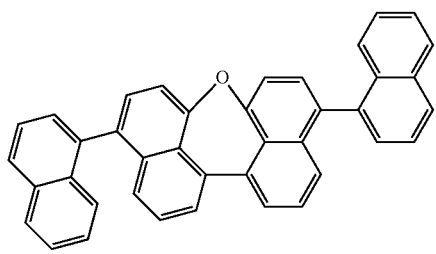
Formula (A-22)
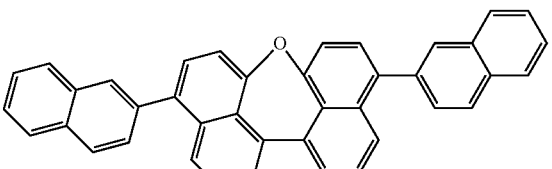
Formula (A-23)
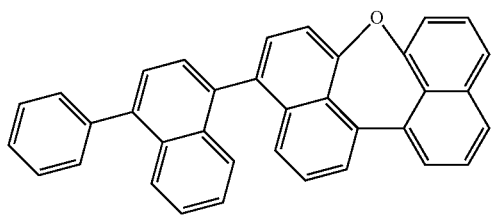
Formula (A-24)
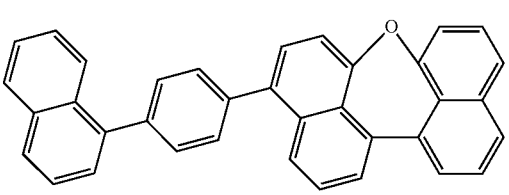
Formula (A-25)
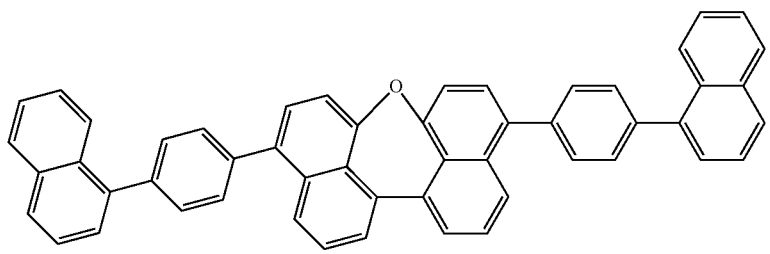
Formula (A-26)
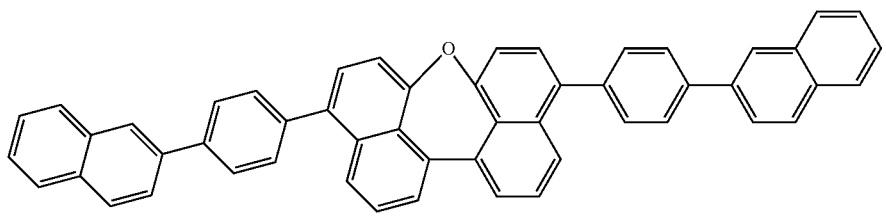
Formula (A-27)
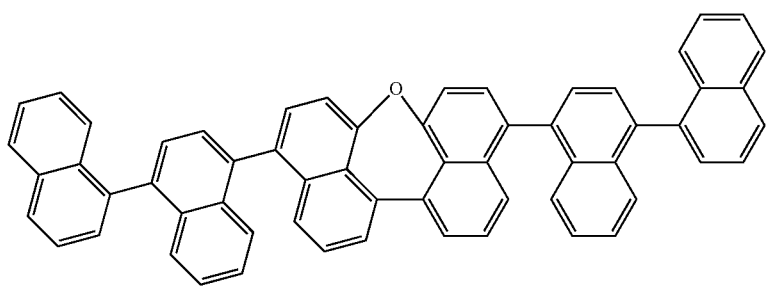

-continued
Formula (A-28)
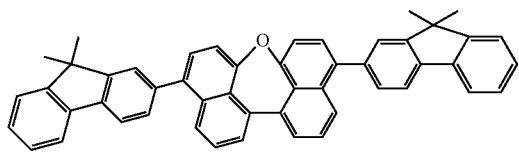
Formula (A-29)
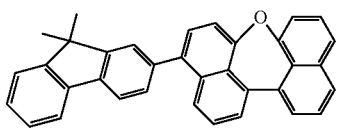
Formula (A-30)
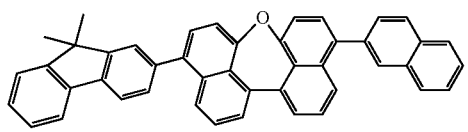
Formula (A-31)
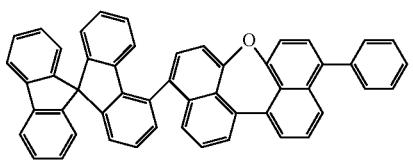
Formula (A-32)
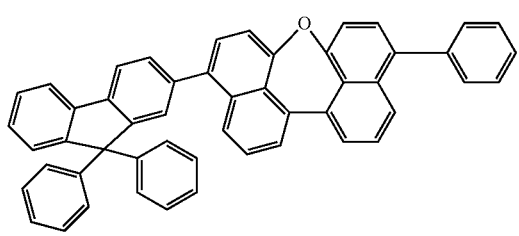
Formula (A-33)
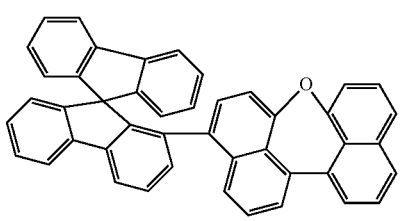
Formula (A-34)
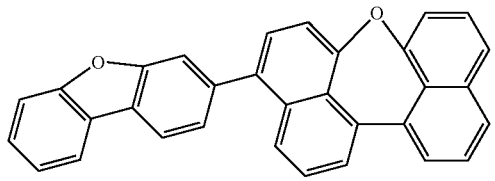
Formula (A-35)
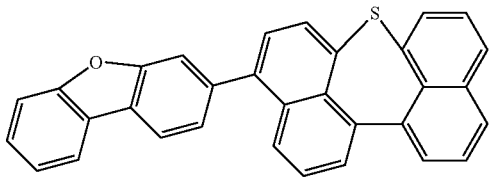
Formula (A-36)
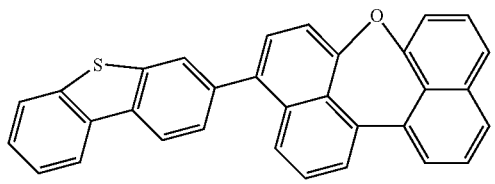
Formula (A-37)
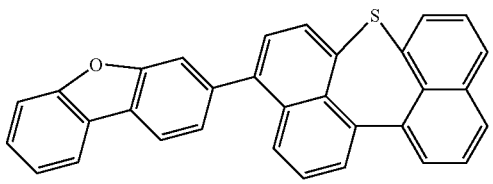
Formula (A-38)
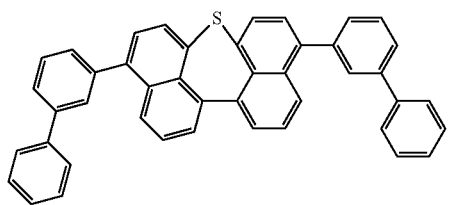
Formula (A-39)
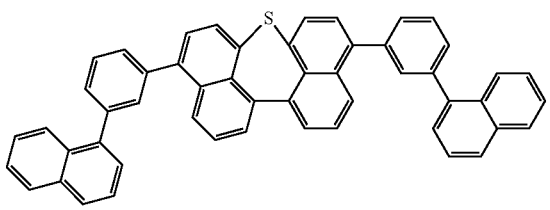
Formula (A-40)
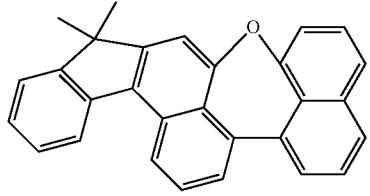
Formula (A-41)
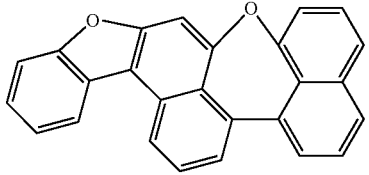

Formula (A-42)
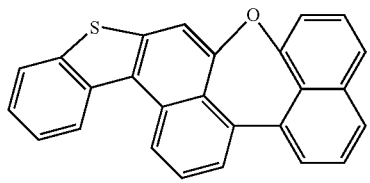
Formula (A-43)
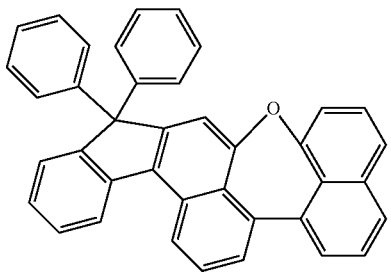
Formula (A-44)
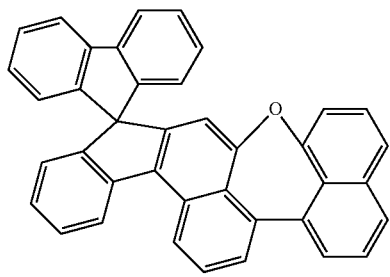
Formula (A-45)
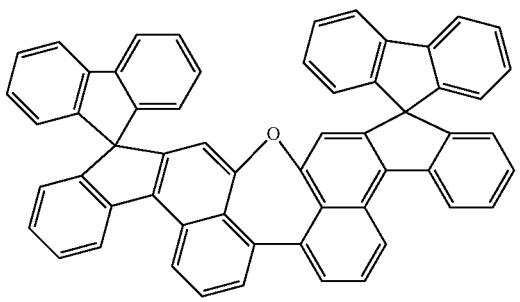
Formula (A-46)
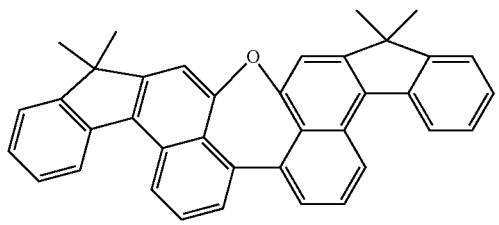
Formula (A-47)
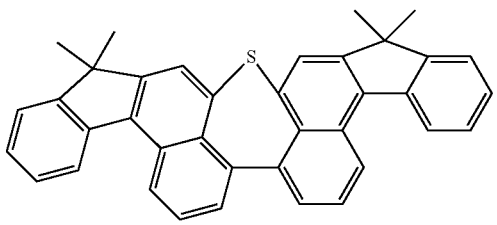
Formula (A-48)
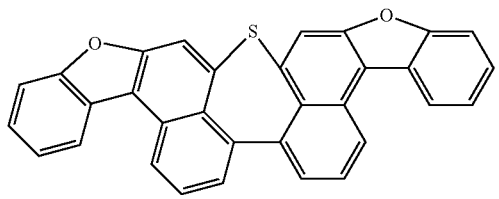
Formula (A-49)
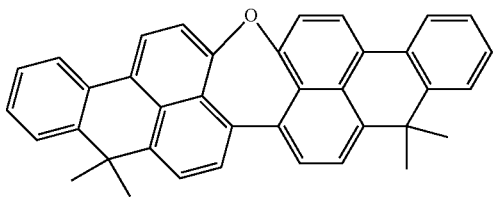
Formula (A-50)
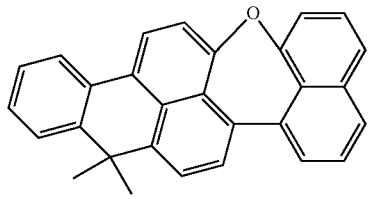
Formula (A-51)
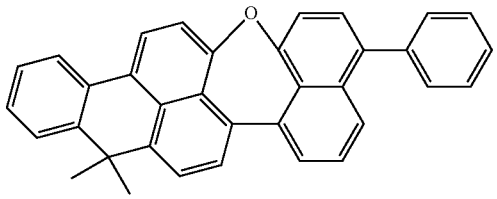
Formula (A-52)
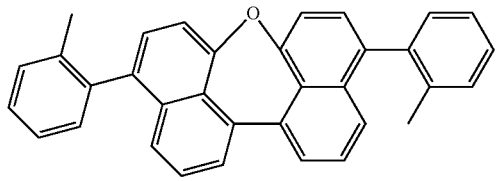
Formula (A-53)
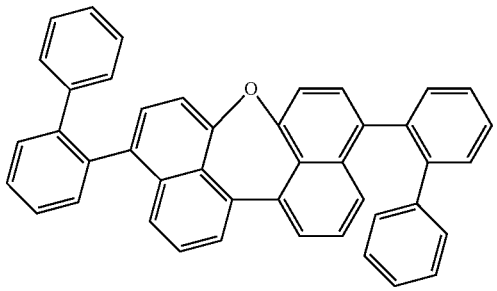

-continued
Formula (A-54)
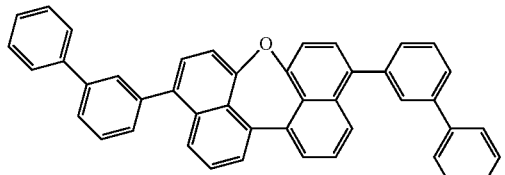
Formula (A-55)
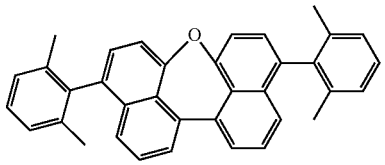
Formula (A-56)
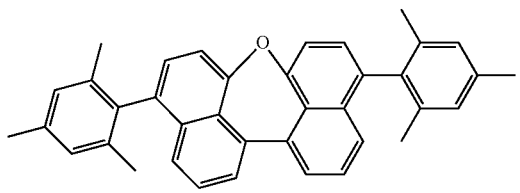
Formula (A-57)
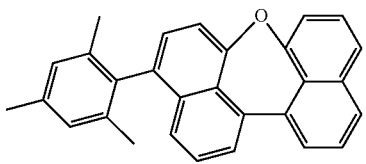
Formula (A-58)
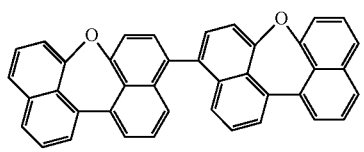
Formula (A-59)
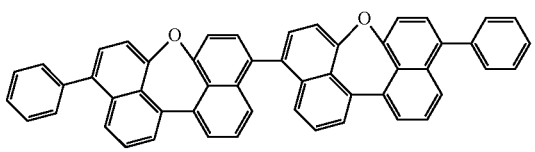
Formula (A-60)
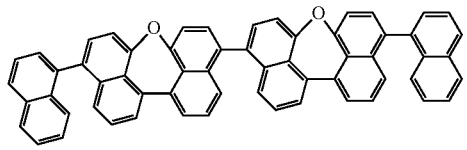
Formula (A-61)
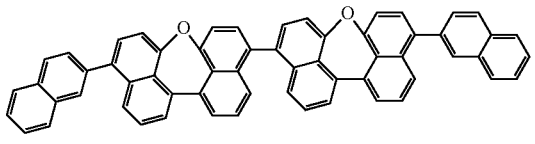
Formula (A-62)
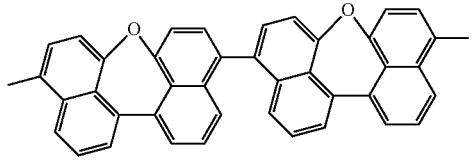
Formula (A-63)
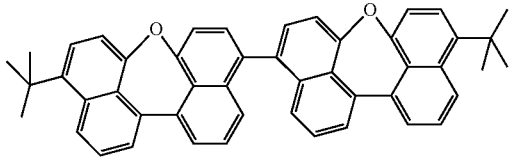
Formula (A-64)
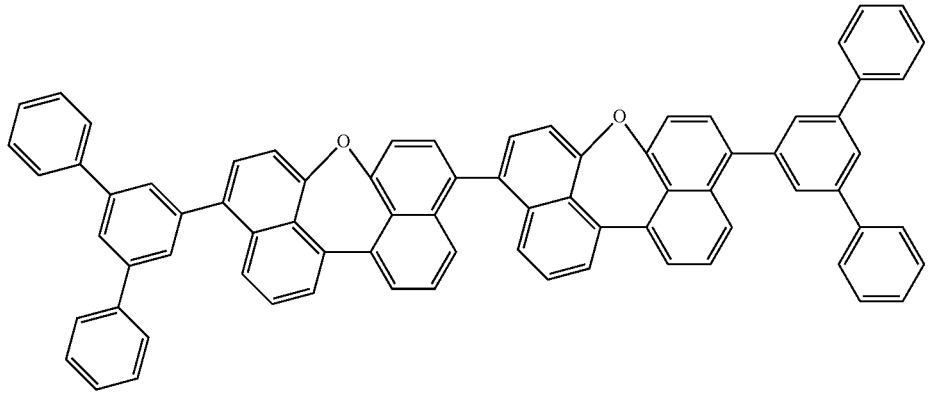
Formula (A-65)
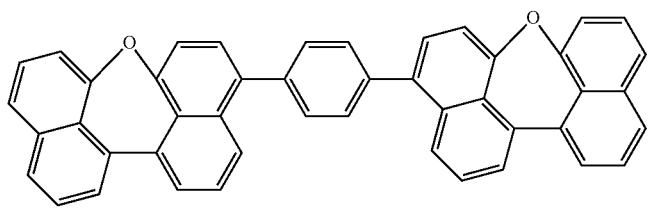

-continued
Formula (A-66)
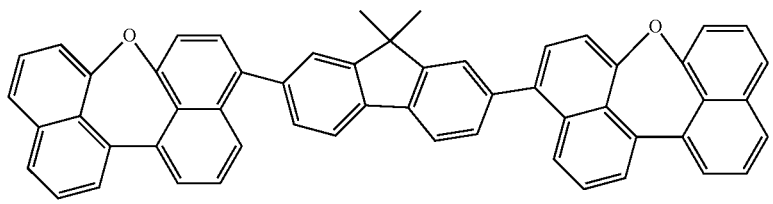
Formula (A-67)
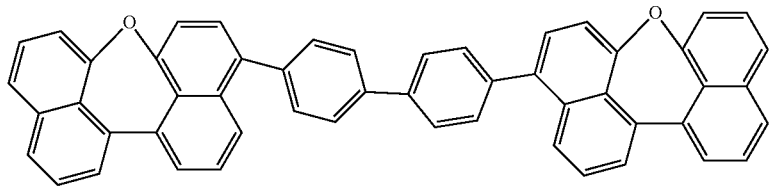
Formula (A-68)
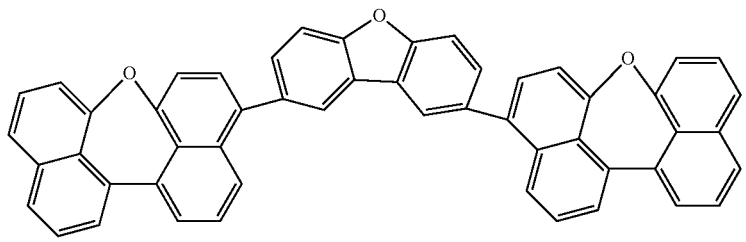
Formula (A-69)
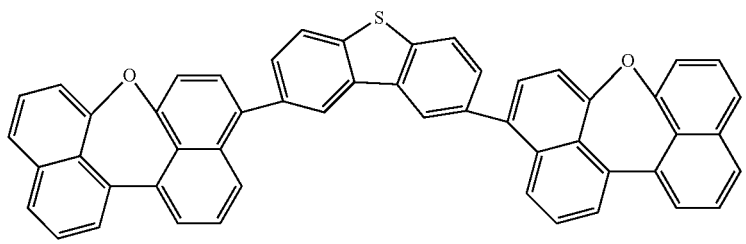
Formula (A-50a)
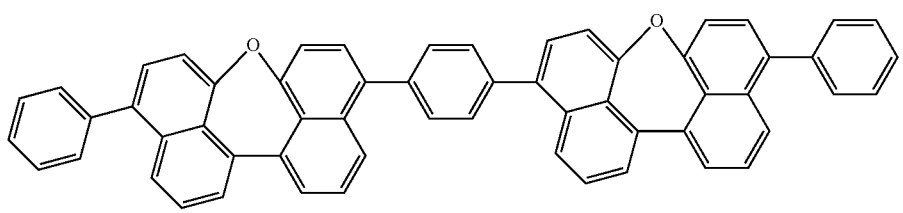
Formula (A-51a)
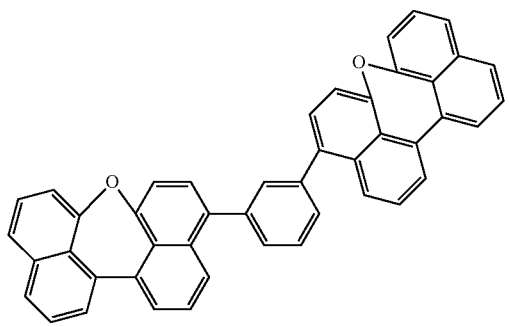
Formula (A-52a)
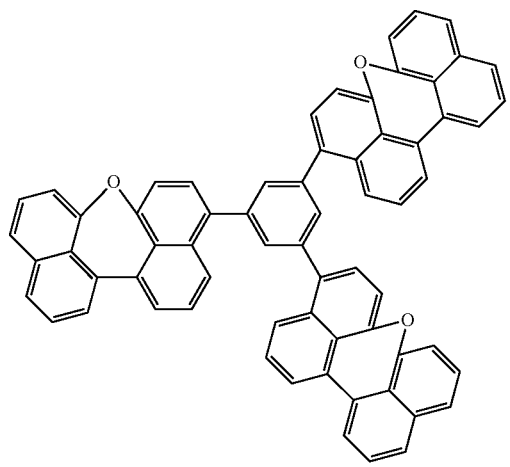

-continued
Formula (A-53a)
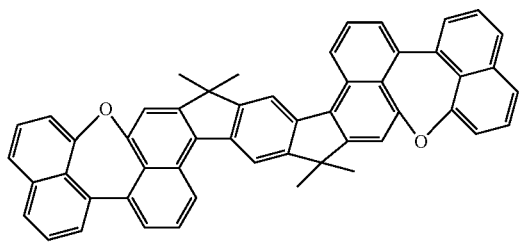
Formula (A-54a)
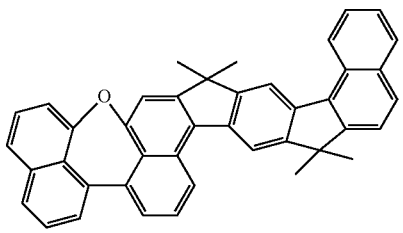
Formula (A-55a)
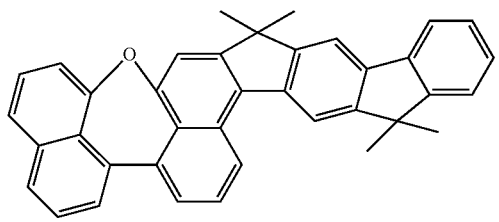
Formula (A-56a)
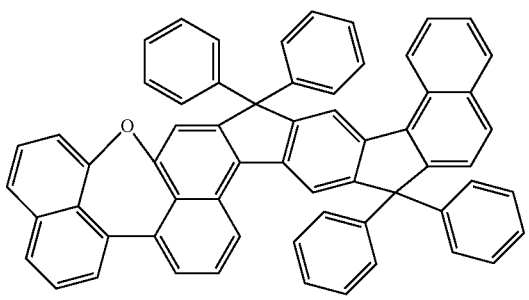
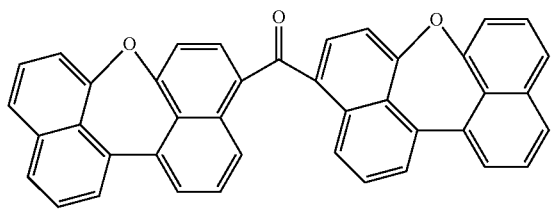
Formula (A-57a)
Formula (A-58a)
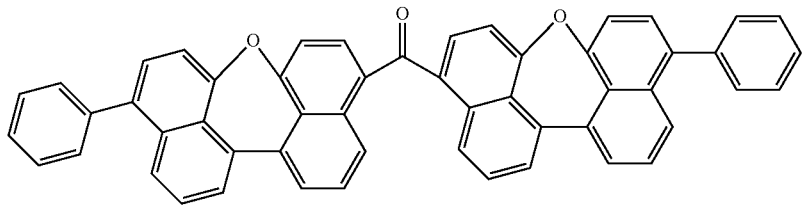
Formula (A-59a)
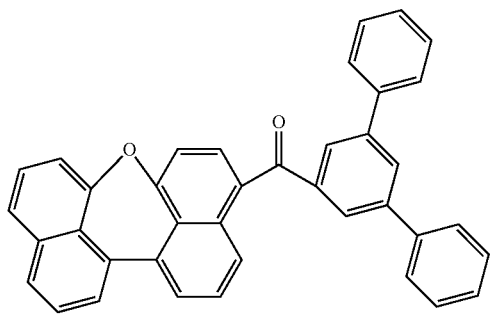
Formula (A-60a)
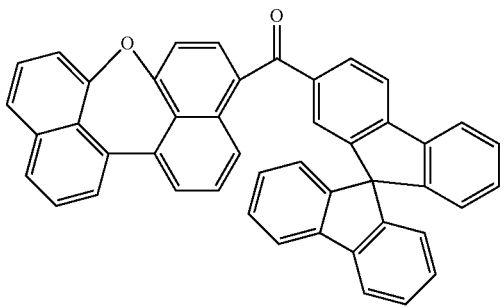

-continued
Formula (A-61a)
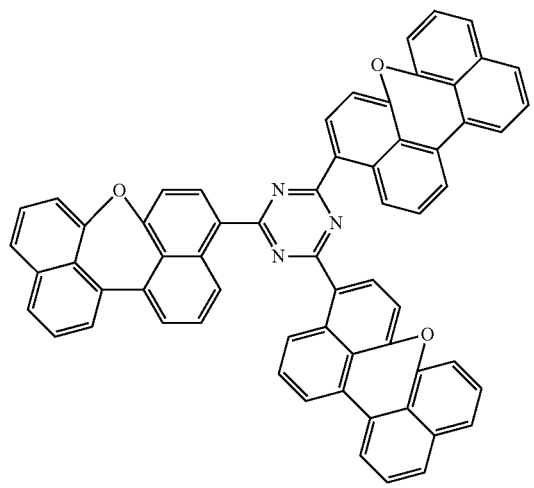
Formula (A-62a)
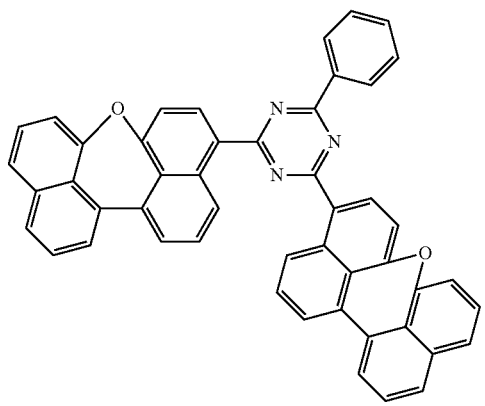
Formula (A-63a)
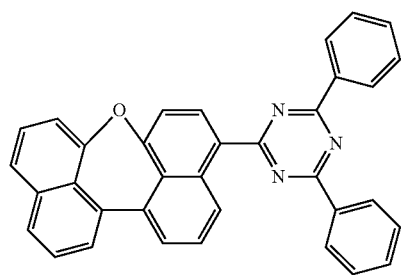
Formula (A-64a)
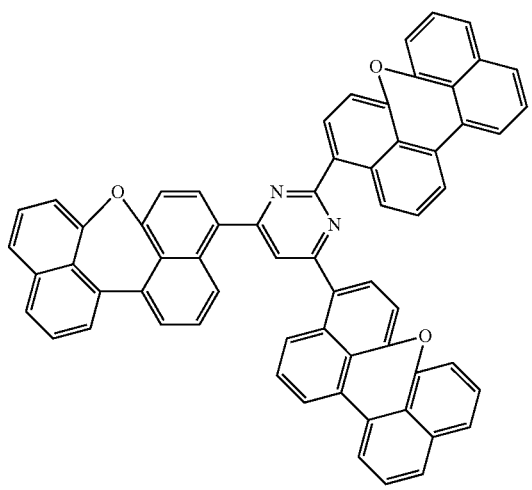
Formula (A-65a)
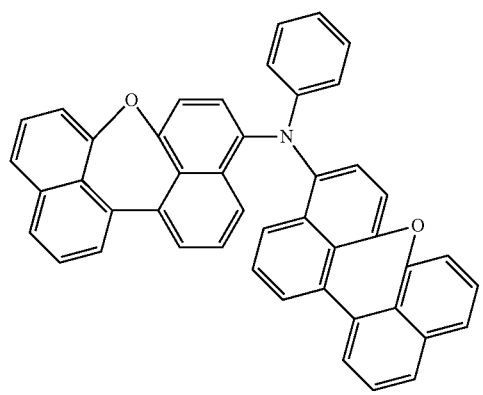
Formula (A-66a)
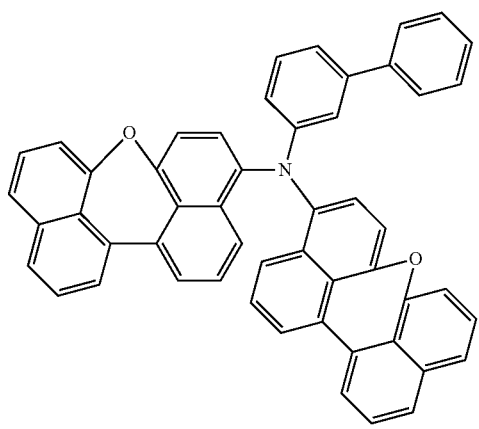

-continued
Formula (A-67a)
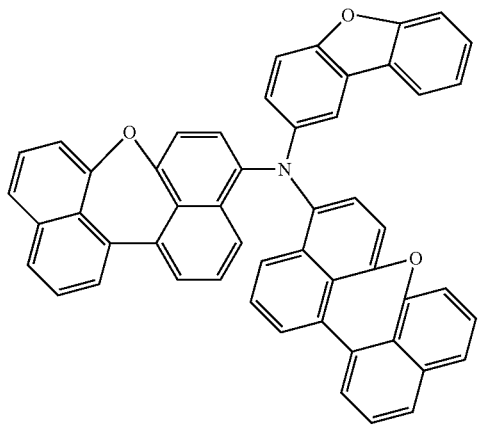
Formula (A-68a)
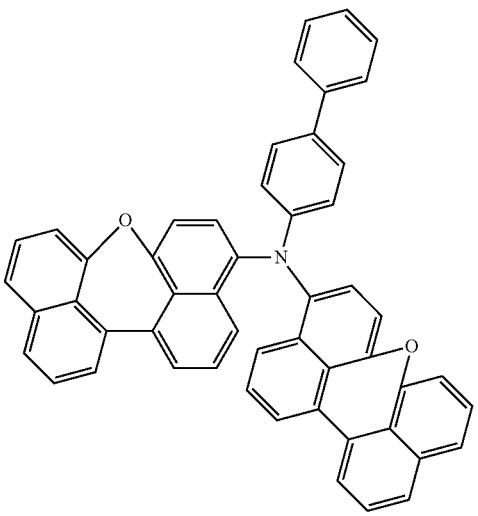
Formula (A-69a)
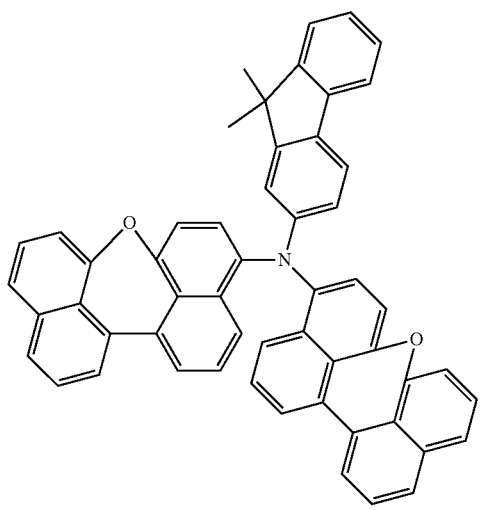
Formula (A-70)
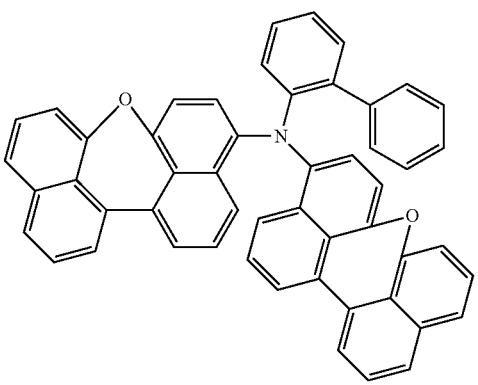
Formula (A-71)
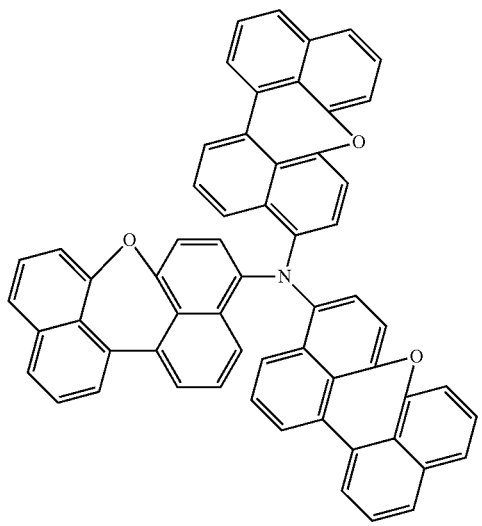
Formula (A-72)
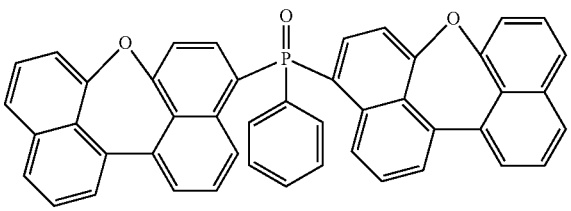

Formula (A-73)
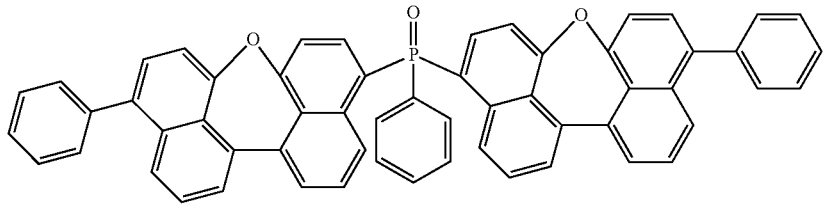
Formula (A-74)
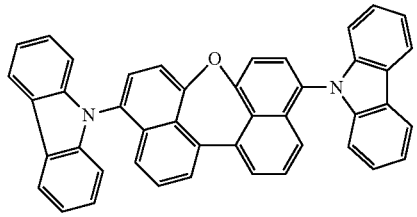
Formula (A-75)
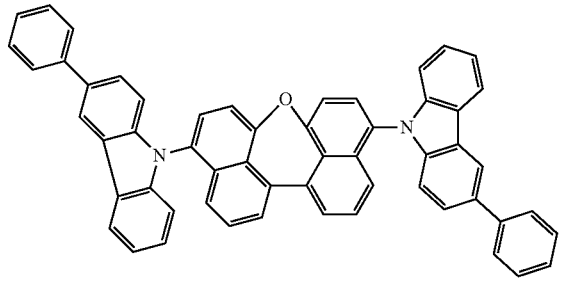
Formula (A-76)
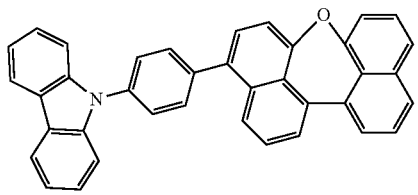
Formula (A-77)
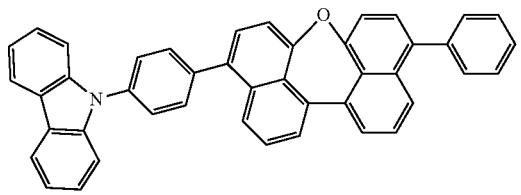
Formula (A-78)
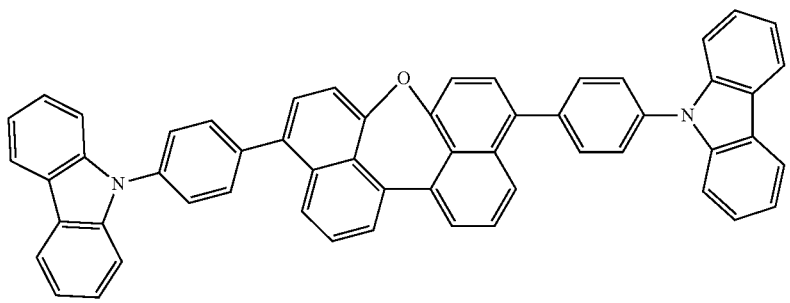
Formula (A-79)
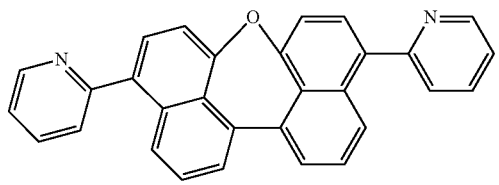
Formula (A-80)
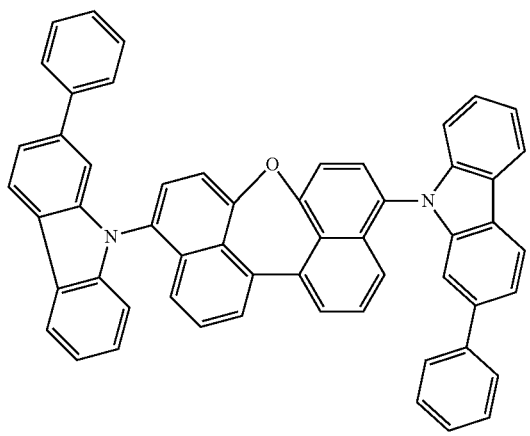

-continued
Formula (A-81)
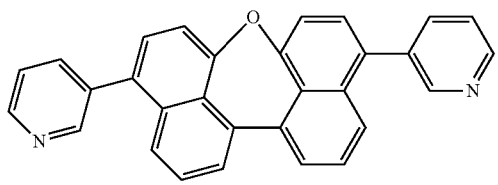
Formula (A-82)
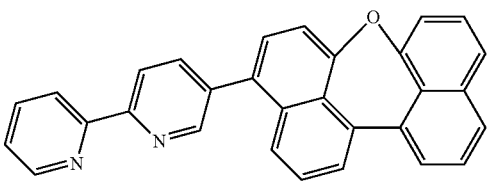
Formula (A-83)
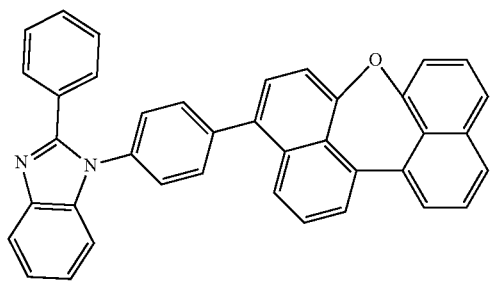
Formula (A-84)
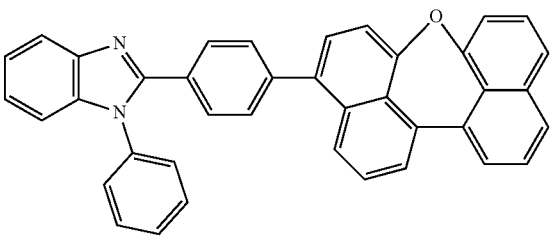
Formula (A-85)
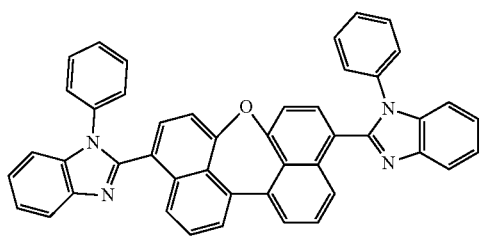
Formula (A-86)
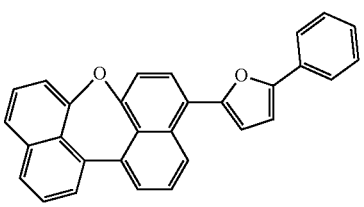
Formula (A-87)
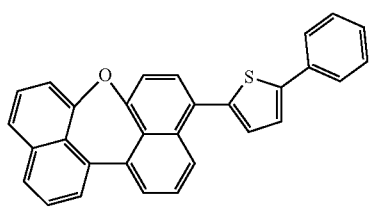
Formula (A-88)
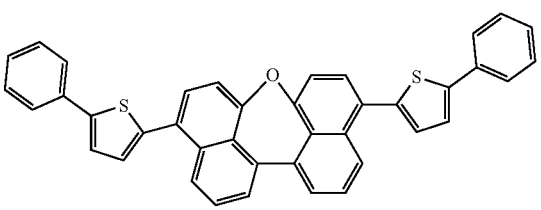
Formula (A-89)
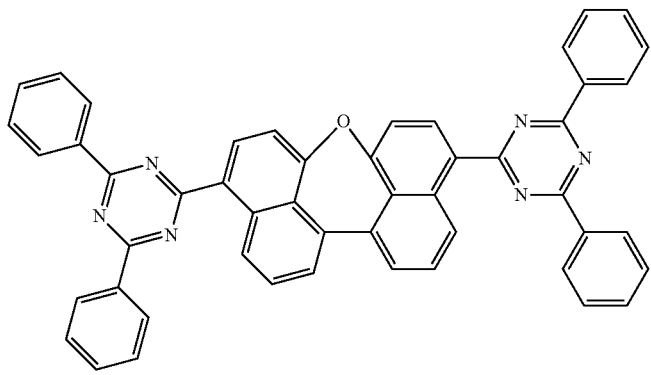

-continued
Formula (A-90)
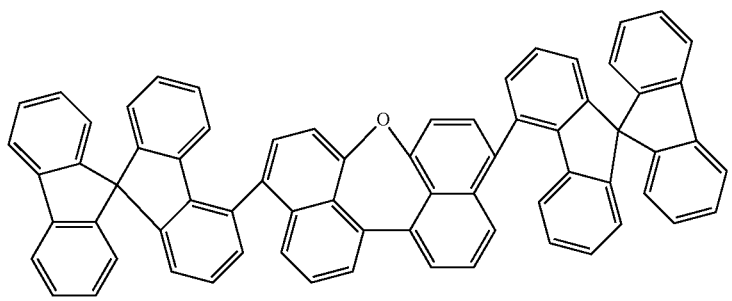
Formula (A-91)
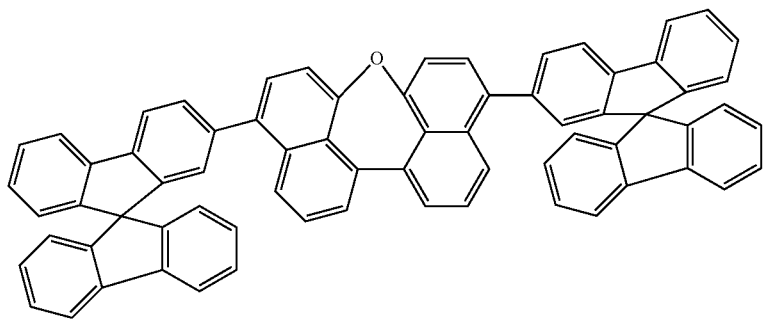
Formula (A-92)
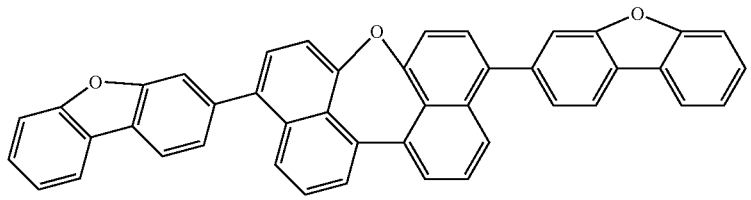
Formula (A-93)
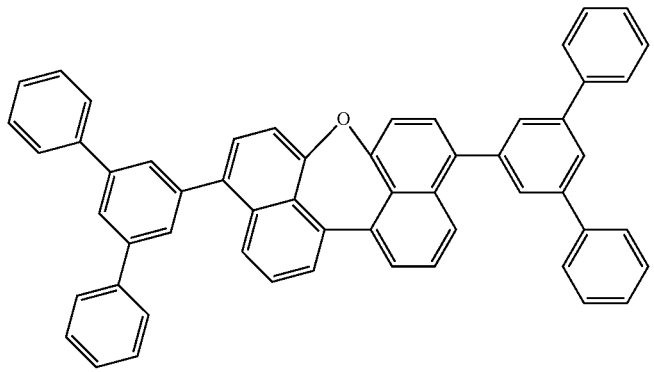
Formula (A-94)
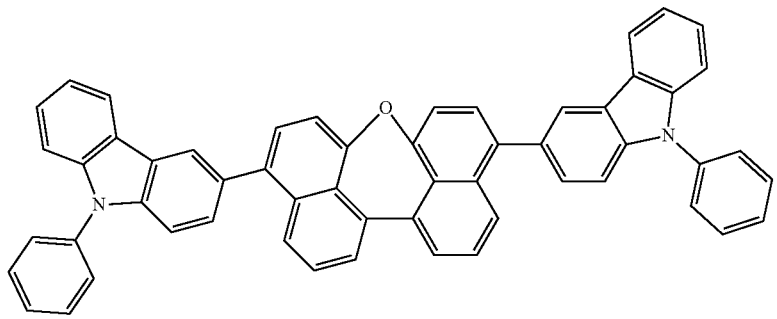

Formula (A-95)
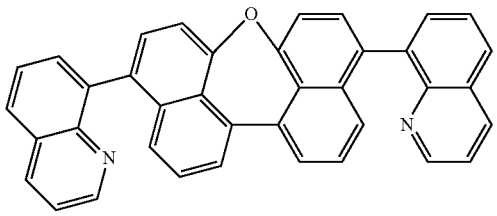
Formula (A-96)
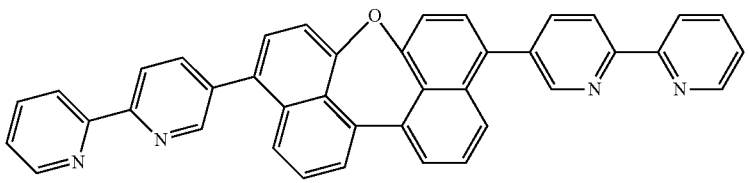
Formula (A-97)
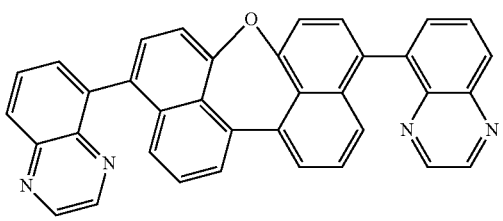
Formula (A-98)
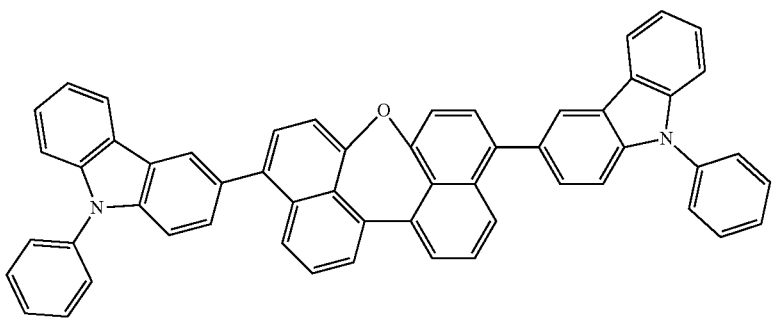
Formula (A-99)
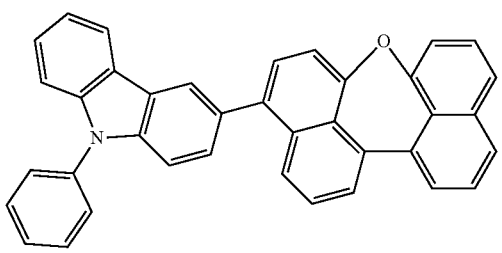
Formula (A-100)
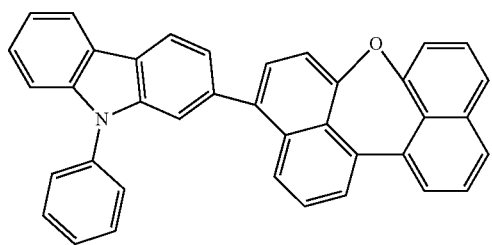
Formula (A-101)
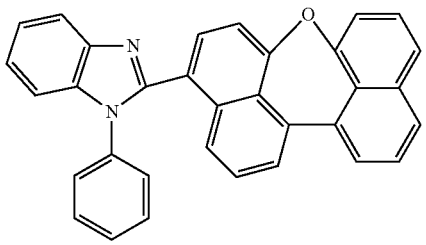
Formula (A-102)
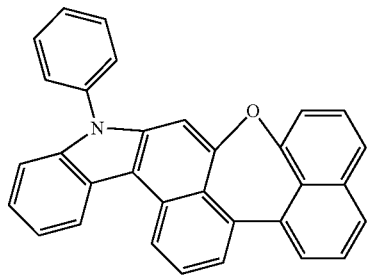

Formula (A-103)
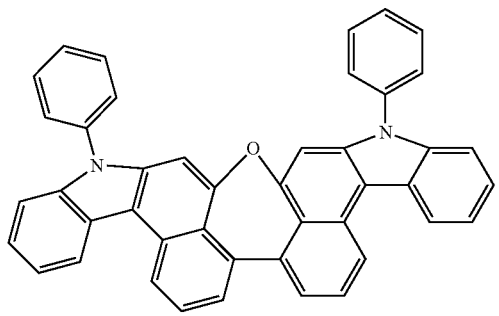
Formula (A-104)
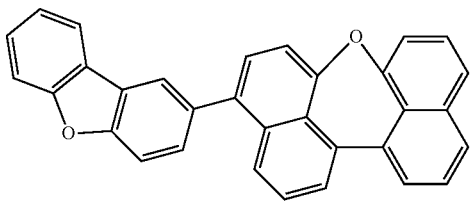
Formula (A-105)
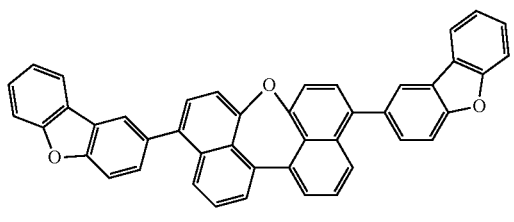
Formula (A-106)
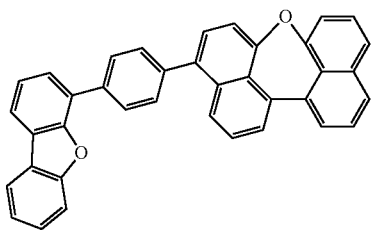
Formula (A-107)
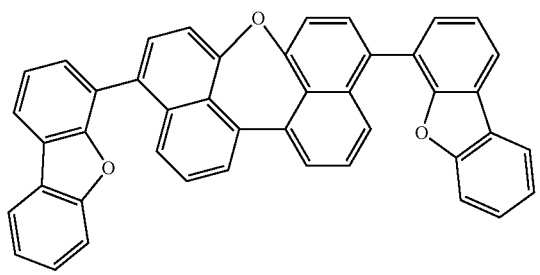
Formula (A-108)
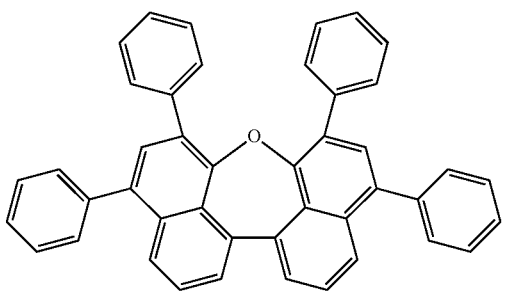
Formula (A-109)
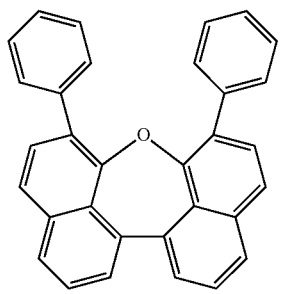
Formula (A-110)
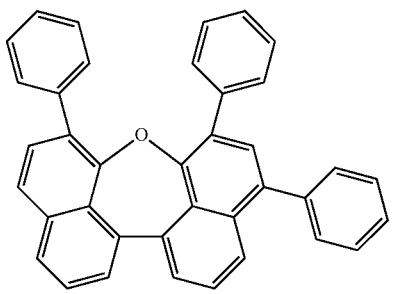
Formula (A-111)
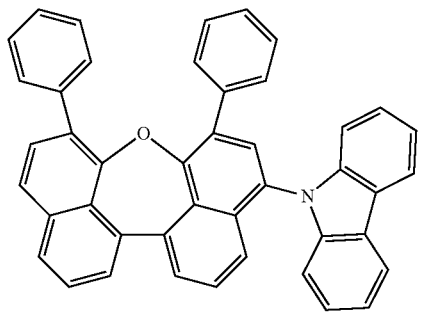
Formula (A-112)
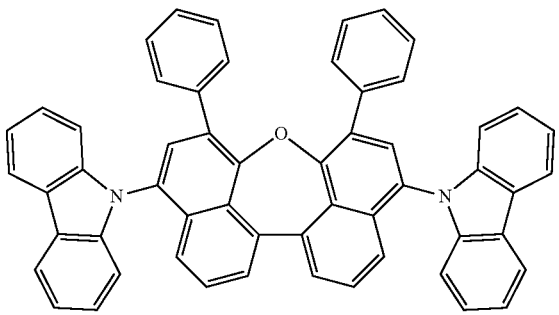

Formula (A-113)
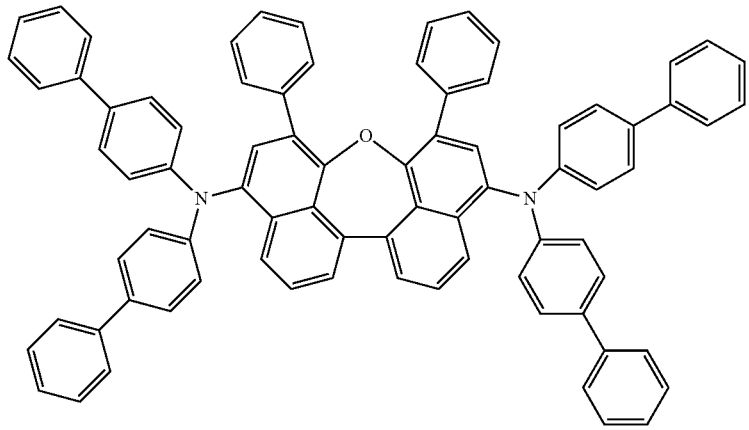
Formula (A-114)
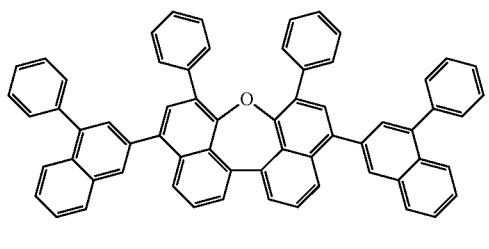
Formula (A-115)
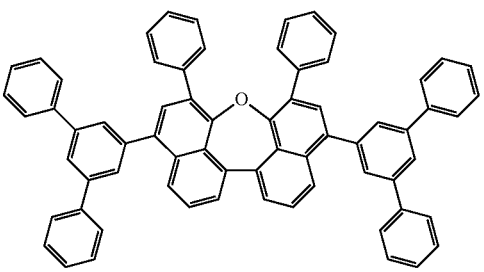
Formula (A-116)
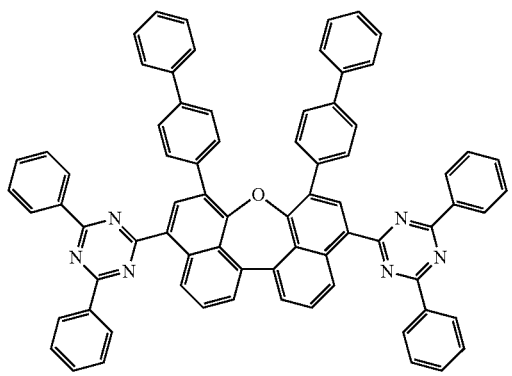
Formula (A-117)
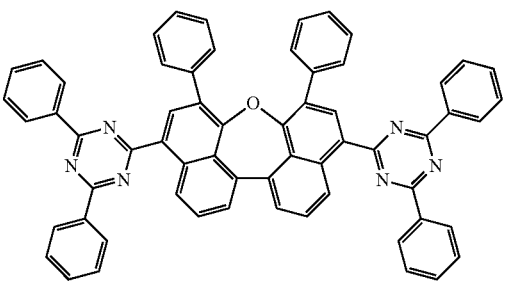
Formula (A-118)
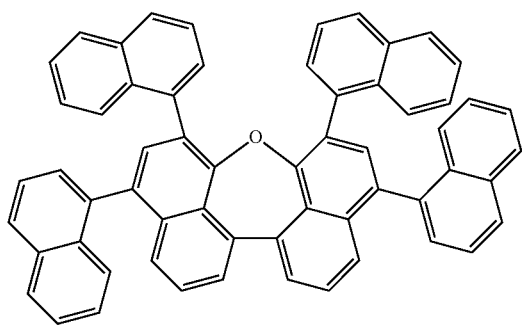
Formula (A-119)
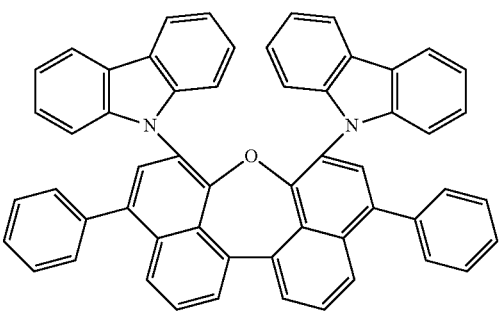

-continued
Formula (A-120)
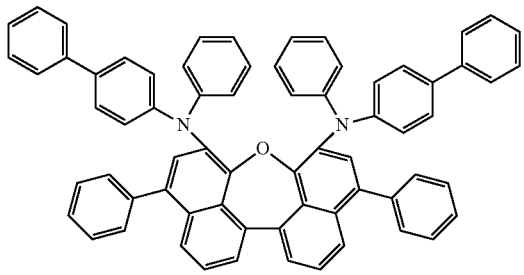
Formula (A-121)
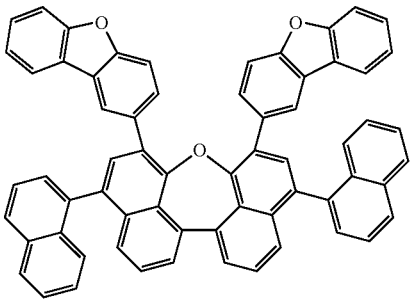
Formula (A-122)
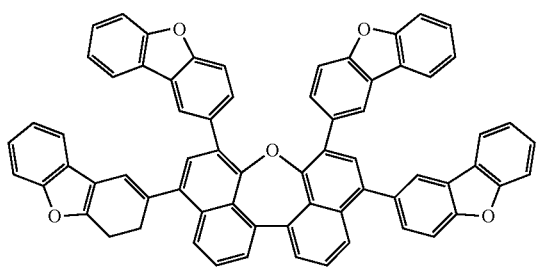
Formula (A-123)
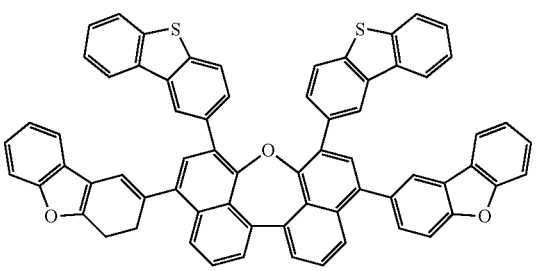
Formula (A-124)
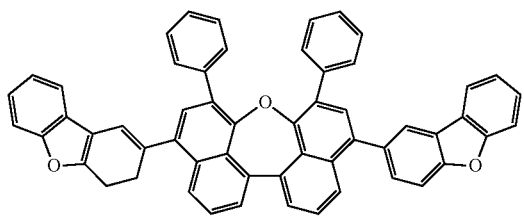
Formula (A-125)
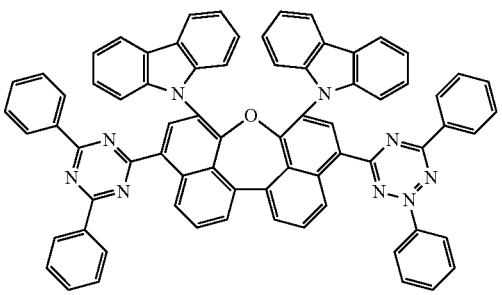
Formula (A-126)
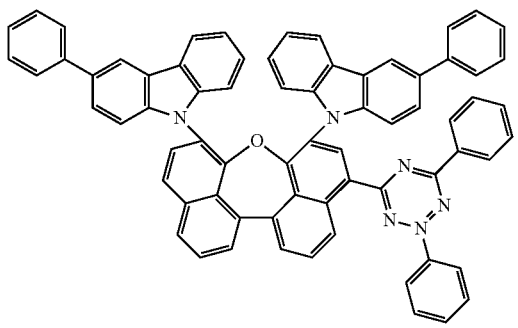
Formula (A-127)
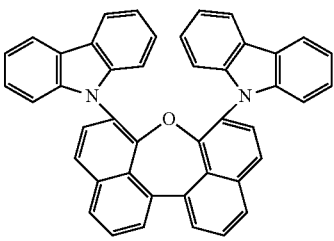

-continued
Formula (A-128)
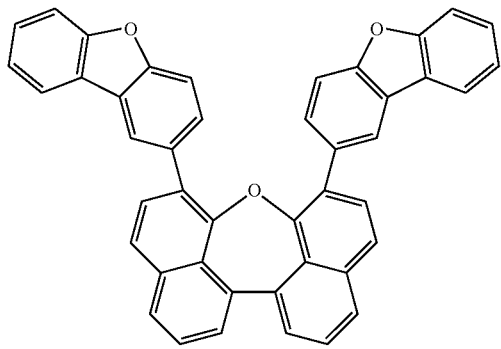
Formula (A-129)
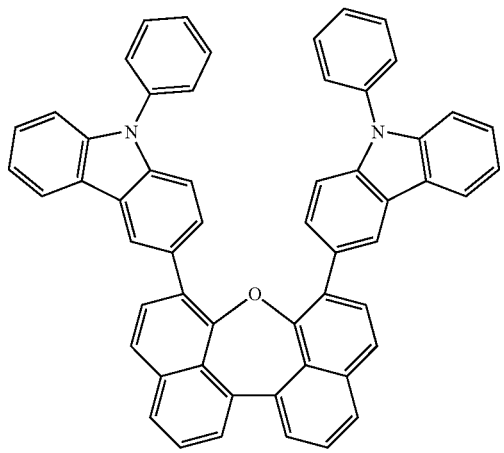
Formula (A-130)
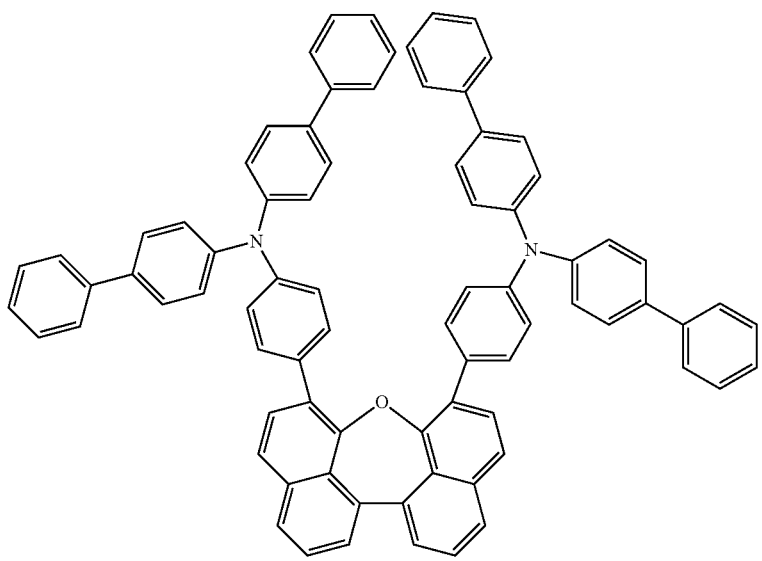
Formula (A-131)
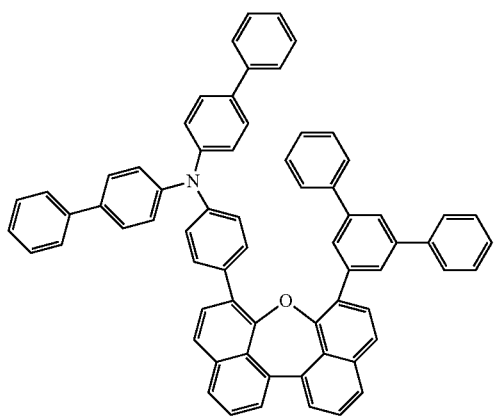
Formula (A-132)
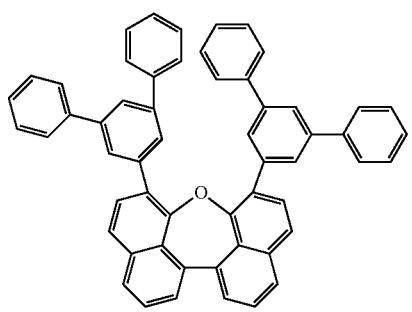

-continued
Formula (A-133)
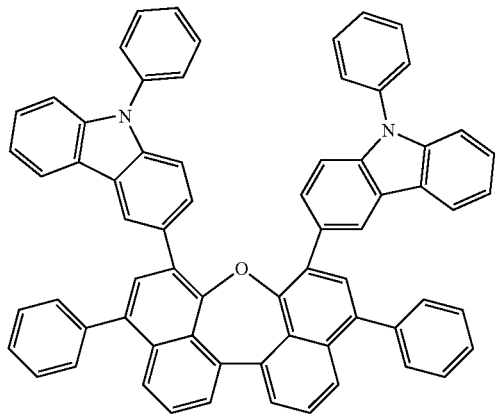
Formula (A-134)
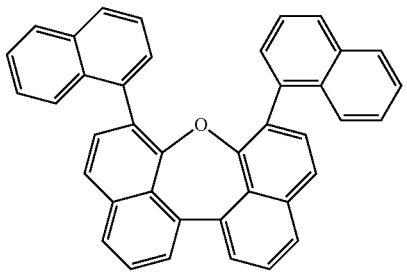
Formula (A-135)
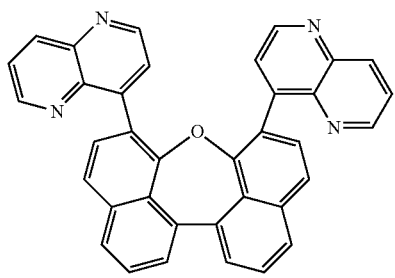
Formula (A-136)
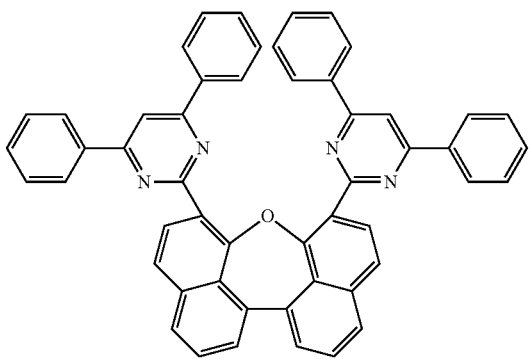
Formula (A-137)
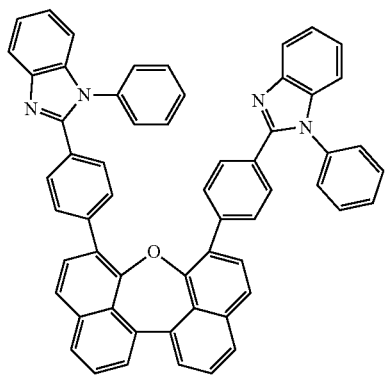
Formula (A-138)
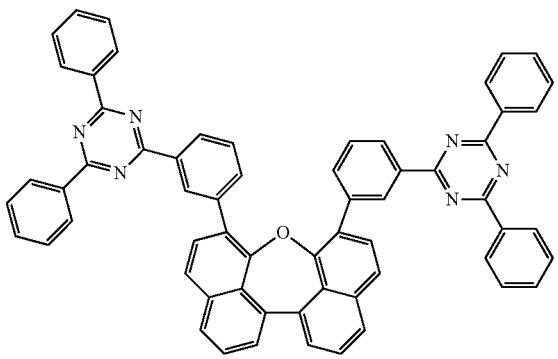

-continued
Formula (A-139)
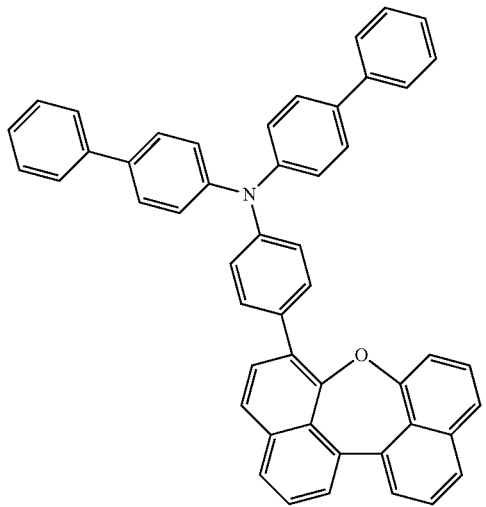
Formula (A-140)
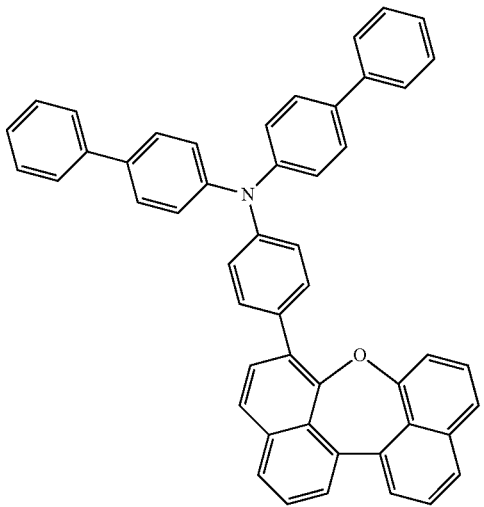
Formula (A-141)
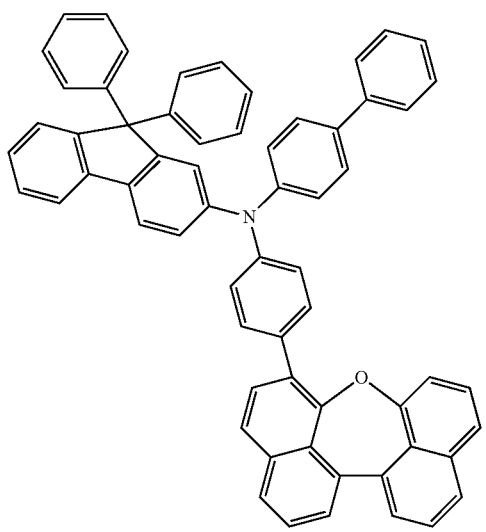
Formula (A-142)
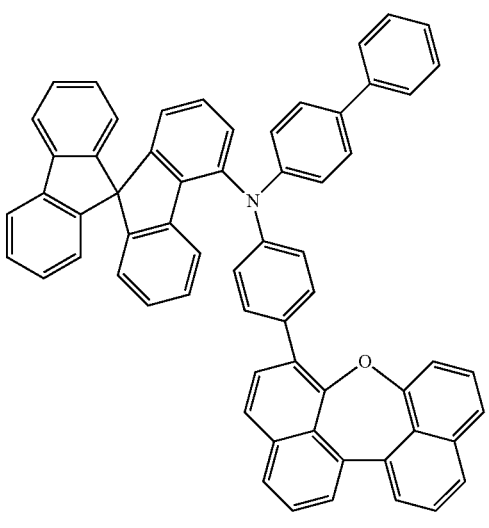
Formula (A-143)
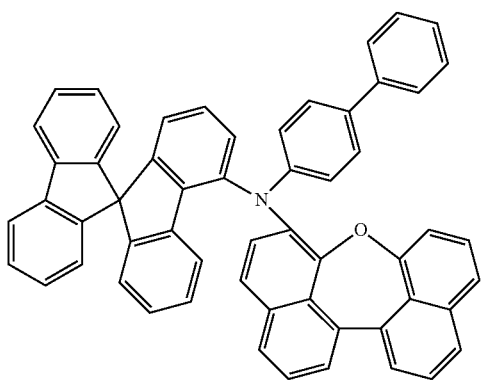
Formula (A-144)
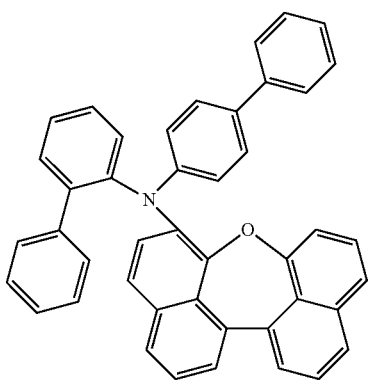

-continued
Formula (A-145)
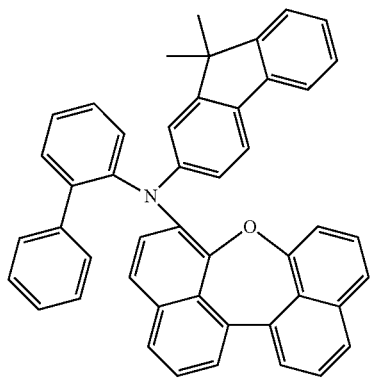
Formula (A-146)
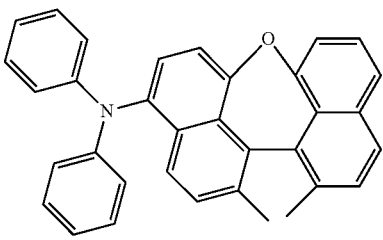
Formula (A-147)
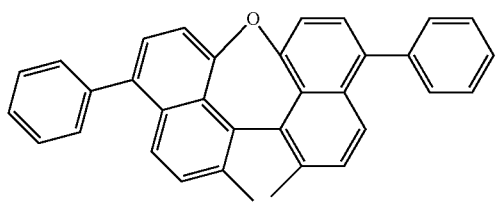
Formula (A-148)
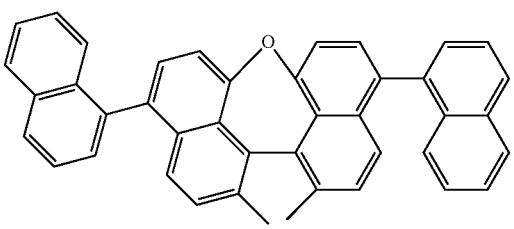
Formula (A-149)
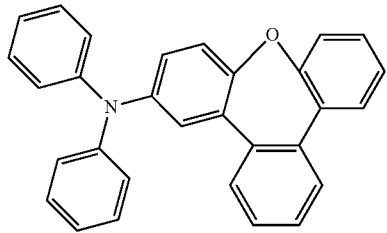
Formula (A-149)
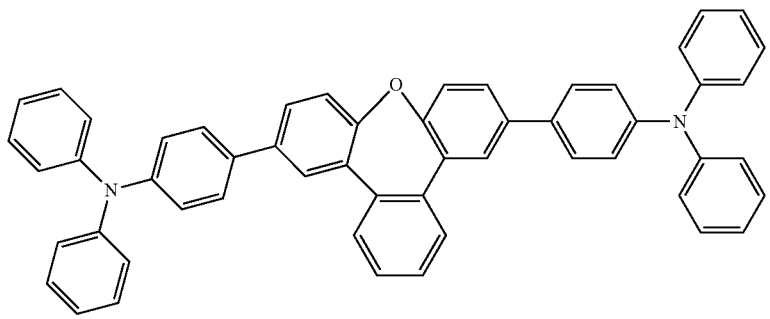
Formula (A-149)
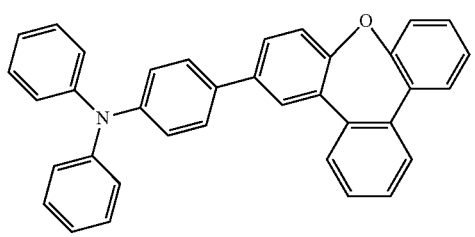
Formula (A-150)
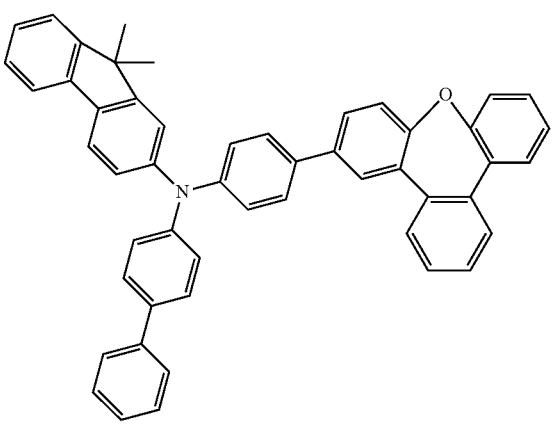

-continued
Formula (A-151)
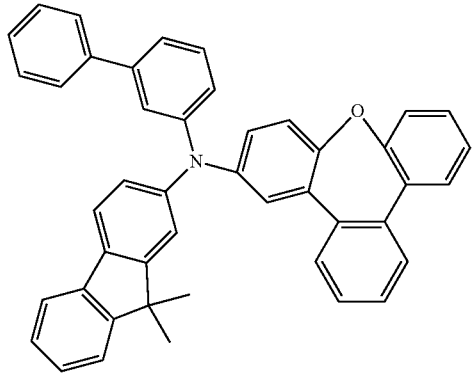
Formula (A-152)
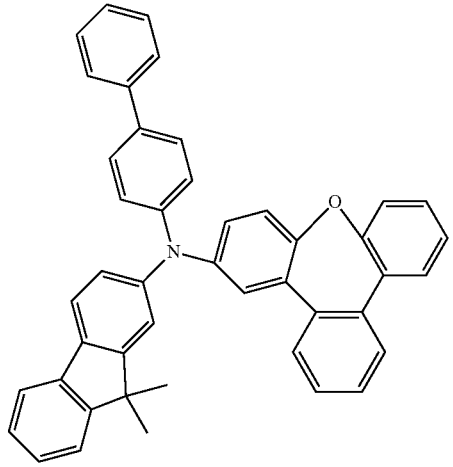
Formula (A-153)
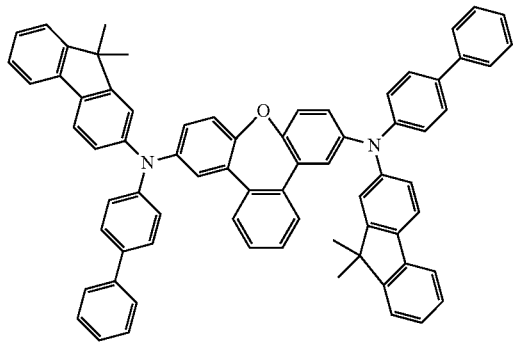
Formula (A-154)
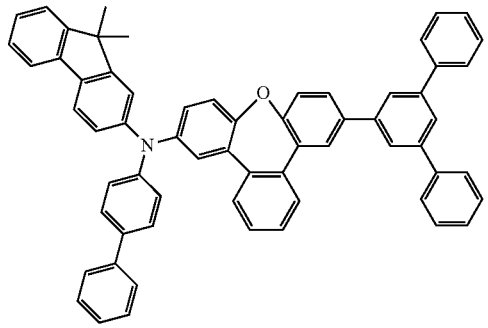
Formula (A-155)
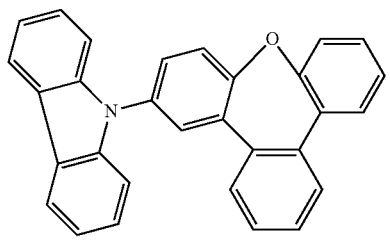
Formula (A-156)
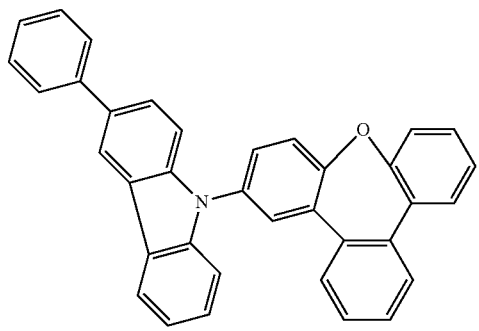
Formula (A-157)
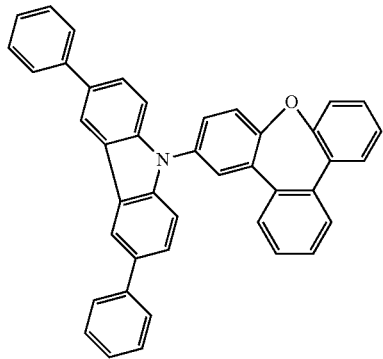
Formula (A-158)
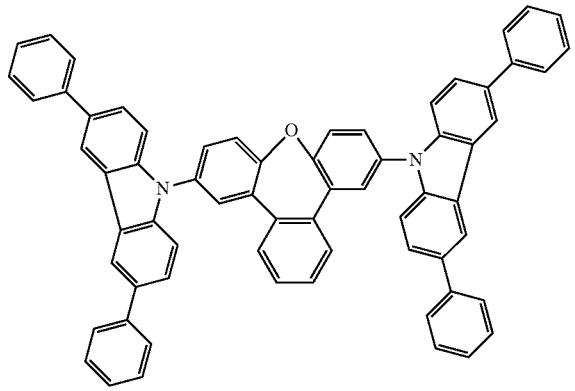

-continued
Formula (A-159)
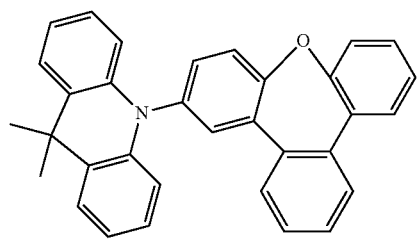
Formula (A-160)
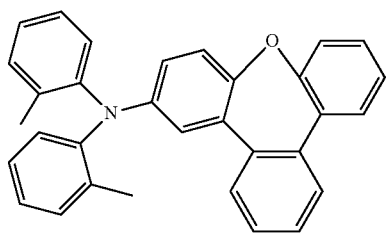
Formula (A-161)
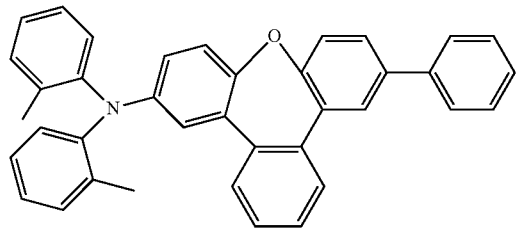
Formula (A-162)
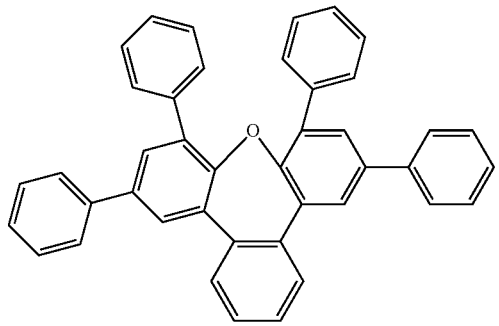
Formula (A-163)
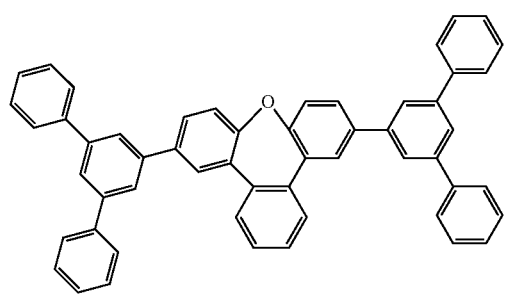
Formula (A-164)
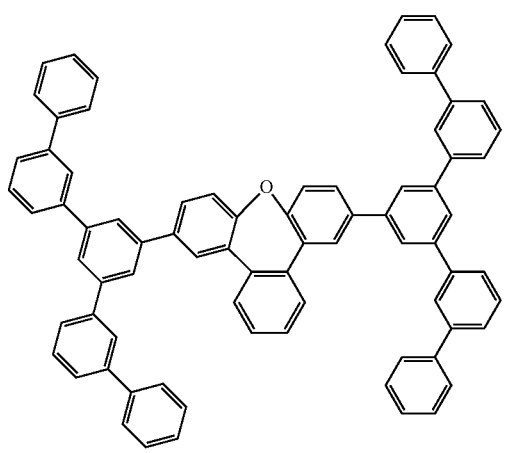
Formula (A-165)
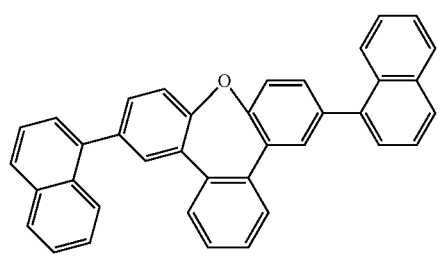
Formula (A-166)
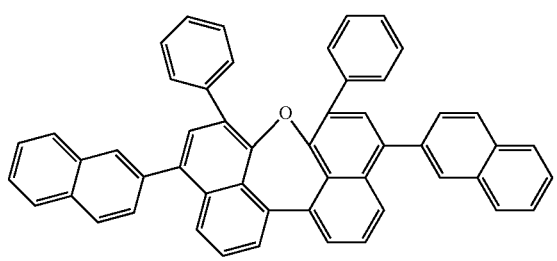
Formula (A-167)
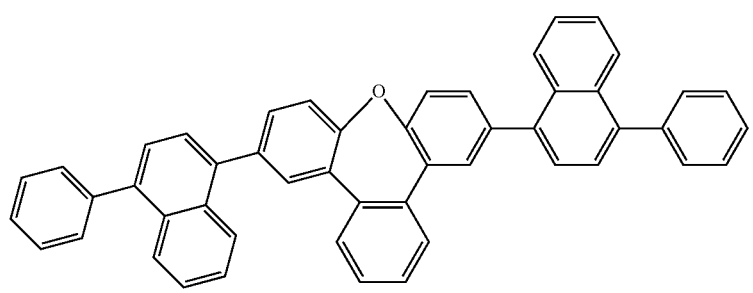

Formula (A-168)
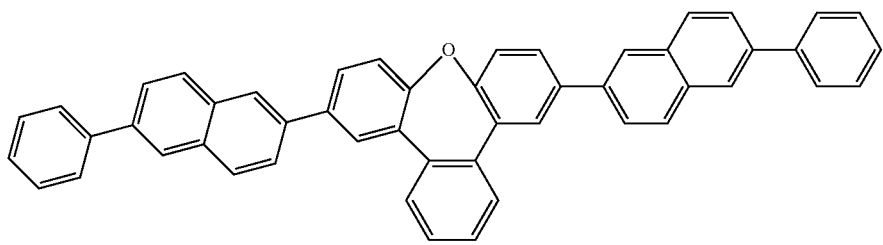
Formula (A-169)
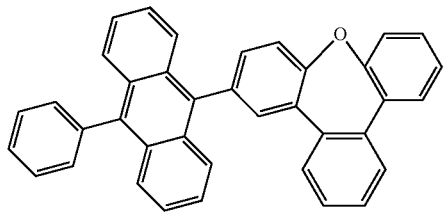
Formula (A-170)
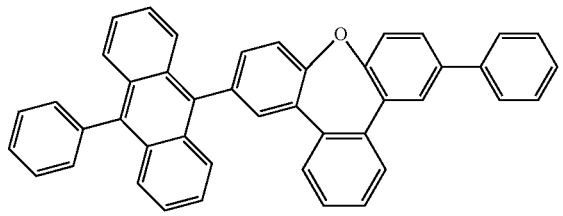
Formula (A-171)
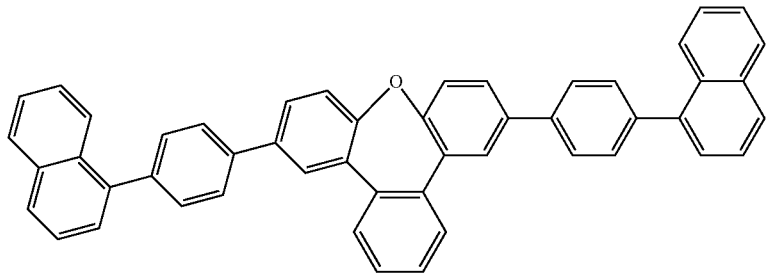
Formula (A-172)
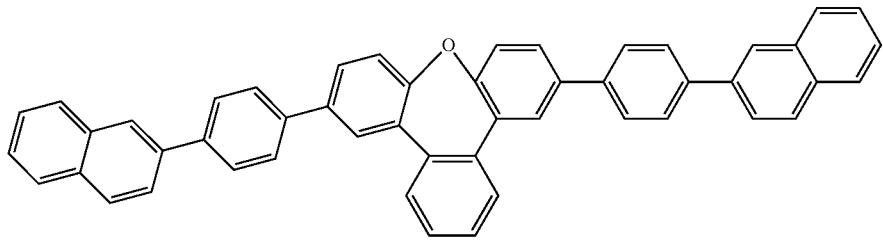
Formula (A-173)
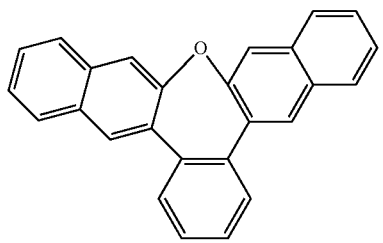
Formula (A-174)
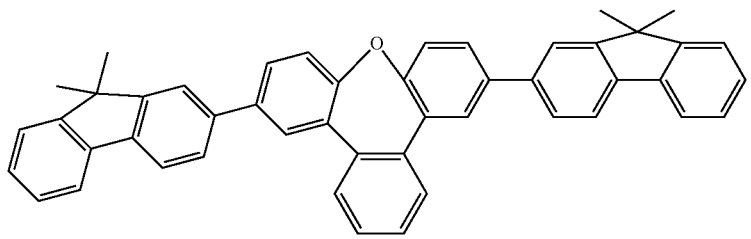

-continued
Formula (A-175)
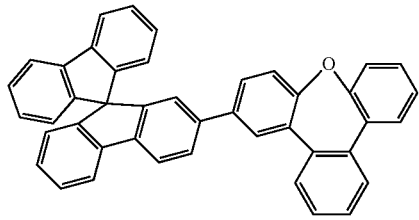
Formula (A-176)
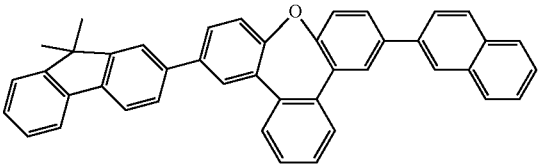
Formula (A-177)
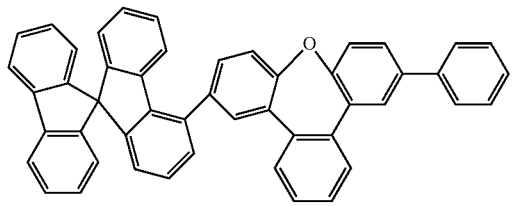
Formula (A-178)
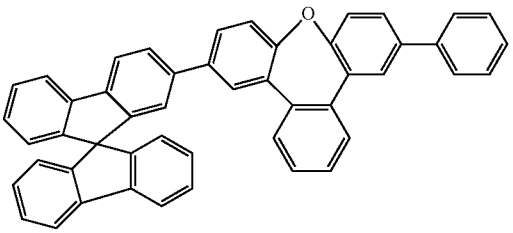
Formula (A-179)
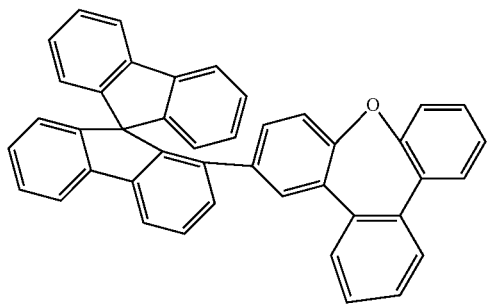
Formula (A-180)
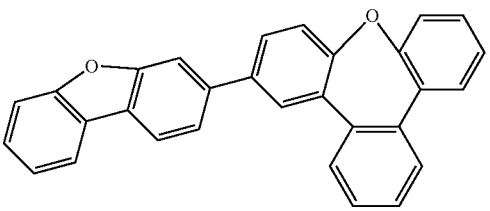
Formula (A-181)
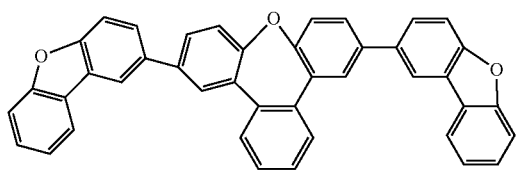
Formula (A-182)
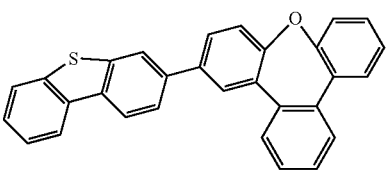
Formula (A-183)
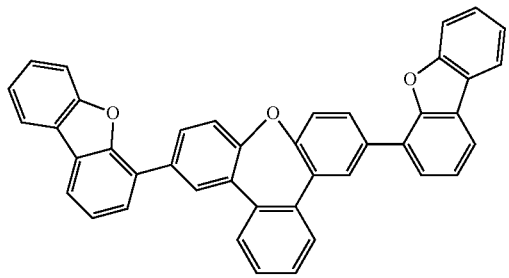
Formula (A-184)
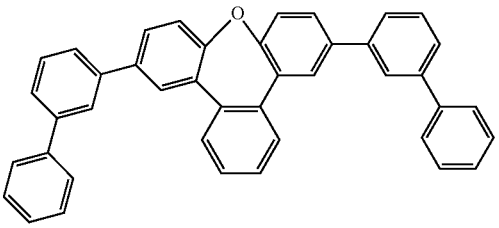
Formula (A-185)
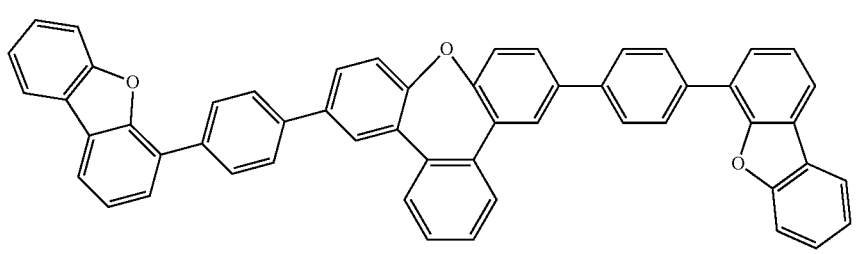

-continued
Formula (A-186)
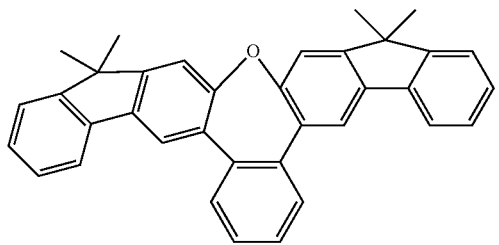
Formula (A-187)
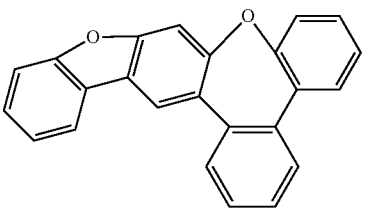
Formula (A-188)
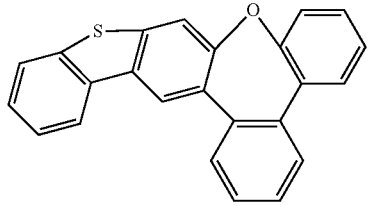
Formula (A-189)
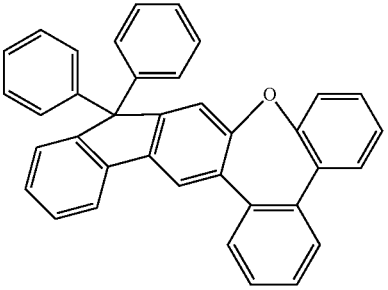
Formula (A-190)
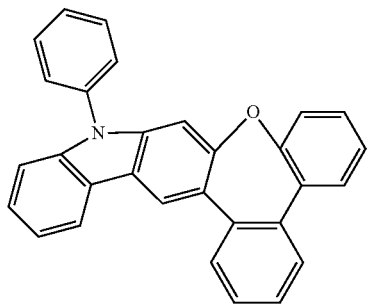
Formula (A-191)
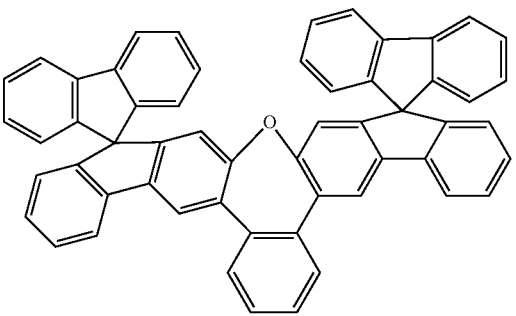
Formula (A-192)
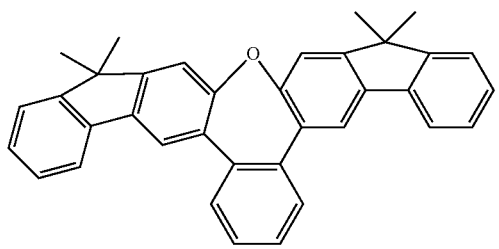
Formula (A-193)
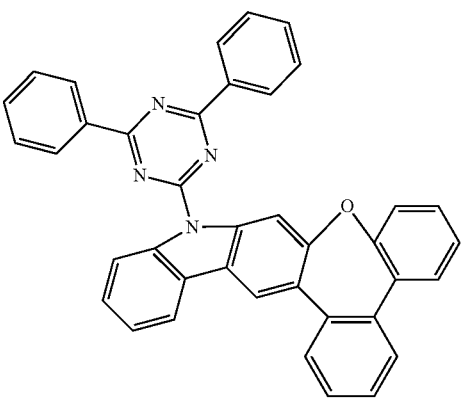
Formula (A-194)
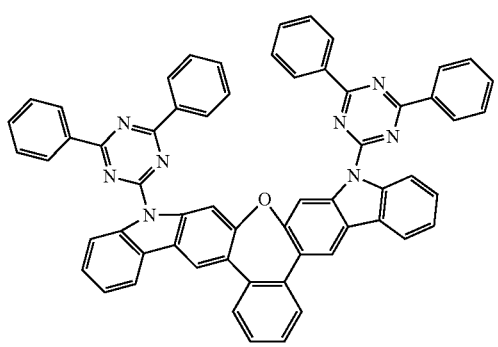
Formula (A-195)
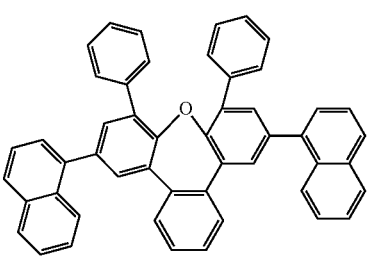

-continued
Formula (A-196)
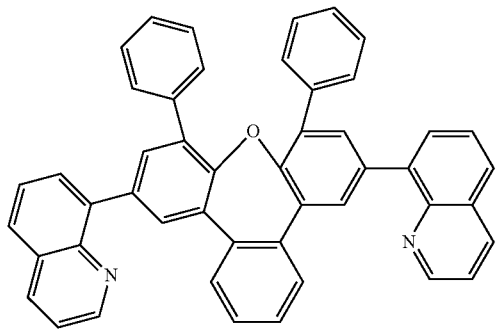
Formula (A-197)
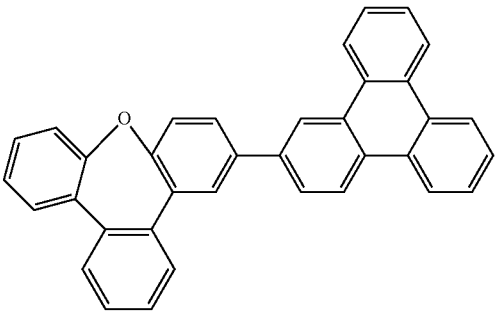
Formula (A-198)
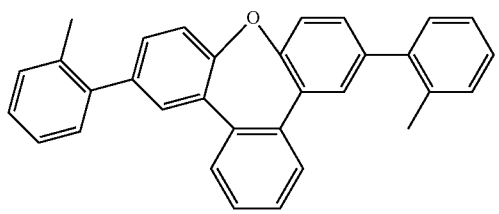
Formula (A-199)
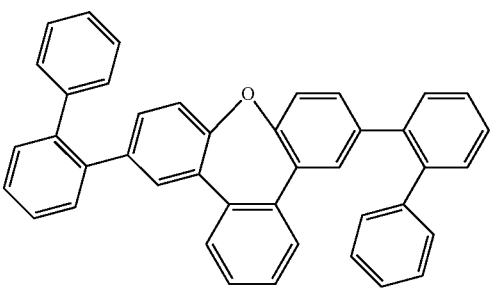
Formula (A-200)
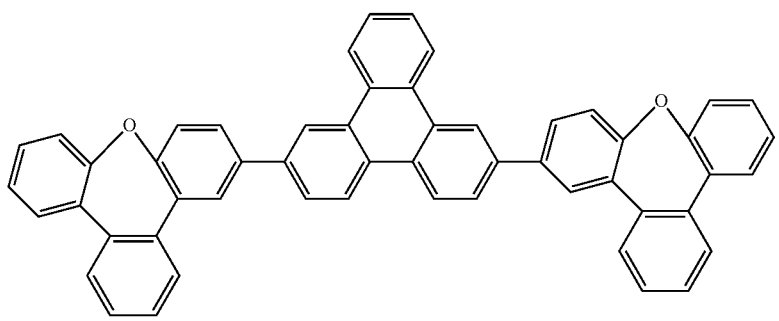
Formula (A-201)
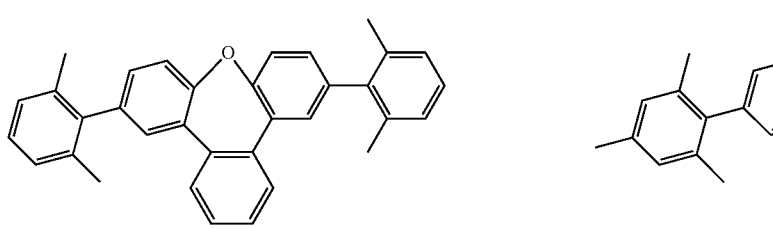
Formula (A-202)
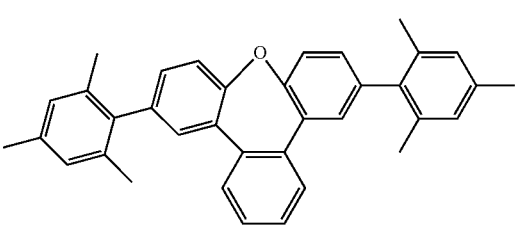
Formula (A-203)
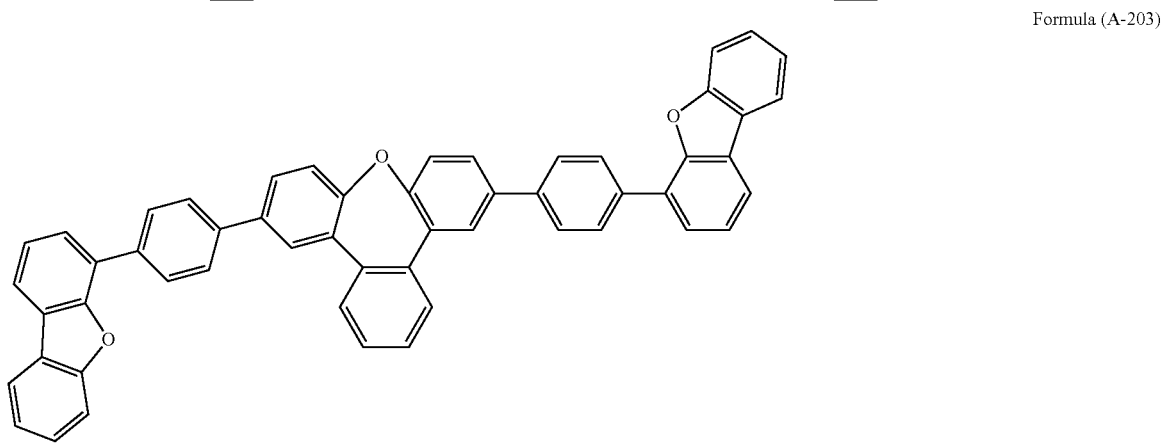

-continued
Formula (A-204)
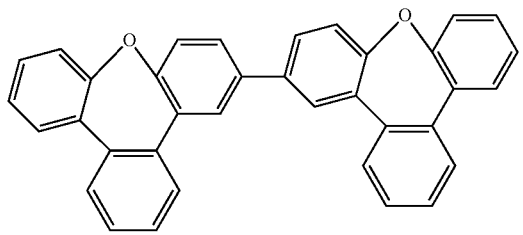
Formula (A-205)
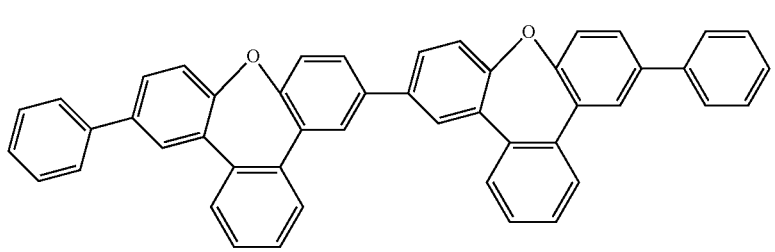
Formula (A-206)
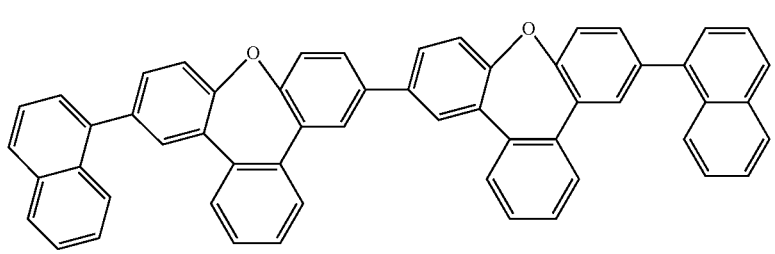
Formula (A-207)
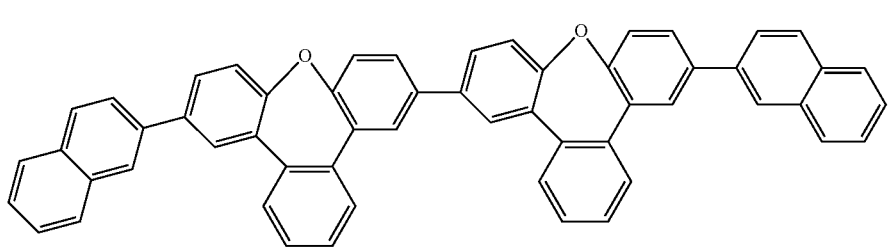
Formula (A-208)
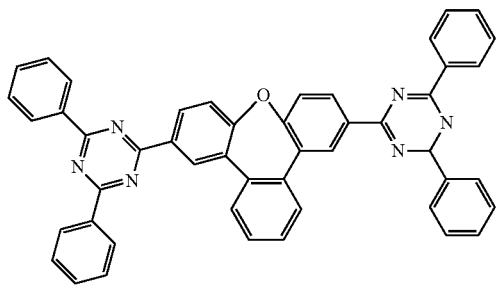
Formula (A-209)
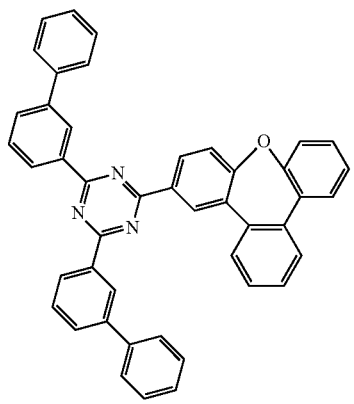

-continued
Formula (A-210)
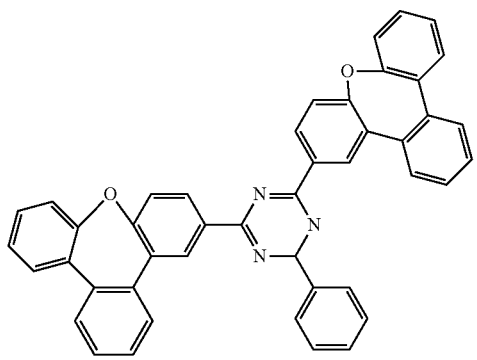
Formula (A-211)
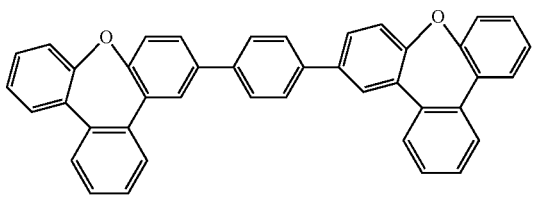
Formula (A-212)
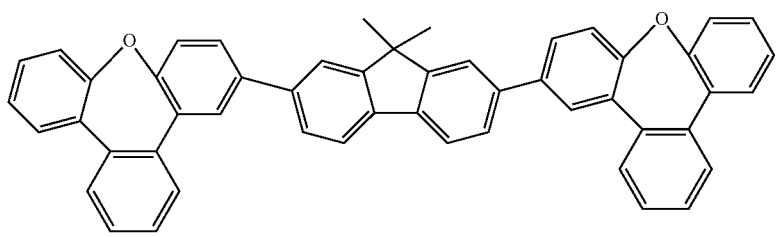
Formula (A-213)
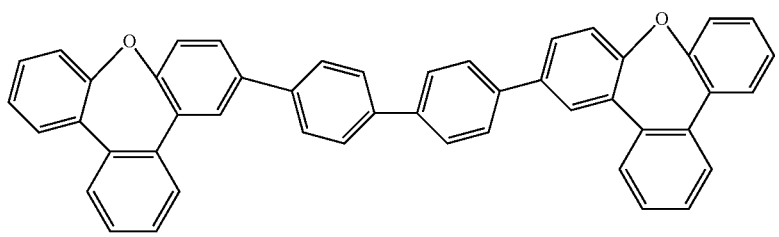
Formula (A-214)
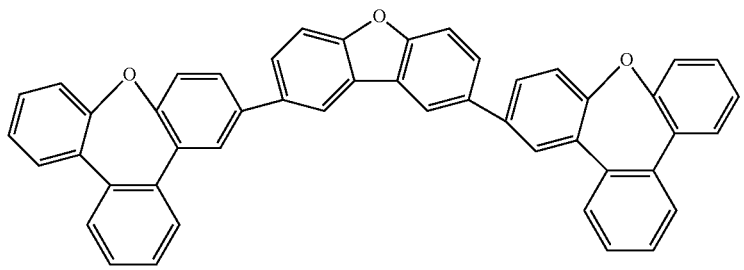
Formula (A-215)
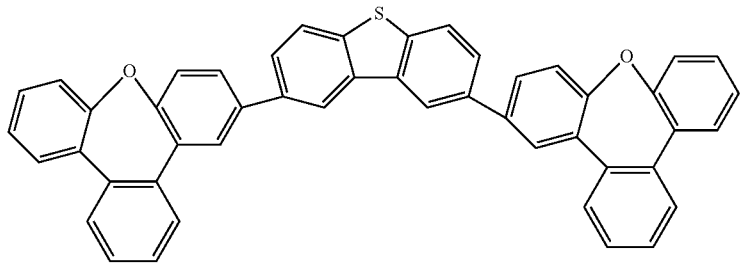
Formula (A-216)
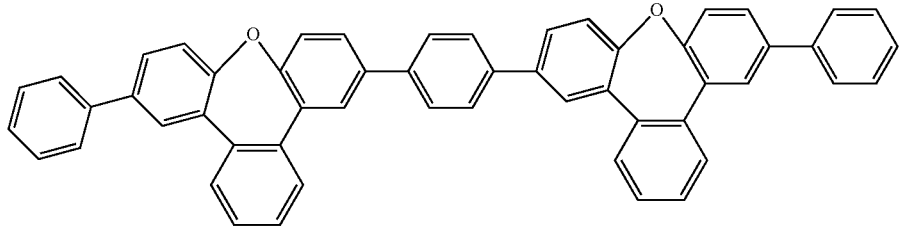

-continued
Formula (A-217)
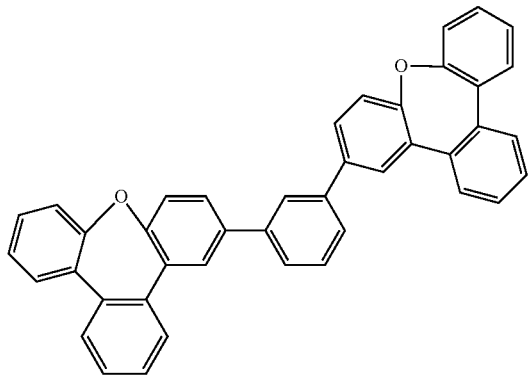
Formula (A-218)
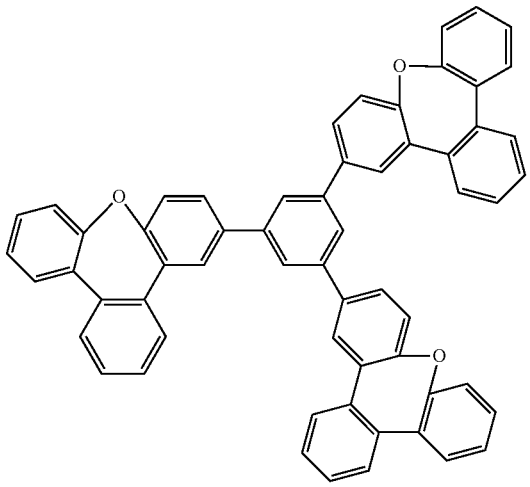
Formula (A-219)
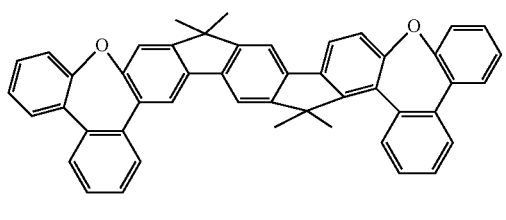
Formula (A-220)
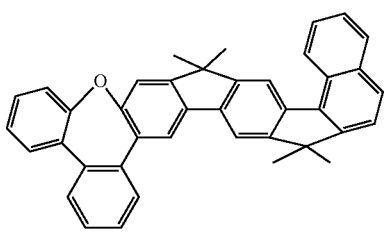
Formula (A-221)
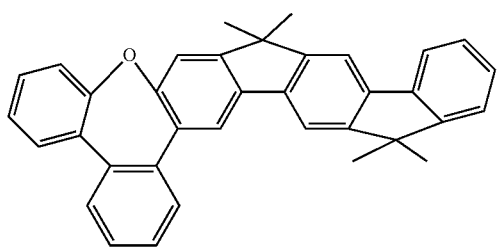
Formula (A-222)
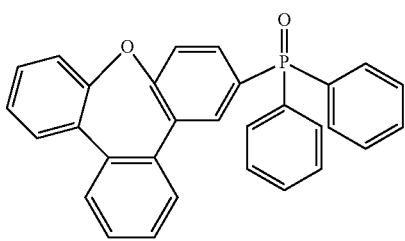
Formula (A-223)
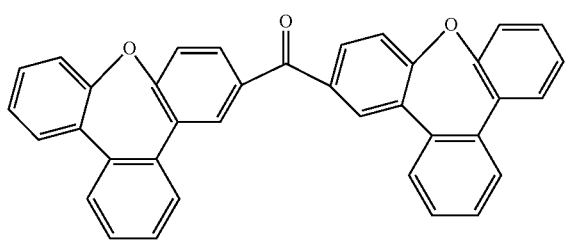
Formula (A-224)
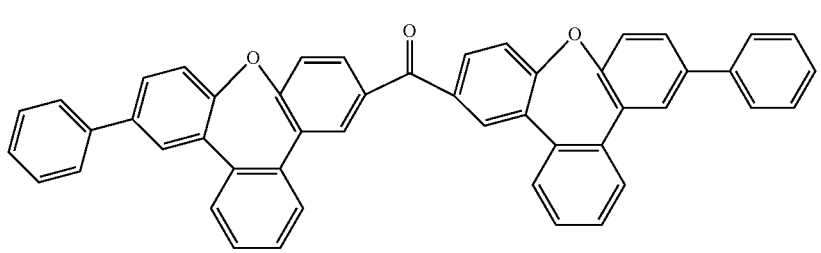

Formula (A-225)
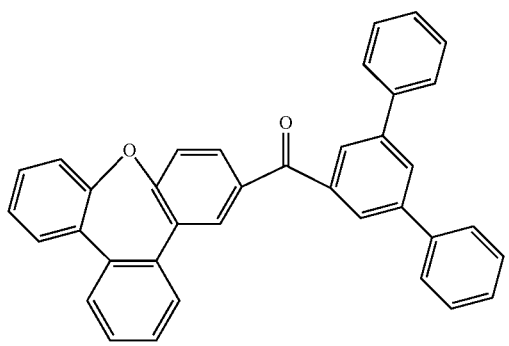
Formula (A-226)
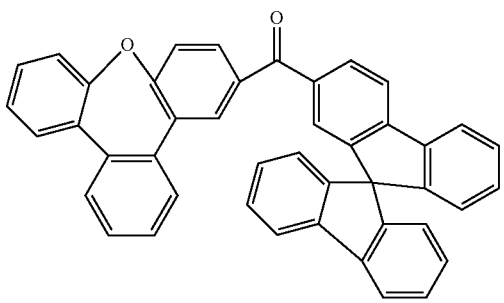
Formula (A-227)
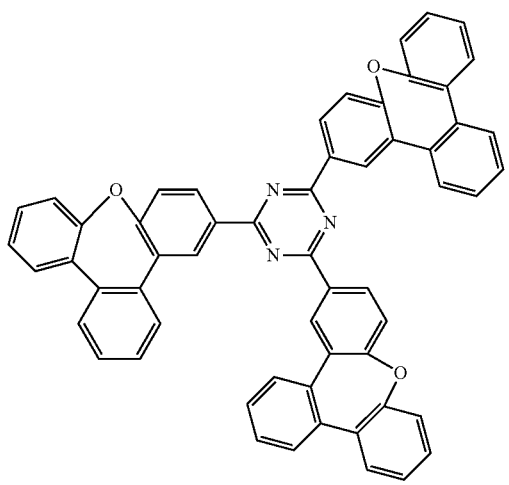
Formula (A-228)
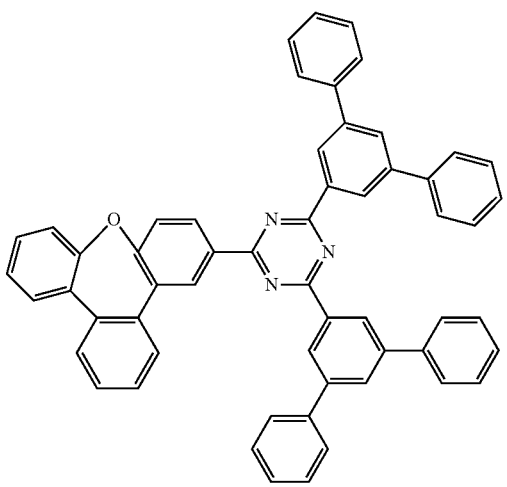
Formula (A-229)
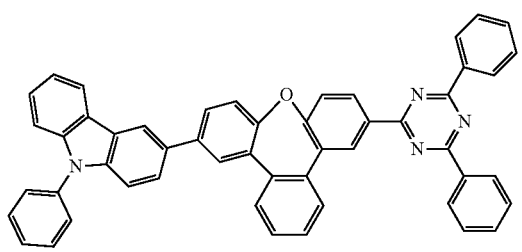
Formula (A-230)
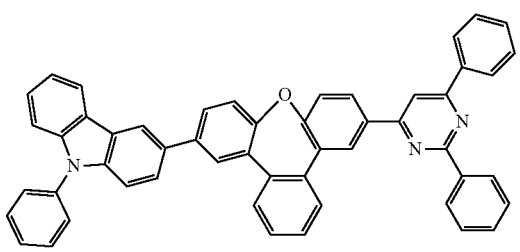
Formula (A-231)
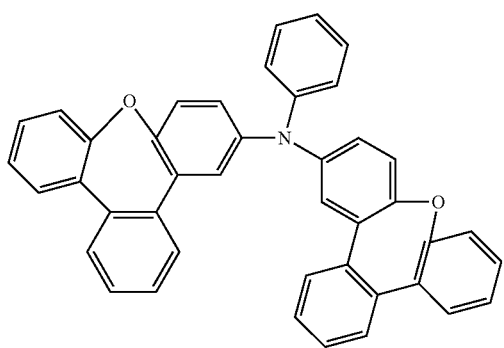
Formula (A-232)
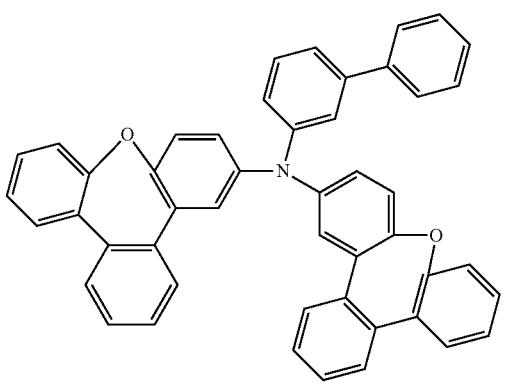

Formula (A-233)
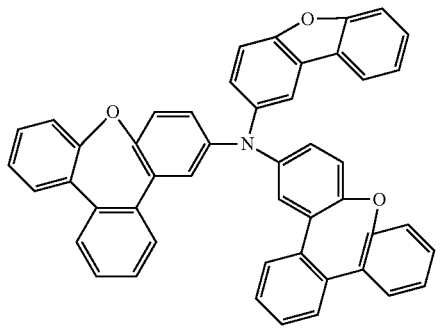
Formula (A-234)
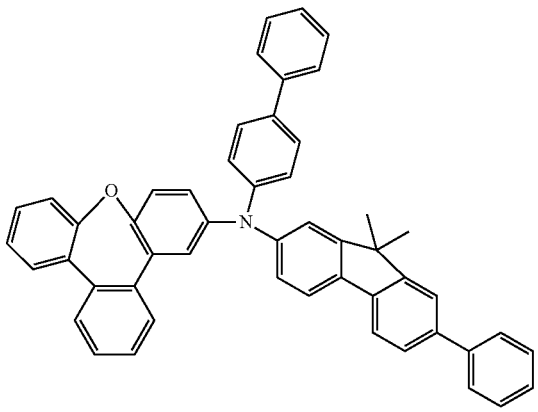
Formula (A-235)
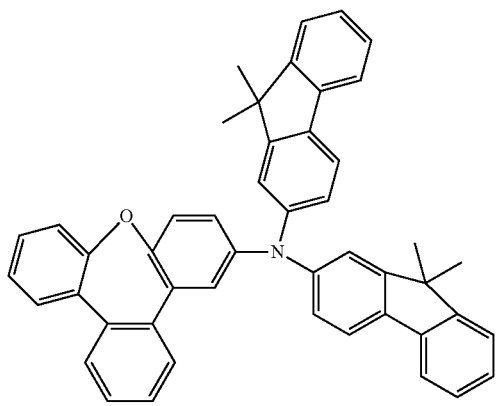
Formula (A-236)
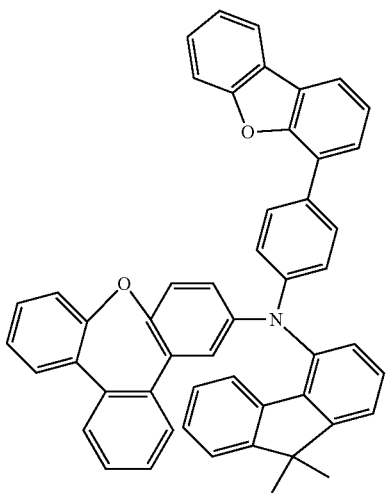
Formula (A-237)
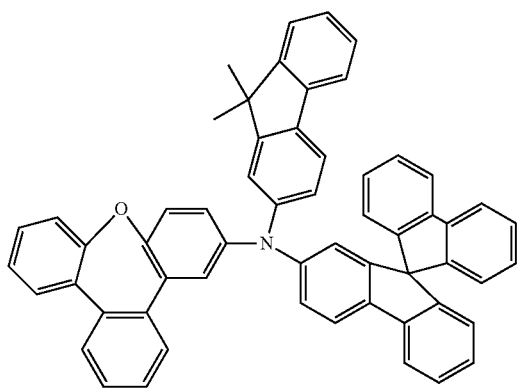
Formula (A-238)
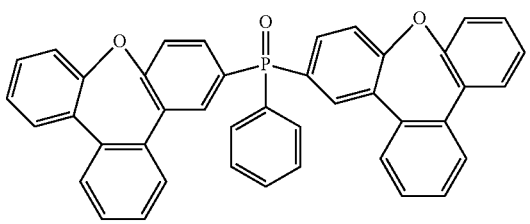
Formula (A-239)
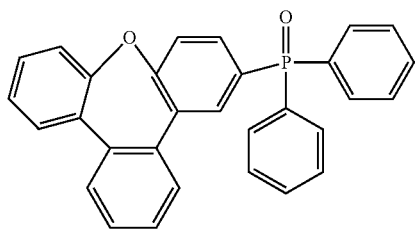
Formula (A-240)
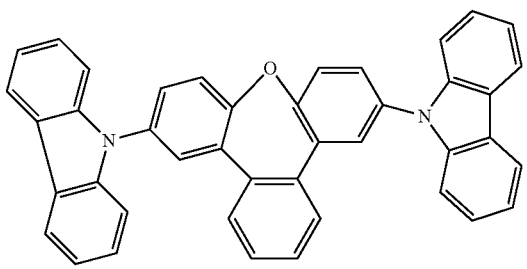

-continued
Formula (A-241)
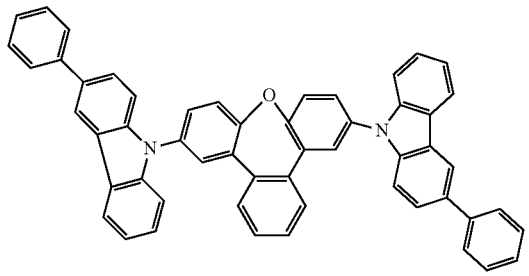
Formula (A-242)
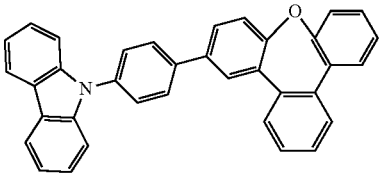
Formula (A-243)
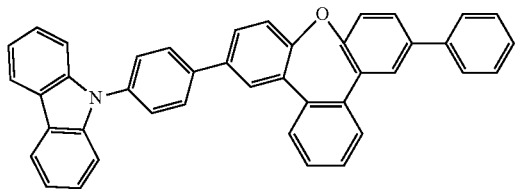
Formula (A-244)
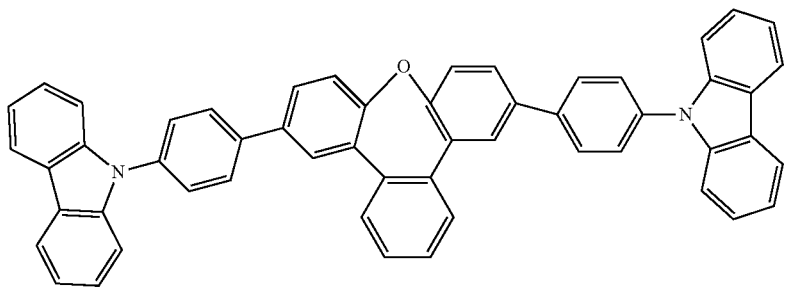
Formula (A-245)
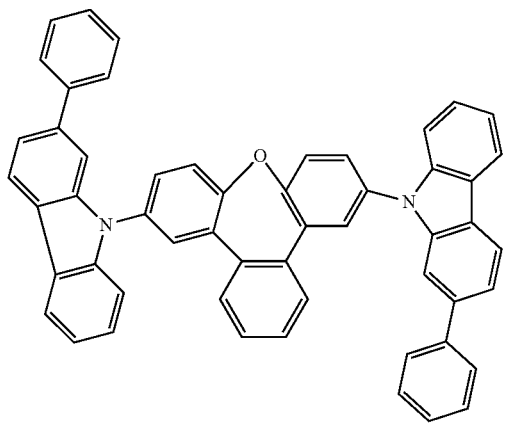
Formula (A-246)
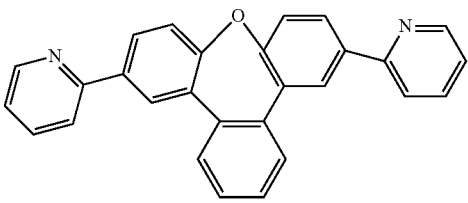
Formula (A-247)
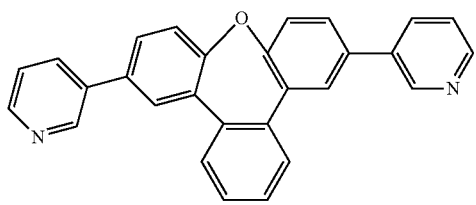
Formula (A-248)
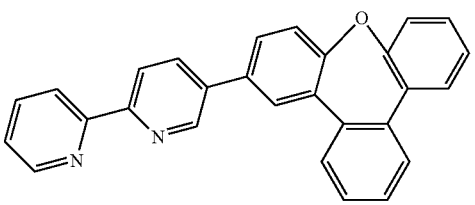

-continued
Formula (A-249)
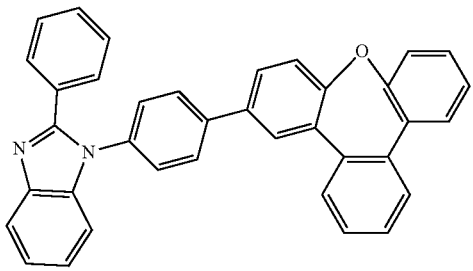
Formula (A-250)
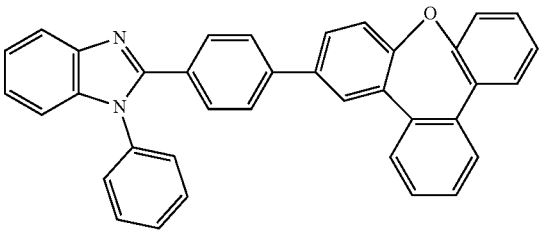
Formula (A-251)
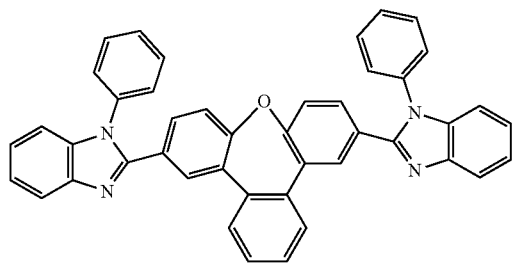
Formula (A-252)
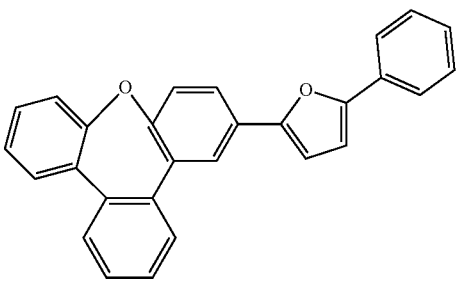
Formula (A-253)
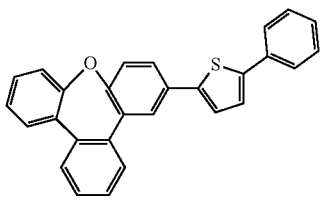
Formula (A-254)
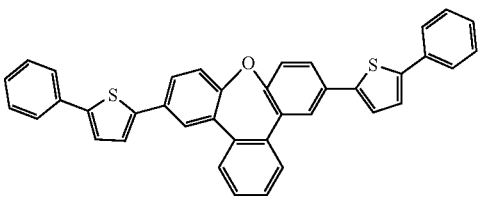
Formula (A-255)
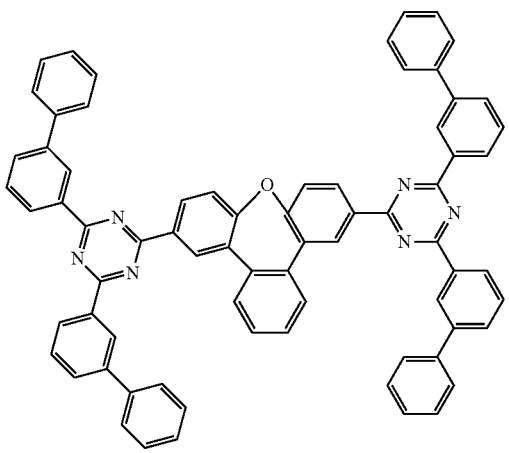
Formula (A-256)
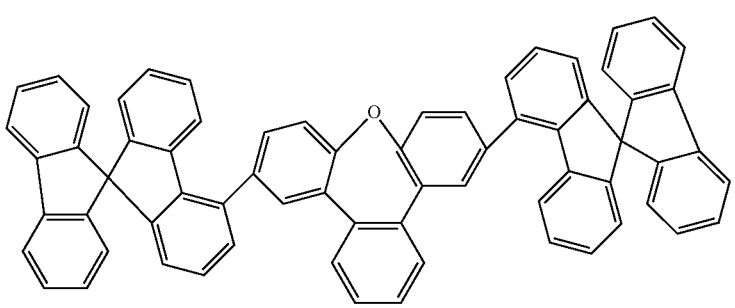

-continued
Formula (A-257)
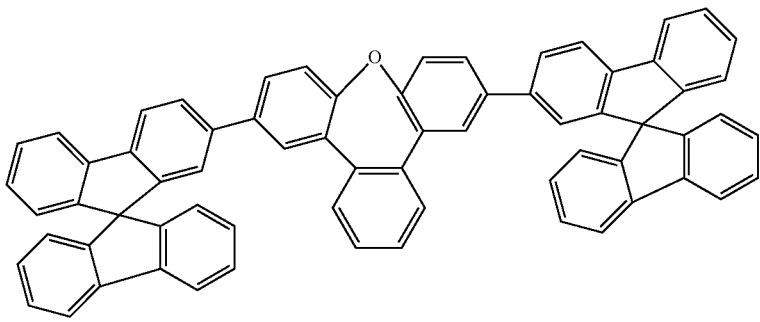
Formula (A-258)
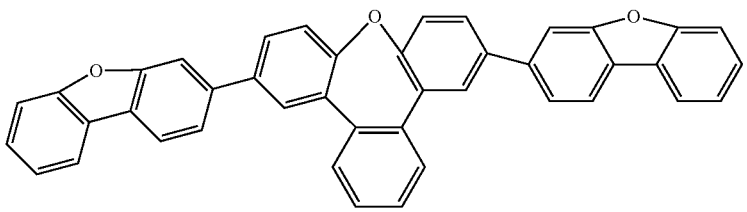
Formula (A-259)
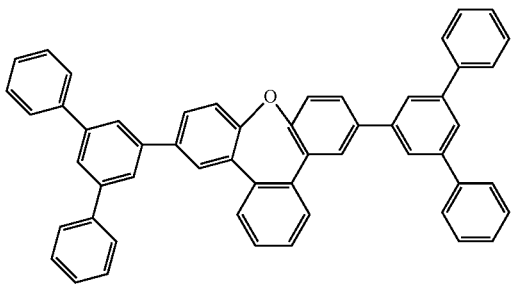
Formula (A-260)
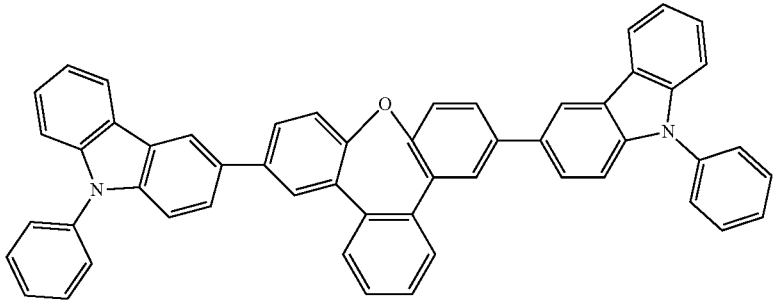
Formula (A-261)
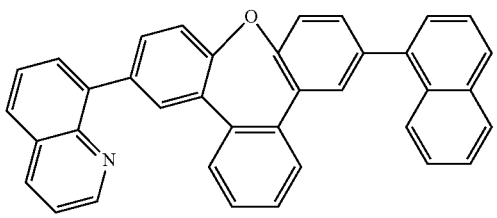
Formula (A-262)
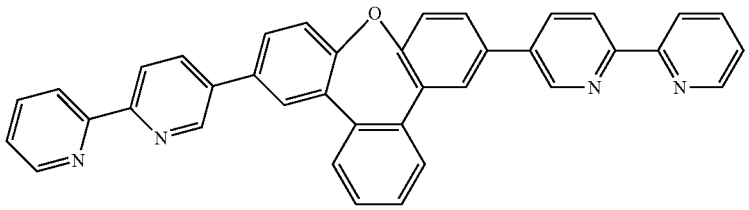

-continued
Formula (A-263)
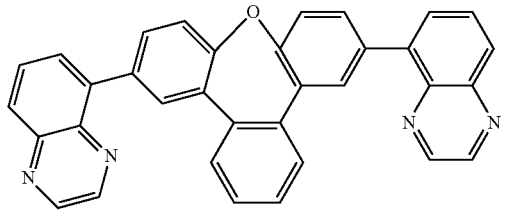
Formula (A-264)
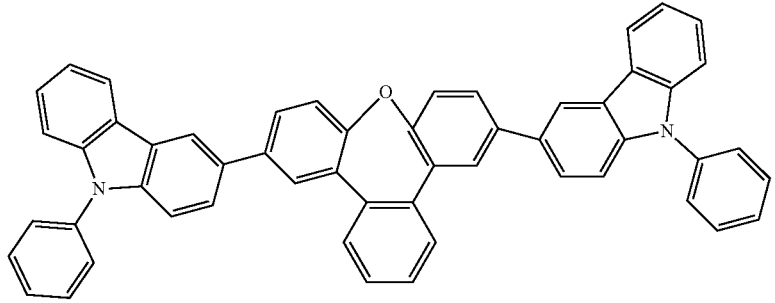
Formula (A-265)
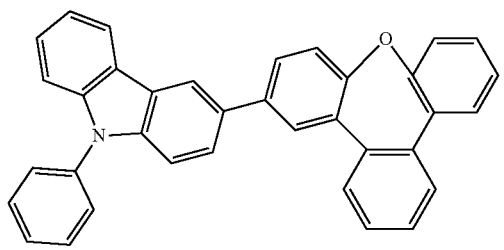
Formula (A-266)
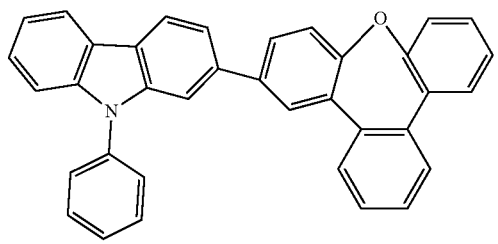
Formula (A-267)
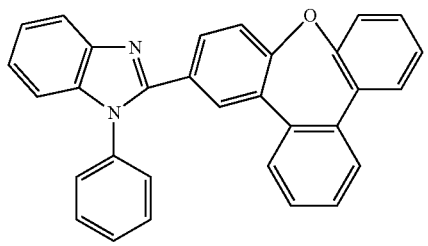
Formula (A-268)
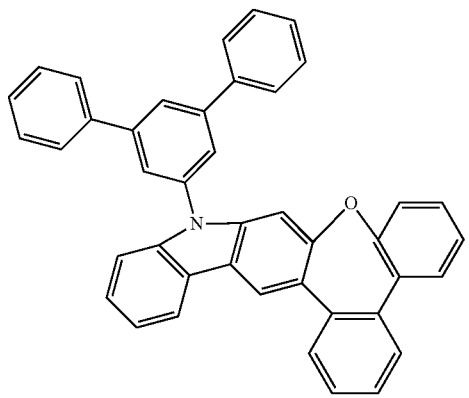
Formula (A-269)
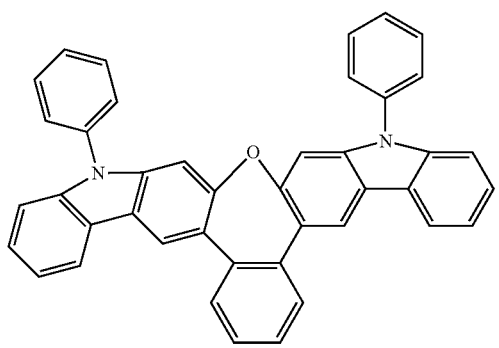
Formula (A-270)
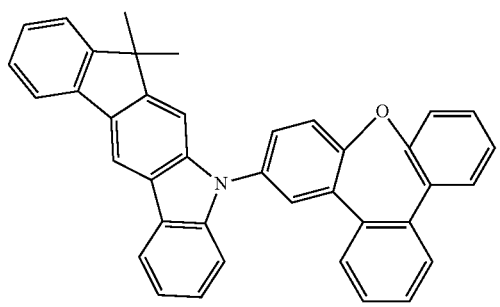

-continued
Formula (A-271)
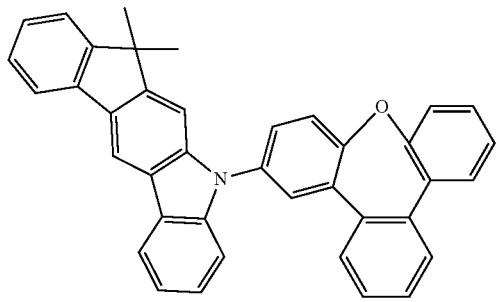
Formula (A-272)
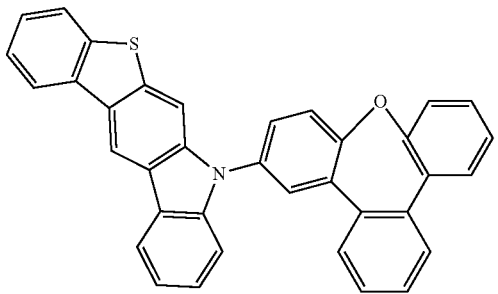
Formula (A-273)
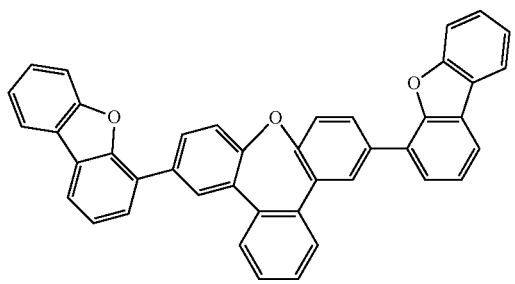
Formula (A-274)
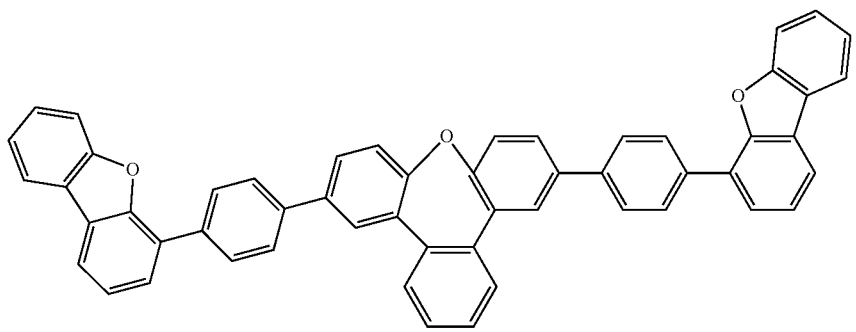
Formula (A-275)
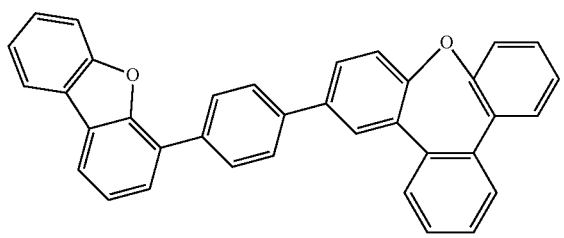
Formula (A-276)
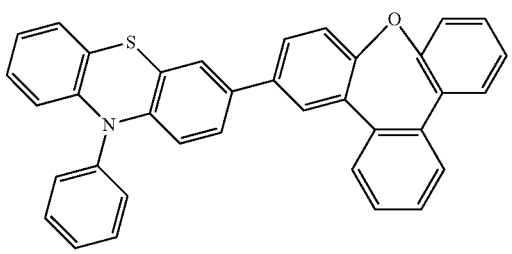
Formula (A-277)
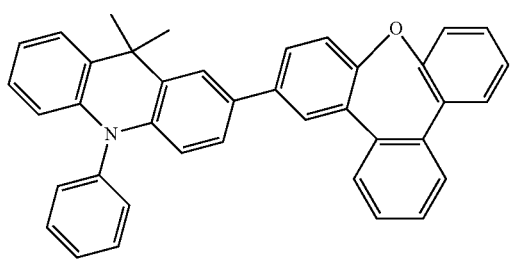
Formula (A-278)
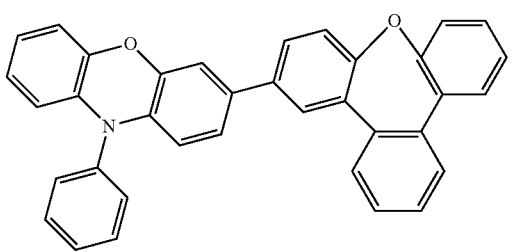

-continued
Formula (A-279)
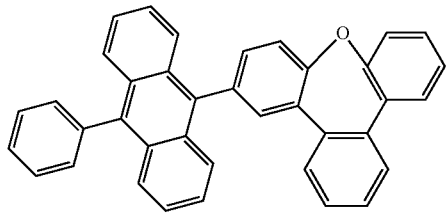
Formula (A-280)
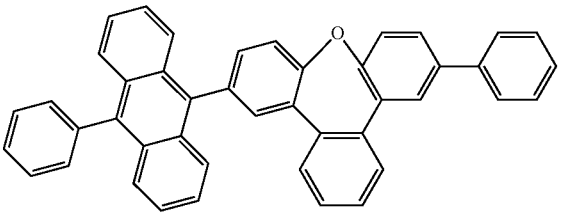
Formula (A-281)
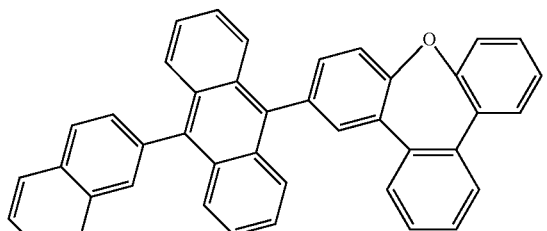
Formula (A-282)
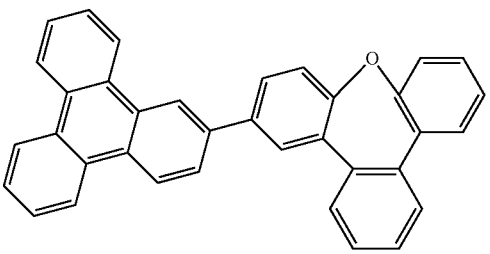
Formula (A-283)
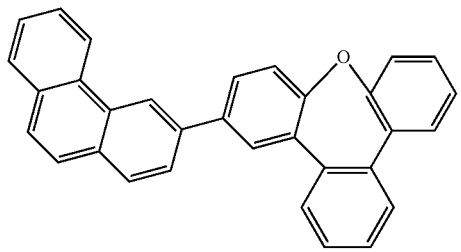
Formula (A-284)
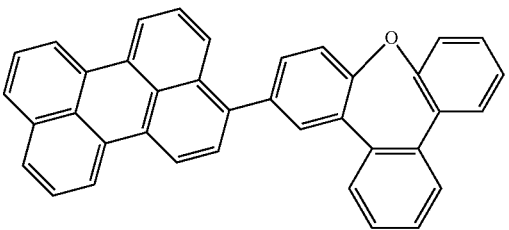
Formula (A-285)
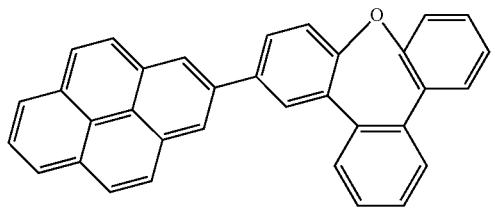
Formula (A-286)
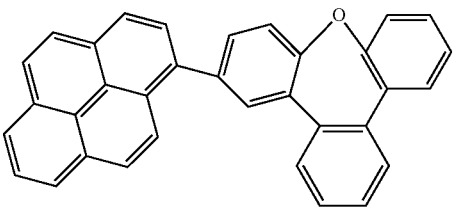
Formula (A-287)
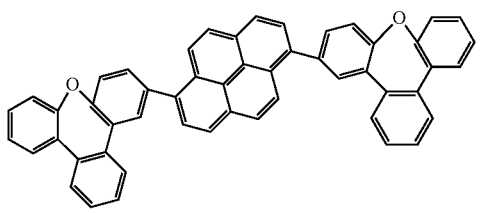
Formula (A-288)
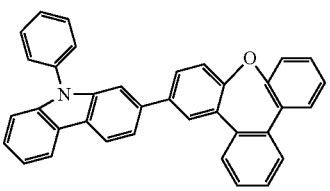
Formula (A-289)
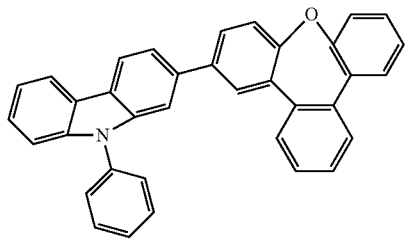
Formula (A-290)
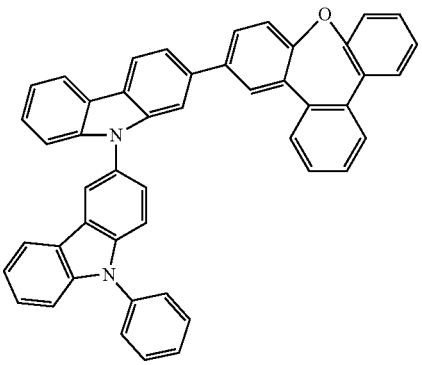

-continued
Formula (A-291)
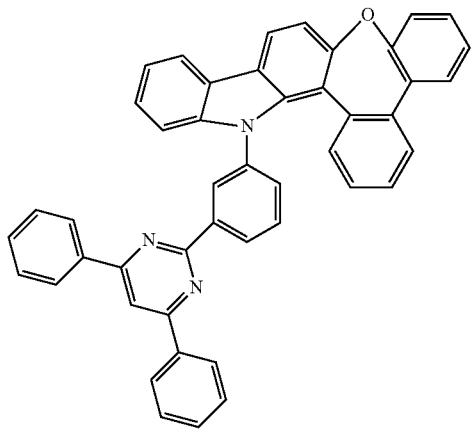
Formula (A-292)
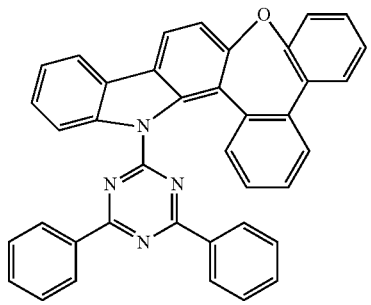
Formula (A-293)
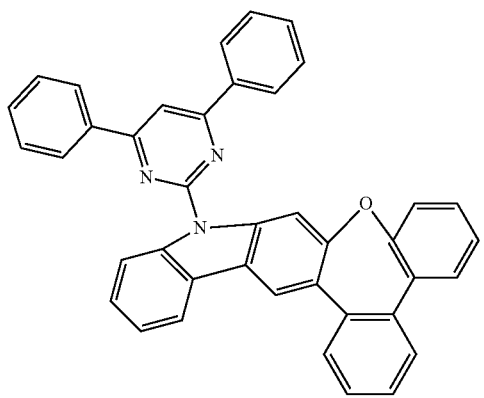
INV-5
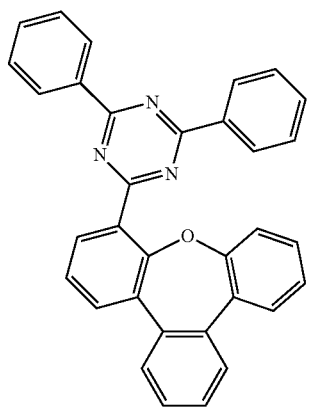
INV-6
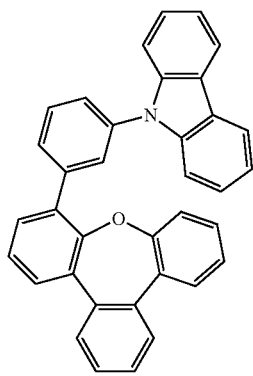
INV-7
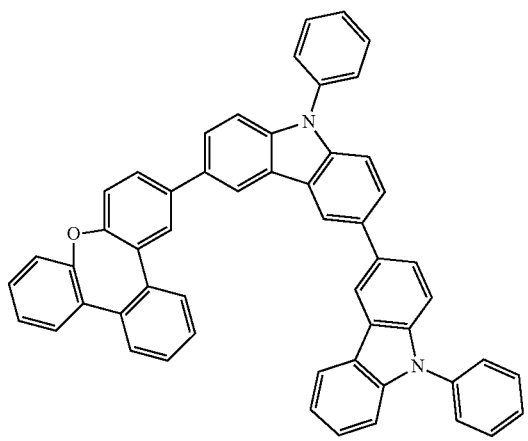

-continued
INV-8
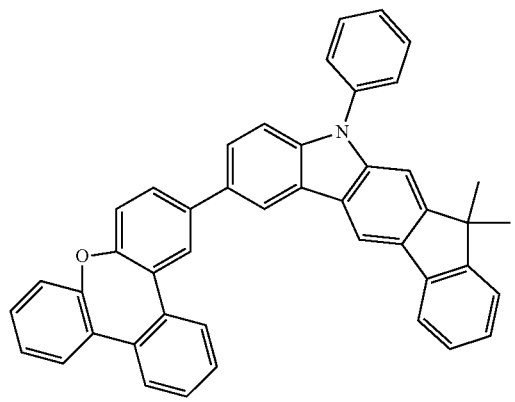
INV-9
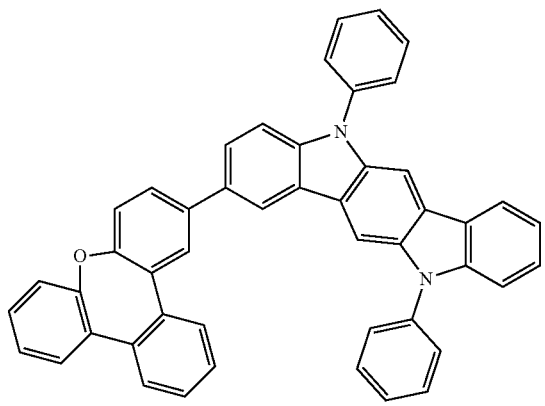
INV-10
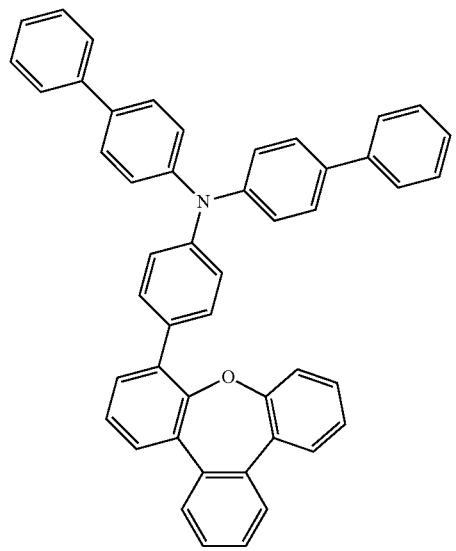
INV-11
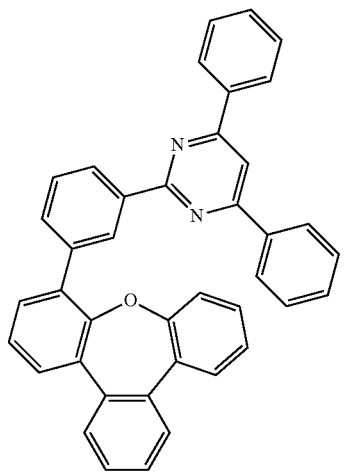
INV-12
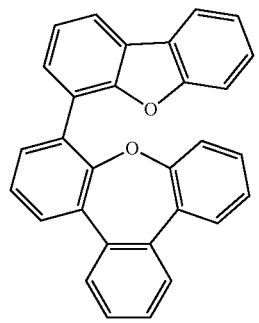
INV-13
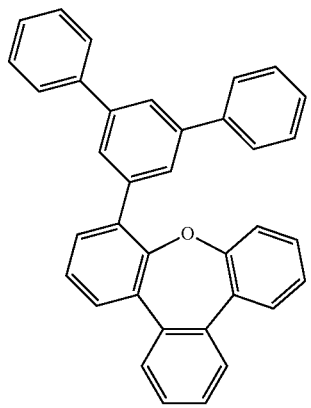

-continued
INV-14
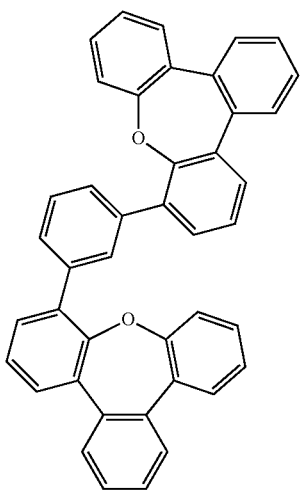
INV-15
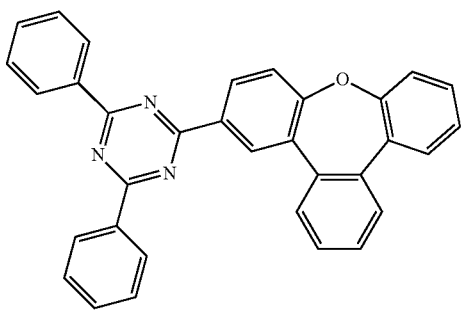
INV-16
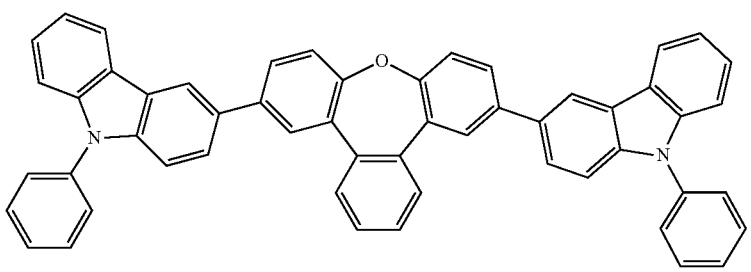
INV-17
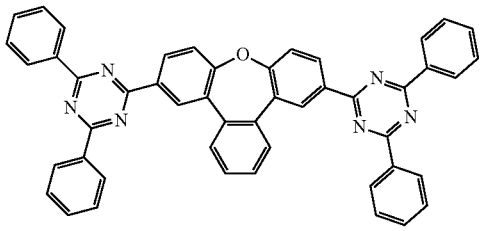
INV-18
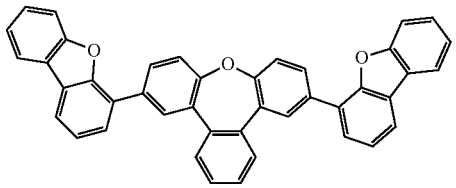
INV-19
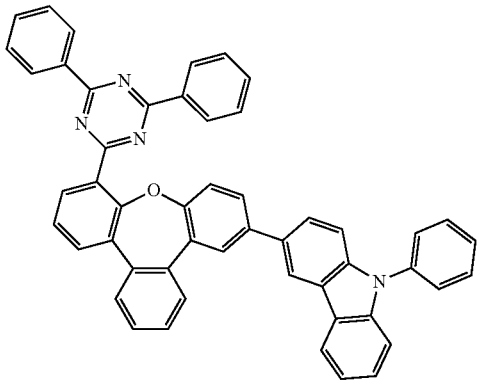
INV-20
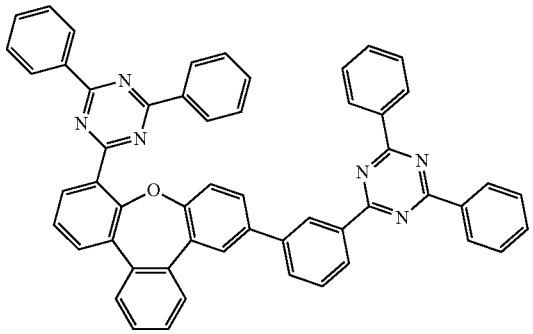

-continued
INV-21
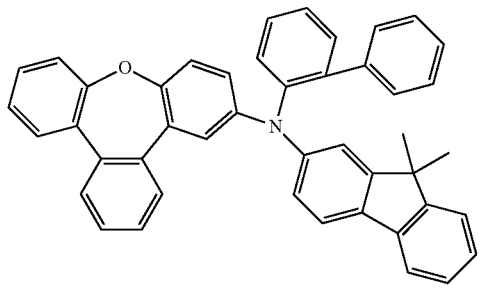
INV-22
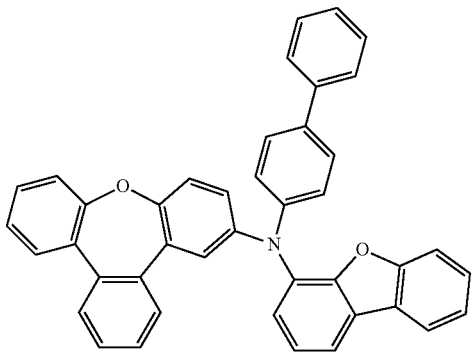
INV-23
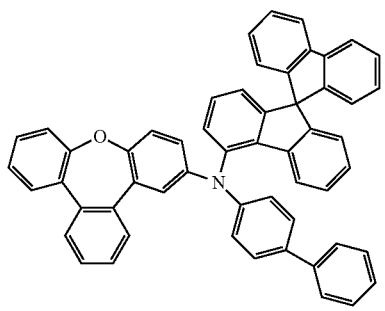
INV-24
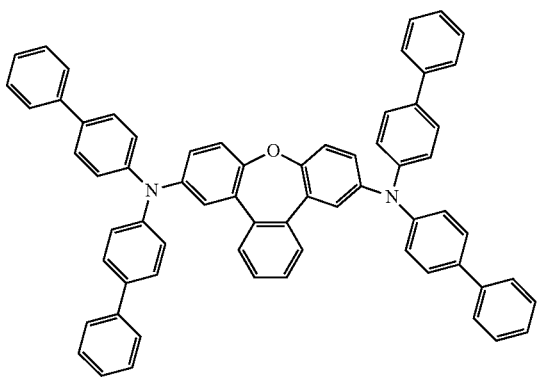
INV-25
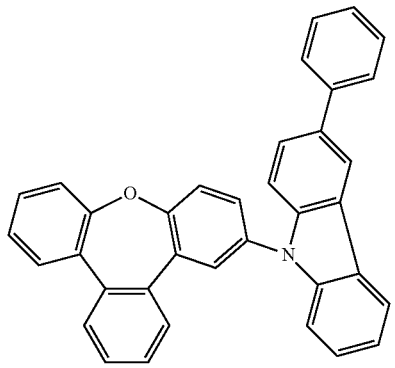
INV-26
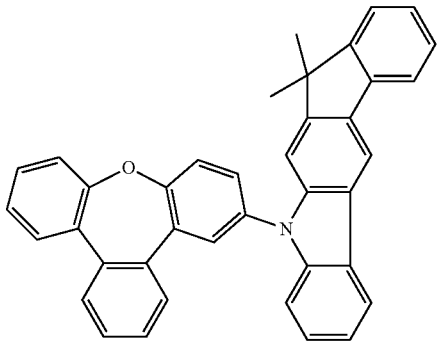
INV-27
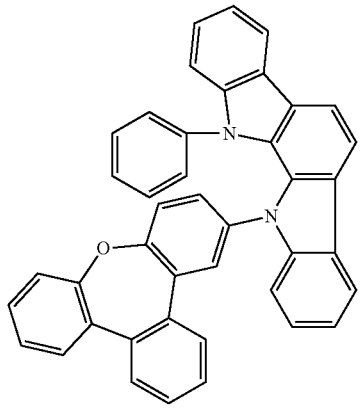
INV-28
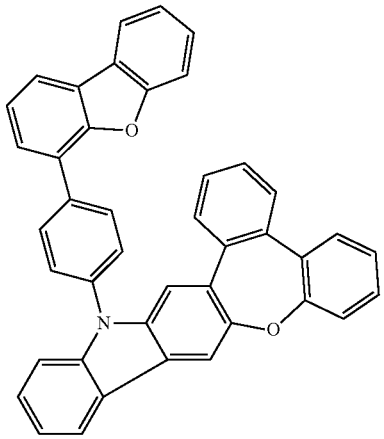

-continued
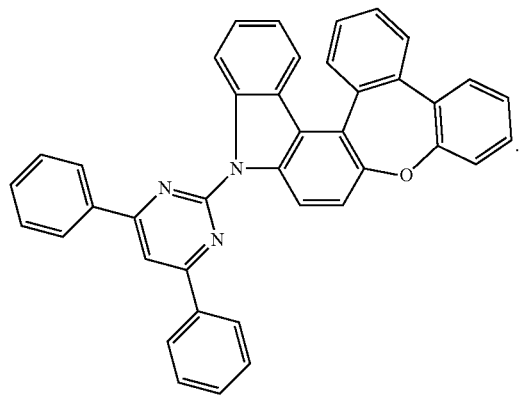
INV-29
* * * * *